(12) United States Patent
Ishibashi et al.

(10) Patent No.: US 8,945,728 B2
(45) Date of Patent: Feb. 3, 2015

(54) ORGANIC COMPOUND, CHARGE-TRANSPORTING MATERIAL, COMPOSITION CONTAINING THE COMPOUND, ORGANIC ELECTROLUMINESCENT ELEMENT, DISPLAY DEVICE, AND LIGHTING DEVICE

(71) Applicant: Mitsubishi Chemical Corporation, Chiyoda-ku (JP)

(72) Inventors: Koichi Ishibashi, Kanagawa (JP); Hideki Gorohmaru, Kanagawa (JP); Wataru Shimizu, Kanagawa (JP); Tomomi Okamoto, Kanagawa (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 14/047,403

(22) Filed: Oct. 7, 2013

(65) Prior Publication Data
US 2014/0034938 A1   Feb. 6, 2014

Related U.S. Application Data

(63) Continuation of application No. PCT/JP2012/059600, filed on Apr. 6, 2012.

(30) Foreign Application Priority Data

Apr. 7, 2011 (JP) ................................. 2011-085501

(51) Int. Cl.
*H01L 51/50* (2006.01)
*H01L 51/00* (2006.01)
(Continued)

(52) U.S. Cl.
CPC .......... *H01L 51/0067* (2013.01); *C07D 239/26* (2013.01); *C07D 403/10* (2013.01);
(Continued)

(58) Field of Classification Search
None
See application file for complete search history.

(56) References Cited

U.S. PATENT DOCUMENTS 6,225,467 B1    5/2001  Esteghamatian et al.
2004/0191191 A1*  9/2004  Ehlis et al. ..................... 424/59
(Continued)

FOREIGN PATENT DOCUMENTS

CN    101287713    10/2008
EP    1 820 801 A1    8/2007
(Continued)

OTHER PUBLICATIONS

Hsiao-Fan Chen et al., "1,3,5-Triazine Derivatives as new Electron Transport-type Host Materials for Highly Efficient Green Phosphorescent OLEDs", Journal of Materials Chemistry, vol. 19, 2009, pp. 8112-8118.
(Continued)

*Primary Examiner* — Gregory Clark
(74) *Attorney, Agent, or Firm* — Oblon, Spivak, McClelland, Maier & Neustadt, L.L.P.

(57) ABSTRACT

The invention provides an organic compound incorporating a specific structure into a pyridine skeleton or a 1,3,5-triazine skeleton and adapting the molecular weight to a specific range, a composition comprising the organic compound and a solvent, organic electroluminescent element comprising a layer that is formed by using the composition, and the uses thereof.

9 Claims, 1 Drawing Sheet

(51) Int. Cl.
    *C07D 239/26*     (2006.01)
    *C07D 403/10*     (2006.01)
    *C07D 405/14*     (2006.01)

(52) U.S. Cl.
    CPC .......... *C07D405/14* (2013.01); *H01L 51/0072* (2013.01); *H01L 51/0073* (2013.01); *H01L 51/0061* (2013.01); *H01L 51/0085* (2013.01); *H01L 51/5012* (2013.01); *Y10S 428/917* (2013.01)
    USPC .......... 428/690; 428/917; 313/504; 313/505; 313/506; 257/40; 257/E51.05; 257/E51.026; 257/E51.032; 548/304.1; 548/418; 548/440; 548/444; 546/18; 546/24; 544/234

(56) References Cited

U.S. PATENT DOCUMENTS

| | | | |
|---|---|---|---|
| 2006/0041126 A1 | 2/2006 | Schafer et al. | |
| 2007/0015007 A1* | 1/2007 | Shin et al. | 428/690 |
| 2008/0124570 A1 | 5/2008 | Kondo et al. | |
| 2009/0096360 A1* | 4/2009 | Tanaka et al. | 313/504 |
| 2009/0236973 A1* | 9/2009 | Yabe et al. | 313/504 |
| 2012/0126692 A1 | 5/2012 | Ise et al. | |

FOREIGN PATENT DOCUMENTS

| | | |
|---|---|---|
| EP | 1 956 008 A1 | 8/2008 |
| JP | 2004-022334 | 1/2004 |
| JP | 2004-031004 | 1/2004 |
| JP | 2006-190759 | 7/2006 |
| JP | 4474493 | 3/2010 |
| JP | 2010-278287 | 12/2010 |
| WO | 2004/039786 | 5/2004 |
| WO | 2011/013843 | 2/2011 |
| WO | 2011/021689 | 2/2011 |

OTHER PUBLICATIONS

Shi-Jian Su et al., "Tuning Energy Levels of Electron-Transport Materials by Nitrogen Orientation for Electrophosphorescent Devices with an 'Ideal' Operating Voltage", Advanced Materials, vol. 22, 2010, pp. 3311-3316.

International Search Report issued May 22, 2012 in PCT/JP2012/059600 filed Apr. 6, 2012.

Extended European Search Report issued Jul. 30, 2014 in Patent Application No. 12768300.1.

Office Action as received in the corresponding Chinese Patent Application No. 201280016418.0 dated Aug. 19, 2014 w/English Translation.

* cited by examiner

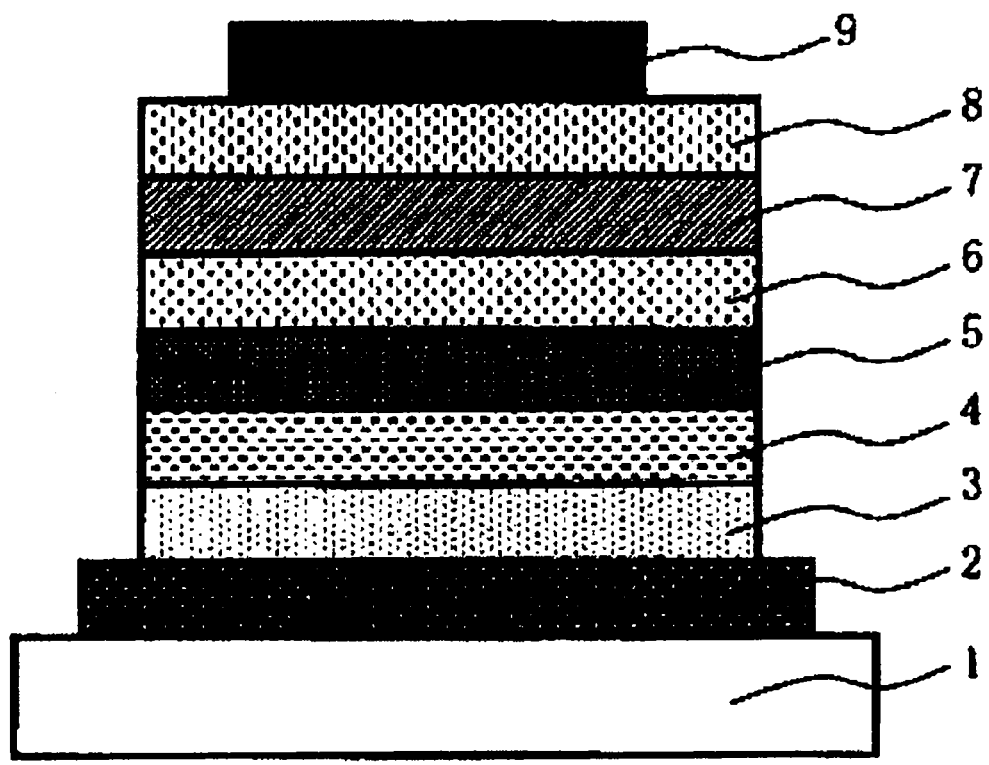

ORGANIC COMPOUND, CHARGE-TRANSPORTING MATERIAL, COMPOSITION CONTAINING THE COMPOUND, ORGANIC ELECTROLUMINESCENT ELEMENT, DISPLAY DEVICE, AND LIGHTING DEVICE

TECHNICAL FIELD

The present invention relates to an organic compound having a specific structure, a charge-transporting material and a composition each containing the compound, an organic electroluminescent element obtained using the compound, a display device, and a lighting device.

BACKGROUND ART

In recent years, organic electroluminescent (EL) elements employing a thin organic film have come to be developed as thin film type electroluminescent elements in place of EL elements employing inorganic materials. An organic electroluminescent element usually has layers such as a hole injection layer, hole-transporting layer, luminescent layer, and electron-transporting layer between the anode and the cathode, and elements which emit light of a color, such as red, green, or blue, suitable for those layers are being developed. Since organic electroluminescent elements emit light by themselves, the elements attain a wide viewing angle and high visibility. The elements are attracting attention also from the standpoints of space saving, etc., because the elements are of the thin film type. In addition, organic electroluminescent elements have a feature that the elements emit light areally unlike the light-emitting diodes and cold-cathode tubes which have hitherto been in practical use. Owing to this feature, use of the elements in lighting devices, the backlights of full-color display devices in which color filters are used, etc. is also attracting attention.

Known as methods for forming the layers of an organic electroluminescent element are a vapor deposition method and a wet film formation method. However, the vapor deposition method has a problem concerning yield when TV receivers, monitors, medium- or large-size full-color panels for illumination, and the like are produced. The wet film formation method is hence suitable for these large-area applications (see patent documents 1 and 2).

For forming each of those layers of an organic electroluminescent element by a wet film formation method, it is desirable that the materials for constituting each layer should dissolve in a solvent and that the element obtained through the wet-process film formation should have high performance. From the standpoint of more efficient production, it is also desirable that the composition including the materials and the solvent should have high stability.

Meanwhile, it is known that pyrimidine derivatives and 1,3,5-triazine derivatives are suitable for use as a charge-transporting material, in particular, a material for organic electroluminescent elements, because these derivatives have high electron-accepting properties and a high electron mobility. For example, patent documents 3 to 6 and no-patent documents 1 and 2 disclose organic electroluminescent elements which employ those derivatives.

CONVENTIONAL ART DOCUMENTS

Patent Documents

Patent Document 1: JP-A-2006-190759
Patent Document 2: JP-A-2010-278287
Patent Document 3: JP-A-2004-031004
Patent Document 4: Japanese Patent No. 4474493
Patent Document 5: U.S. Pat. No. 6,225,467
Patent Document 6: JP-A-2004-022334

Non-Patent Documents

Non-Patent Document 1: *Journal of Materials Chemistry*, Vol. 19, pp. 8112-8118, 2009
Non-Patent Document 2: *Advanced Materials*, Vol. 22, pp. 3311-3316, 2010

SUMMARY OF THE INVENTION

Problems that the Invention is to Solve

However, the conventional materials have low solubility in organic solvents and, hence, it is difficult to produce an element by a wet film formation method using a composition containing both any of those materials and a solvent. Even if the composition can be used to produce an element, this composition has poor storage stability and hence does not render efficient production possible.

The present invention eliminates such problems of the conventional art techniques above. Subjects for the invention are: to improve the solubility in solvents of organic compounds having a pyrimidine framework and a 1,3,5-triazine framework; to improve the storage stability of a composition constituted of such organic compound and a solvent; and to provide an organic electroluminescent element which has a layer formed from the composition by a wet film formation method and which shows high performance in terms of luminescent efficiency, driving life, durability, etc. A further subject for the invention is to provide a display device and a lighting device which each include the organic electroluminescent element.

Means for Solving the Problems

The present inventors diligently made investigations in order to overcome the problems. As a result, the inventors have found that by introducing specific structures into the pyrimidine framework and 1,3,5-triazine framework, the solubility of the compound in solvents is greatly improved and the storage stability of the composition containing the compound and a solvent is heightened, and that the organic electroluminescent element having an organic layer formed from the composition by a wet film formation method has a low operating voltage and a high luminescent efficiency. The invention has been thus accomplished.

That is, the gist of the invention resides in the following [1] to [13].

[1] An organic compound which is represented by the following general formula (1), has a molecular weight of 750 or more and 2,000 or less, and has one or no carbazolyl group in the molecule:

[Ka 1]

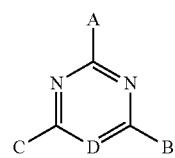

(1)

wherein

A, B, and C each independently are selected from substituents represented by the following general formulae (2-1) to (2-5):

—Ar¹—X¹  (2-1)

Ar²—Ar³—X²  (2-2)

—Ar⁴—Ar⁵—Ar⁶—X³  (2-3)

—Ar⁷—Ar⁸—Ar⁹—Ar¹⁰—X⁴  (2-4)

—Ar¹¹—Ar¹²—Ar¹³—Ar¹⁴—Ar¹⁵—X⁵  (2-5)

wherein Ar¹ represents a 1,2-phenylene group or 1,3-phenylene group, which may have a substituent, Ar² to Ar¹⁵ each independently represent a 1,2-phenylene group, 1,3-phenylene group, or 1,4-phenylene group, which may have a substituent, X¹ represents an aromatic hydrocarbon group which has 10 or more carbon atoms and may have a substituent, or a carbazolyl group which may have a substituent, and X² to X⁵ each independently represent an aromatic hydrocarbon group which may have a substituent, a carbazolyl group which may have a substituent, a dibenzofuranyl group which may have a substituent, or a dibenzothienyl group which may have a substituent, with the proviso that A, B, and C each contain at least one of a 1,2-phenylene group and a 1,3-phenylene group, and that A, B, and C do not simultaneously represent the same group; and D represents CH or a nitrogen atom.

[2] The organic compound according to the item [1] above, wherein in general formulae (2-2) to (2-5), the substituents represented by Ar² to Ar¹⁵ each independently are a 1,3-phenylene group or a 1,4-phenylene group.

[3] The organic compound according to the item 1 or 2 above, wherein in general formulae (2-1) to (2-5), the substituents represented by Ar¹, Ar³, Ar⁶, Ar¹⁰, and Ar¹⁵ are 1,3-phenylene groups.

[4] The organic compound according to any one of the items [1] to [3] above, wherein A, B, and C in general formula (1) are a different substituent from each other.

[5] An organic compound which is represented by the following general formula (3), has a molecular weight of 750 or more and 2,000 or less, and has one or no carbazolyl group in the molecule:

[Ka 2]

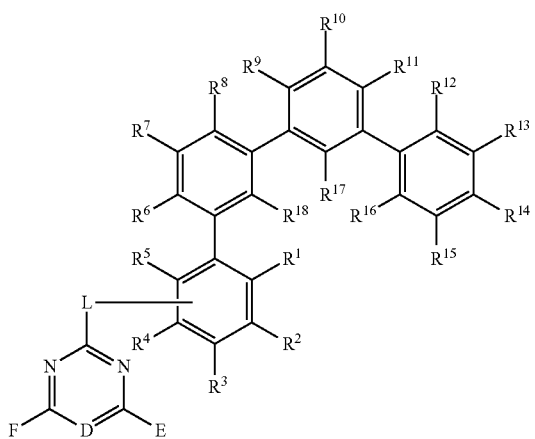

(3)

wherein
D represents CH or a nitrogen atom;

E and F each independently are selected from substituents represented by the following general formulae (4-1) to (4-6):

—X⁶  (4-1)

—Ar¹⁶—X⁷  (4-2)

—Ar¹⁷—Ar¹⁸—X⁸  (4-3)

—Ar¹⁹—Ar—Ar²¹—X⁹  (4-4)

—Ar²²—Ar²³—Ar²⁴—Ar²⁵—X¹⁰  (4-5)

—Ar²⁶—Ar²⁷—Ar²⁸—Ar²⁹—Ar³⁰—X¹¹  (4-6)

wherein Ar¹⁶ represents a 1,2-phenylene group or 1,3-phenylene group, which may have a substituent, Ar¹⁷ to Ar³⁰ each independently represent a 1,2-phenylene group, 1,3-phenylene group, or 1,4-phenylene group, which may have a substituent, and X⁶ to X¹¹ each independently represent an aromatic hydrocarbon group which may have a substituent, a carbazolyl group which may have a substituent, a dibenzofuranyl group which may have a substituent, or a dibenzothienyl group which may have a substituent, with the proviso that E and F each contain at least one of a 1,2-phenylene group and a 1,3-phenylene group;

L represents a direct bond or a divalent aromatic hydrocarbon group which may have a substituent, and forms a bond with any one of the substitution positions of R¹ to R⁵;

R¹ to R⁵ each independently represent a bond with L, a hydrogen atom, a phenyl group which may have a substituent, a dibenzofuranyl group which may have a substituent, a dibenzothienyl group which may have a substituent, an alkyl group, a silyl group, a fluorine atom, or a perfluoroalkyl group; and R⁶ to R¹⁸ each represent a hydrogen atom, a phenyl group which may have a substituent, a dibenzofuranyl group which may have a substituent, a dibenzothienyl group which may have a substituent, an alkyl group, a silyl group, a fluorine atom, or a perfluoroalkyl group.

[6] The organic compound according to the item [5] above, wherein in general formulae (4-3) to (4-6), the substituents represented by Ar¹⁷ to Ar³⁰ each independently are a 1,3-phenylene group or a 1,4-phenylene group.

[7] The organic compound according to the item [5] or [6] above, wherein in general formulae (4-2) to (4-6), the substituents represented by Ar¹⁶, Ar¹⁸, Ar²¹, Ar²⁵, and Ar³⁰ are 1,3-phenylene groups.

[8] A charge-transporting material which comprises the organic compound according to any one of the items [1] to [7] above.

[9] A composition which comprises the organic compound according to any one of the items [1] to [7] above and a solvent.

[10] An organic electroluminescent element which comprises an anode, a cathode, and one or more organic layers disposed between the anode and the cathode, wherein at least one of the organic layers is a layer formed from the composition according to the item [9] above.

[11] The organic electroluminescent element according to the item [10] above, wherein the layer formed from the composition according to claim 9 is a luminescent layer.

[12] A display device which comprises the organic electroluminescent element according to the item [10] or [11] above.

[13] A lighting device which comprises the organic electroluminescent element according to the item [10] or [11] above.

Effects of the Invention

The organic compound of the invention, which has a pyrimidine framework or 1,3,5-triazine framework into which specific substituents have been introduced, has high solubility in solvents, and a composition constituted of this organic compound and a solvent has excellent storage stability. Furthermore, by using the composition, an even thin film can be formed by a wet film formation method, making it possible to provide an organic electroluminescent element having a long life, low operating voltage, and high luminescent efficiency. Moreover, the organic electroluminescent element of the invention is expected to be used in applications which take advantage of the feature of a surface light emitter, such as lighting devices, white-light sources (e.g., the light sources of copiers, the backlights of liquid-crystal displays or instruments, and color-filter display devices), display boards, and marker lamps. This organic electroluminescent element is thought to have an exceedingly high technical value.

BRIEF DESCRIPTION OF THE DRAWING

FIG. 1 is a sectional view which diagrammatically shows one example of the structure of an organic electroluminescent element of the invention.

MODES FOR CARRYING OUT THE INVENTION

Modes for carrying out the invention are explained below in detail. However, the invention should not be construed as being limited to the following modes, and the invention can be variously modified within the gist of the invention.

In this description, "% by weight" has the same meaning as "% by mass", and "weight ratio" has the same meaning as "mass ratio".

Explanation of Terms

In the invention, the mere expression "aromatic ring" includes both an aromatic hydrocarbon ring and an aromatic heterocycle.

In the invention, the expression "may have a substituent" means that one or more substituents may be possessed.

The term "group derived from a ring" in the invention means either a monovalent group obtained by removing one hydrogen atom from the ring or a divalent group obtained by removing two hydrogen atoms from the ring. For example, the expression "a group which is derived from a benzene ring and may have a substituent" means a phenyl group which may have a substituent, when that group has a valence of 1, or means a phenylene group which may have a substituent, when that group has a valence of 2. There are no particular limitations on the positions of bonds unless otherwise indicated, and the divalent group derived from a benzene ring include a 1,2-phenylene group, 1,3-phenylene group, and 1,4-phenylene group.

The term "wet film formation method" in the invention means a method in which a film is formed by a wet process such as, for example, spin coating, dip coating, die coating, bar coating, blade coating, roll coating, spray coating, capillary coating, ink-jet printing, screen printing, gravure printing, or flexographic printing. Preferred of these film formation techniques are spin coating, spray coating, and ink-jet printing. This is because these techniques are suited to the liquid nature characteristics of compositions for wet film formation to be used for organic electroluminescent elements.

[Organic Compound of the Invention]

The organic compound of the invention is an organic compound characterized by being represented by the following general formula (1) or (3), having a molecular weight of 750 or more and 2,000 or less, and having one or no carbazolyl group in the molecule (hereinafter often referred to as "organic compound of the invention").

[Ka 3]

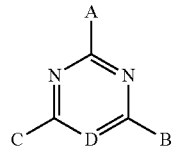

(1)

In general formula (1),

A, B, and C each independently are selected from substituents represented by the following general formulae (2-1) to (2-5).

—Ar$^1$—X$^1$ (2-1)

—Ar$^2$—Ar$^3$—X$^2$ (2-2)

—Ar$^4$—Ar$^5$—Ar$^6$—X$^3$ (2-3)

—Ar$^7$—Ar$^8$—Ar$^9$—Ar$^{10}$—X$^4$ (2-4)

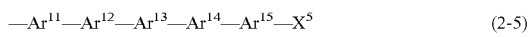

—Ar$^{11}$—Ar$^{12}$—Ar$^{13}$—Ar$^{14}$—Ar$^{15}$—X$^5$ (2-5)

In general formulae (2-1) to (2-5), Ar$^1$ represents a 1,2-phenylene group or 1,3-phenylene group which may have a substituent, and Ar$^2$ to Ar$^{15}$ each independently represent a 1,2-phenylene group, 1,3-phenylene group, or 1,4-phenylene group which may have a substituent.

X$^1$ represents an aromatic hydrocarbon group which has 10 or more carbon atoms and may have a substituent or a carbazolyl group which may have a substituent, and X$^2$ to X$^5$ each independently represent an aromatic hydrocarbon group which may have a substituent, a carbazolyl group which may have a substituent, a dibenzofuranyl group which may have a substituent, or a dibenzothienyl group which may have a substituent.

D represents CH or a nitrogen atom. Namely, when D is CH, the organic compound of the invention is a compound having a pyrimidine ring framework, and when D is a nitrogen atom, the organic compound of the invention is a compound having a 1,3,5-triazine ring framework.

However, the following should be noted. From the standpoint of making the compound have a molecular structure with reduced symmetry and have a larger number of stable conformations and thereby improving the solubility thereof in solvents, A, B, and C each contain at least one 1,2-phenylene group which may have a substituent or at least one 1,3-phenylene group which may have a substituent, and A, B, and C do not simultaneously represent the same group, that is, the case where A=B=C is excluded.

[Ka 4]

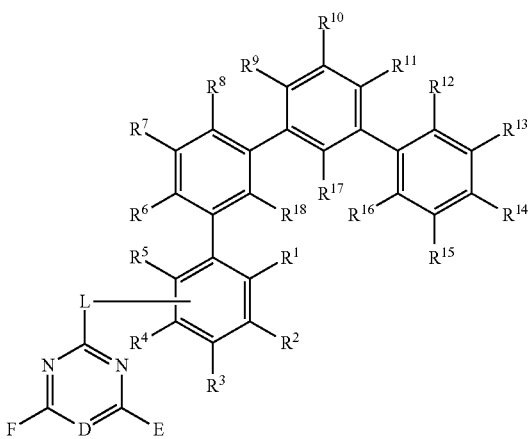

(3)

In general formula (3),

D represents CH or a nitrogen atom. Namely, when D is CH, the organic compound of the invention is a compound having a pyrimidine ring framework, and when D is a nitrogen atom, the organic compound of the invention is a compound having a 1,3,5-triazine ring framework.

E and F each independently are selected from substituents represented by the following general formulae (4-1) to (4-6).

 (4-1)

 (4-2)

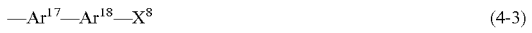 (4-3)

 (4-4)

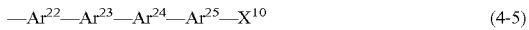 (4-5)

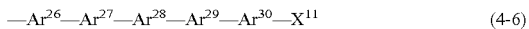 (4-6)

In general formulae (4-1) to (4-6), $Ar^{16}$ represents a 1,2-phenylene group or 1,3-phenylene group which may have a substituent, and $Ar^{17}$ to $Ar^{30}$ each independently represent a 1,2-phenylene group, 1,3-phenylene group, or 1,4-phenylene group which may have a substituent.

$X^6$ to $X^{11}$ each independently represent an aromatic hydrocarbon group which may have a substituent, a carbazolyl group which may have a substituent, a dibenzofuranyl group which may have a substituent, or a dibenzothienyl group which may have a substituent.

However, E and F each contain a 1,2-phenylene group and/or a 1,3-phenylene group.

$R^1$ to $R^5$ each independently represent a hydrogen atom, a phenyl group which may have a substituent, a dibenzofuranyl group which may have a substituent, a dibenzothienyl group which may have a substituent, an alkyl group, a silyl group, a fluorine atom, or a perfluoroalkyl group, and $R^6$ to $R^{18}$ each represent a hydrogen atom, a phenyl group which may have a substituent, a dibenzofuranyl group which may have a substituent, a dibenzothienyl group which may have a substituent, an alkyl group, a silyl group, a fluorine atom, or a perfluoroalkyl group.

L represents a direct bond or a divalent aromatic hydrocarbon group which may have a substituent, and forms a bond with any one of the substitution positions of $R^1$ to $R^5$.

<$Ar^1$ to $Ar^{30}$>

In general formulae (2-1) and (4-2), although $Ar^1$ and $Ar^{16}$ each are a 1,2-phenylene group which may have a substituent or a 1,3-phenylene group which may have a substituent, it is especially preferred that $Ar^1$ and $Ar^{16}$ each should be a 1,3-phenylene group which may have a substituent, from the standpoint of durability.

In general formulae (2-2) to (2-5) and general formulae (4-3) to (4-6), although $Ar^2$ to $Ar^{15}$ and $Ar^{17}$ to $Ar^{30}$ each independently are a 1,2-phenylene group which may have a substituent, a 1,3-phenylene group which may have a substituent, or a 1,4-phenylene group which may have a substituent, it is preferred from the standpoint of durability that these groups each should be a 1,3-phenylene group which may have a substituent or a 1,4-phenylene group which may have a substituent. In particular, from the standpoint of further improving the solubility in organic solvents, it is preferred that $Ar^3$, $Ar^6$, $Ar^{10}$, $Ar^{15}$, $Ar^{18}$, $Ar^{21}$, $Ar^{25}$, and $Ar^{30}$ in general formulae (2-2) to (2-5) and in general formulae (4-3) to (4-6) each should be a 1,3-phenylene group which may have a substituent.

<$X^1$ to $X^{11}$>

In general formula (2-1), the aromatic hydrocarbon group having 10 or more carbon atoms which constitutes $X^1$ preferably is an aromatic hydrocarbon group having 10-30 carbon atoms, and especially preferably is a group derived from a fused ring composed of two to five 6-membered monocycles fused together.

Examples of the aromatic hydrocarbon group of $X^1$ include groups derived from a naphthalene ring, anthracene ring, phenanthrene ring, perylene ring, tetracene ring, pyrene ring, benzpyrene ring, chrysene ring, triphenylene ring, and fluoranthene ring. Preferred of these are groups derived from a naphthalene ring and a phenanthrene ring, from the standpoint that the organic compound in which $X^1$ is such a group has a relatively low triplet excitation level and relatively high solubility in organic solvents.

The reason why the aromatic hydrocarbon groups having 9 or less carbon atoms (e.g., a group derived from a benzene ring) are excluded from $X^1$ is as follows. Since the substituent represented by general formula (2-1) has a smaller overall size than the substituents represented by general formulae (2-2) to (2-5), the solvation energy which the substituent receives from solvent molecules is low. It is therefore desirable that the substituent which constitutes $X^1$ should be a substituent that greatly improves solubility. For example, groups derived from a naphthalene ring and phenanthrene ring are known to improve both solubility in organic solvents and film quality, because these groups show higher steric hindrance with other rings bonded thereto than groups derived from a benzene ring (see, for example, JP-A-2011-26237).

The position of the site where the aromatic hydrocarbon group of $X^1$ is bonded to $Ar^1$ is not particularly limited. However, from the standpoints of chemical stability and charge-transporting properties, it is preferred that when $X^1$ is, for example, a naphthyl group, this group should have been bonded at the 1-position of the naphthalene ring, and that when $X^1$ is a phenanthyl group, this group should have been bonded at the 9- or 10-position of the phenanthrene ring.

In general formula (2-1), the position of the site where the carbazolyl group ("carbazolyl group" means a "group derived from a carbazole ring") which constitutes $X^1$ is bonded to $Ar^1$ is not particularly limited. However, from the standpoints of chemical stability and charge-transporting properties, it is preferred that the group should have been bonded at the 2-, 3-, 6-, or 9-position of the carbazole ring, and it is more preferred that the group should have been bonded at the 2- or 9-position.

In general formulae (2-2) to (2-5) and general formulae (4-1) to (4-6), the aromatic hydrocarbon groups which constitute $X^2$ to $X^{11}$ preferably are aromatic hydrocarbon groups having 6-30 carbon atoms, and especially preferably are groups derived from a 6-membered monocycle or from a fused ring composed of two to five 6-membered monocycles fused together.

Examples of the aromatic hydrocarbon groups of $X^2$ to $X^{11}$ include groups derived from a benzene ring, naphthalene ring, anthracene ring, phenanthrene ring, perylene ring, tetracene ring, pyrene ring, benzpyrene ring, chrysene ring, triphenylene ring, and fluoranthene ring. Preferred of these are groups derived from a benzene ring, naphthalene ring, and phenanthrene ring, from the standpoint that the organic compound in which $X^2$ to $X^{11}$ are such groups has a relatively low triplet excitation level and relatively high solubility in organic solvents.

There are no particular limitations on the sites where the aromatic hydrocarbon groups constituting $X^2$ to $X^5$ and $X^7$ to $X^{11}$ are bonded respectively to $Ar^3$, $Ar^6$, $Ar^{10}$, $Ar^{15}$, $Ar^{16}$, $Ar^{18}$, $Ar^{21}$, $Ar^{25}$, and $Ar^{30}$, and on the site where the aromatic hydrocarbon group constituting $X^6$ is bonded to the 1,3,5-triazine ring or pyrimidine ring. However, from the standpoints of chemical stability and charge-transporting properties, it is preferred that when $X^2$ to $X^{11}$ each are, for example, a naphthyl group, this group should have been bonded at the 1-position of the naphthalene ring, and that when $X^2$ to $X^{11}$ each are a phenanthyl group, this group should have been bonded at the 9- or 10-position of the phenanthrene ring.

In general formulae (2-2) to (2-5) and general formulae (4-1) to (4-6), there are no particular limitations on the sites where the carbazolyl groups constituting $X^2$ to $X^5$ and $X^7$ to $X^{11}$ are bonded respectively to $Ar^3$, $Ar^6$, $Ar^{10}$, $Ar^{15}$, $Ar^{16}$, $Ar^{18}$, $Ar^{21}$, $Ar^{25}$, and $Ar^{30}$, and on the site where the carbazolyl group constituting $X^6$ is bonded to the 1,3,5-triazine ring or pyrimidine ring. However, from the standpoints of chemical stability and charge-transporting properties, it is preferred that each carbazolyl group should have been bonded at the 2-, 3-, 6-, or 9-position of the carbazole ring, and it is more preferred that each carbazolyl group should have been bonded at the 2- or 9-position.

In general formulae (2-2) to (2-5) and general formulae (4-1) to (4-6), there are no particular limitations on the sites where the dibenzofuranyl groups ("dibenzofuranyl group" means a "group derived from a dibenzofuran ring") or dibenzothienyl groups ("dibenzothienyl group" means a "group derived from a dibenzothiophene ring") which constitute $X^2$ to $X^5$ and $X^7$ to $X^{11}$ are bonded respectively to $Ar^3$, $Ar^6$, $Ar^{10}$, $Ar^{15}$, $Ar^{16}$, $Ar^{18}$, $Ar^{21}$, $Ar^{25}$, and $Ar^{30}$, and on the site where the dibenzofuranyl group or dibenzothienyl group which constitutes $X^6$ is bonded to the 1,3,5-triazine ring or pyrimidine ring. However, from the standpoints of chemical stability and charge-transporting properties, it is preferred that each dibenzofuranyl or dibenzothienyl group should have been bonded at the 2- or 4-position of the dibenzofuran ring or dibenzothiophene ring, and it is more preferred that the group should have been bonded at the 4-position.

<L>

Substituent L in general formula (3) represents a direct bond or a divalent aromatic hydrocarbon group which may have a substituent (a divalent arylene group which may have a substituent); one end of the L is bonded to the 1,3,5-triazine ring or pyrimidine ring, and the other end is bonded to the benzene ring at the substitution position of any of $R^1$ to $R^5$ in place of the one of $R^1$ to $R^5$. Especially preferred of these bonds, from the standpoints of solubility and durability, is the bond formed at the substitution position of any of $R^2$ to $R^4$. Examples of the divalent aromatic hydrocarbon group of L include a 1,2-phenylene group, 1,3-phenylene group, 1,4-phenylene group, 4,4'-biphenylylene, 4,3'-biphenylylene, 3,4'-biphenylylene, and 3,3'-biphenylylene. Preferred of these are a 1,3-phenylene group and a 3,3'-biphenylylene group, from the standpoint that the organic compound in which L is either of these groups has relatively high solubility in organic solvents.

<$R^1$ to $R^{18}$>

Substituents $R^1$ to $R^5$ in general formula (3) each independently represent a bond with L, a phenyl group which may have a substituent, a dibenzofuranyl group which may have a substituent, a dibenzothienyl group which may have a substituent, an alkyl group, a silyl group, a fluorine atom, or a perfluoroalkyl group. $R^6$ to $R^{18}$ each independently represent a hydrogen atom, a phenyl group which may have a substituent, a dibenzofuranyl group which may have a substituent, a dibenzothienyl group which may have a substituent, an alkyl group, a silyl group, a fluorine atom, or a perfluoroalkyl group (of these groups, the phenyl, dibenzofuranyl, and dibenzothienyl groups may further have an alkyl group, a silyl group, a fluorine atom, or a perfluoroalkyl group). With respect to the site where the dibenzofuranyl group or dibenzothienyl group is bonded to each aromatic ring, the same explanation as given above applies.

The alkyl group preferably is an alkyl group having 1-20 carbon atoms, and examples thereof include methyl, ethyl, propyl, isopropyl, butyl, isobutyl, sec-butyl, tert-butyl, pentyl, hexyl, octyl, cyclohexyl, decyl, and octadecyl. More preferred of these, from the standpoint of durability, are alkyl groups having up to 4 carbon atoms, such as methyl, ethyl, and tert-butyl.

The silyl group preferably is a silyl group to which one or more alkyl groups having 1-4 carbon atoms or one or more aryl groups having 6-20 carbon atoms have been bonded. Examples thereof include triisopropylsilyl, triphenylsilyl, dimethylphenylsilyl, and tert-butyldiphenylsilyl. Of these, triphenylsilyl is preferred from the standpoint of durability.

The term "perfluoroalkyl group" means an alkyl substituent in which the hydrogen atoms as components of the alkyl group have been wholly replaced by fluorine atoms. This substituent preferably is a perfluoroalkyl group having 1-4 carbon atoms, and examples thereof include trifluoromethyl and pentafluoroethyl. Of these, trifluoromethyl is more preferred from the standpoint of durability.

<Substituents>

Examples of the substituents which may be possessed by $Ar^1$ to $Ar^{30}$ and by $X^1$ to $X^{11}$ in general formulae (2-1) to (2-5) and general formulae (4-1) to (4-6) include a phenyl group, dibenzofuranyl group, dibenzothienyl group, alkyl group, silyl group, fluorine atom, and perfluoroalkyl group (of these groups, the phenyl, dibenzofuranyl, and dibenzothienyl groups may further have an alkyl group, a silyl group, a fluorine atom, or a perfluoroalkyl group). It is preferred, from the standpoint of durability, that the substituents each should be a phenyl group, alkyl group, or silyl group among those. With respect to the site where the dibenzofuranyl group or dibenzothienyl group is bonded to each of the $Ar^1$ to $Ar^{30}$ and $X^1$ to $X^{11}$, the same explanation as given above applies. The alkyl group, silyl group, and perfluoroalkyl group are the same as those described above in the section <$R^1$ to $R^{18}$>.

<A, B, and C>

Substituents A, B, and C in general formula (1) each are a substituent that includes at least one 1,2-phenylene group which may have a substituent or at least one 1,3-phenylene group which may have a substituent, and the case where substituents A, B, and C all are the same is excluded. From the standpoint of reducing the symmetry of the molecule to improve solubility in organic solvents and improve the amorphousness of the material, it is more preferred that substituents A, B, and C in general formula (1) should differ from each other, that is, A, B, and C are substituents in which any two are not the same. The expression "not the same" herein means that substituents A, B, and C differ in at least one of the kind of the aromatic ring constituting the substituent, the substituent possessed by the aromatic ring, the order of bonding of the aromatic ring to other groups, and the positions of the bonding sites.

<Carbazolyl Group>

It is preferred that the organic compound of the invention should have only one carbazolyl group or no carbazolyl group.

<Molecular Weight>

The molecular weight of the organic compound of the invention is usually 2,000 or less, preferably 1,500 or less, more preferably 1,300 or less, and is usually 750 or higher, preferably 800 or higher. When the molecular weight thereof exceeds the upper limit, there are cases where this organic compound contains an increased amount of impurities which generated in synthesis steps and the increased impurity content makes it difficult to highly purify the material (that is, to remove deteriorators). In case where the molecular weight thereof is lower than the lower limit, the result is considerable decreases in solubility, glass transition temperature, melting point, vaporization temperature, film-forming properties, film quality, etc. Consequently, there is a possibility that the organic electroluminescent element might have considerably impaired heat resistance.

<Glass Transition Temperature>

From the standpoints of making the organic compound of the invention have enhanced solubility in organic solvents to ensure the storage stability of a composition containing both the compound and an organic solvent and of ensuring the thermal durability of the organic electroluminescent element to be formed using the composition, it is preferred that the organic compound of the invention should have a glass transition temperature (hereinafter often referred to as "Tg") of 70-125° C. The Tg thereof is more preferably 75-125° C.

In the invention, glass transition temperature (Tg) can be measured by differential scanning calorimetry (DSC) under the following conditions.

<Measurement of Glass Transition Temperature>

Apparatus: DSC 6220, manufactured by SII Nano Technology Inc.

Sample amount: about 4 mg

Sample vessel: sample vessel for liquids, made of aluminum

Atmosphere: $N_2$, 50 mL/min

Temperature range: room temperature to 300° C.

Heating rate: 10° C./min

As will be described later, it is easy to regulate the organic compound of the invention so as to have a glass transition temperature within that preferred temperature range, when the organic compound has only one carbazolyl group or has no carbazolyl group.

SPECIFIC EXAMPLES

Preferred specific examples of the organic compound of the invention are shown below. However, the organic compound of the invention should not be construed as being limited to the following compounds shown as examples.

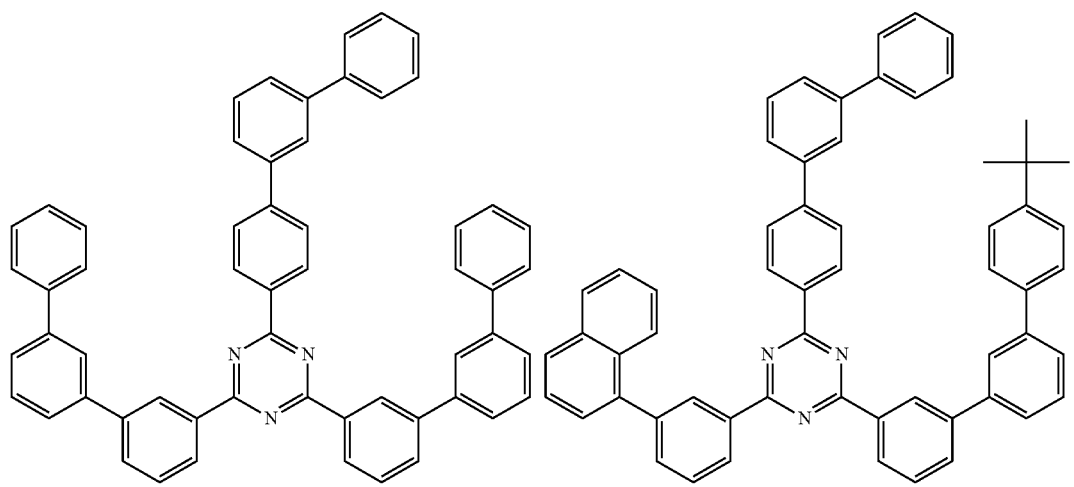

[Ka 5]

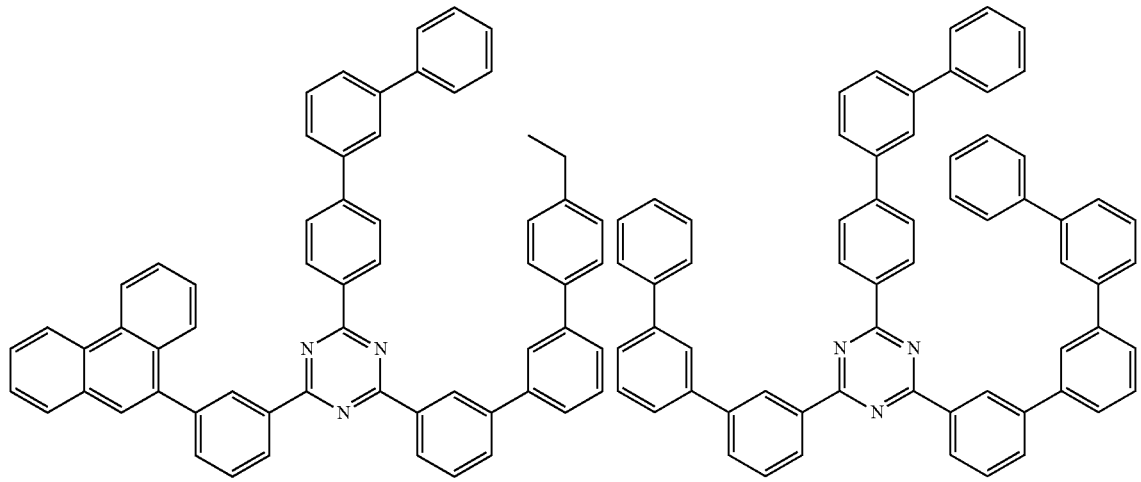
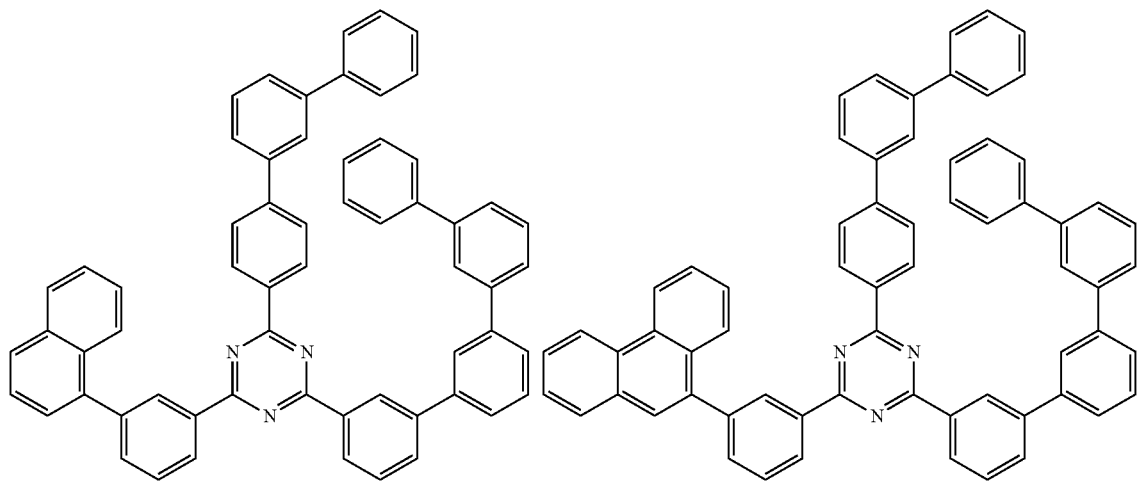
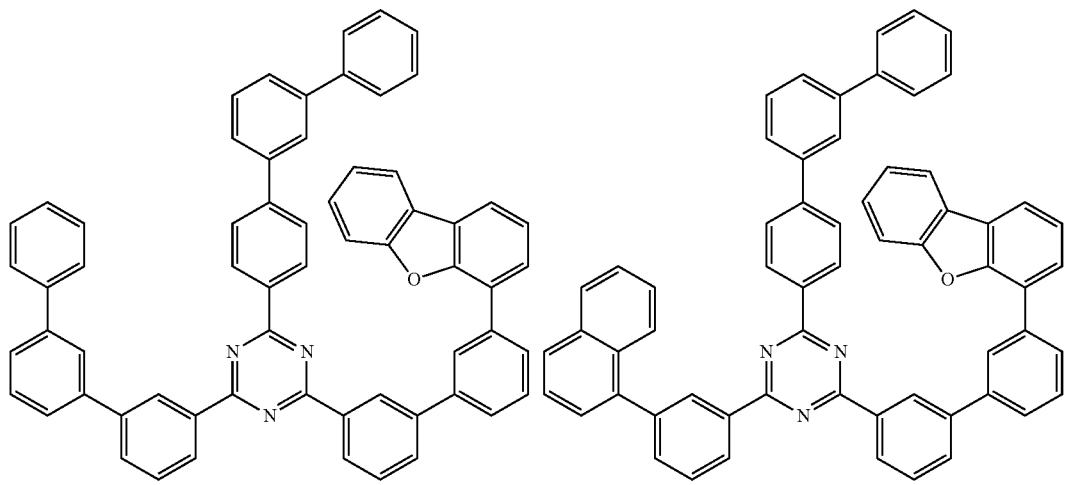

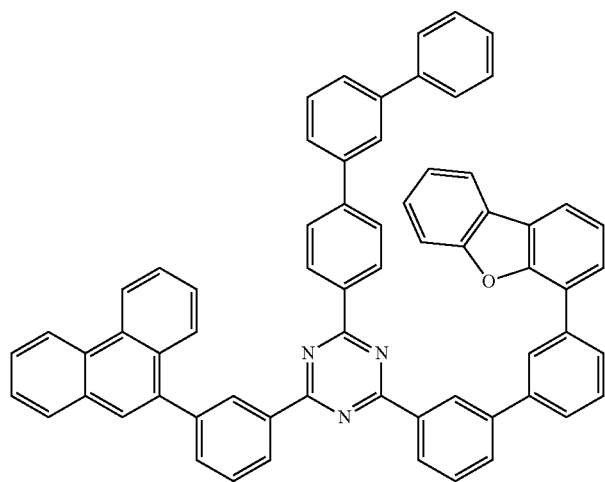
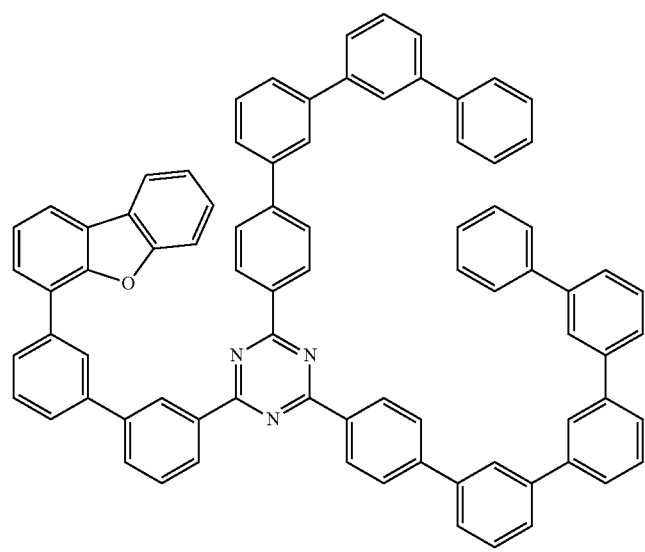
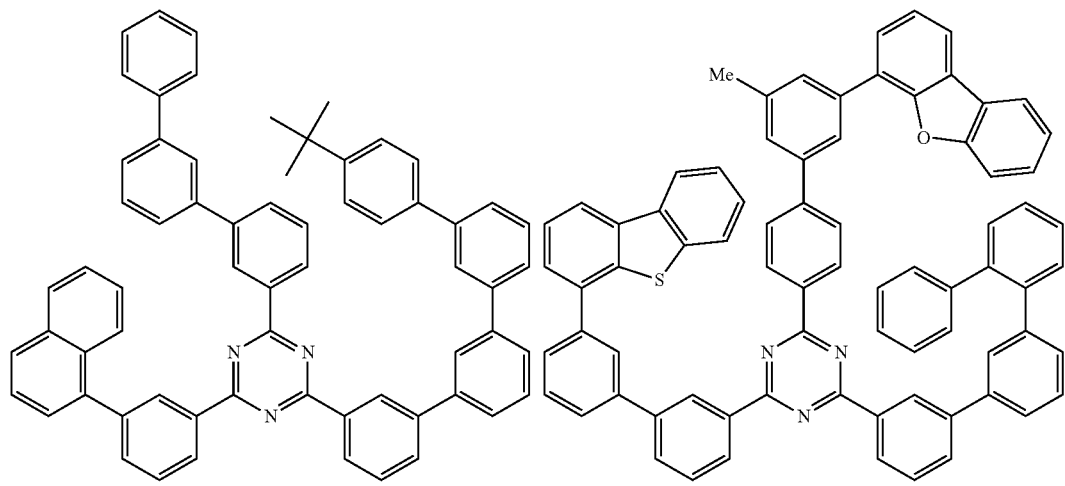

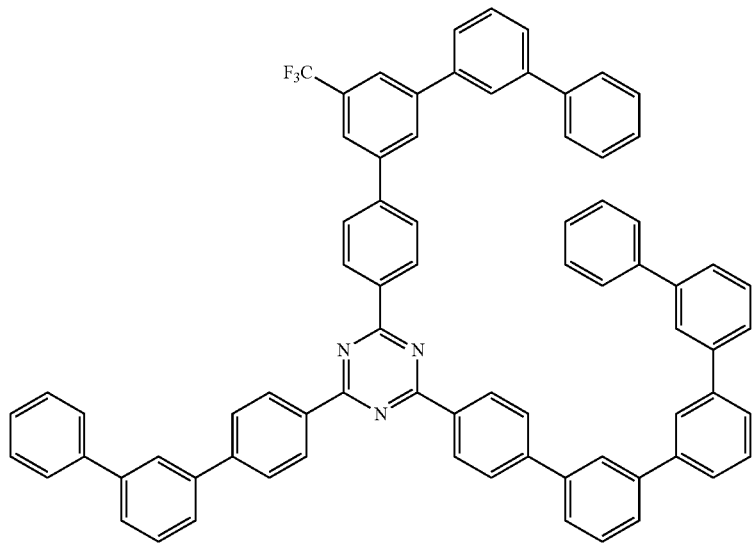
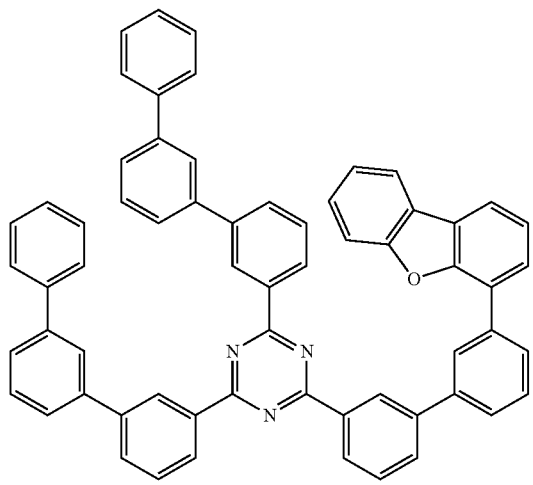
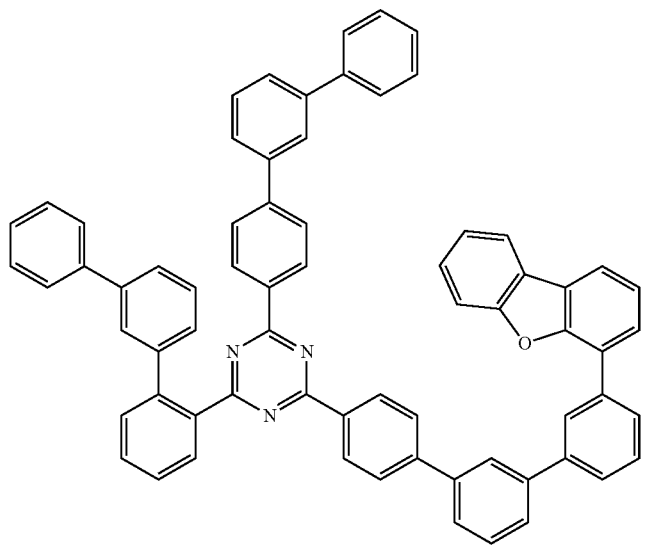

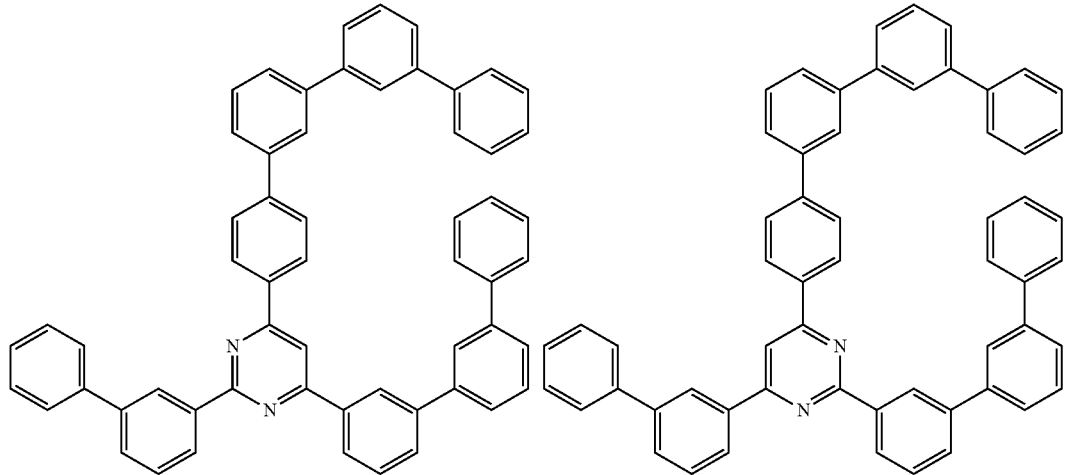
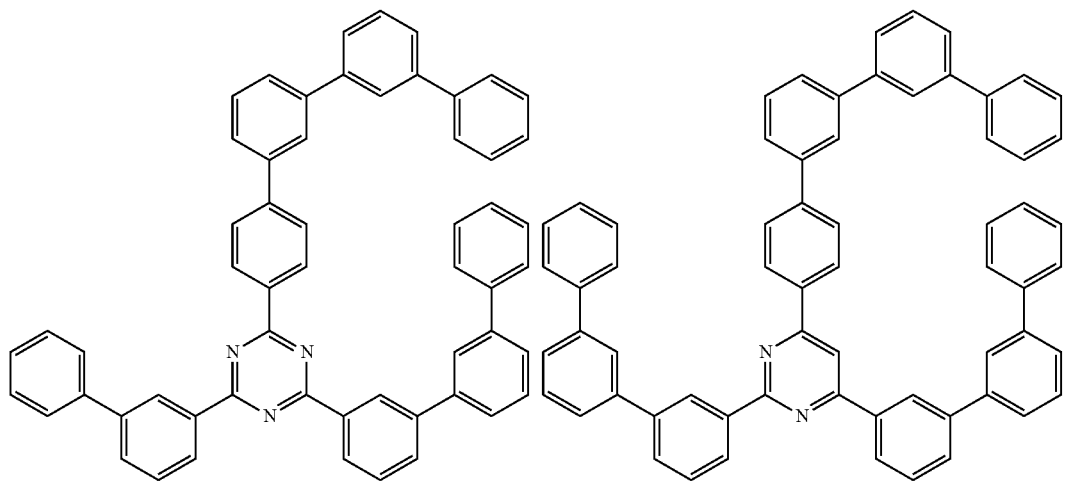
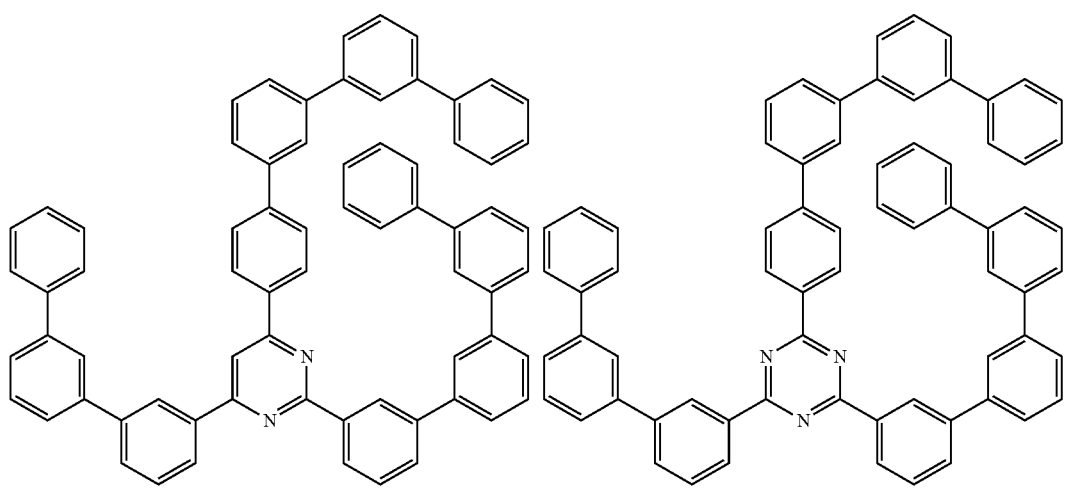

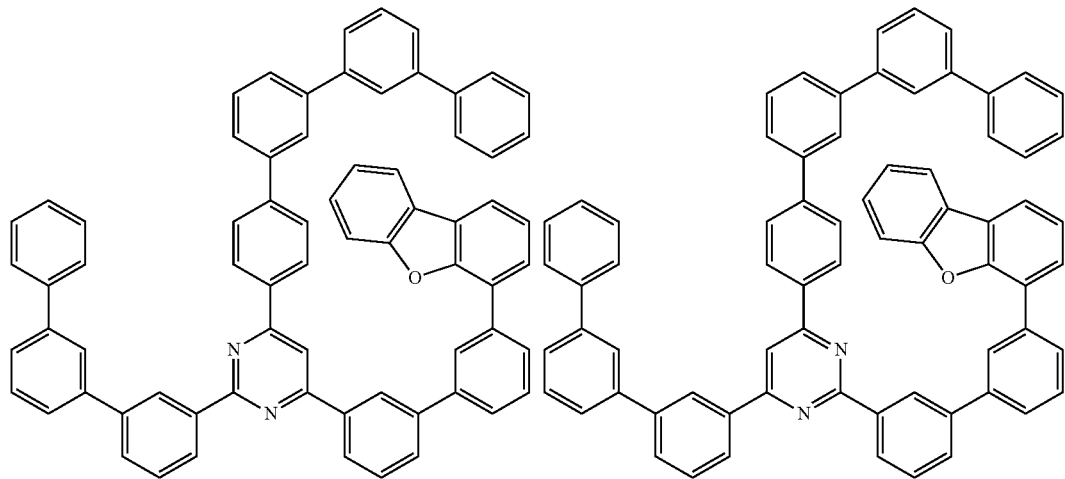
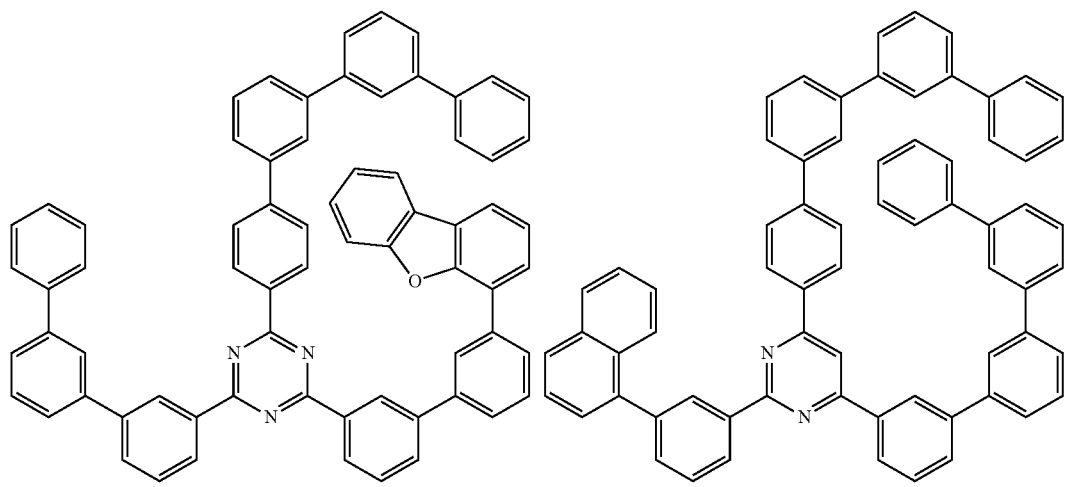
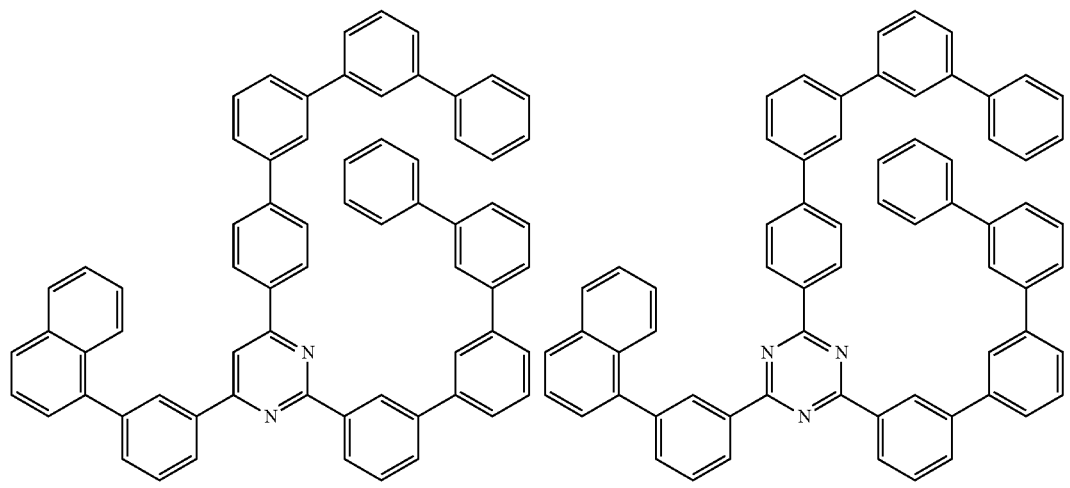

-continued
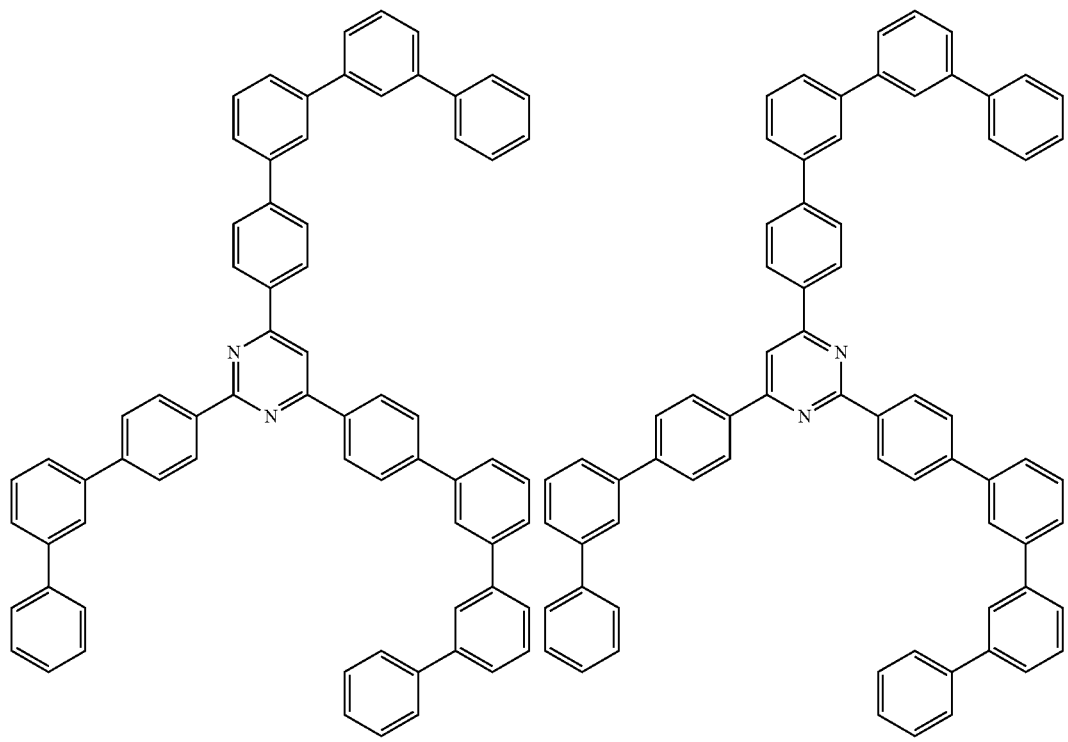
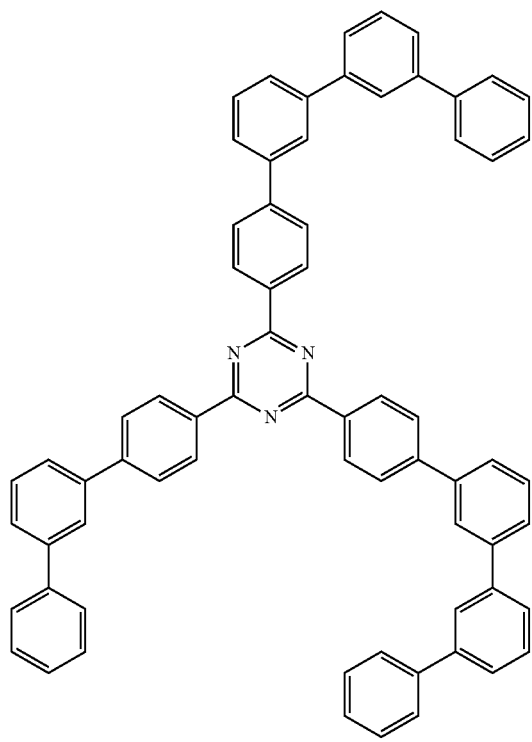

[Ka 7]
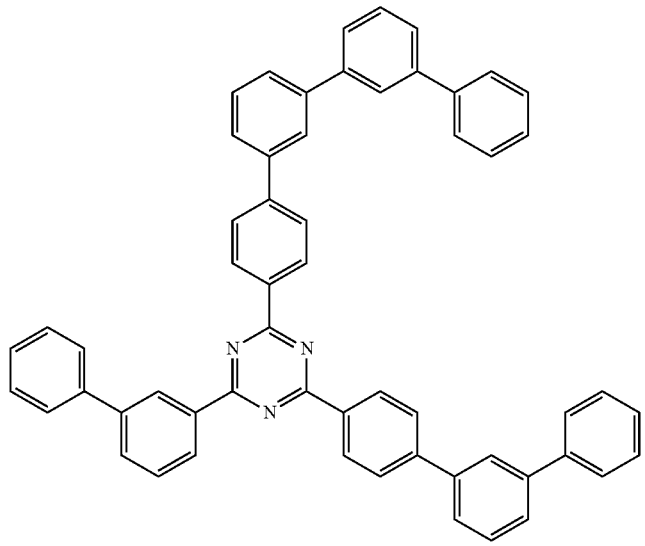
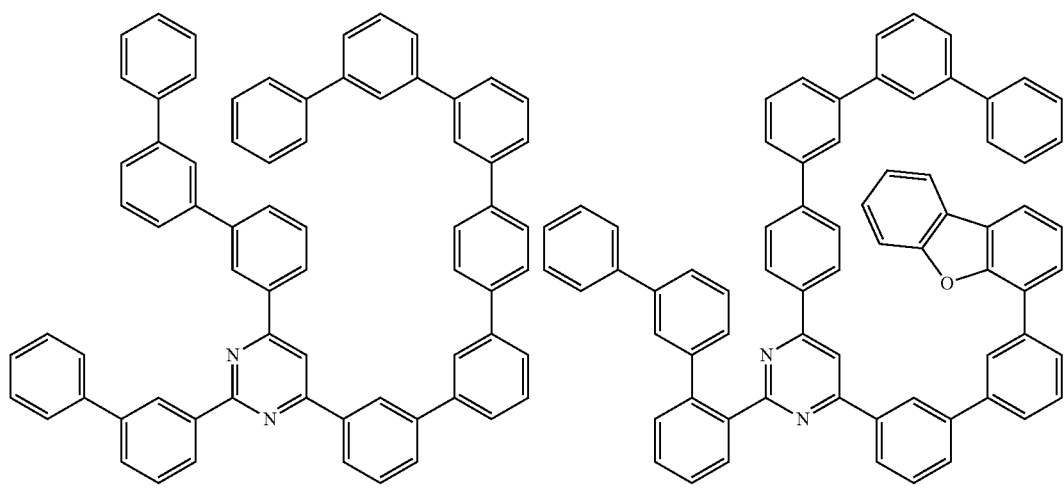
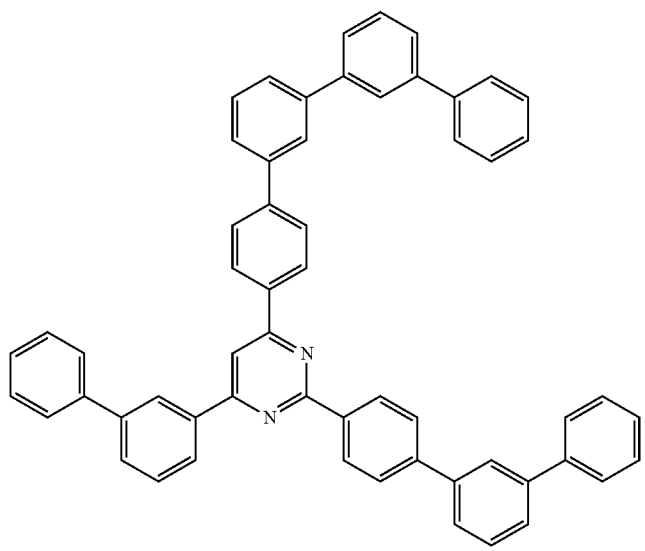

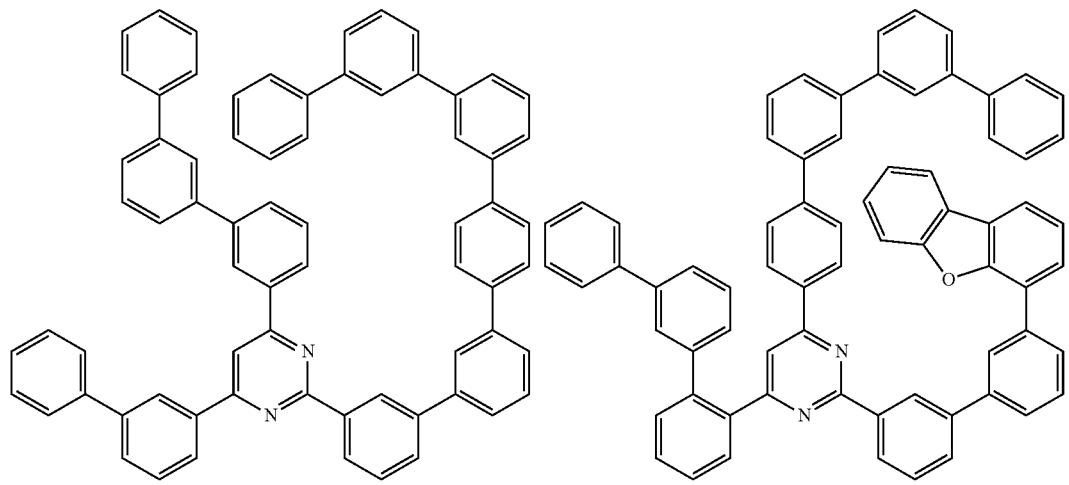
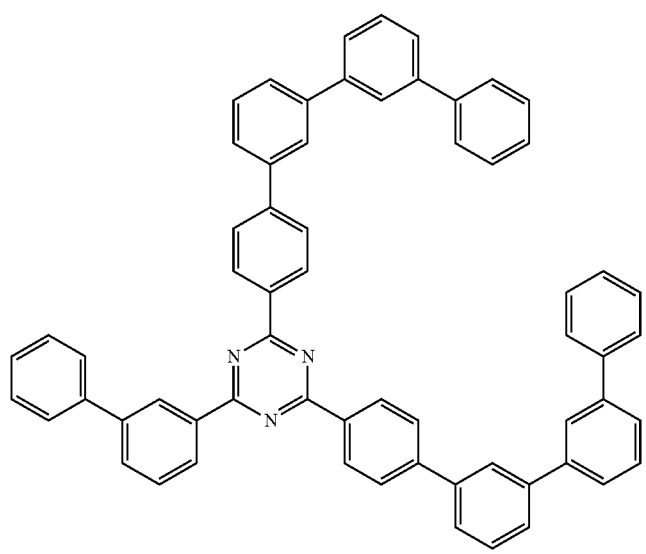
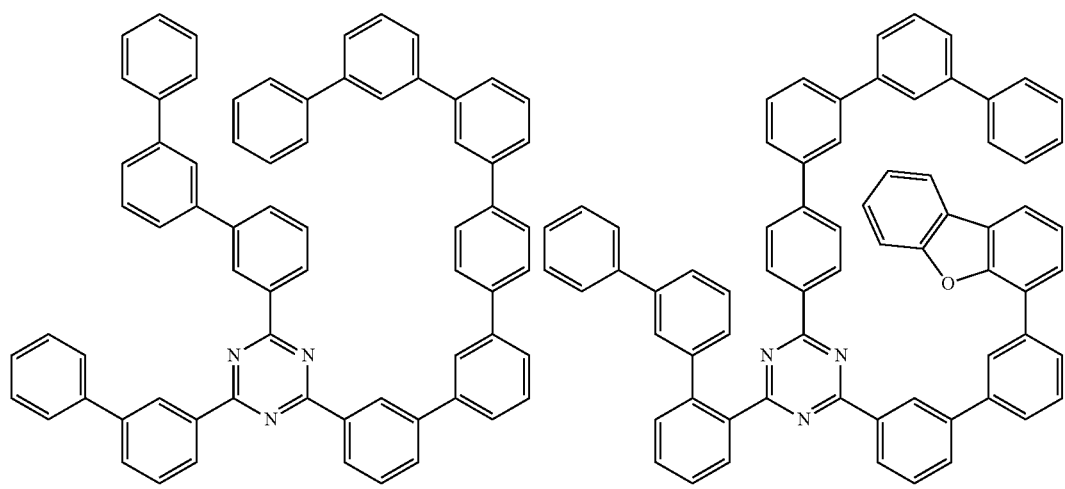

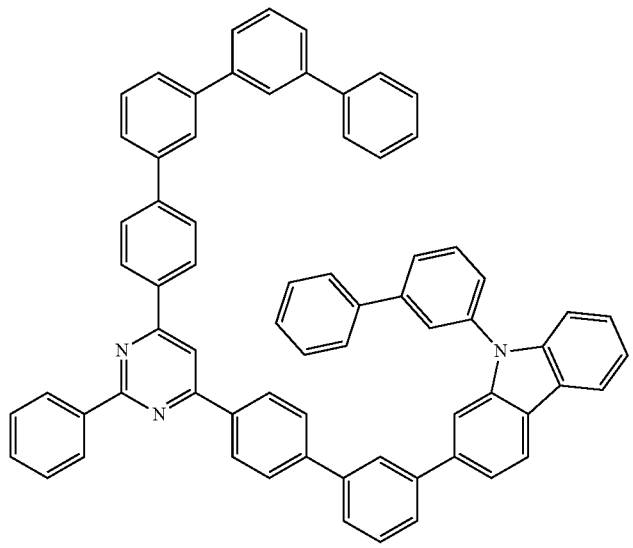 [SMILES: c1ccc(-c2cccc(-c3cccc(-c4ccc(-c5cc(-c6ccccc6)nc(-c6ccc(-c7cccc(-c8ccc9c%10ccccc%10n(-c%10cccc(-c%11ccccc%11)c%10)c9c8)c7)cc6)n5)cc4)c3)c2)cc1]
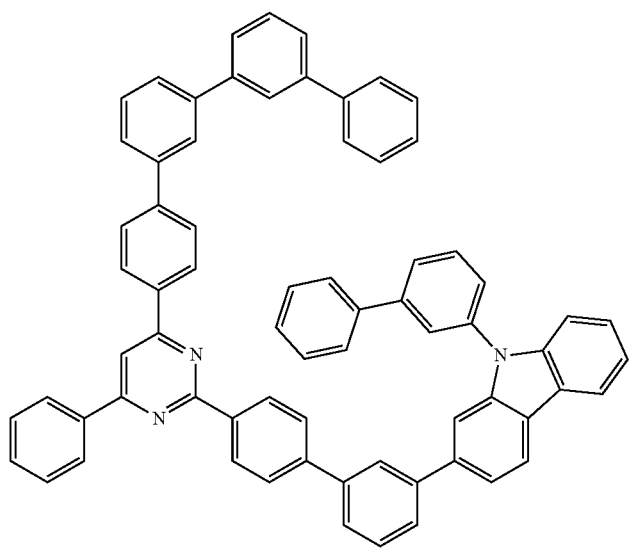
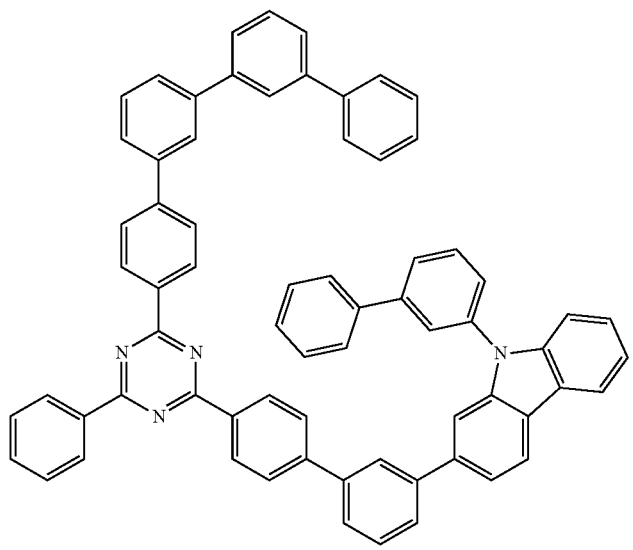

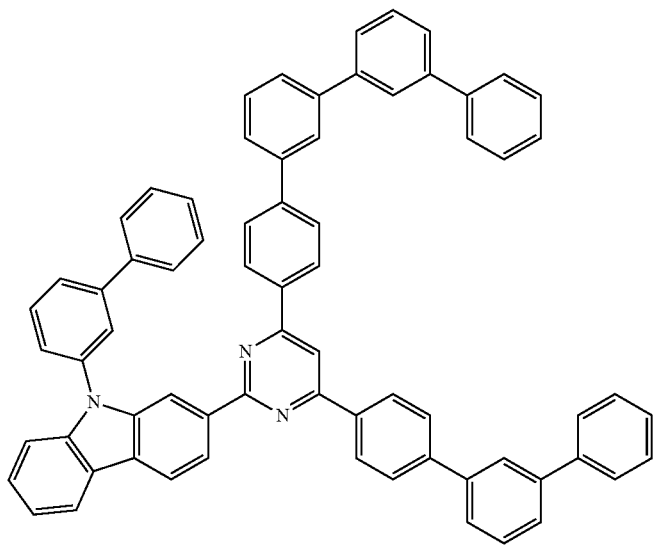
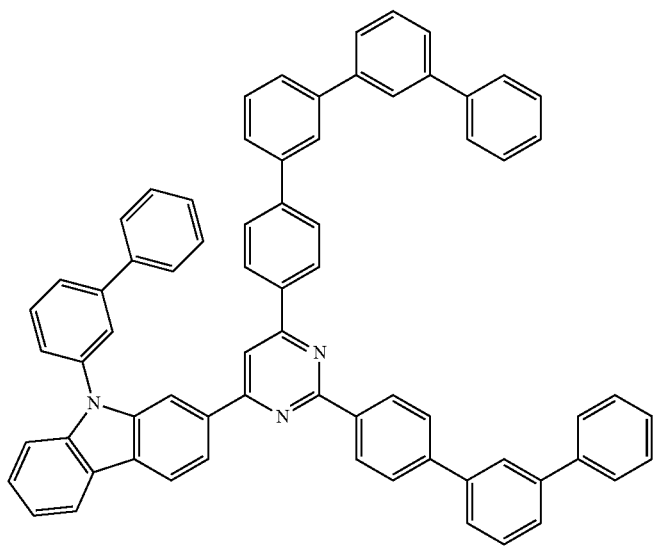
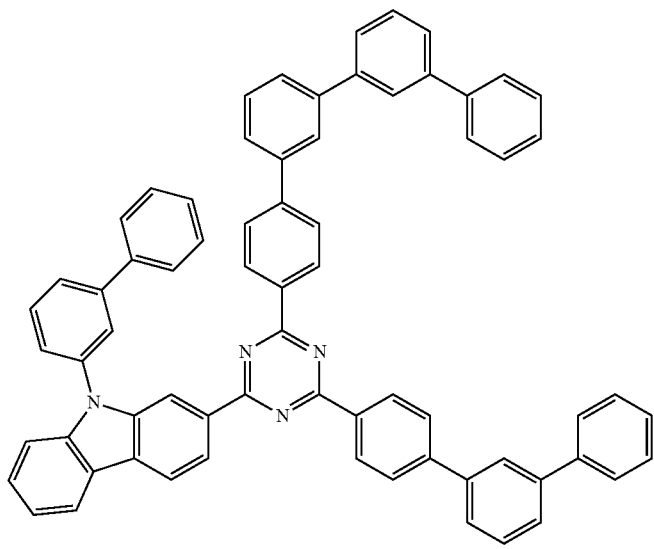

[Ka 8]
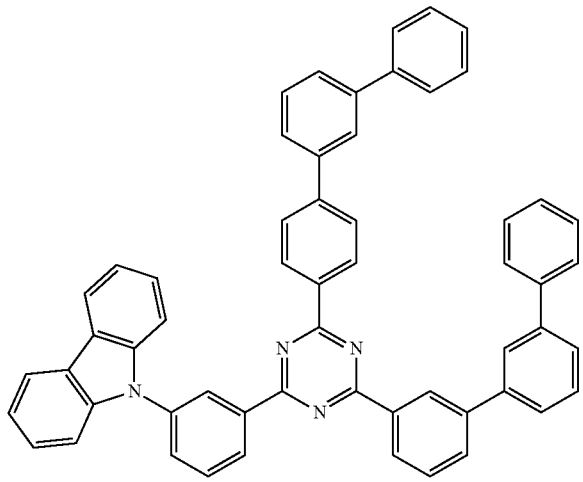
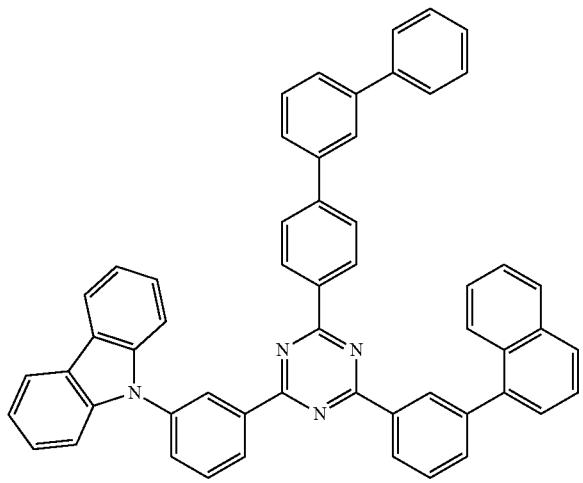
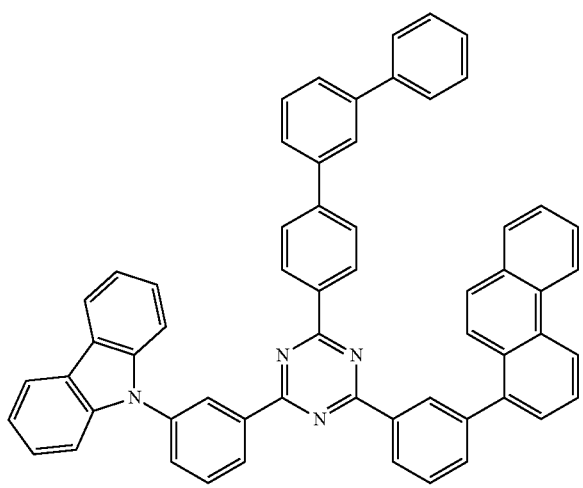

-continued
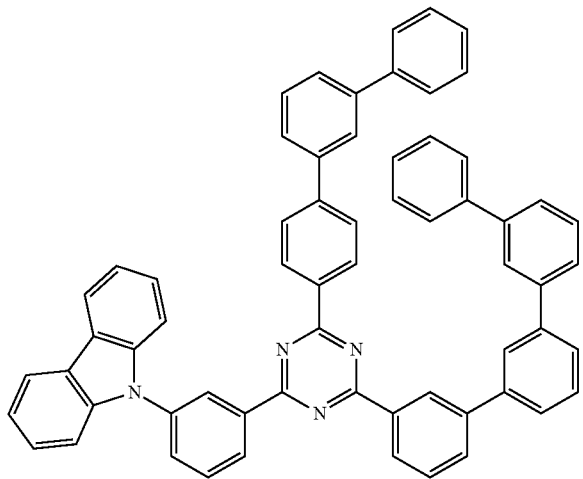
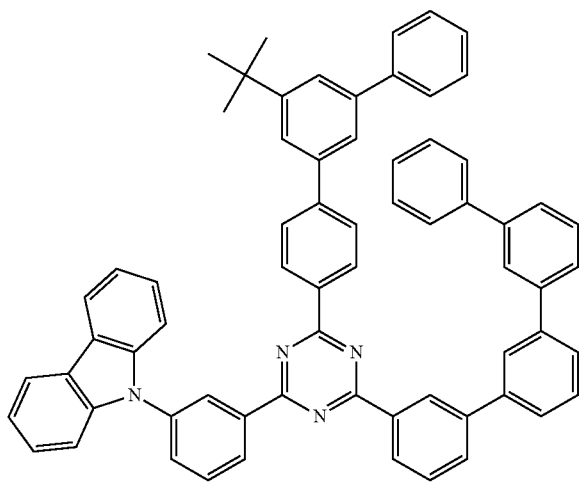
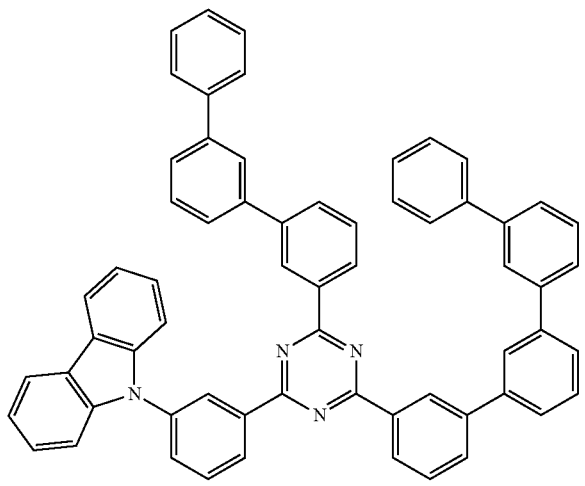

-continued
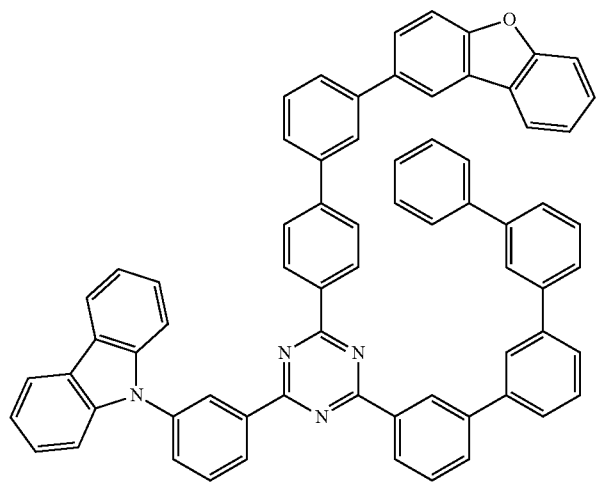
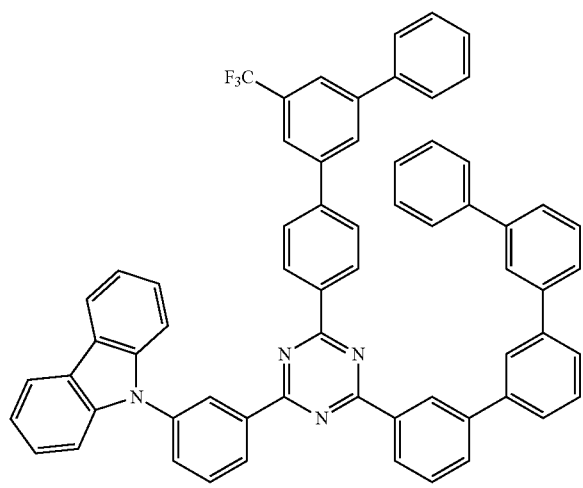
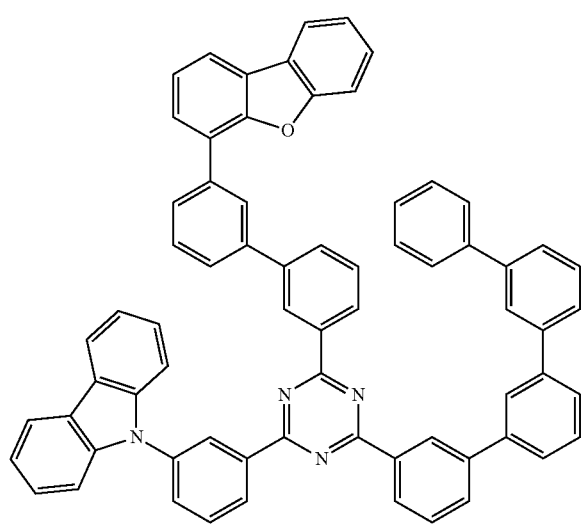

-continued
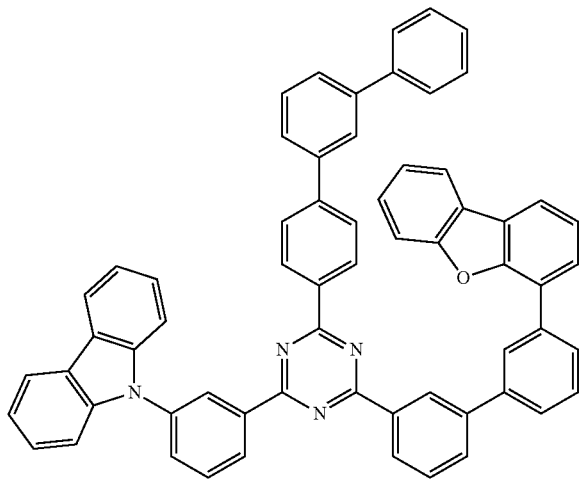
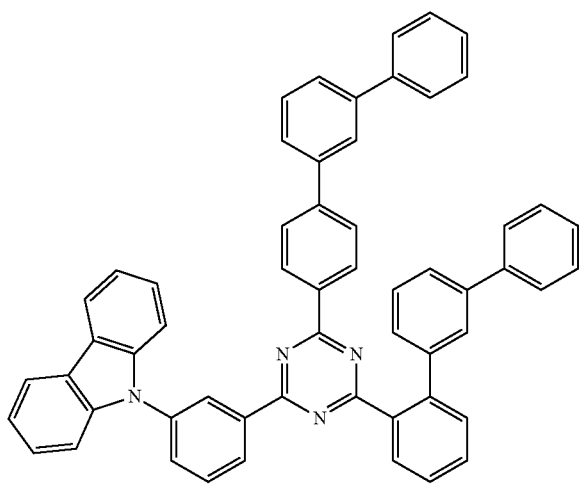
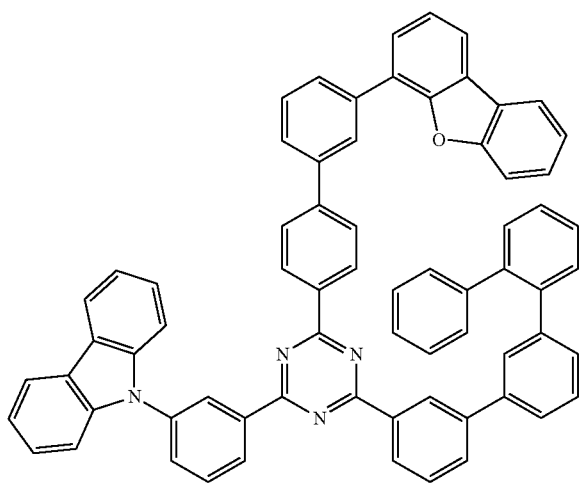

-continued
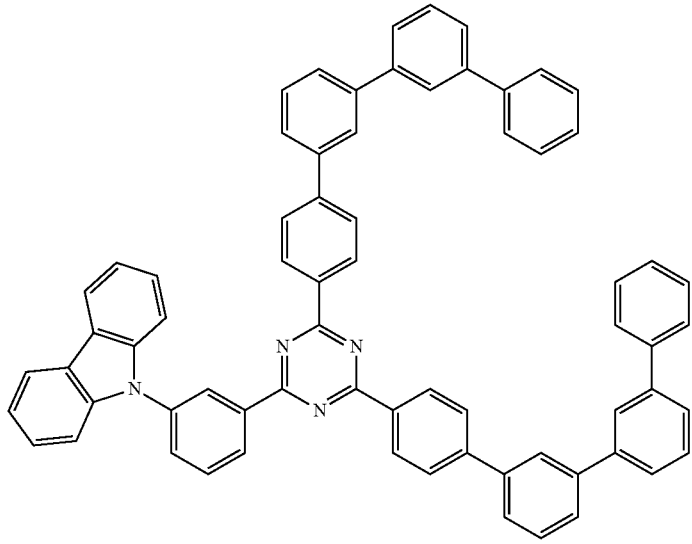
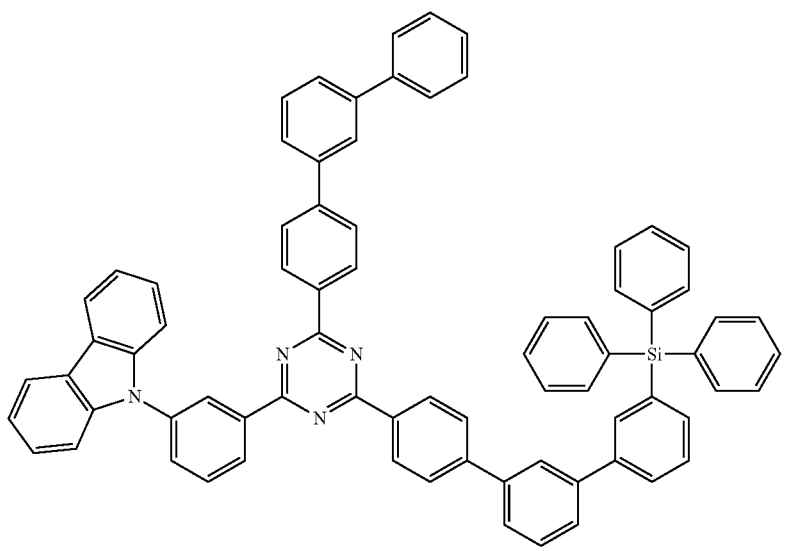
[Ka 9]
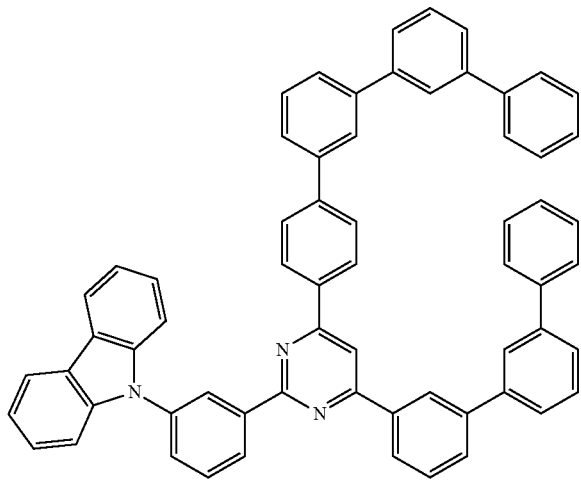

-continued
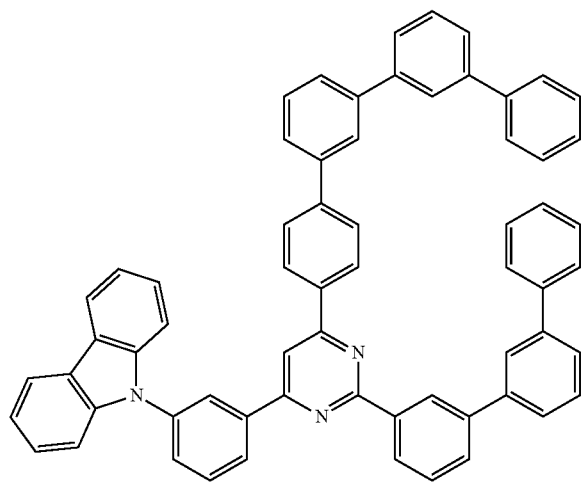
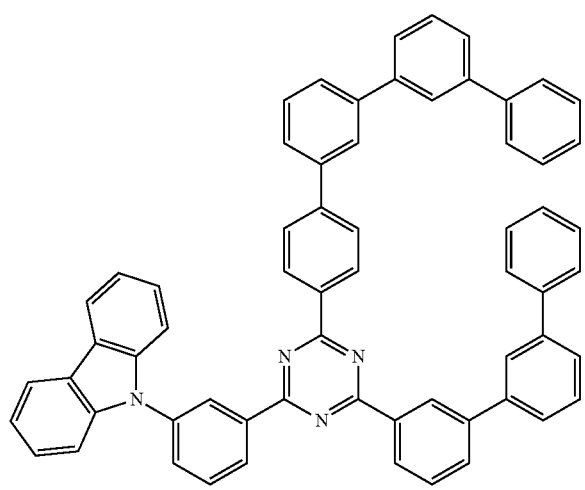
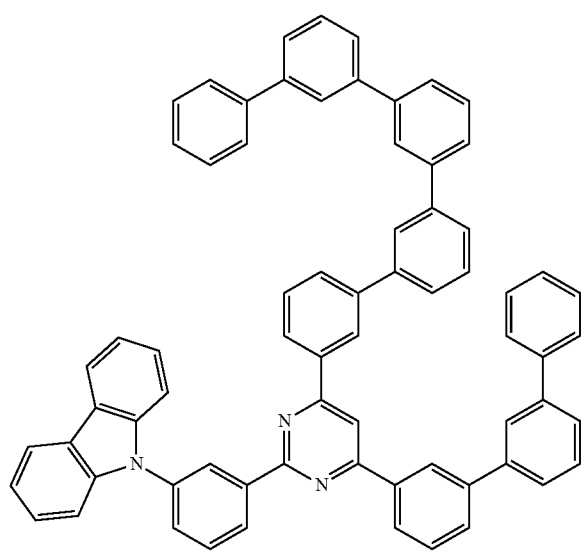

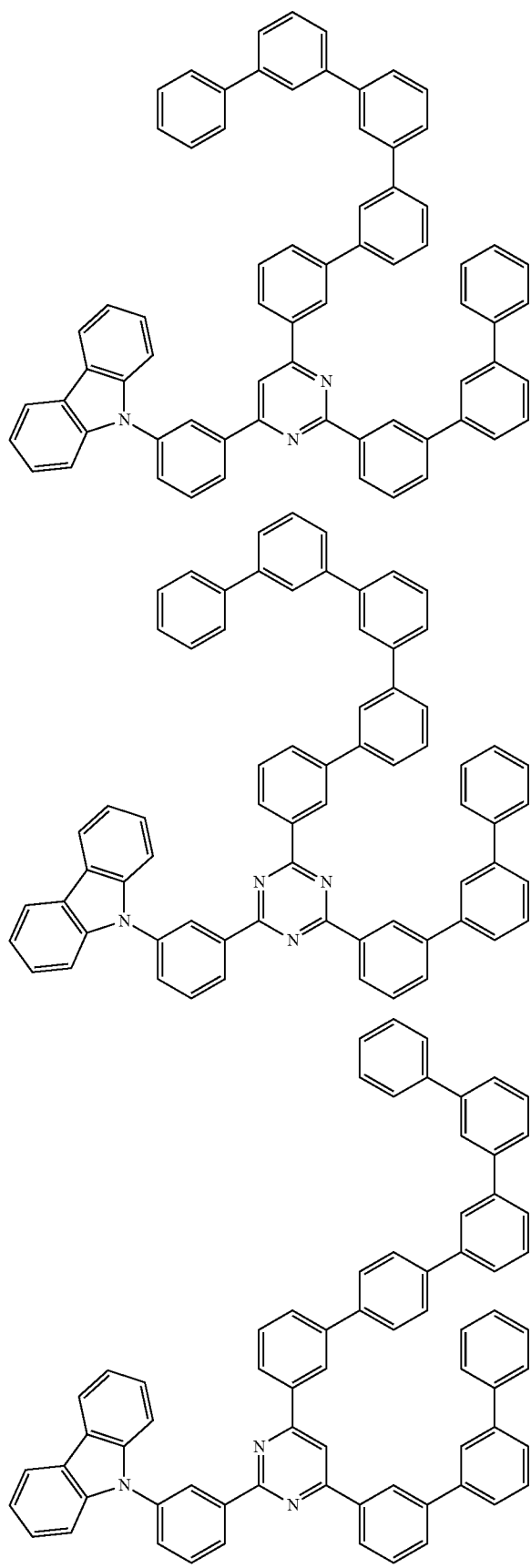

-continued
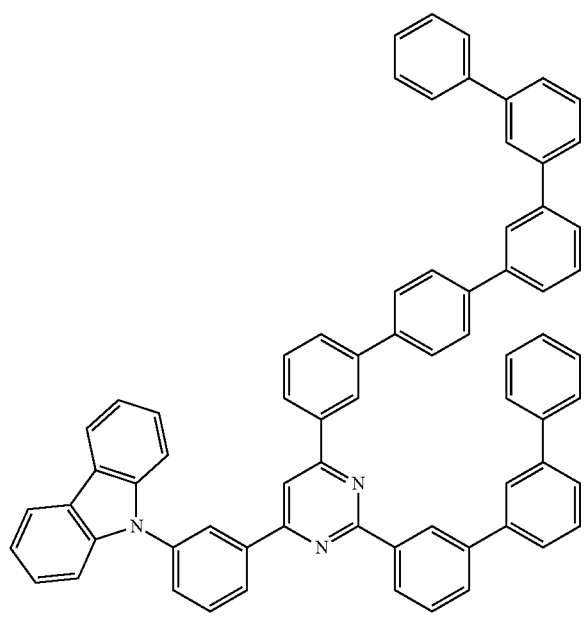
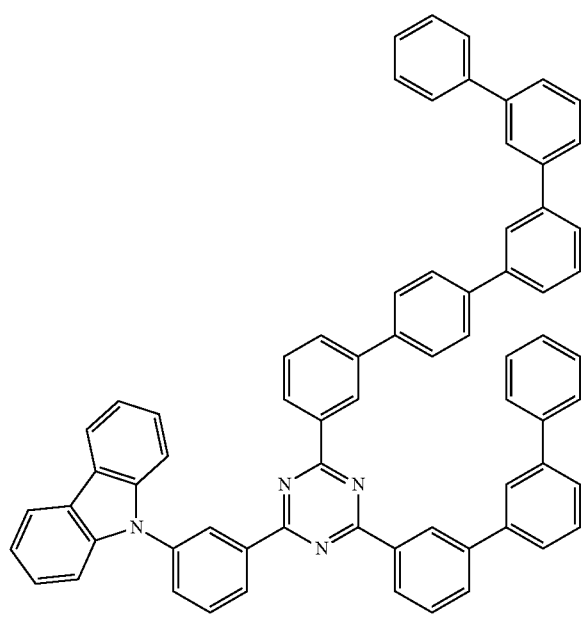
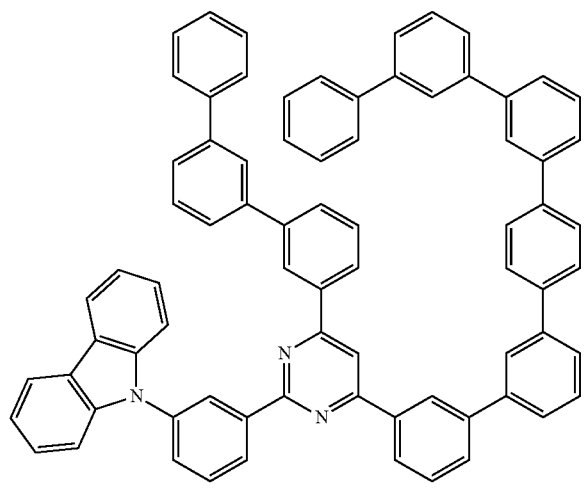

-continued
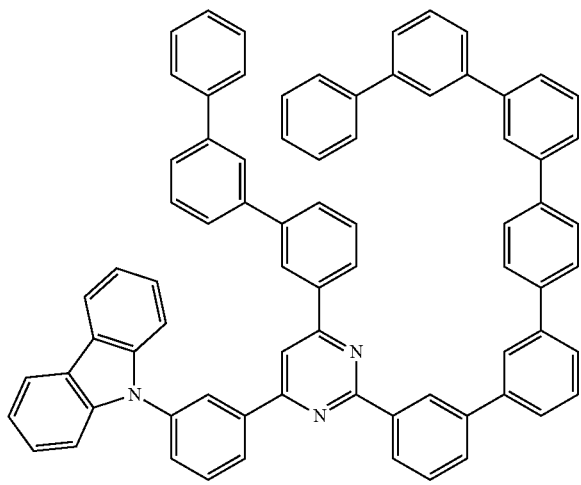
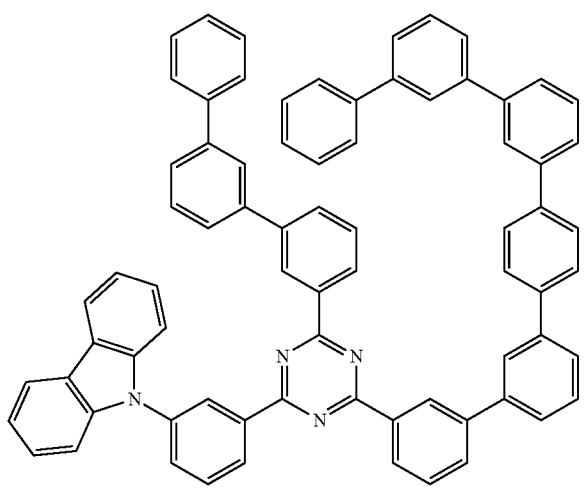
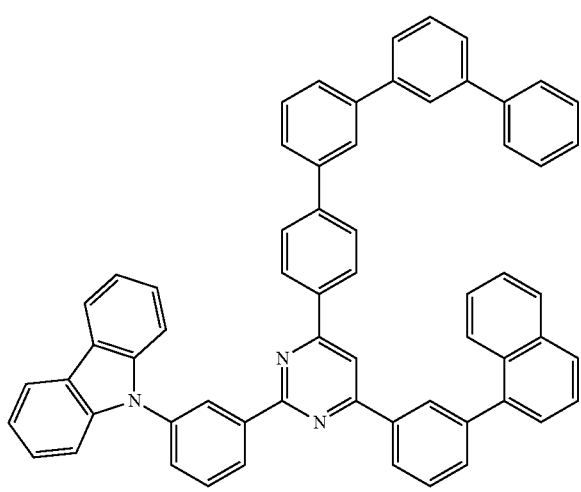

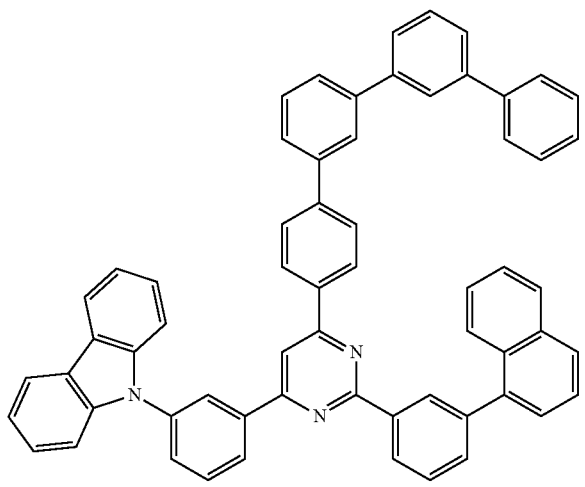
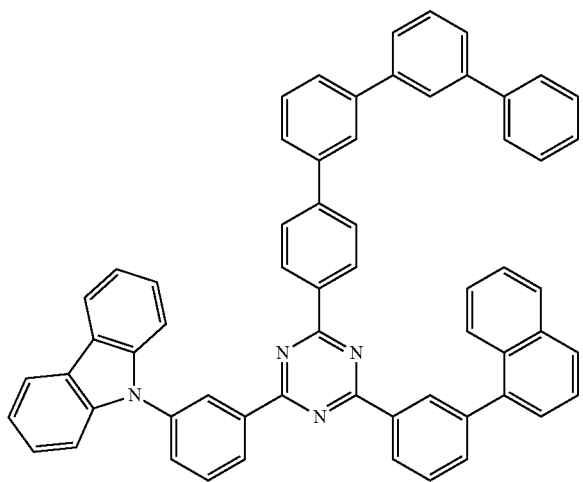
[Ka 10]
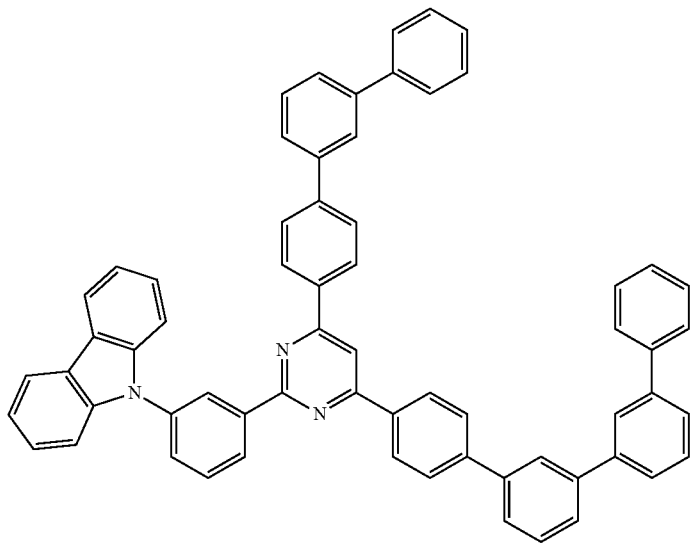

-continued
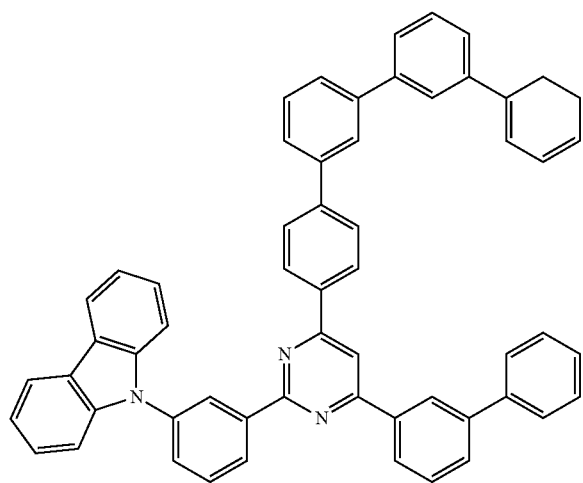
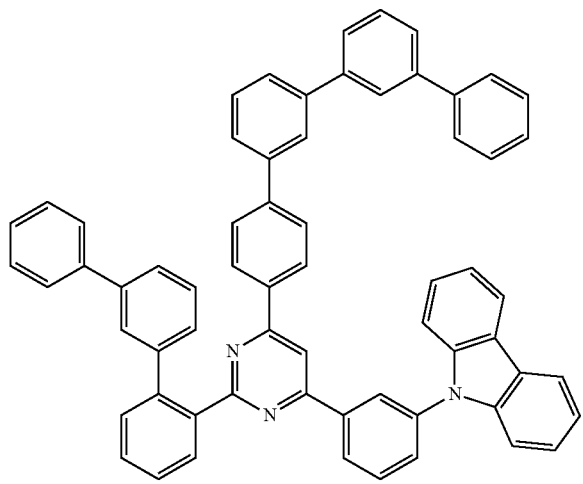
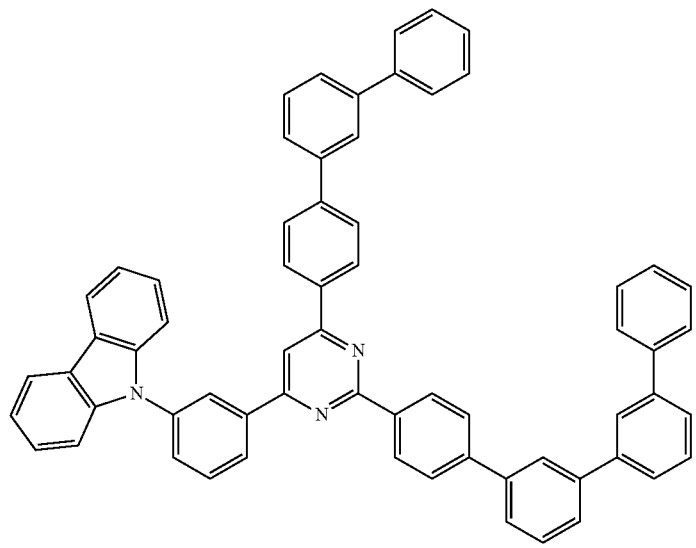

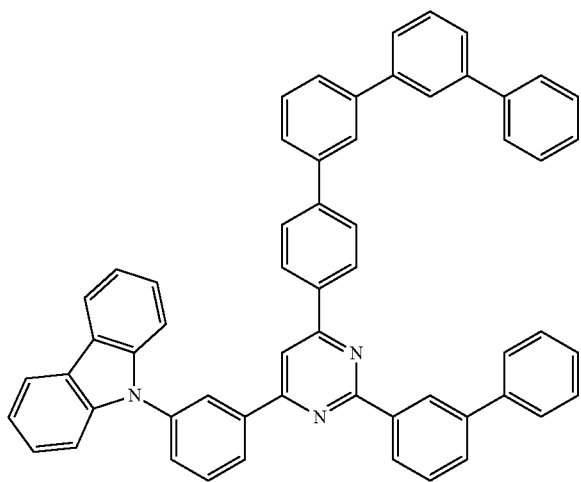
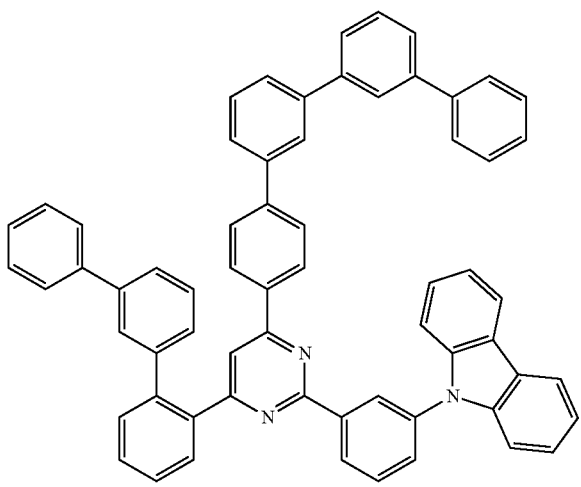
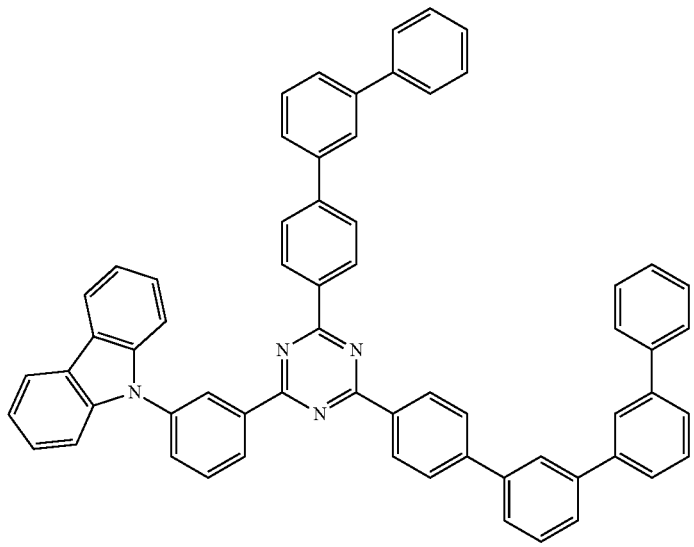

-continued
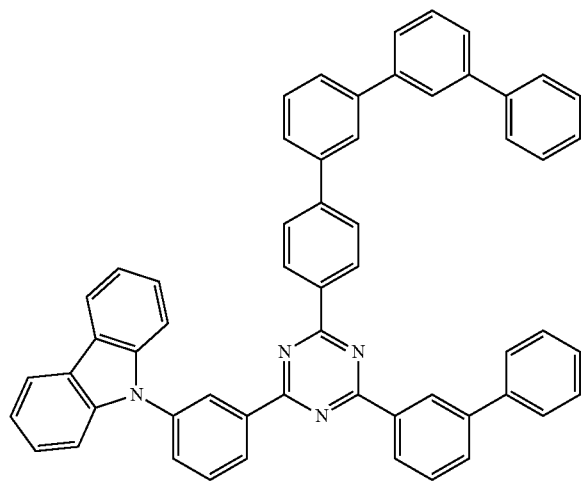
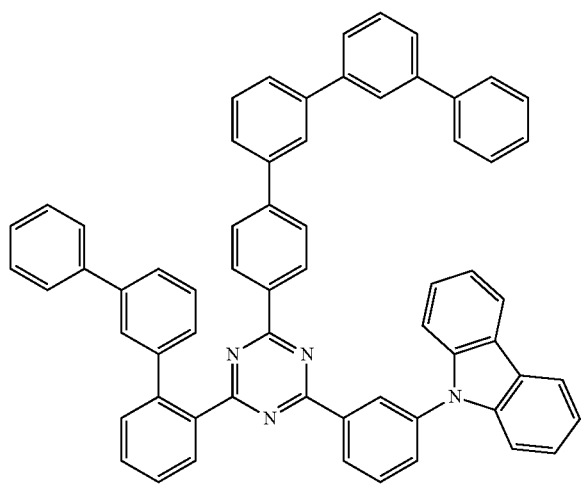
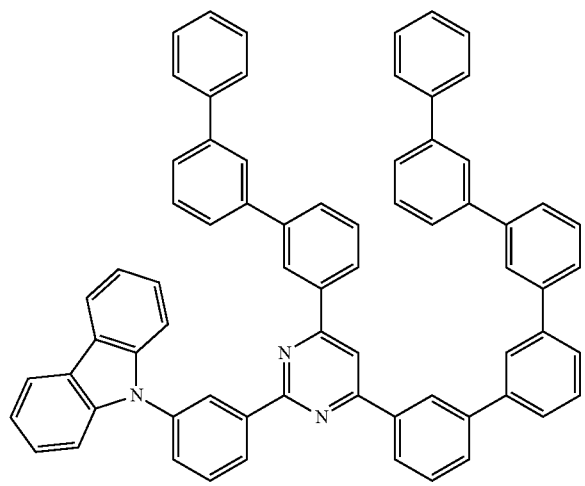

-continued
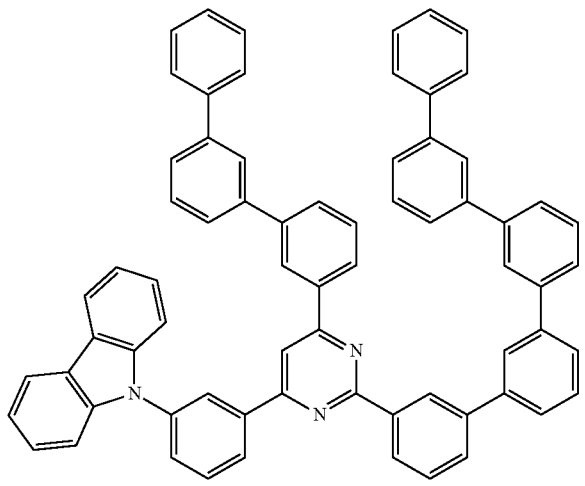
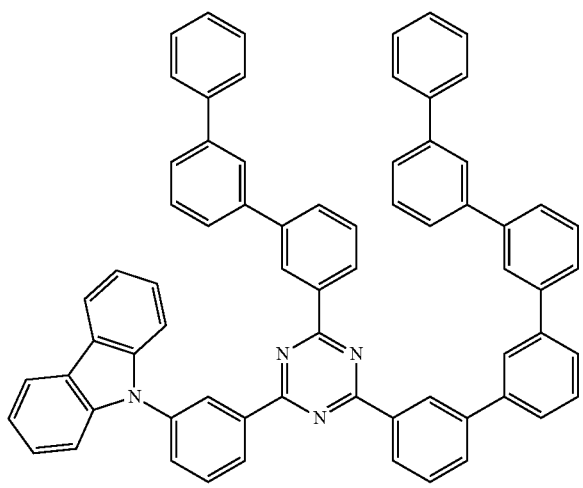
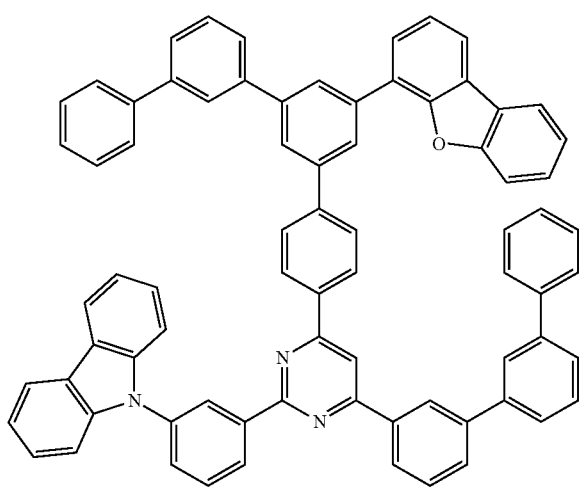

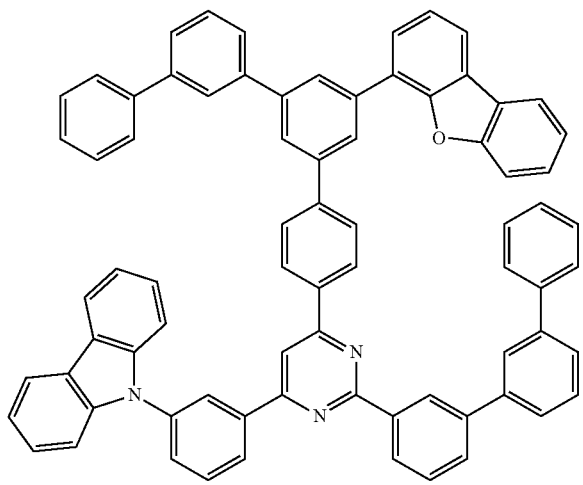
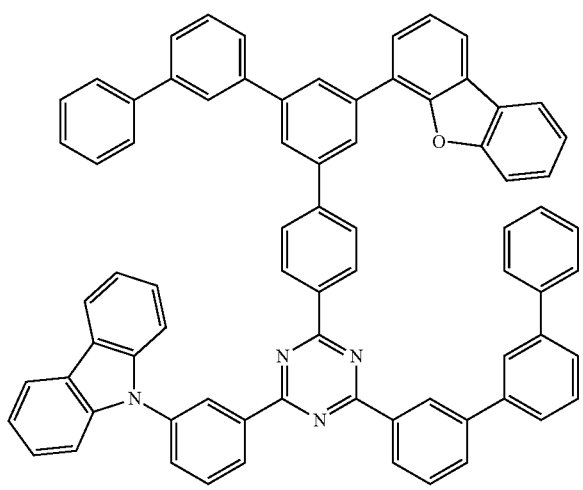
[Ka 11]
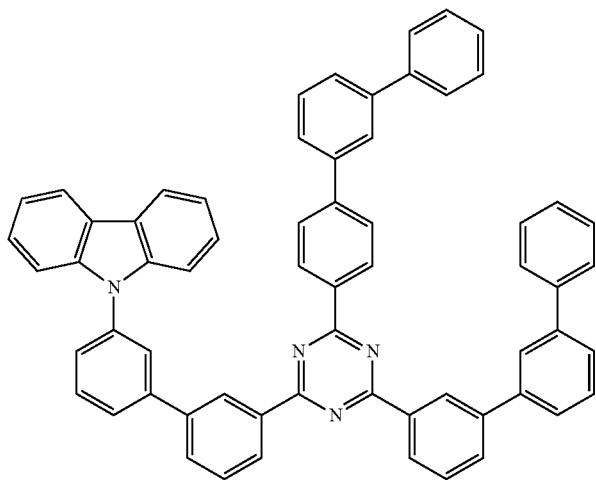

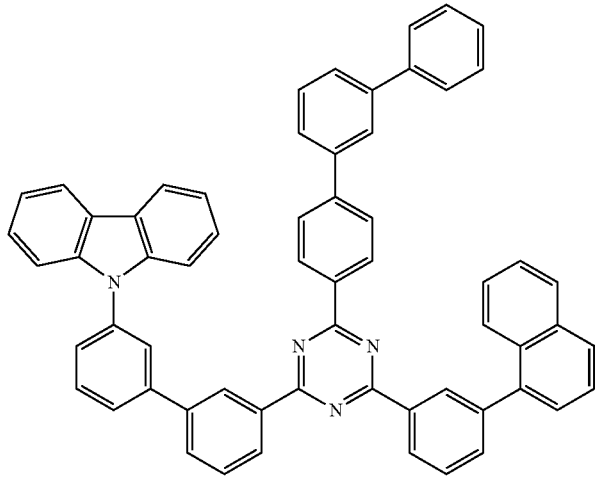
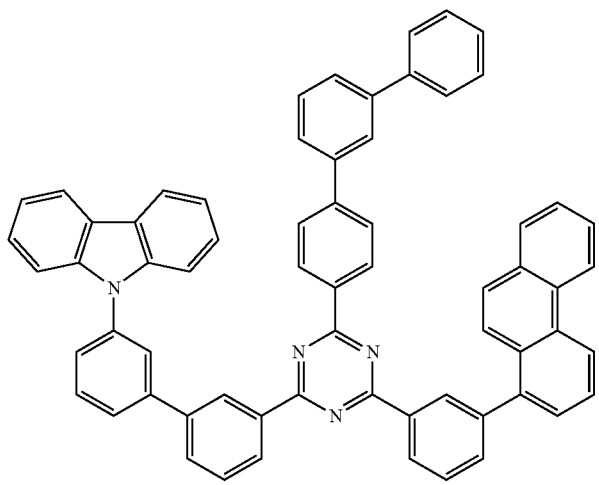
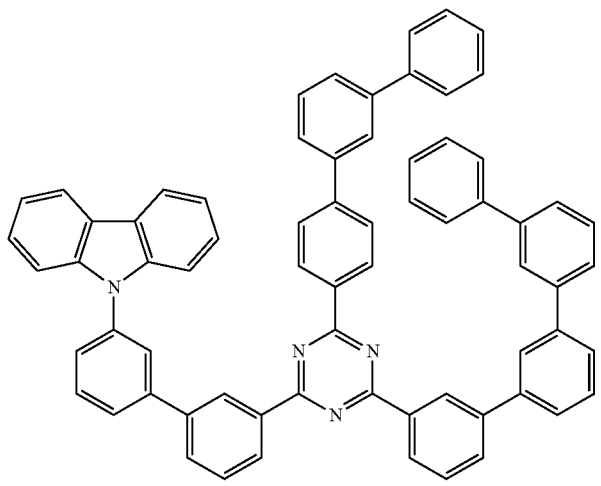

-continued
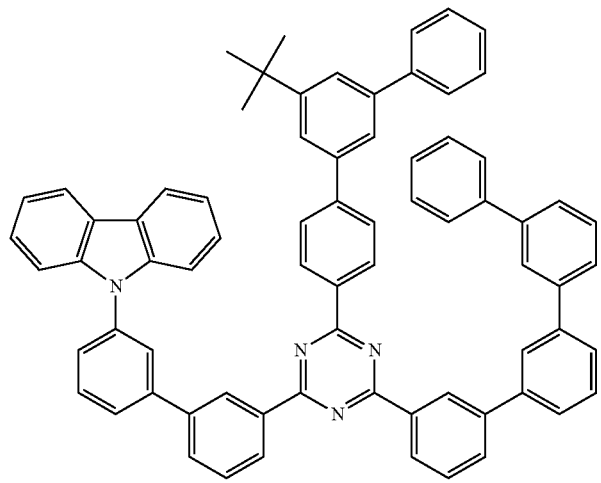
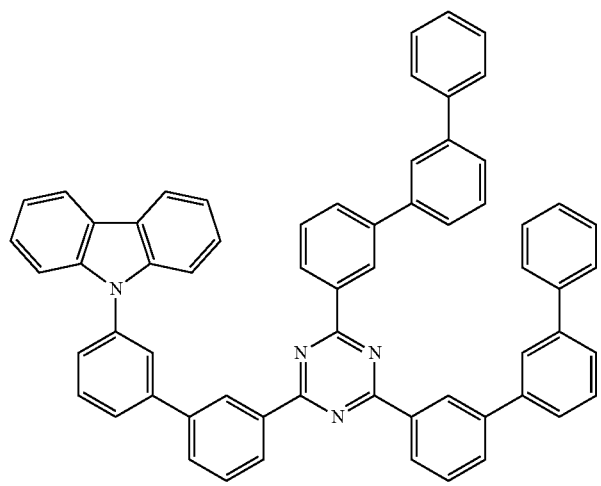
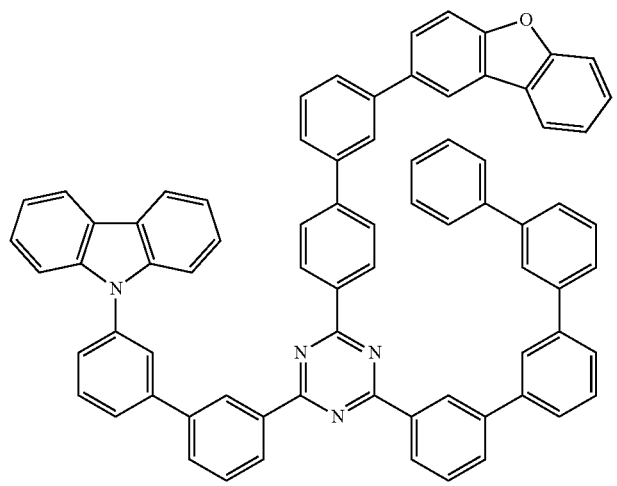

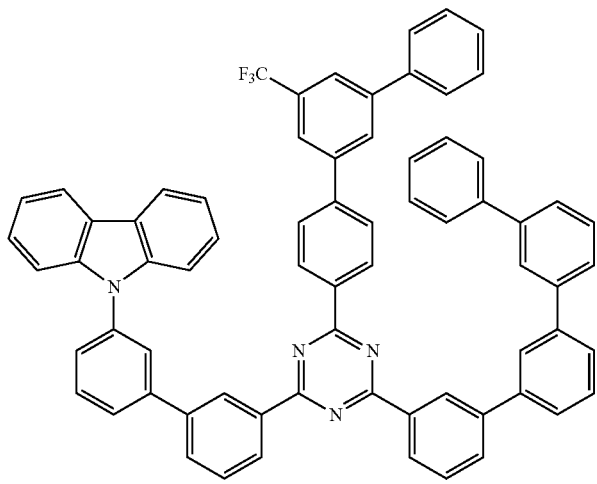
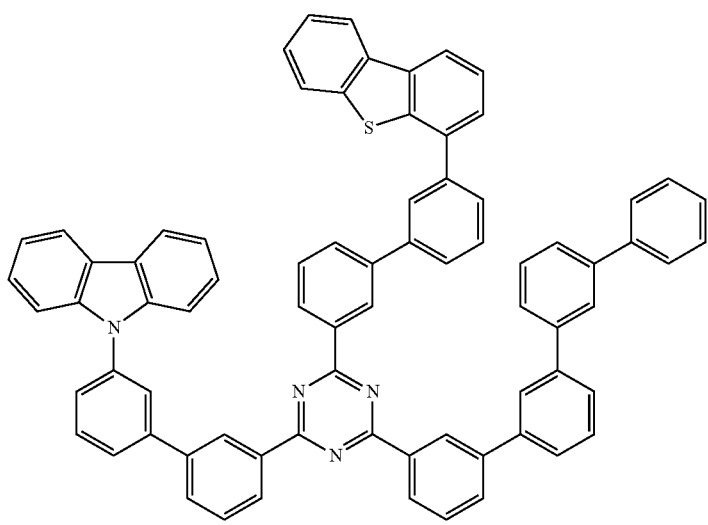
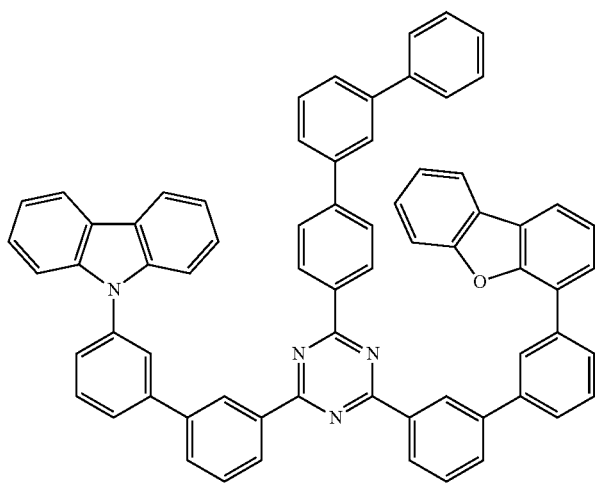

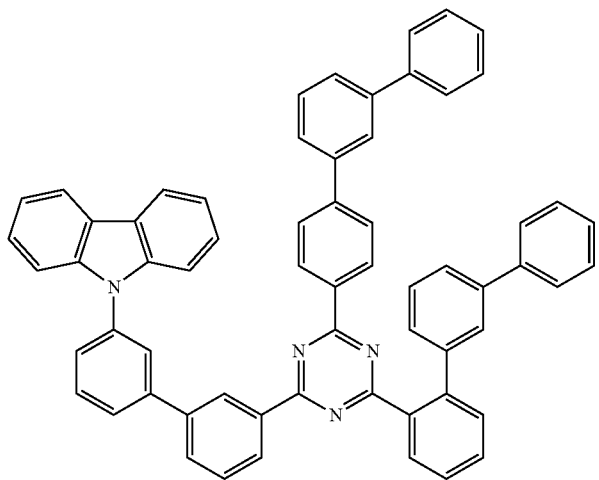
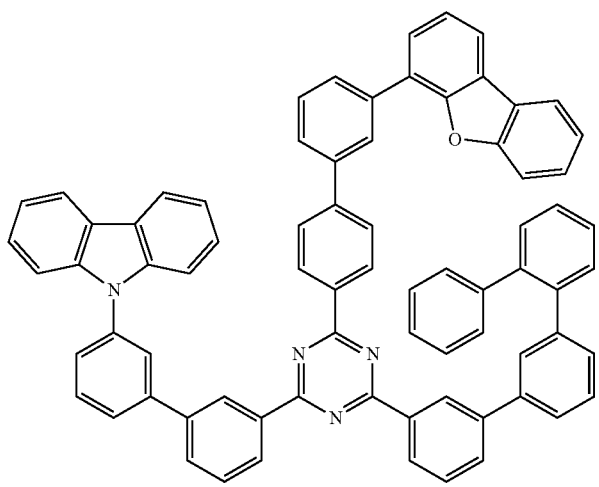
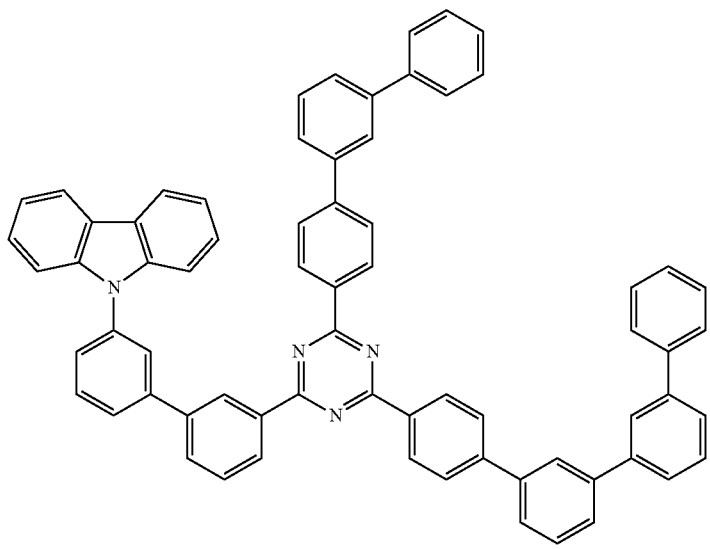

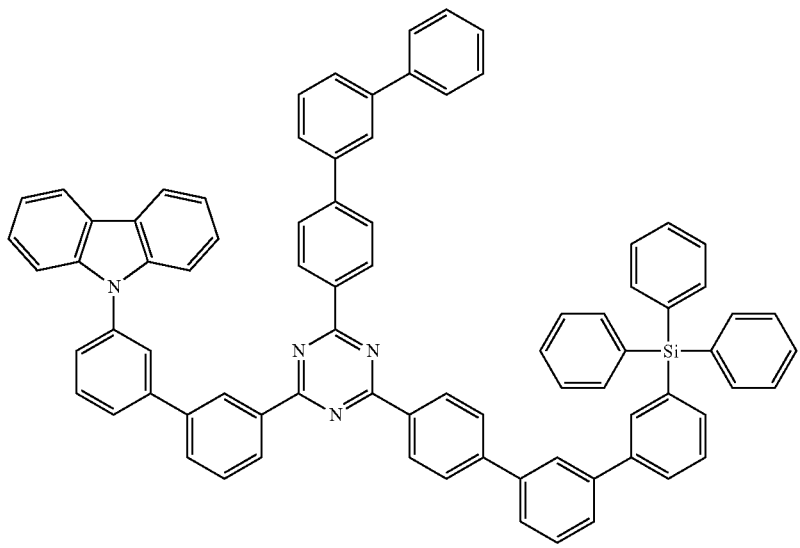
[Ka 12]
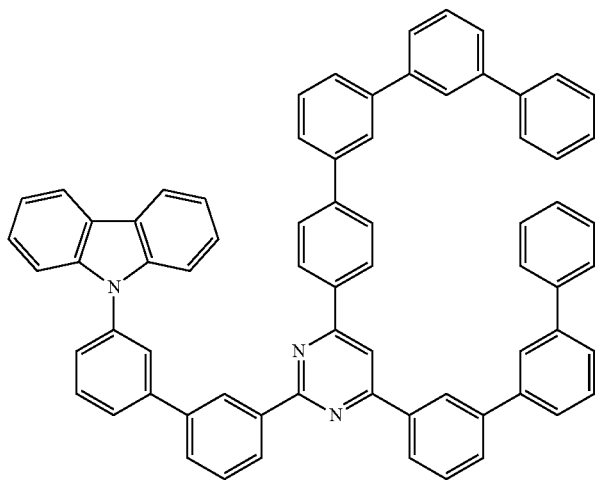
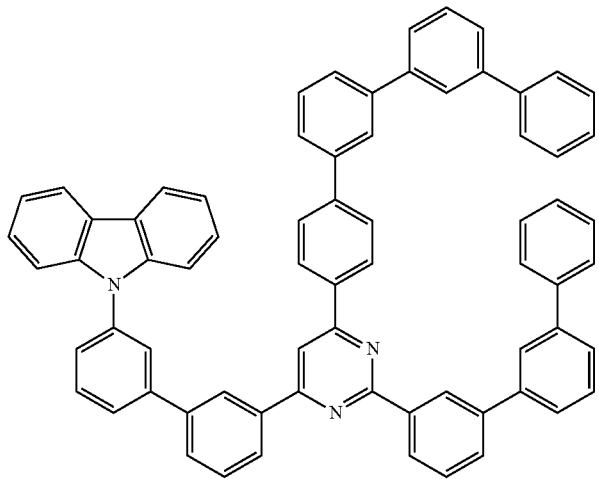

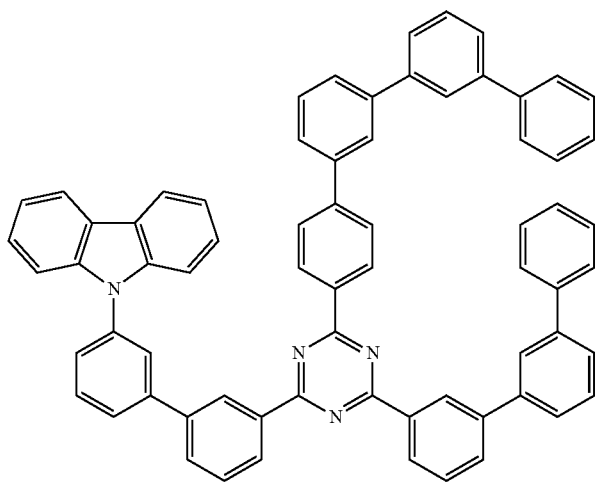
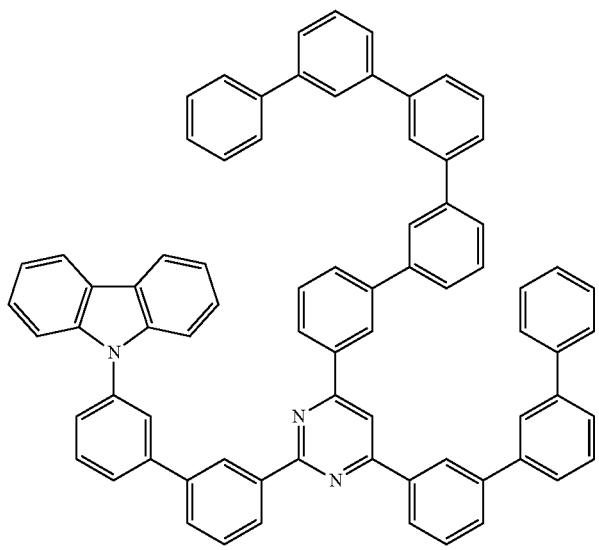
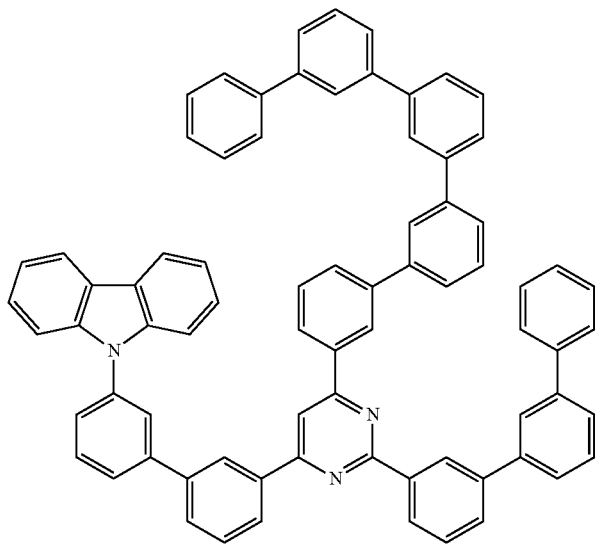

-continued
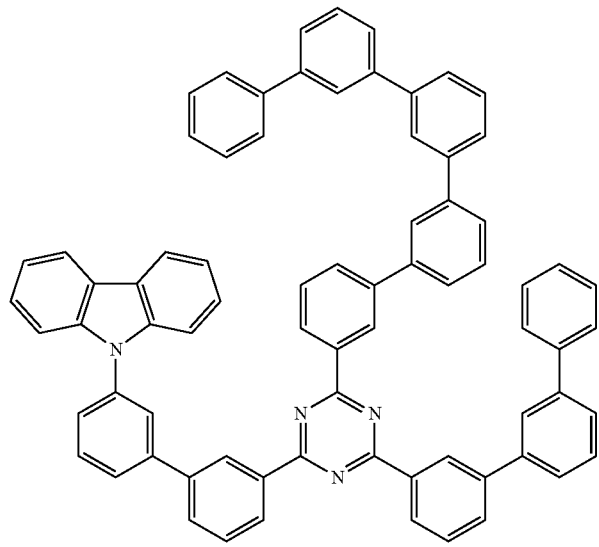
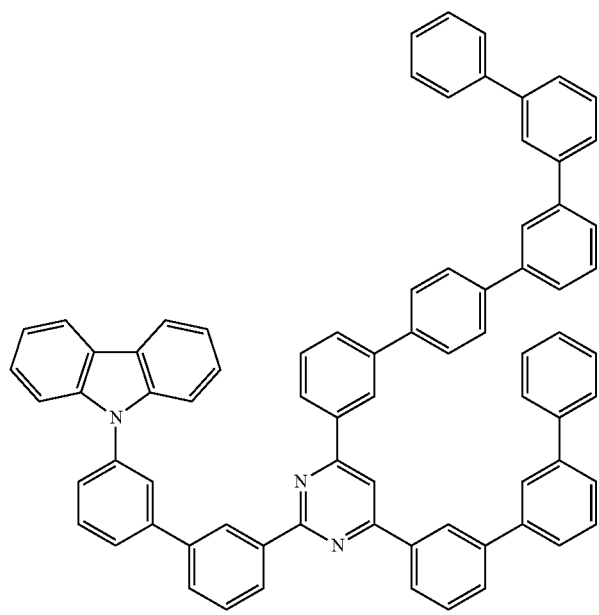

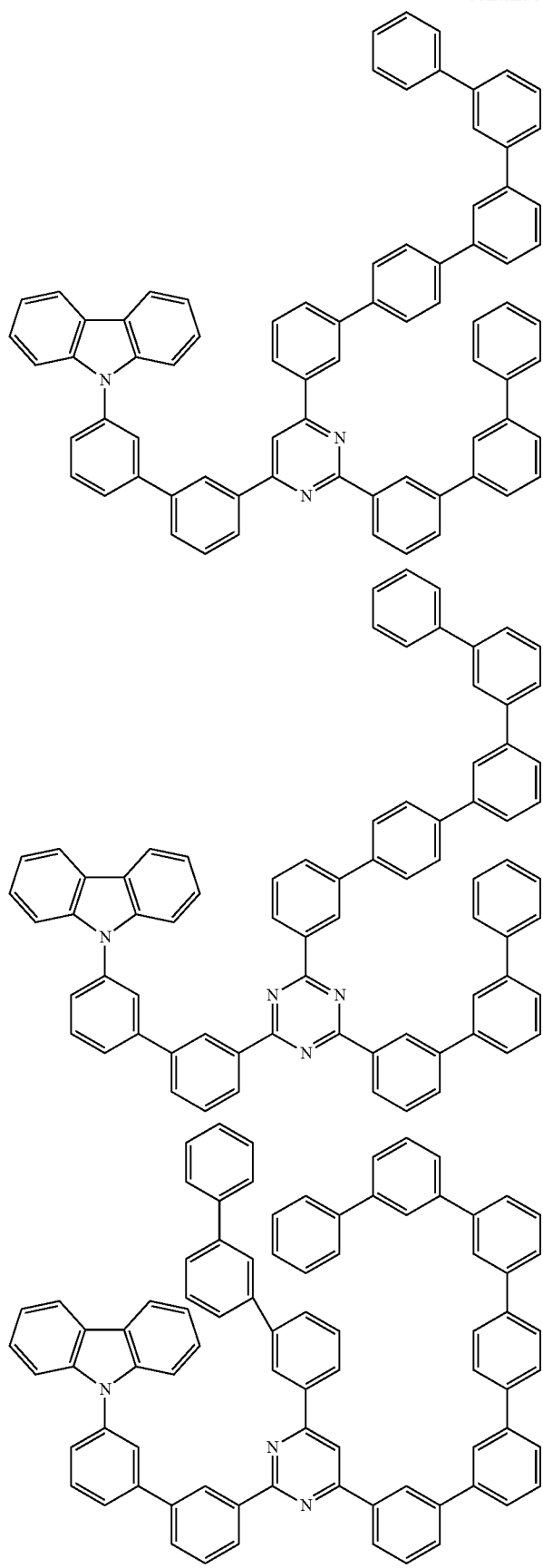

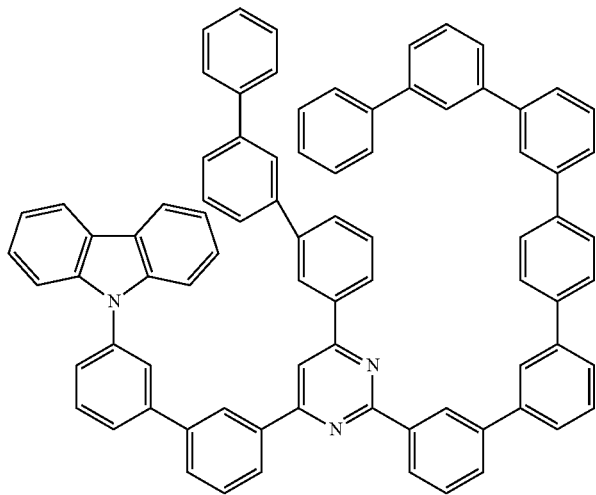
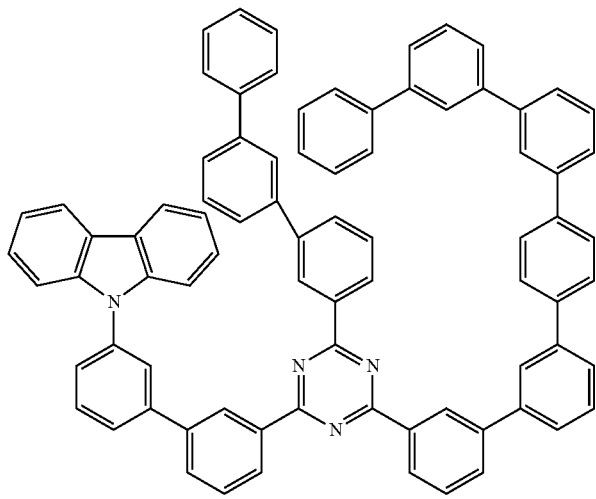
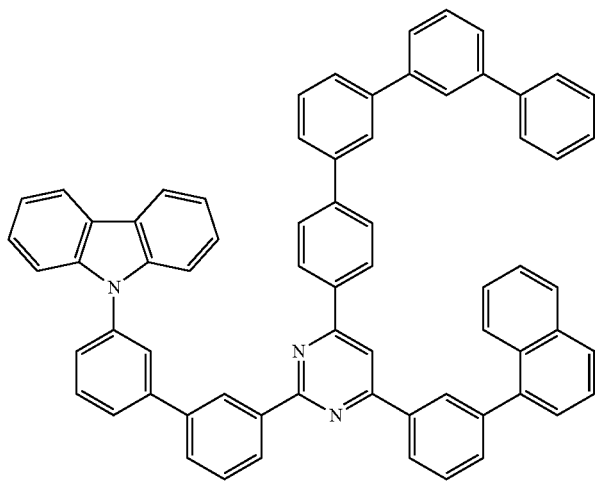

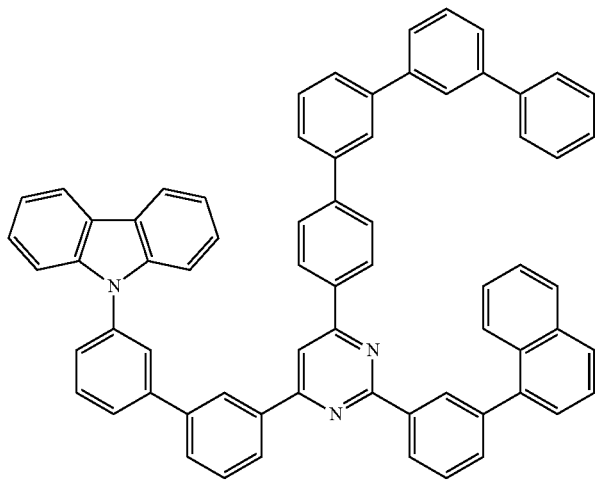
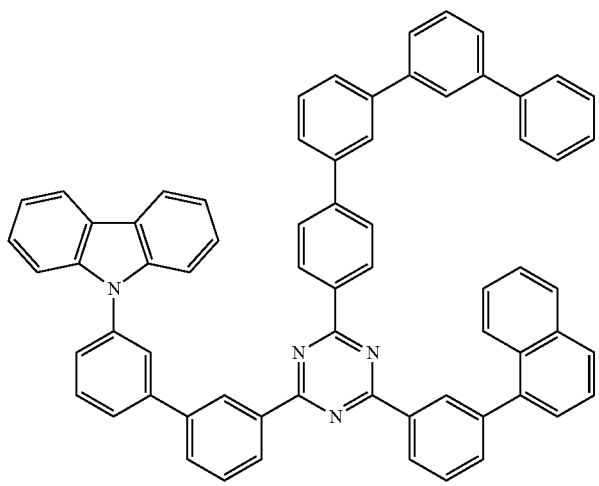
[Ka 13]
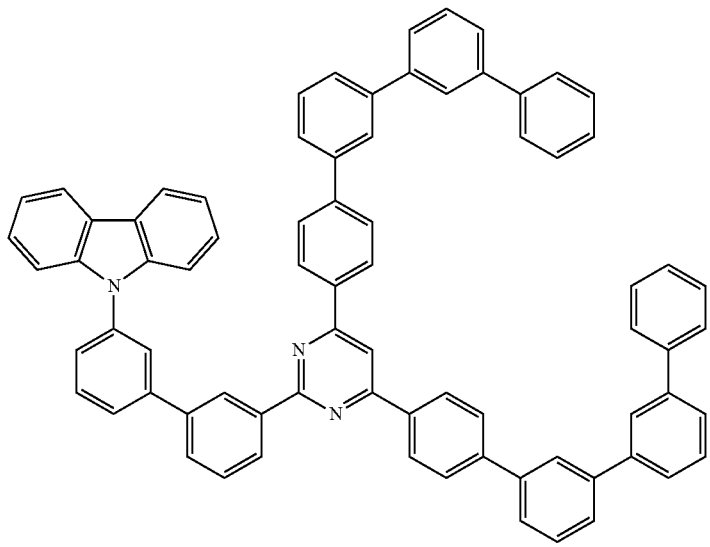

-continued
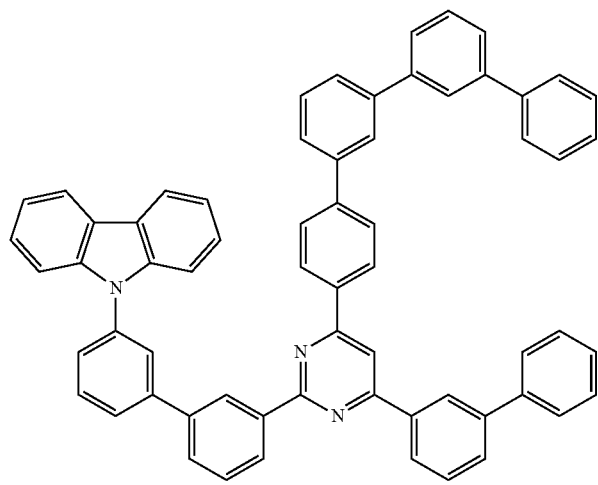
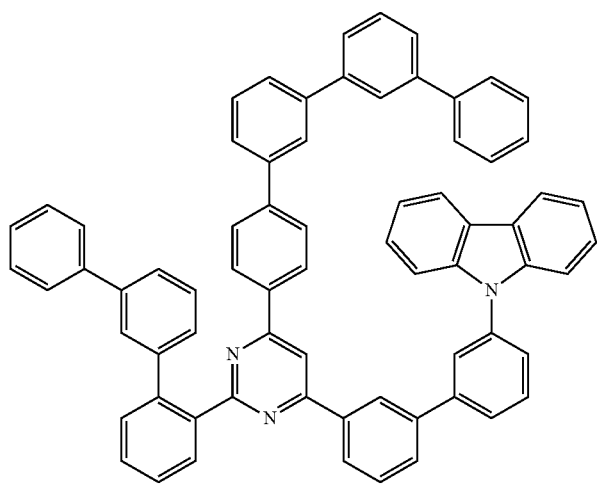
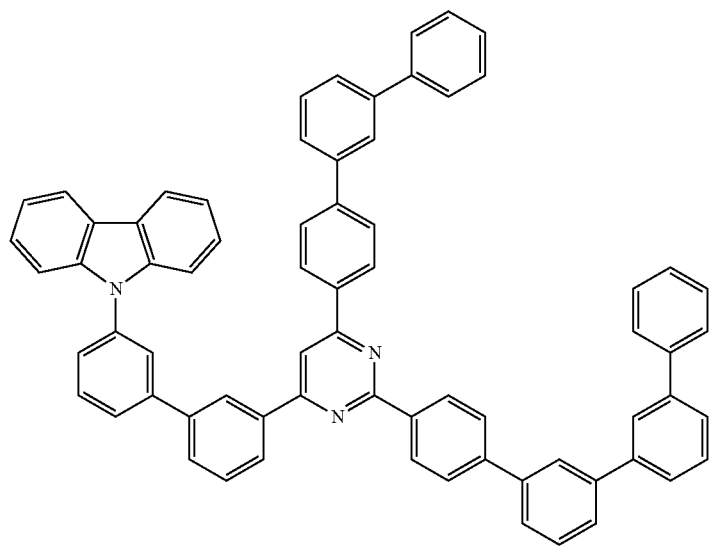

-continued
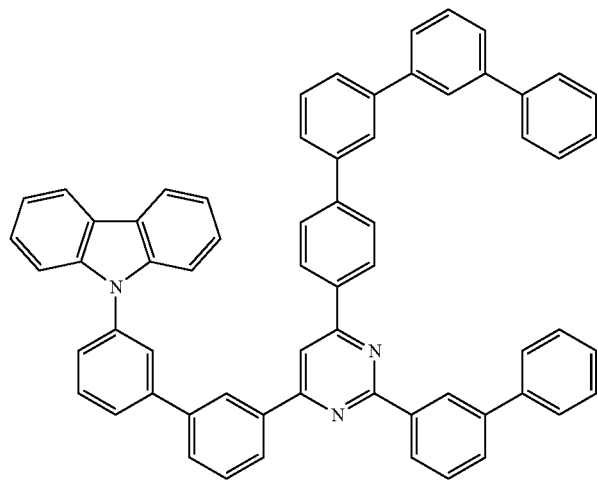
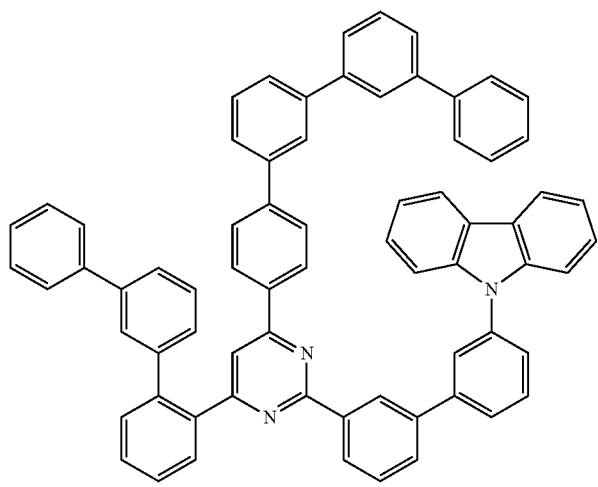
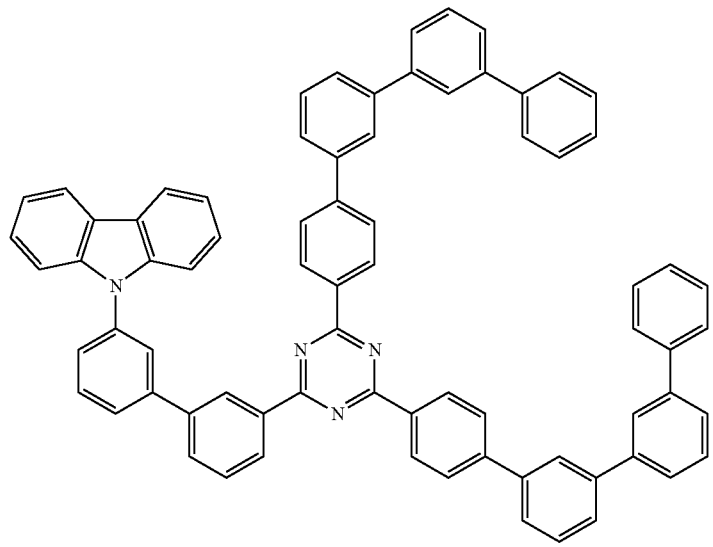

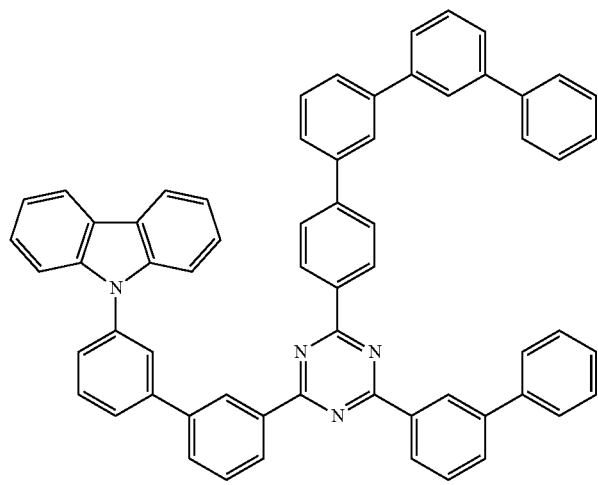
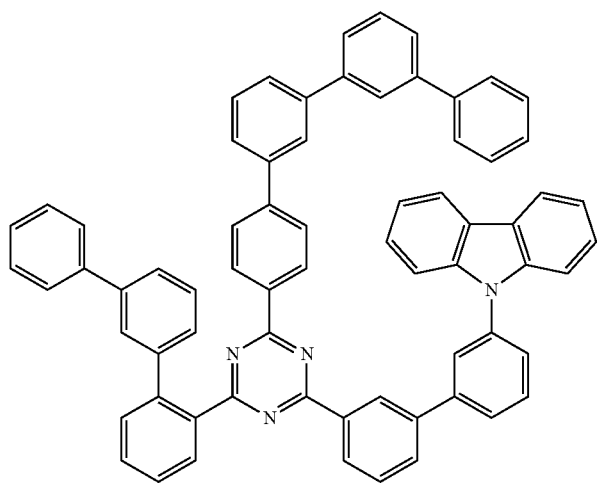
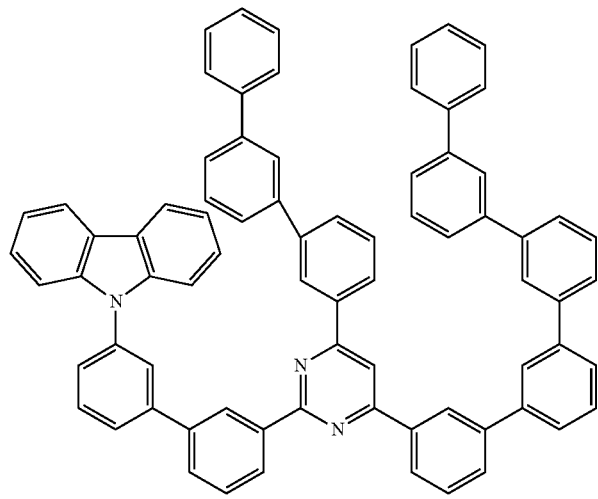

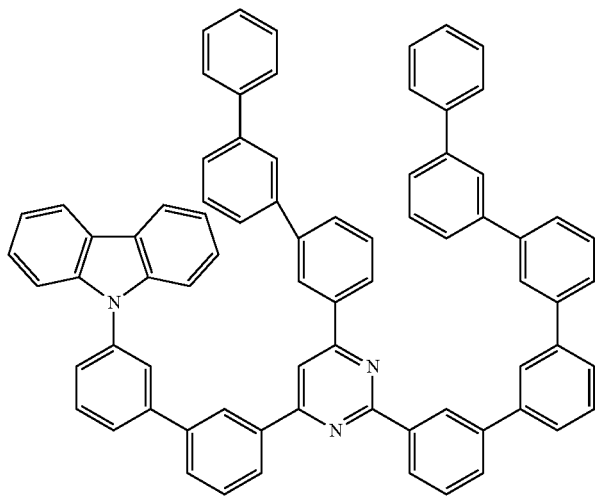
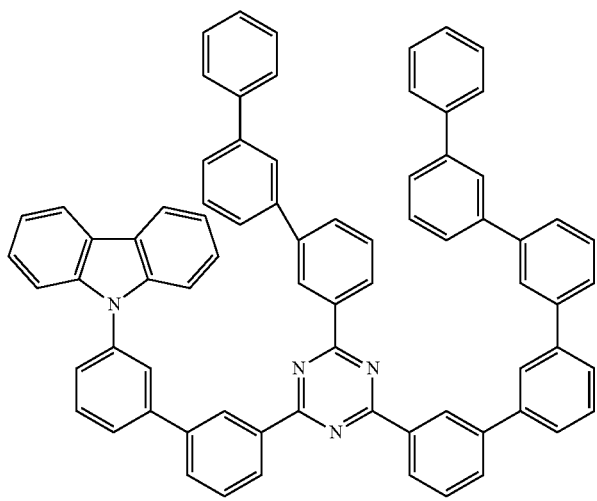
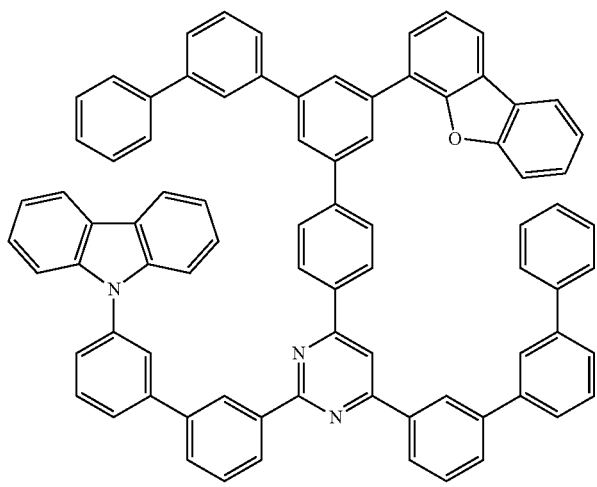

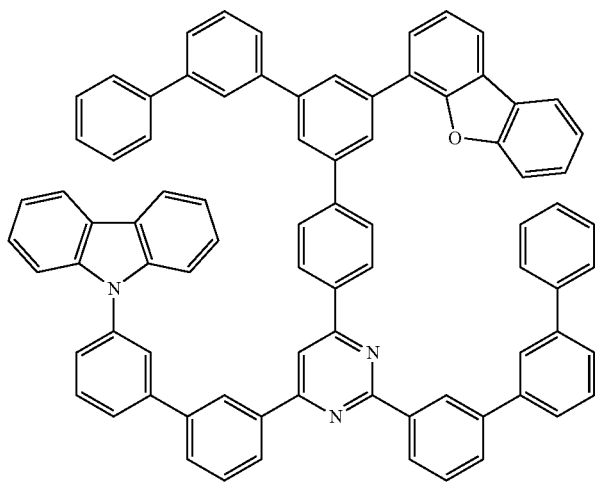
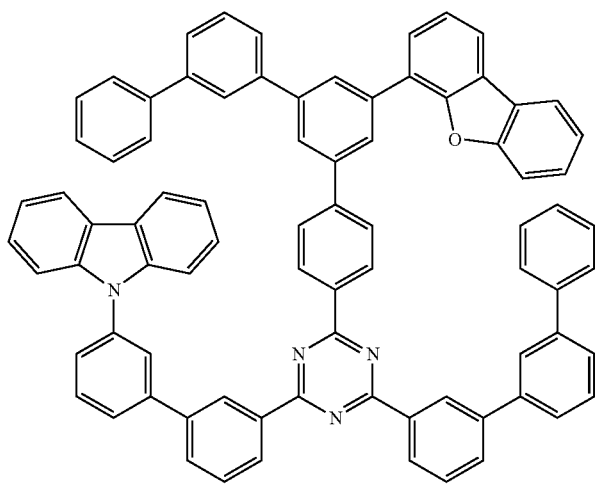
[Ka 14]
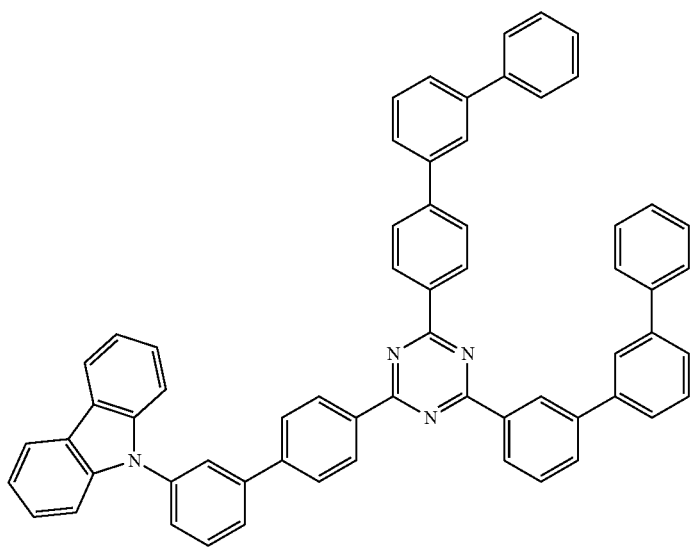

-continued
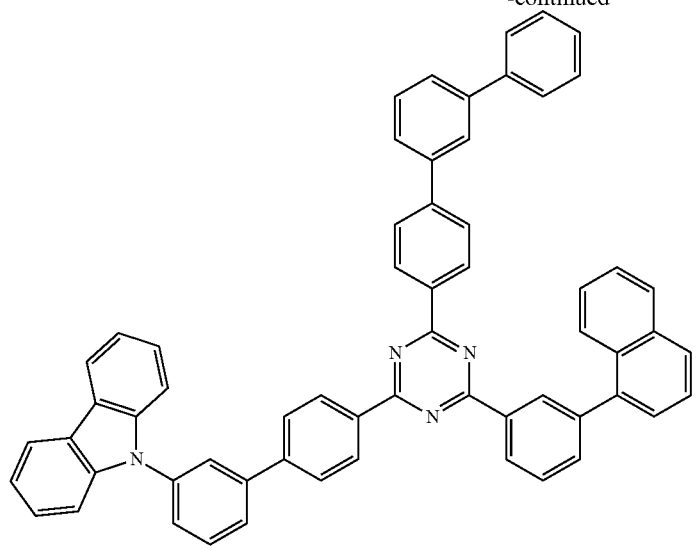
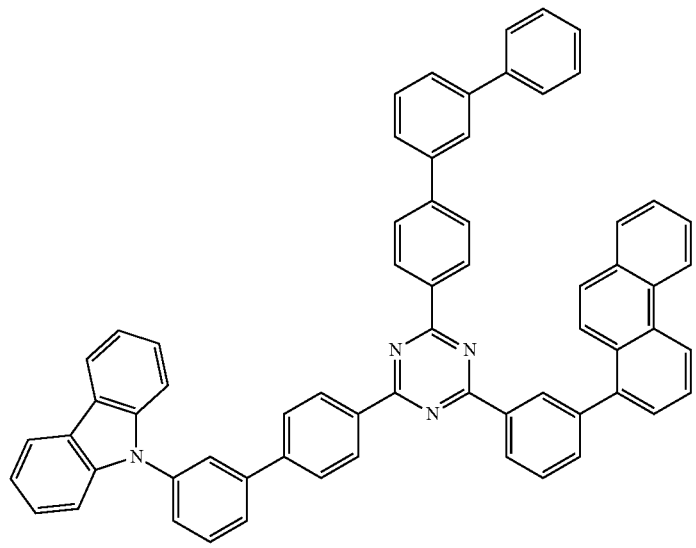
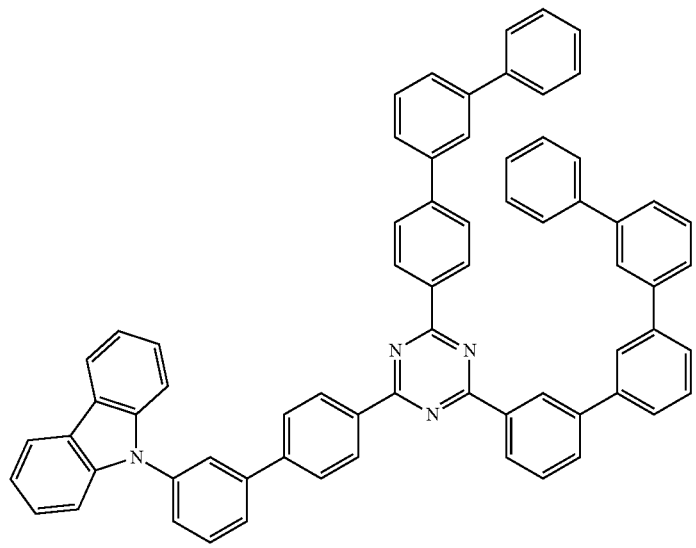

-continued
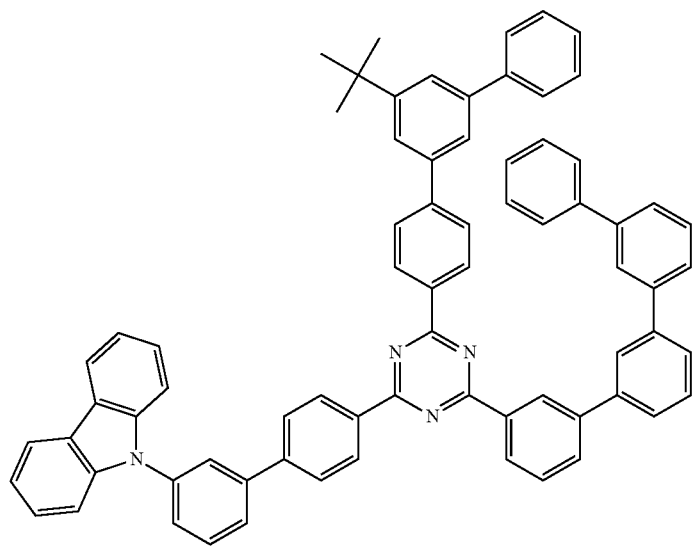
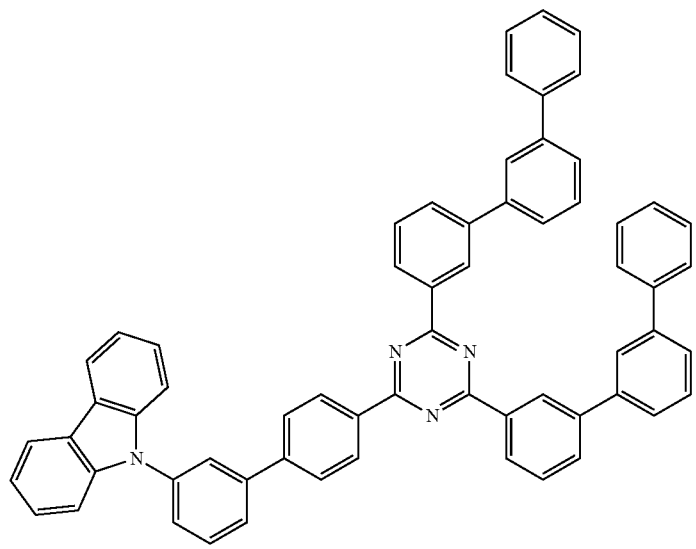
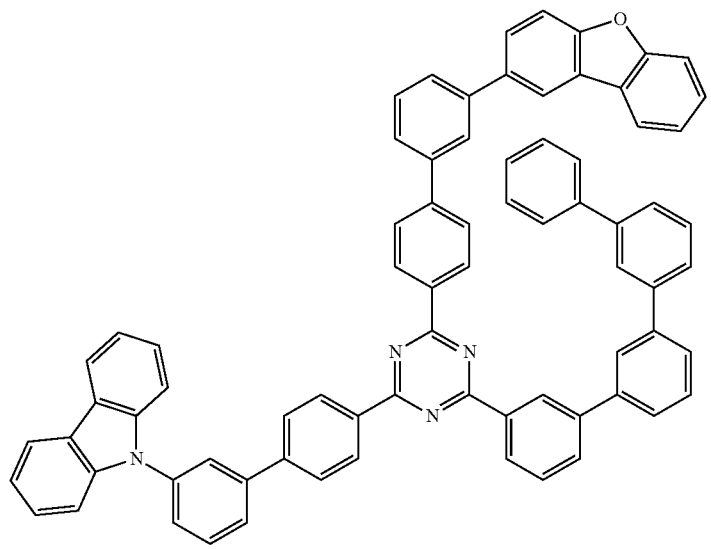

-continued
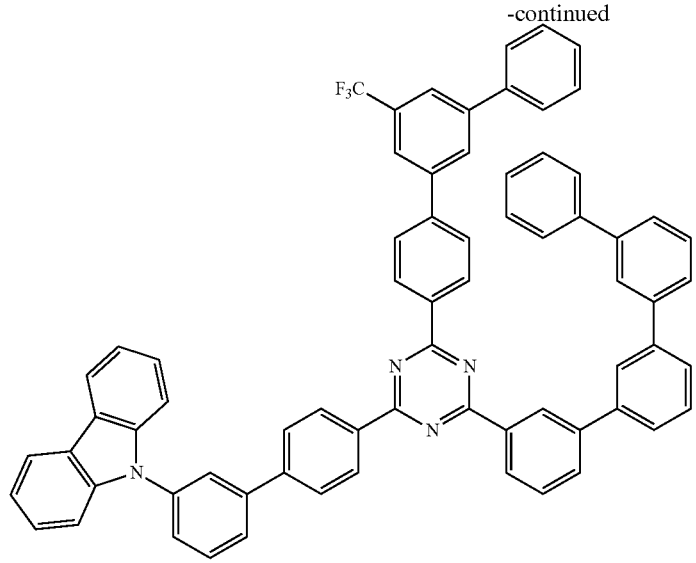
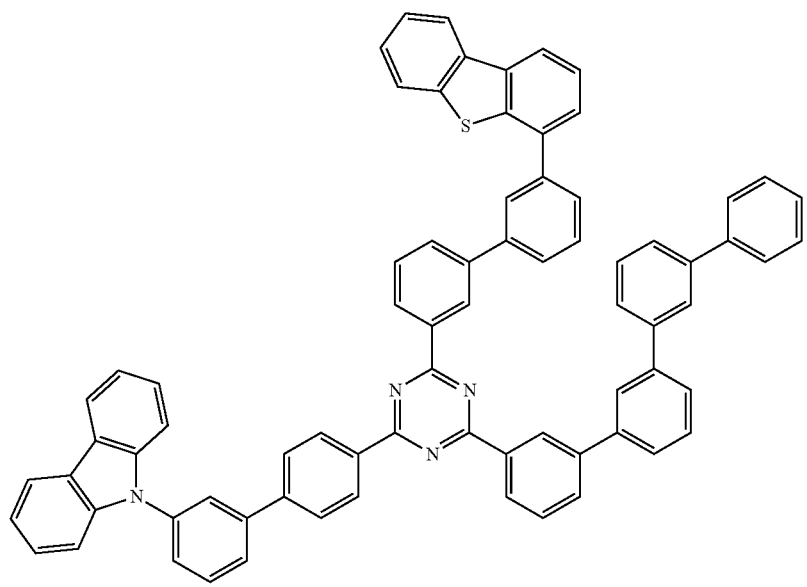
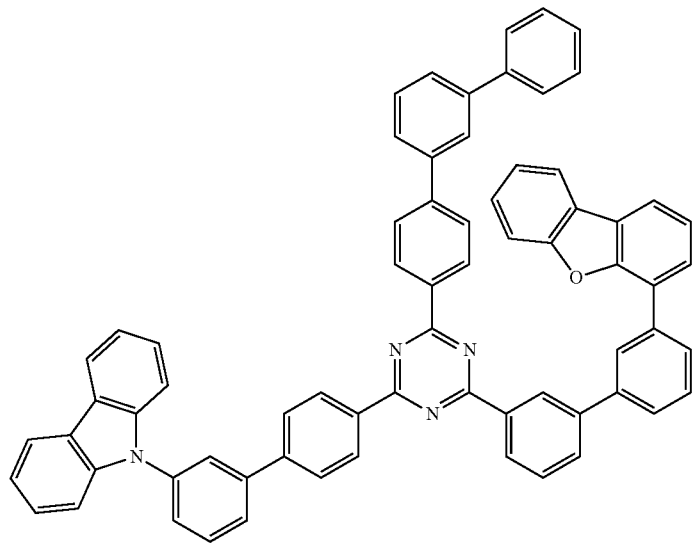

-continued
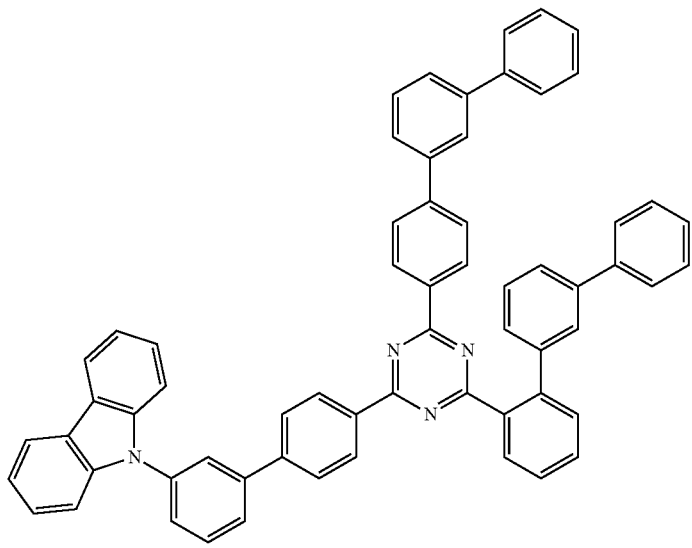
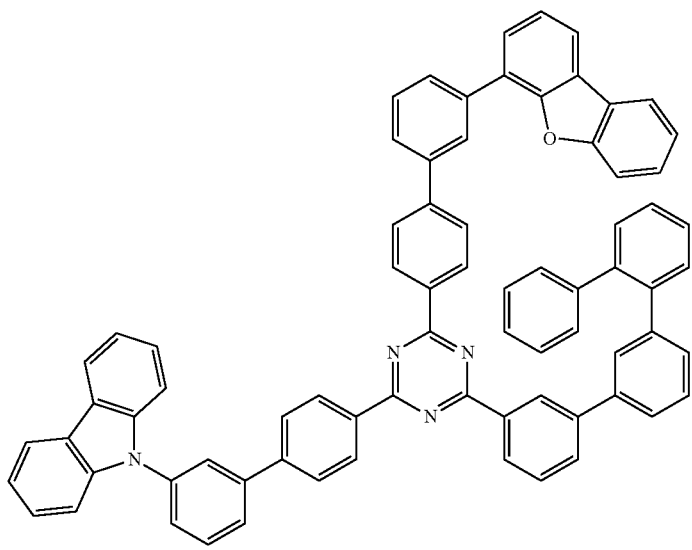
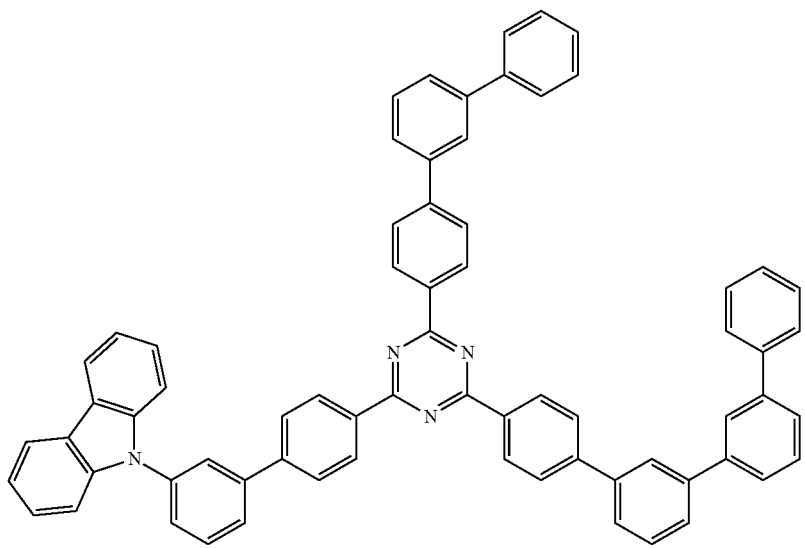

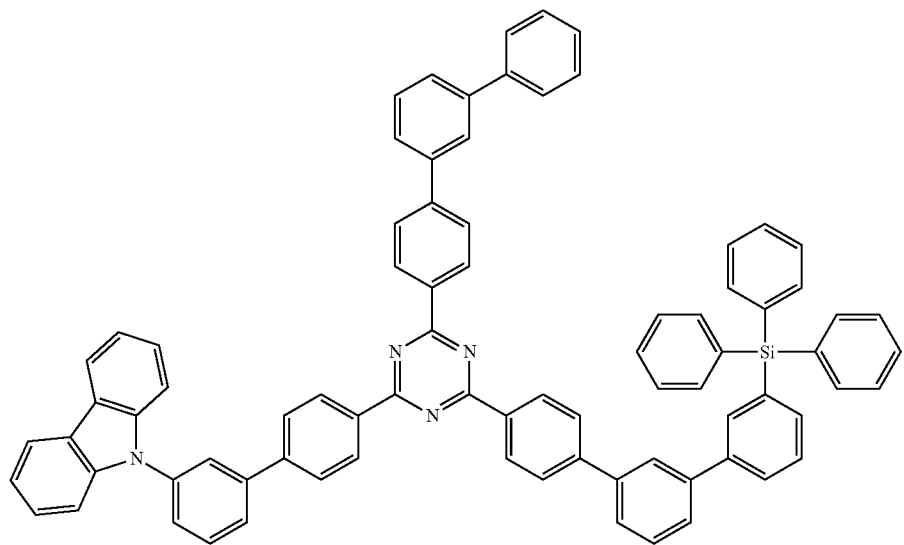
[Ka 15]
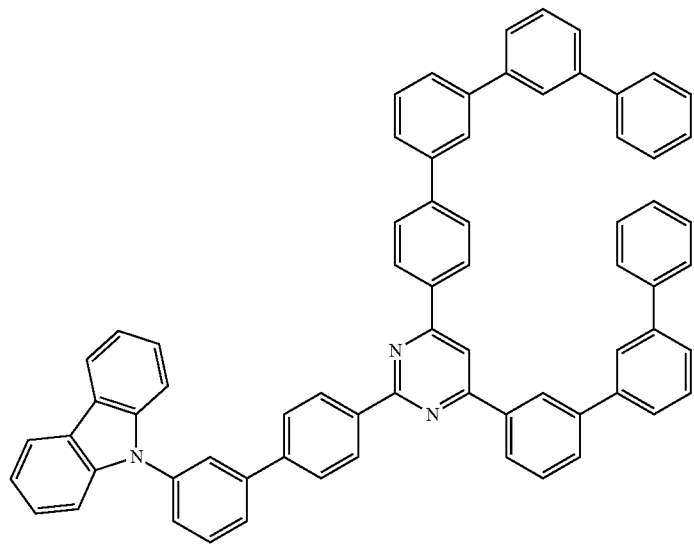
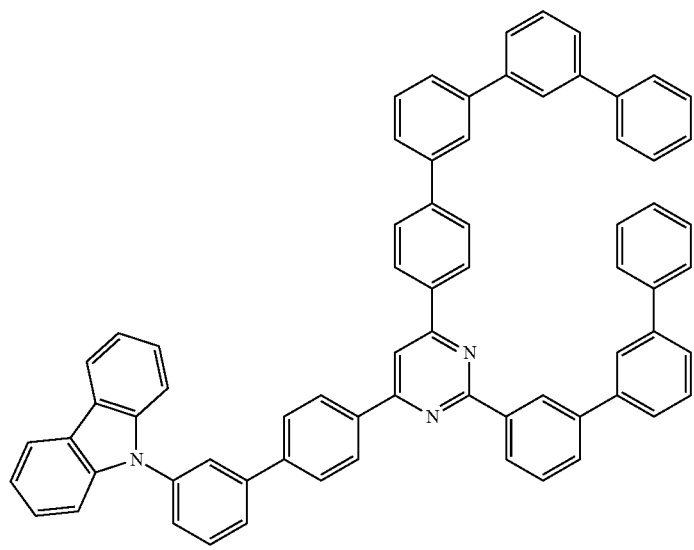

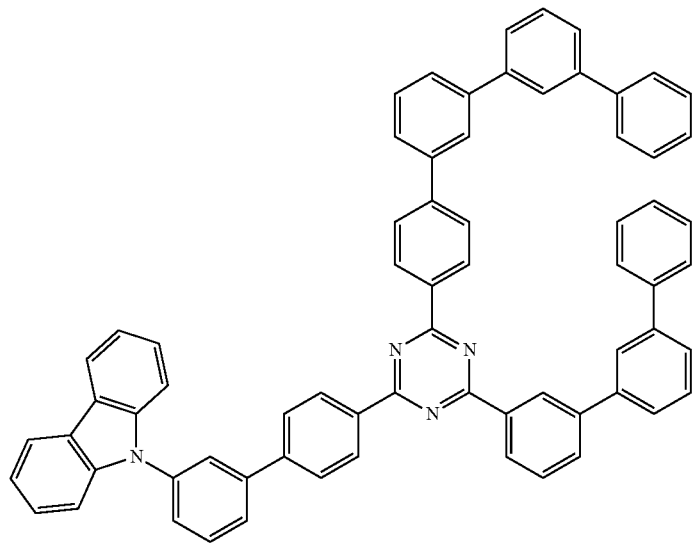
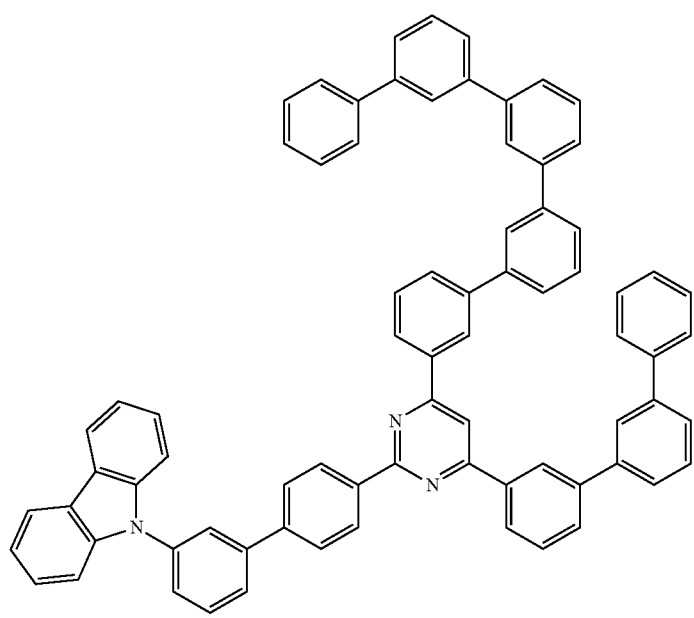

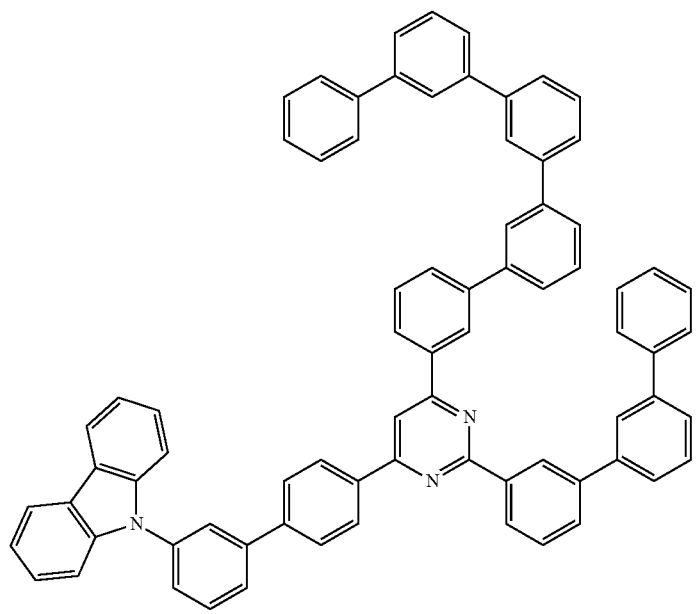
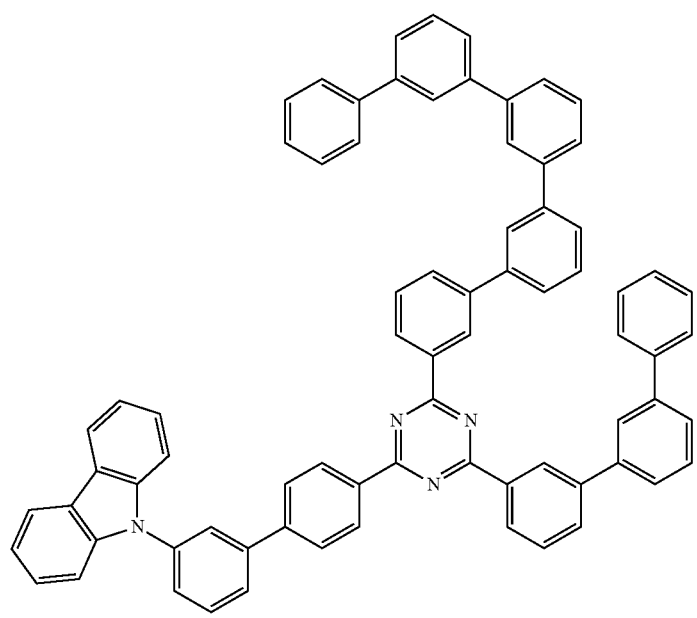

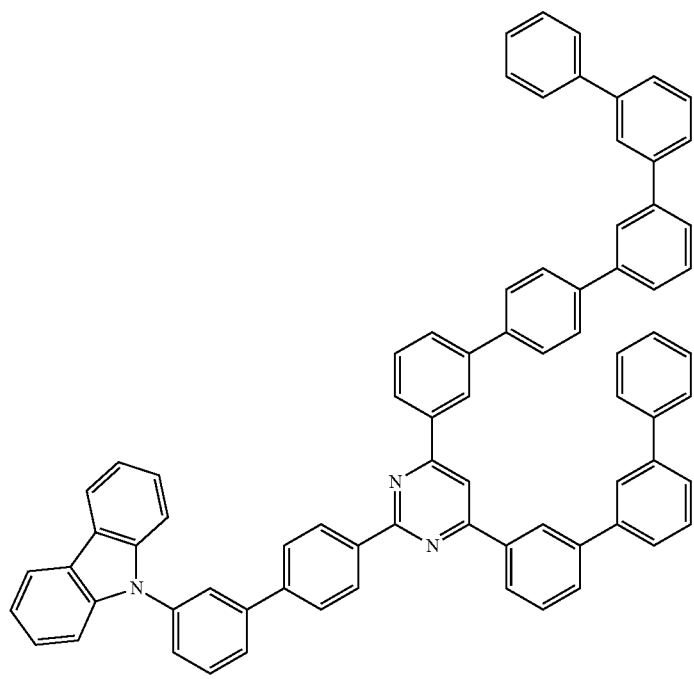
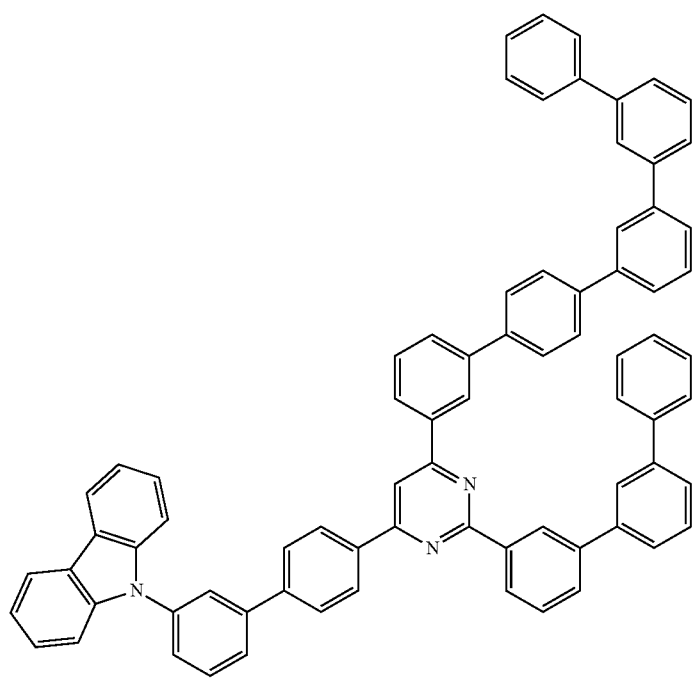

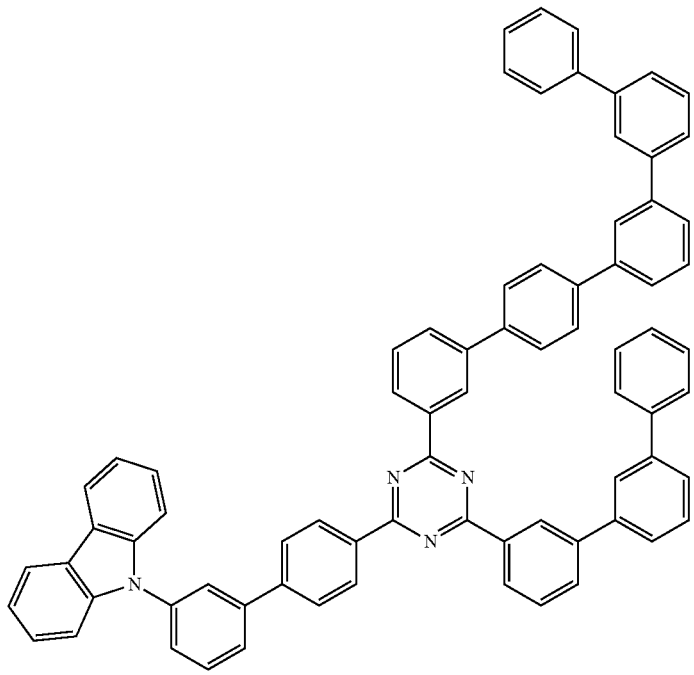
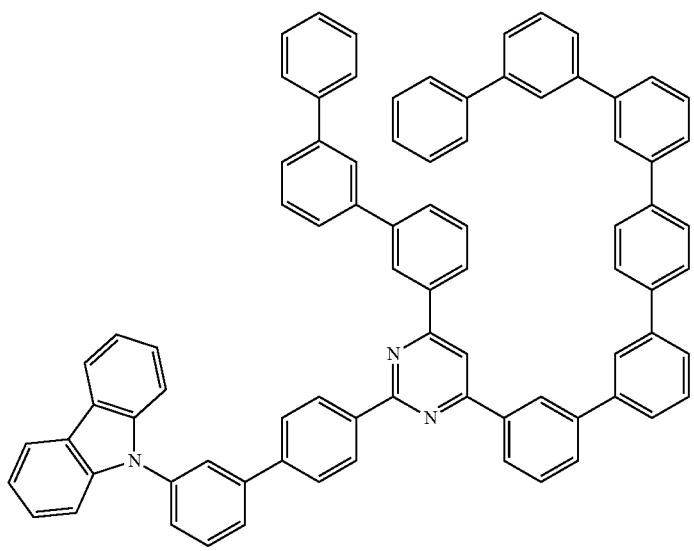

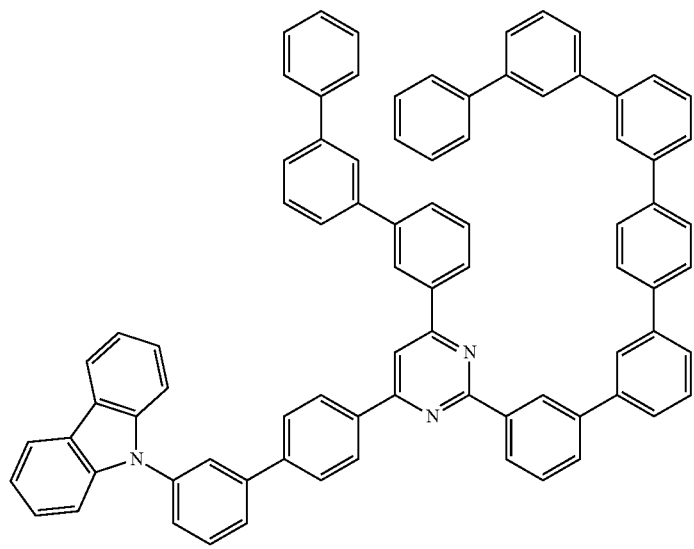
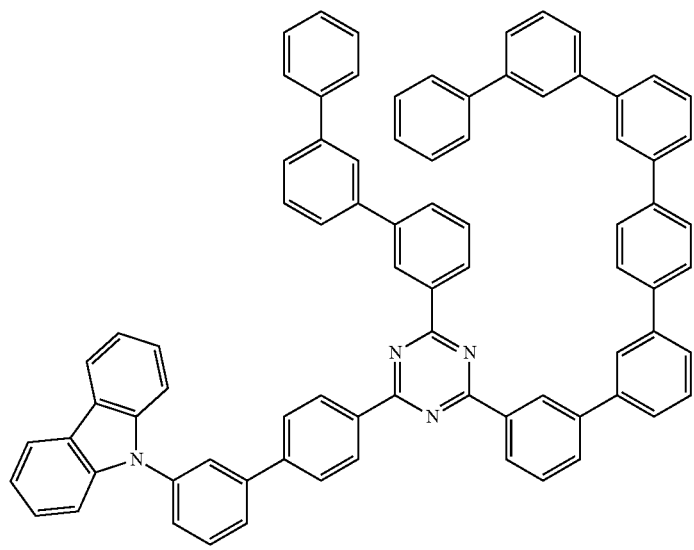
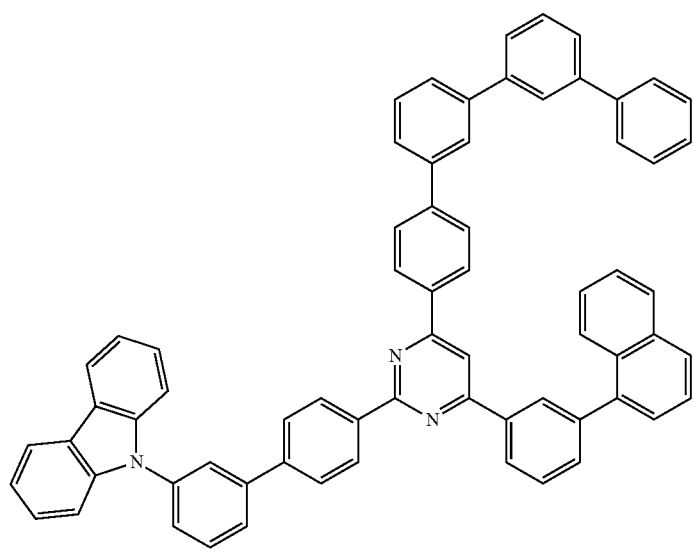

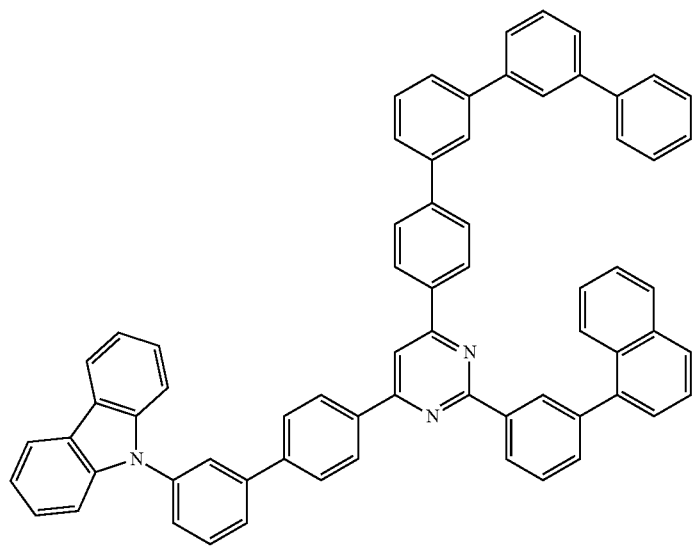
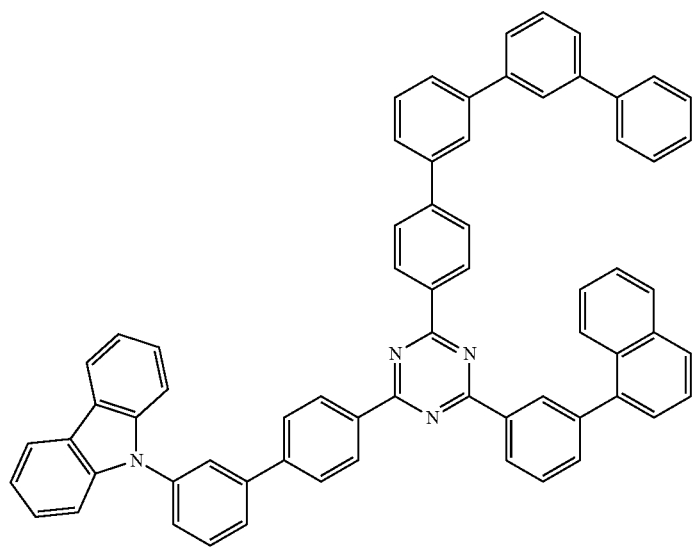
[Ka 16]
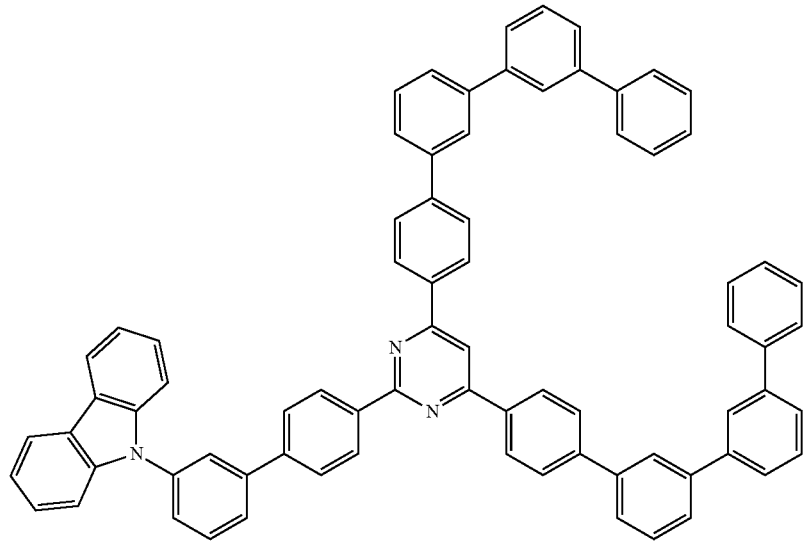

-continued
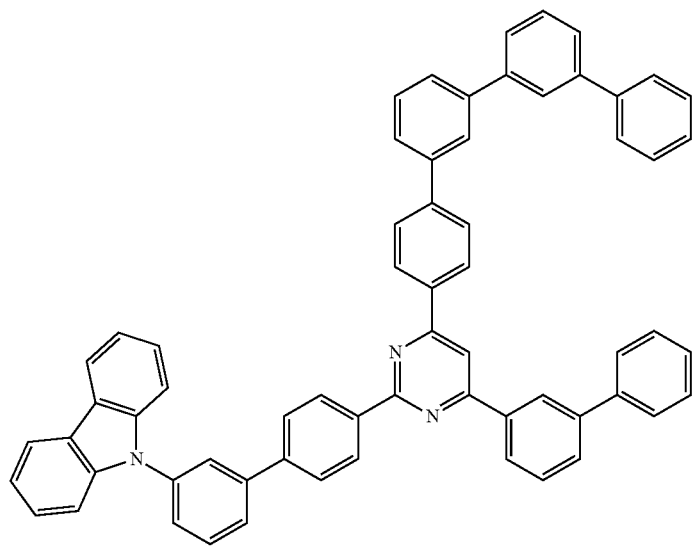
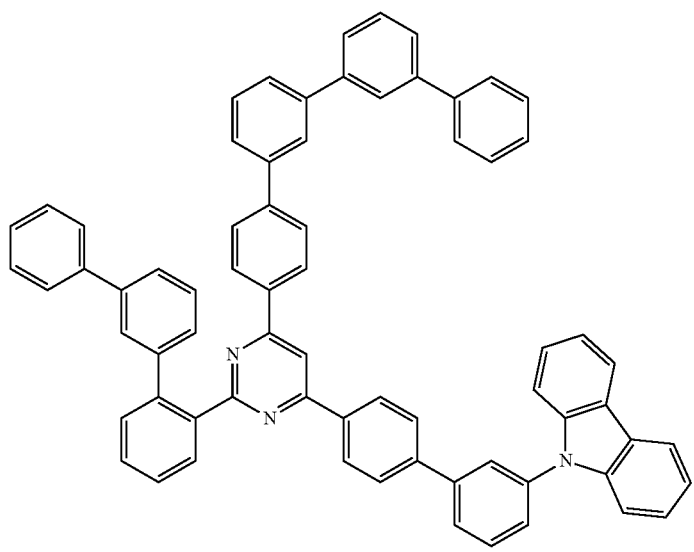
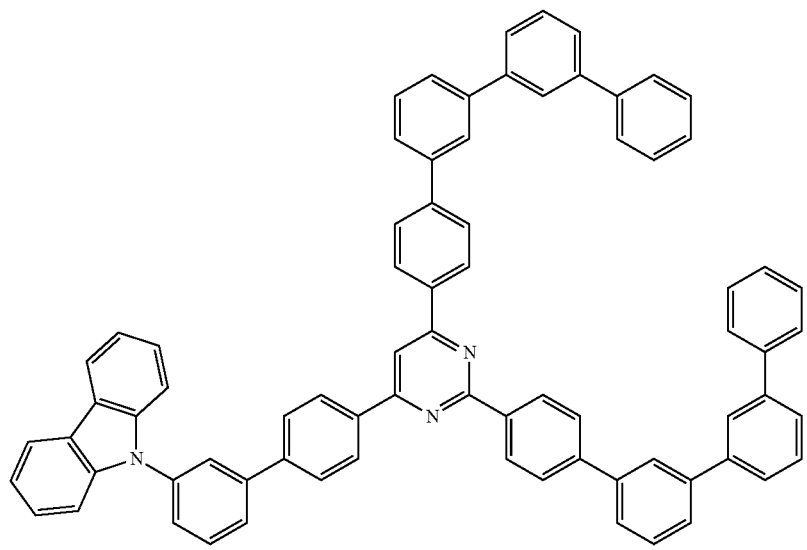

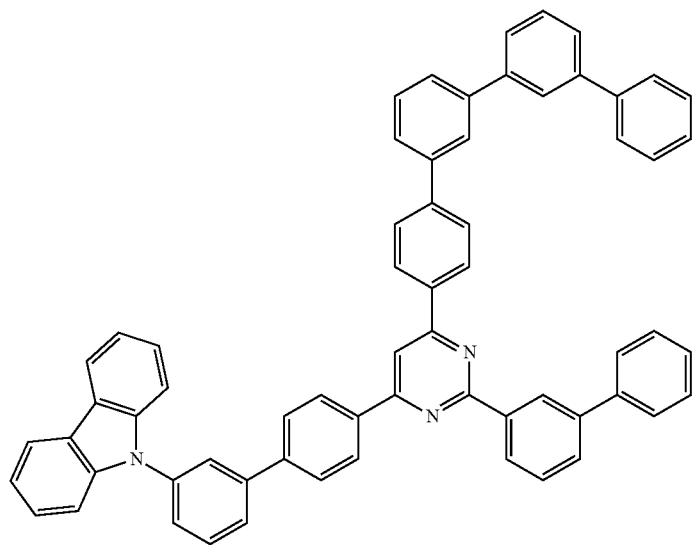
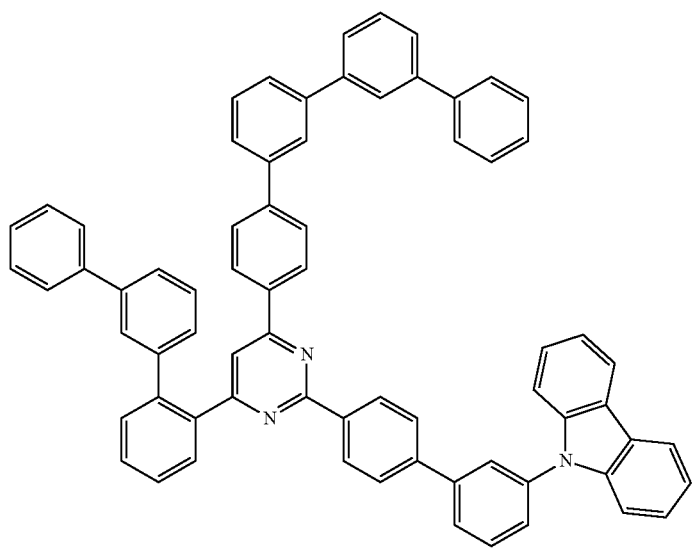
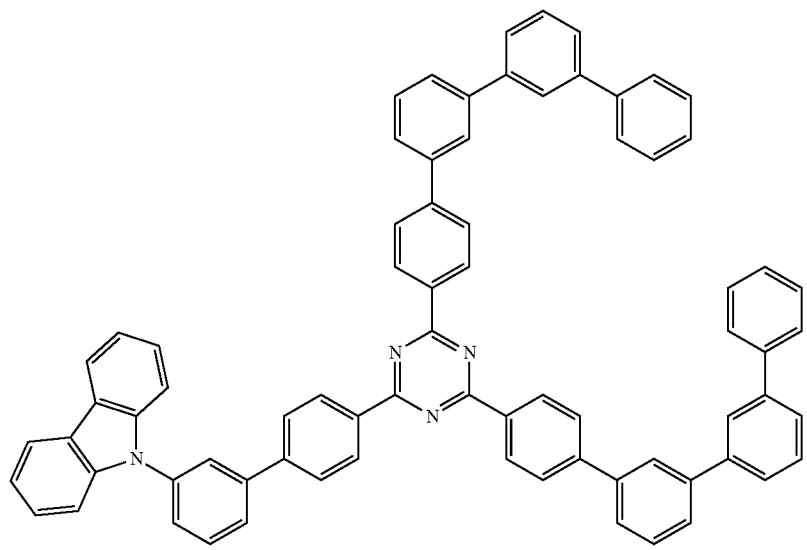

-continued
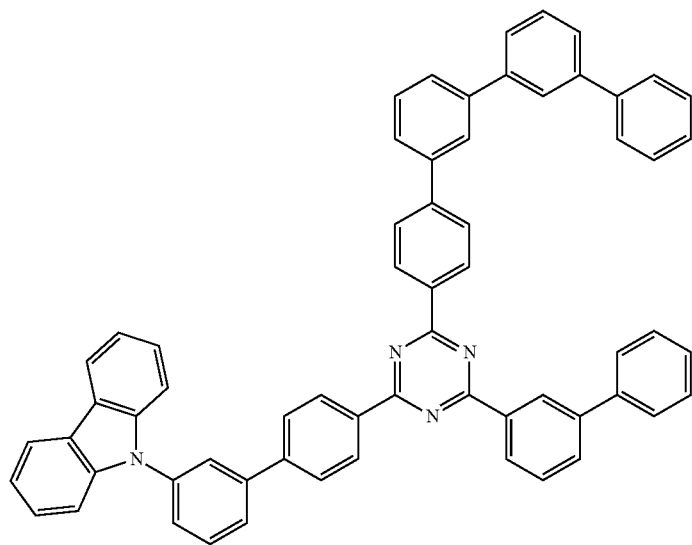
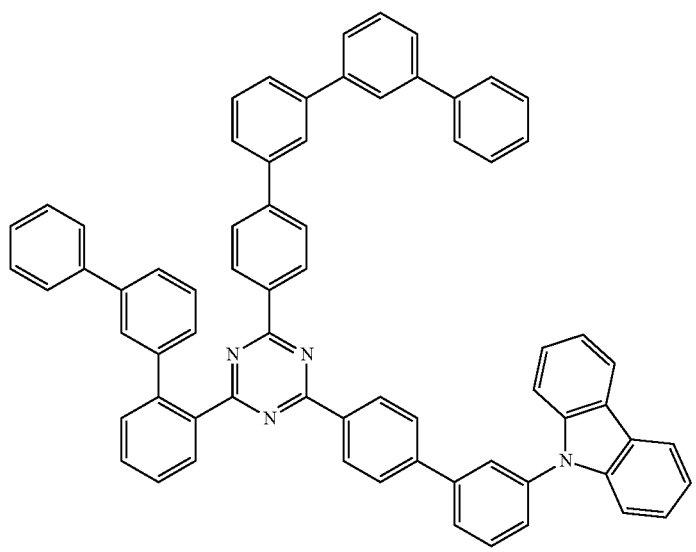
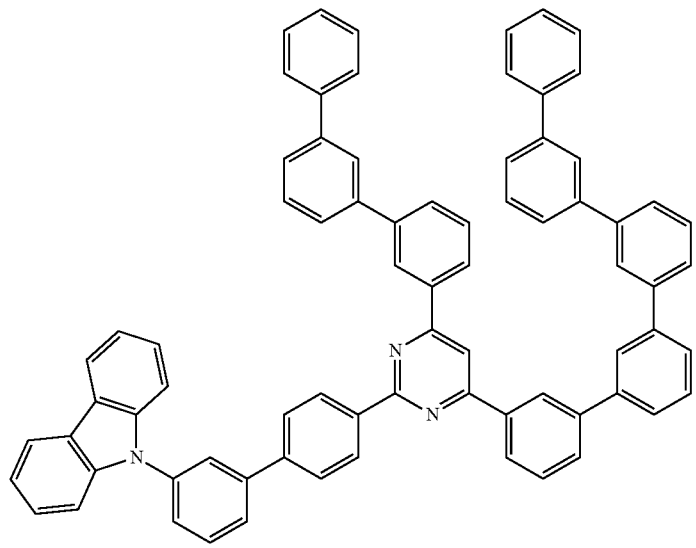

-continued
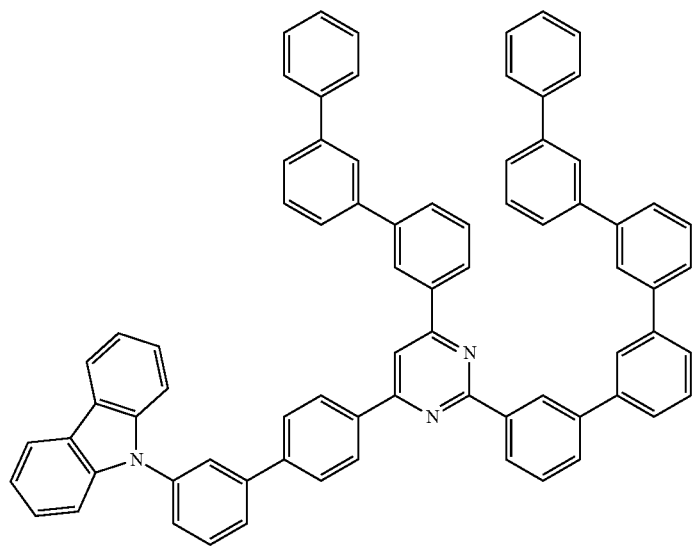
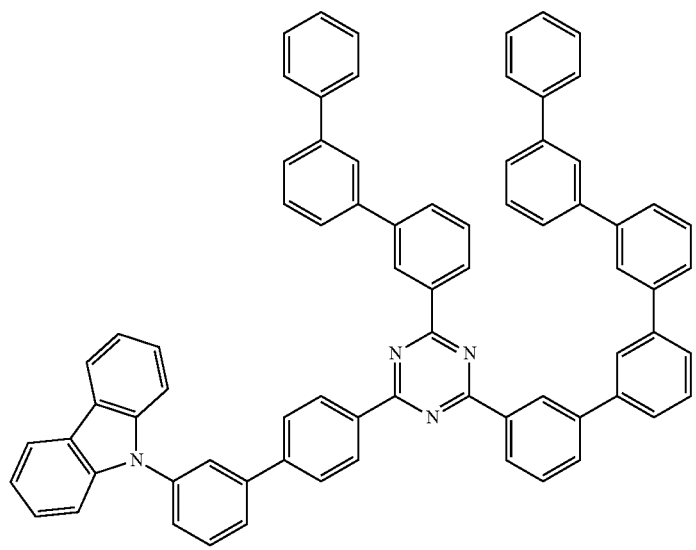
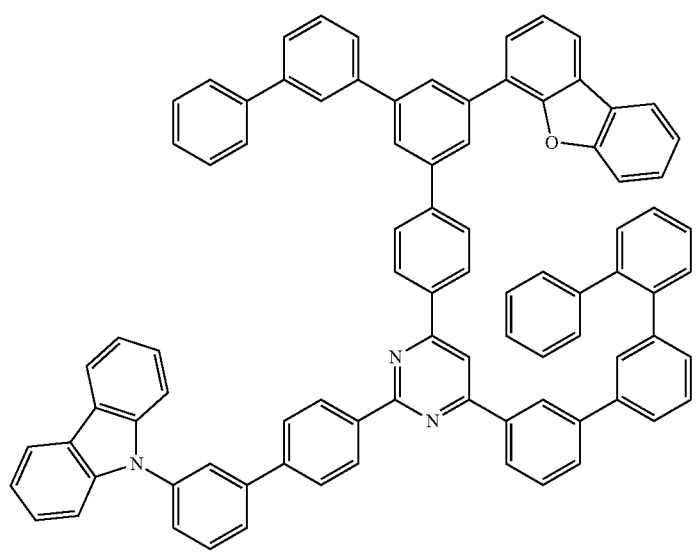

-continued

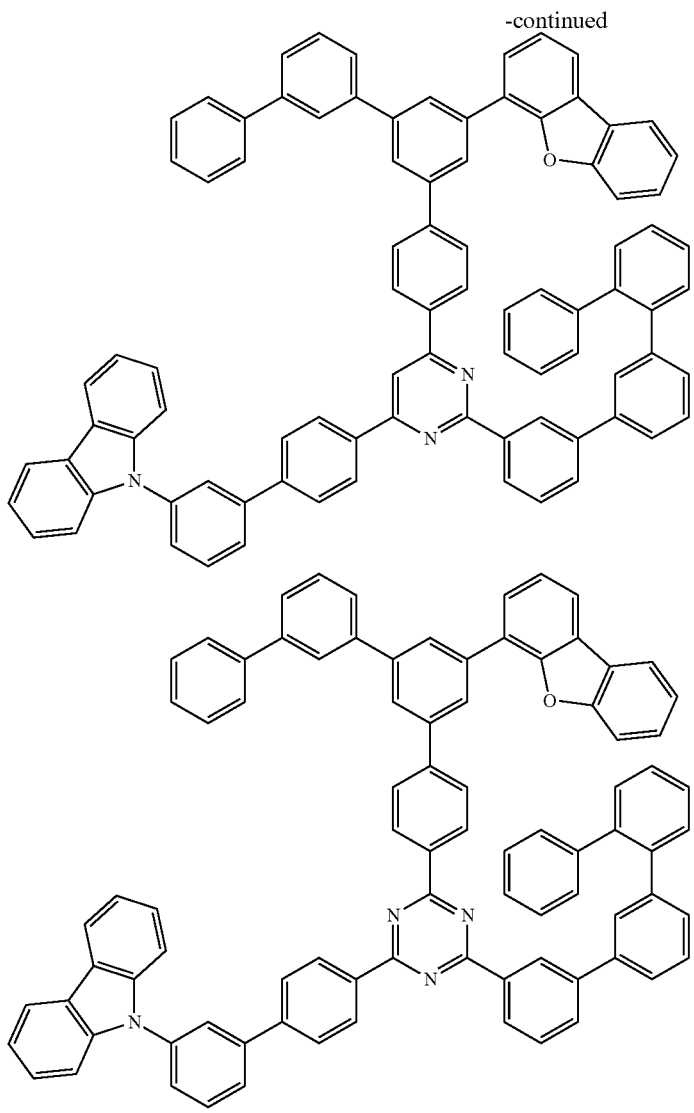

<Synthesis Methods>

The organic compound represented by general formula (1) of the invention can be synthesized, for example, by a suitable combination of the known methods shown below.

(Method A: Method for Synthesis from Aryl Cyanide)

Reference: *Advanced Materials*, Vol. 22, pp. 3311-3316, 2010

(Method B: Method for Synthesis from Trihalogenotriazine)

Reference: *Journal of Organic Chemistry*, Vol. 67, No. 24, pp. 8424-8429, 2002; *Synthetic Metals*, Vol. 122, No. 3, pp. 485-493, 2001; *Organic Letters*, Vol. 3, No. 15, pp. 2419-2421, 2001; *Organic Letters*, Vol. 10, No. 5, pp. 709-712, 2008; and *Chemistry of Materials*, Vol. 18, pp. 204-213, 2006

[Ka 17]

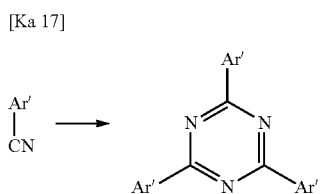

(In the formulae, Ar' represents an aromatic hydrocarbon group which may have any substituent, and the Ar' groups may be the same or different.)

[Ka 18]

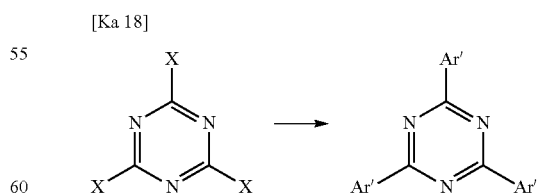

(In the formulae, X represents any of a fluorine atom, chlorine atom, bromine atom, and iodine atom, and the X atoms may be the same or different. Ar' represents an aromatic hydrocarbon group which may have any substituent, and the Ar' groups may be the same or different.)

(Method C: Method for Synthesis from Trichloropyrimidine)

[Ka 19]

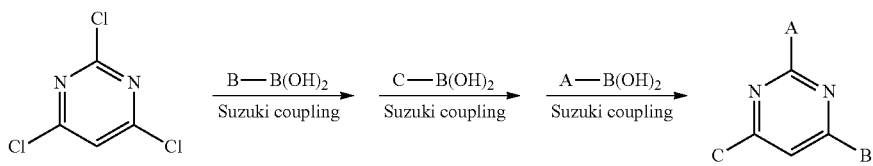

Namely, an organic compound represented by general formula (1) can be synthesized by reacting the starting compound in stages using the method described in *J. Org. Chem.*, Vol. 66, pp. 7125-7128, 2001.

Besides those methods, use can be made of the methods described or cited in *Hetero Kan No Kagaku—Iyakuhin No Kiso* (Kunieda et al., Kagaku-Dojin Publishing Company, Inc., 2002), *Shinpen Hetero Kan Kagōbutsu Kisohen, Ōyōhen* (Yamanaka et al., Kodansha Ltd., 2004), etc.

<Mechanism of the Effects of the Organic Compound of the Invention>

The mechanism by which the desired effects of the invention are produced by configuring the chemical structure of the organic compound of the invention has not been elucidated in detail. However, the mechanism is presumed to be as follows.

The "solubility of a compound" means the weight of the dissolved compound determined by mixing the compound with any solvent and measuring the weight of the compound dissolved in the solvent when the mixture is in a solid-liquid equilibrium state. Consequently, the solubility of a compound can be discussed by comparing the free energy of the compound in a solid state with the free energy of the compound in the state of having been dissolved in a solvent. In general, the solubility of a compound is improved by (1) rendering the free energy of the solid-state compound instable and (2) stabilizing the free energy of the compound dissolved in a solvent. The free energy of the solid-state compound is approximately equal to the total energy of the interaction between the molecules, and the free energy of the compound dissolved in a solvent is approximately equal to the solvation energy which the compound receives from the solvent molecules.

[Ka 20]

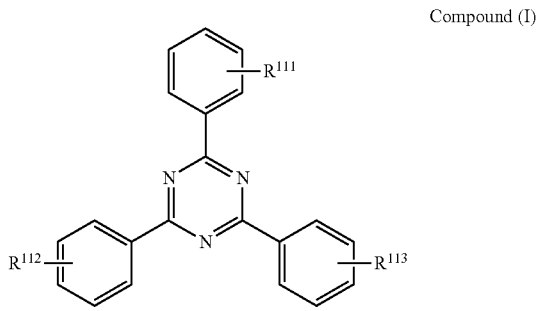

Compound (I)

In a compound (I) which has a 2,4,6-triphenyl-1,3,5-triazine moiety as a partial structure, the 1,3,5-triazine ring as the central framework has no hydrogen atom and, hence, no steric hindrance occurs between this ring and the hydrogen atoms present on each phenyl group bonded to the ring, and the triazine ring and the three benzene rings have a substantially planar molecular structure as a stable conformation (see, for example, *Synthetic Metals*, Vol. 122, No. 3, pp. 485-493, 2001; and *Chemical Communications*, Vol. 46, No. 27, pp. 4902-4904, 2010). Because of this, the compound (I) in a solution shows reduced fluctuations in molecular structure due to molecular movements and receives a reduced amount of solvation energy from the solvent molecules. In addition, molecules of the compound (I) are apt to be stacked due to intermolecular $\pi/\pi$ stacking, resulting in exceedingly high crystallinity. Consequently, this compound is thought to generally have low solubility. Similarly, with respect to 2,4,6-triphenylpyrimidine also, no steric hindrance occurs between the pyrimidine ring and the hydrogen atoms present on a phenyl group (one of the three phenyl groups), and it is thought that the pyrimidine ring and the one benzene ring have a substantially planar molecular structure as a stable conformation. This compound is consequently thought to have low solubility in solvents. Meanwhile, 2,4,6-triphenylpyridine cannot have a planar structure as a stable conformation and hence has high solubility in solvents. (See Reference Example 1 and Comparative Example 2, which will be given later. Regardless of the same substituents, the pyridine derivative gave a composition having higher storage stability.)

It is thought from the tendency described above that the following three methods are usable as methods for improving the solubility of a 1,3,5-triazine compound and a pyrimidine compound. Although an explanation is given here only on the 1,3,5-triazine compound (I), the same lines of design can be applied to pyrimidine compounds. Namely, the three methods, which relate to the three substituents $R^{111}$ to $R^{113}$ to be introduced into the three phenyl groups of the compound (I), are: (i) to regulate these substituents so as to be substituents which cause a high steric hindrance that inhibits the intermolecular $\pi/\pi$ stacking; (ii) to reduce the molecular symmetry to thereby render the crystal structure more instable and cause fluctuations in the molecular structure which the molecules of the solid-state compound can take, thereby rendering the free energy of the solid-state compound instable; and (iii) to regulate the substituents $R^{111}$ to $R^{113}$ so as to be substituents which are as large as possible, thereby increasing the solvation energy which the compound (I) receives from an organic solvent.

Examples which correspond to the first method (i) include a method in which the substituents A, B, and C in general formula (1) each are represented by general formula (2-1) in which $Ar^1$ is a 1,2-phenylene group or a 1,3-phenylene group and $X^1$ is an aromatic hydrocarbon group having 10 or more carbon atoms or a carbazolyl group. It is presumed that these substituents show a high steric hindrance with the rings bonded thereto and, hence, bring about larger angles of torsion with the central framework, resulting in inhibition of the intermolecular $\pi/\pi$ stacking of central frameworks.

Examples which correspond to the second method (ii) include a method in which the substituents A to C, E, and F that constitute general formulae (1) and (3) each have a 1,2-phenylene group and/or a 1,3-phenylene group. These substituents have low symmetry, in contrast to the 1,4-phenylene group, which is a highly symmetric substituent, and are hence apt to cause fluctuations in the molecular structure of the solid-state compound.

Examples which correspond to the third method (iii) include a method in which the organic compound of the invention is represented by general formula (1) wherein the substituents each are any of substituents of general formulae (2-1) to (2-5) and in which the compound represented by general formula (3) has a structure including at least four benzene rings linked together. It is presumed that since the three substituents introduced into the 1,3,5-triazine framework or pyrimidine framework are the specific substituents according to the invention, each substituent receives an increased amount of solvation energy from organic solvents and this organic compound hence has improved solubility in solvents.

Meanwhile, the term "glass transition temperature" means the temperature at which a compound which is amorphous at room temperature undergoes a change in state. At temperatures not lower than the glass transition temperature, the amorphous compound has reduced rigidity and viscosity and shows enhanced flowability. Namely, in the case of a compound having a high glass transition temperature, a large amount of energy is required for the molecules to become flowable. On the other hand, in the case of a compound having a low glass transition temperature, a relatively limited amount of energy is required for the molecules to become flowable. Usually, in the case of a low-molecular compound having a molecular weight of 2,000 or less, that the molecules become flowable is nothing but the release of the molecules in the material from the interaction between the molecules. Namely, it is presumed that the glass transition temperature of a compound can be regarded as an index to the free energy of the compound in a solid state.

The present inventors diligently made investigations from this standpoint. As a result, the inventors have found that a compound in which specific structures have been introduced into a pyrimidine framework and a 1,3,5-triazine framework and which has been made to have a molecular weight of 750 or more and 2,000 or less has a relatively low glass transition temperature, has improved solubility in solvents, and gives a composition which contains this compound and a solvent and which has satisfactory storage stability. The inventors have further found that an organic electroluminescent element produced using this composition has a long life, low operating voltage, and high luminescent efficiency.

Since glass transition temperature is related to the mobility of the molecules, the glass transition temperature of a compound depends on the molecular weight of the compound, the framework which constitutes each molecule, and the kinds of the substituents. The inventors have found that a compound having a pyrimidine framework and a 1,3,5-triazine framework has a relatively low glass transition temperature when the three substituents which constitute the molecule are constituted of general formula (1) or (3) and when the compound has only one carbazolyl group or no carbazolyl group in the molecule. The reason why the presence of one or less carbazole ring in the molecule has resulted in a decrease in glass transition temperature is presumed to be as follows. A carbazole ring, which has high polarity and high planeness as compared with other aromatic rings, brings about a relatively strong interaction between molecules. A compound having two or more carbazole rings disadvantageously undergoes an enhanced interaction between the molecules due to intermolecular association and hence has an elevated glass transition temperature. Meanwhile, a compound having one or less carbazole ring in the molecule has reduced energy of interaction between molecules and hence has a lowered glass transition temperature.

For the reasons described above, the following effects are presumed to be brought about: the organic compound of the invention represented by general formula (1) or (3) has high solubility in organic solvents; the composition containing this compound and a solvent has excellent storage stability; and the organic electroluminescent element produced using the composition has a long life and high efficiency and can be operated at a low voltage.

<Applications>

It is preferred that the organic compound of the invention should be used as a light-emitting material or a charge-transporting material (charge-transporting compound). It is also preferred that the organic compound should be used as a light-emitting material or a charge-transporting material in the luminescent layer of an organic electroluminescent element. It is especially preferred that the organic compound should be used as a charge-transporting material.

Since the organic compound of the invention has higher solubility in organic solvents than conventionally known pyrimidine compounds or 1,3,5-triazine compounds, it is preferred that a composition containing this compound and an organic solvent should be prepared and this composition be used as a composition for forming an organic layer by a wet film formation method. In particular, it is especially preferred to use the composition for producing an organic electroluminescent element by a wet film formation method and for producing a display device and a lighting device each including the element, because production processes can be simplified therewith.

<Composition Containing Organic Compound of the Invention>

The composition of the invention contains the organic compound of the invention and a solvent. Only one of the organic compounds of the invention described above may be contained in the composition of the invention, or two or more thereof may be contained in combination in the composition. Even when the composition of the invention contains the organic compound of the invention as a charge-transporting material, this composition can further contain a compound which has conventionally been used as a charge-transporting material.

<Solvent>

The solvent which can be contained in the composition of the invention preferably is a volatile liquid ingredient that is used in order to form an organic layer by a wet film formation method.

This solvent is not particularly limited so long as the organic compound of the invention, which is a solute, and ingredients used according to need, e.g., a charge-transporting material and a light-emitting material, dissolve therein satisfactorily. However, preferred solvents include the following.

Examples thereof include: alkanes such as n-decane, cyclohexane, ethylcyclohexane, decalin, and bicyclohexane; aromatic hydrocarbons such as toluene, xylene, mesitylene, cyclohexylbenzene, and tetralin; halogenated aromatic hydrocarbons such as chlorobenzene, dichlorobenzene, and trichlorobenzene; aromatic ethers such as 1,2-dimethoxybenzene, 1,3-dimethoxybenzene, anisole, phenetole, 2-methoxytoluene, 3-methoxytoluene, 4-methoxytoluene, 2,3-dimethylanisole, 2,4-dimethylaminsole, and diphenyl ether; aromatic esters such as phenyl acetate, phenyl propionate, methyl benzoate, ethyl benzoate, propyl benzoate, and n-butyl benzoate; alicyclic ketones such as cyclohexanone, cyclooctanone, and fenchone; alicyclic alcohols such as cyclohexanol and cyclooctanol; aliphatic ketones such as methyl ethyl ketone and dibutyl ketone; aliphatic alcohols such as butanol and hexanol; and aliphatic ethers such as tetrahydrofuran, 1,4-dioxane, ethylene glycol dimethyl ether, ethylene glycol diethyl ether, and propylene glycol 1-monomethyl ether acetate (PGMEA).

Preferred of these are aromatic hydrocarbons such as toluene, xylene, mesitylene, cyclohexylbenzene, and tetralin, from the standpoint that these compounds are low in the solubility of water therein and these compounds do not readily alter.

In organic devices including organic electroluminescent elements, a large number of materials which are considerably deteriorated by moisture (e.g., cathodes) are used. The presence of water in the composition is hence undesirable because there is a possibility that water remains in the dried film to reduce the characteristics of the elements.

Examples of methods for obtaining a composition having a reduced water content include to dehydrate the solvent beforehand by distillation or with a desiccant, etc., to use nitrogen gas sealing, and to use a solvent in which water has low solubility. Preferred of these is to use a solvent in which water has low solubility, because the phenomenon in which the solution film absorbs atmospheric moisture to blush in the step of wet-process film formation can be avoided. From this standpoint, it is preferred that the composition to which this embodiment is applied should contain a solvent in which the solubility of water therein at 25° C. is, for example, 1% by weight or less, preferably 0.1% by weight or less, in an amount of 10% by weight or larger based on the composition.

For diminishing the decrease in film formation stability due to solvent vaporization from the composition during wet-process film formation, it is effective to use a solvent having a boiling point of 100° C. or higher, preferably 150° C. or higher, more preferably 200° C. or higher, as the solvent of the composition. Meanwhile, for obtaining a more even film, it is necessary that the solvent should vaporize at a moderate rate from the liquid film just after film formation. For this purpose, it is effective to use a solvent having a boiling point which is usually 80° C. or higher, preferably 100° C. or higher, more preferably 120° C. or higher, and is usually lower than 270° C., preferably lower than 250° C., more preferably lower than 230° C.

A solvent which satisfies those requirements, i.e., the requirements concerning the property of dissolving solutes therein, vaporization rate, and water solubility therein, may be used alone. However, in the case where a solvent which satisfies all these requirements cannot be selected, two or more solvents can be used as a mixture thereof.

In the composition of the invention, the content of the solvent, based on 100% by weight the composition, is preferably 10% by weight or higher, more preferably 50% by weight or higher, especially preferably 80% by weight or higher, and is preferably 99.99% by weight or less, more preferably 99.8% by weight or less, especially preferably 99.5% by weight or less. In case where the content of the solvent is less than the lower limit, there is a possibility that the composition might have too high viscosity, resulting in a decrease in applicability in film formation. On the other hand, in case where the content of the solvent exceeds the upper limit, there is a tendency that the film obtained through solvent removal after film formation has a thickness which is far smaller than an expected thickness, resulting in difficulties in film formation.

<Light-Emitting Material>

It is preferred that the composition of the invention should further contain a light-emitting material.

The term "light-emitting material" means an ingredient which mainly emits light in the composition of the invention, and the light-emitting material corresponds to the dopant ingredient in organic EL devices, e.g., organic electroluminescent elements. In the case where usually 10-100%, preferably 20-100%, more preferably 50-100%, most preferably 80-100%, of the quantity of light (unit: $cd/m^2$) emitted from the composition is attributable to a component material thereof, this component is defined as a light-emitting material.

As the light-emitting material, any desired known material is applicable. Although fluorescent materials or phosphorescent materials can be used alone or as a mixture of two or more thereof, phosphorescent materials are preferred from the standpoint of internal quantum efficiency.

It is important to reduce the symmetry or stiffness of the molecule of the light-emitting material or to introduce an oleophilic substituent, e.g., an alkyl group, for the purpose of improving the solubility in solvents.

Examples of fluorescent dyes which give blue luminescence include perylene, pyrene, anthracene, coumarin, p-bis (2-phenylethenyl)benzene, and derivatives thereof. Examples of green fluorescent dyes include quinacridone derivatives and coumarin derivatives. Examples of yellow fluorescent dyes include rubrene and perimidone derivatives. Examples of red fluorescent dyes include DCM compounds, benzopyran derivatives, rhodamine derivatives, benzothioxanthene derivatives, and azabenzothioxanthene.

Examples of the phosphorescent materials include organometallic complexes which contain the atoms of metals selected from Groups 7 to 11 of the periodic table.

Preferred examples of the metal atoms in the phosphorescent organometallic complexes which contain the atoms of metals selected from Groups 7 to 11 of the periodic table include ruthenium, rhodium, palladium, silver, rhenium, osmium, iridium, platinum, and gold. Preferred examples of these organometallic complexes include compounds represented by the following formula (II) or formula (III).

$$ML_{(q-j)}L'_j \qquad (II)$$

(In formula (II), M represents a metal atom, and q represents the valence of the metal atom. L and L' each represent a bidentate, and j represents 0, 1, or 2.)

[Ka 21]

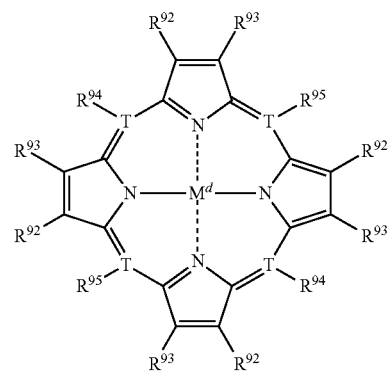

(III)

(In formula (III), $M^d$ represents a metal atom, and T represents a carbon atom or a nitrogen atom. $R^{92}$ to $R^{95}$ each independently represent a substituent. However, when T is a nitrogen atom, $R^{94}$ and $R^{95}$ are absent.)

First, the compounds represented by formula (II) are explained.

In formula (II), M represents any desired metal atom. Preferred examples thereof include the metal atoms enumerated above as examples of the metal atoms selected from Groups 7 to 11 of the periodic table.

The bidentates L and L' in formula (II) represent ligands respectively having the following partial structures.

[Ka 22]

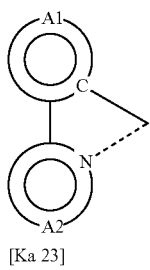

L

[Ka 23]

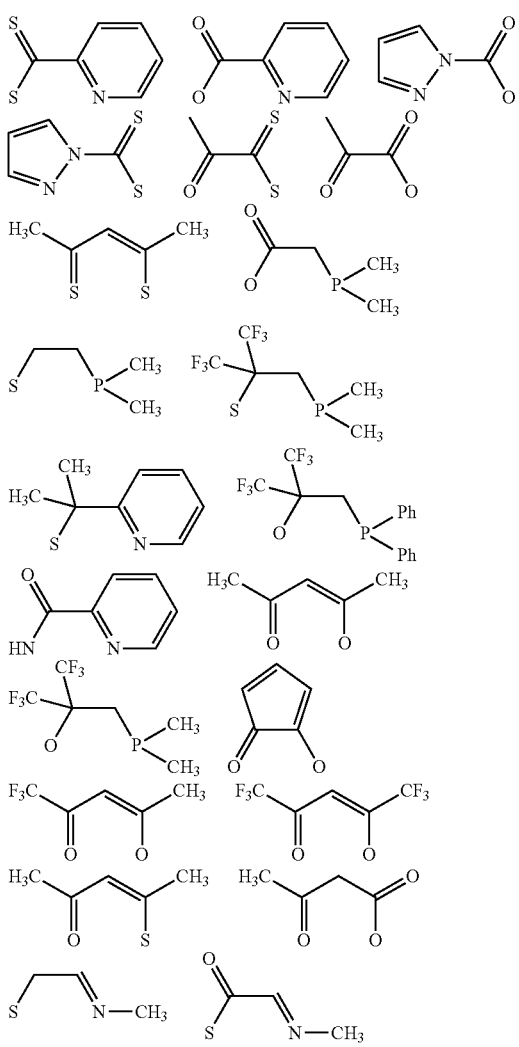

L'

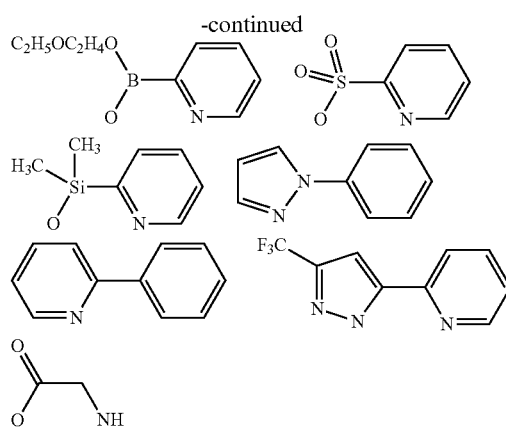

Especially preferred examples of the L' include the following, from the standpoint of the stability of the complex.

[Ka 24]

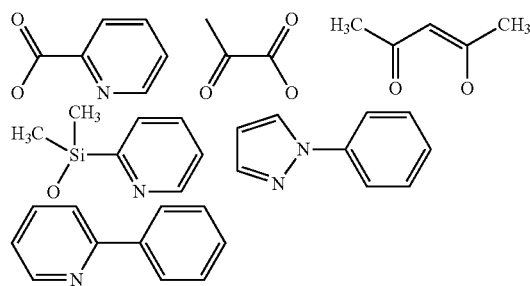

In the partial structure of the L and L', ring A1 represents an aromatic hydrocarbon group or an aromatic heterocyclic group, and these groups may have a substituent. Ring A2 represents a nitrogen-containing aromatic heterocyclic group, and this group may have a substituent.

In the case where rings A1 and A2 have substituents, preferred examples of the substituents include: halogen atoms such as fluorine atom; alkyl groups such as methyl and ethyl; alkenyl groups such as vinyl; alkoxycarbonyl groups such as methoxycarbonyl and ethoxycarbonyl; alkoxy groups such as methoxy and ethoxy; aryloxy groups such as phenoxy and benzyloxy; dialkylamino groups such as dimethylamino and diethylamino; diarylamino groups such as diphenylamino; carbazolyl; acyl groups such as acetyl; haloalkyl groups such as trifluoromethyl; cyano; and aromatic hydrocarbon groups such as phenyl, naphthyl, and phenanthyl.

More preferred examples of the compounds represented by formula (II) include compounds represented by the following formulae (IIa), (IIb), and (IIc).

[Ka 25]

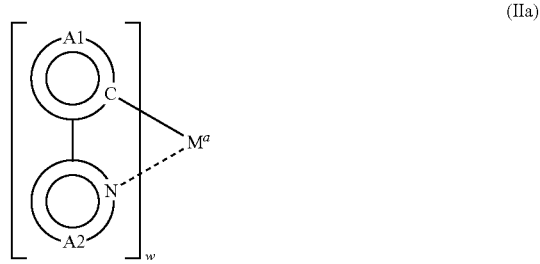

(IIa)

(In formula (IIa), $M^a$ represents the same metal atom as the M contained in formula (II), and w represents the valence of the metal atom. Ring A1 represents an aromatic hydrocarbon group which may have a substituent, and ring A2 represents a nitrogen-containing aromatic heterocyclic group which may have a substituent.)

[Ka 26]

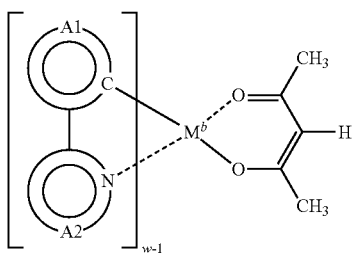

(IIb)

(In formula (IIb), $M^b$ represents the same metal atom as the M contained in formula (II), and w represents the valence of the metal atom. Ring A1 represents an aromatic hydrocarbon group which may have a substituent or an aromatic heterocyclic group which may have a substituent, and ring A2 represents a nitrogen-containing aromatic heterocyclic group which may have a substituent.)

[Ka 27]

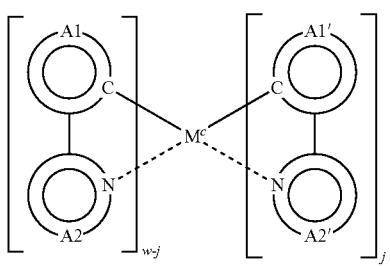

(IIc)

(In formula (IIc), $M^c$ represents the same metal atom as the M contained in formula (II), and w represents the valence of the metal atom. Symbol j represents 0, 1, or 2. Ring A1 and ring A1' each independently represent an aromatic hydrocarbon group which may have a substituent or an aromatic heterocyclic group which may have a substituent. Furthermore, ring A2 and ring A2' each independently represent a nitrogen-containing aromatic heterocyclic group which may have a substituent.)

Preferred examples of the groups represented by ring A1 and ring A2 in formulae (IIa), (IIb), and (IIc) include phenyl, biphenyl, naphthyl, anthryl, thienyl, furyl, benzothienyl, benzofuryl, pyridyl, quinolyl, isoquinolyl, and carbazolyl.

Preferred examples of the groups represented by ring A2 and ring AT include pyridyl, pyrimidyl, pyrazyl, triazyl, benzothiazole, benzoxazole, benzimidazole, quinolyl, isoquinolyl, quinoxalyl, and phenanthridyl.

Furthermore, examples of substituents which may be possessed by the compounds represented by formulae (IIa), (III)), and (IIc) include: halogen atoms such as fluorine atom; alkyl groups such as methyl and ethyl; alkenyl groups such as vinyl; alkoxycarbonyl groups such as methoxycarbonyl and ethoxycarbonyl; alkoxy groups such as methoxy and ethoxy; aryloxy groups such as phenoxy and benzyloxy; dialkylamino groups such as dimethylamino and diethylamino; diarylamino groups such as diphenylamino; carbazolyl; acyl groups such as acetyl; haloalkyl groups such as trifluoromethyl; and cyano.

When the substituents are alkyl groups, the number of carbon atoms of each group is usually 1-6. When the substituents are alkenyl groups, the number of carbon atoms of each group is usually 2-6. When the substituents are alkoxycarbonyl groups, the number of carbon atoms of each group is usually 2-6. When the substituents are alkoxy groups, the number of carbon atoms of each group is usually 1-6. When the substituents are aryloxy groups, the number of carbon atoms of each group is usually 6-14. When the substituents are dialkylamino groups, the number of carbon atoms of each group is usually 2-24. When the substituents are diarylamino groups, the number of carbon atoms of each group is usually 12-28. When the substituents are acyl groups, the number of carbon atoms of each group is usually 1-14. When the substituents are haloalkyl groups, the number of carbon atoms of each group is usually 1-12.

These substituents may be linked to each other to form a ring. An example is the case in which a substituent possessed by ring A1 is bonded to a substituent possessed by ring A2 or a substituent possessed by ring A1' is bonded to a substituent possessed by ring AT, thereby forming one fused ring. Examples of such a fused ring include a 7,8-benzoquinoline group.

More preferred examples of the substituents of ring A1, ring A1', ring A2, and ring A2', among those substituents, include alkyl groups, alkoxy groups, aromatic hydrocarbon groups, cyano, halogen atoms, haloalkyl groups, diarylamino groups, and carbazolyl.

Preferred examples of the $M^a$, $M^b$, and $M^c$ in formulae (IIa), (IIb), and (IIc) include ruthenium, rhodium, palladium, silver, rhenium, osmium, iridium, platinum, or gold.

Specific examples of the organometallic complexes represented by formula (II), (IIa), (IIb), or (IIc) are shown below. However, the organometallic complexes should not be construed as being limited to the following compounds (in the following, Ph represents phenyl).

[Ka 28]

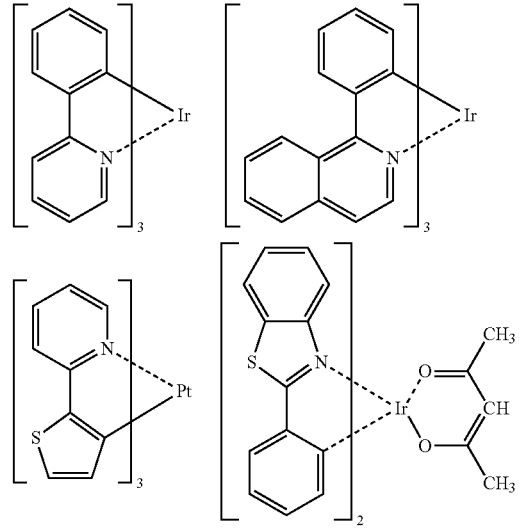

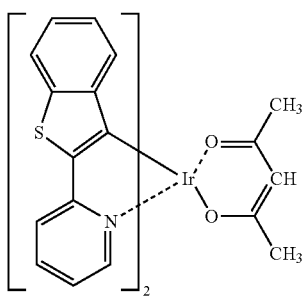
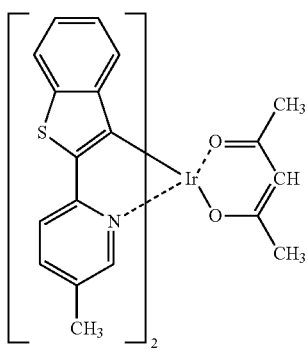
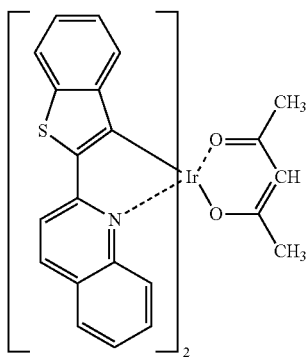
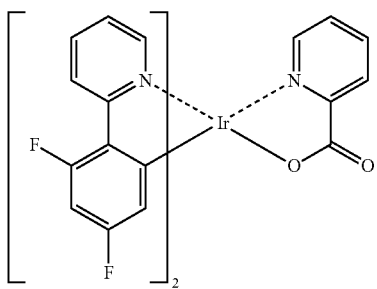
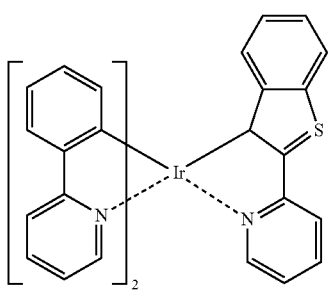
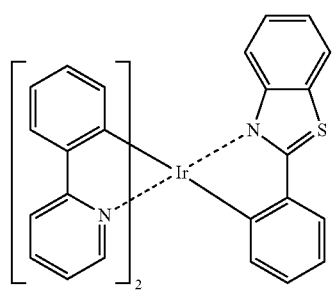
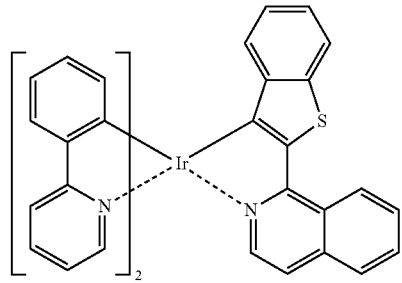
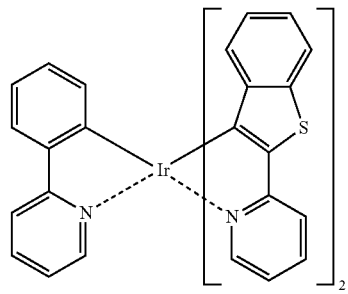
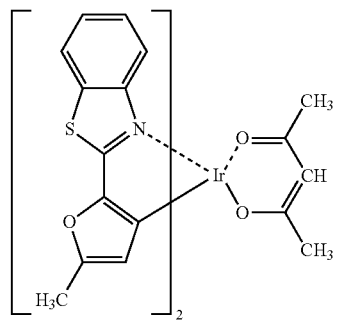
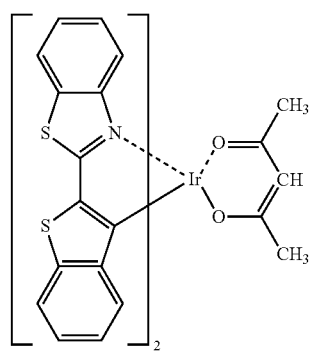

[Ka 29]
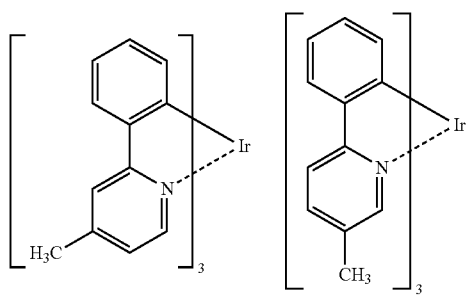
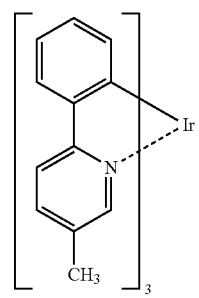
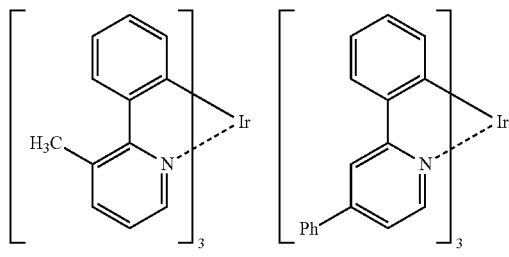
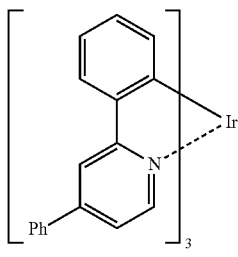
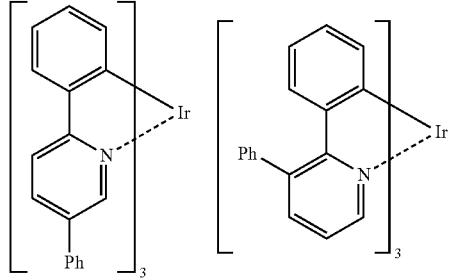
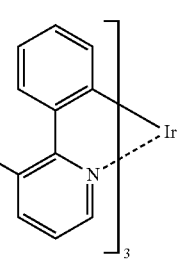
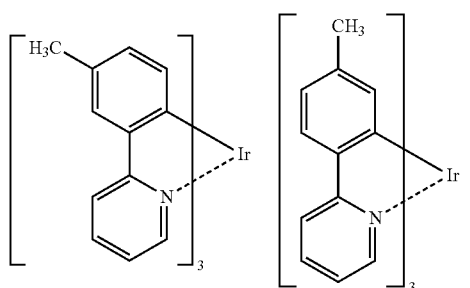
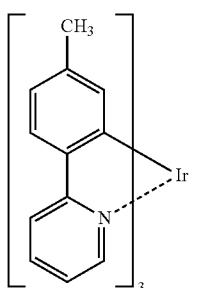
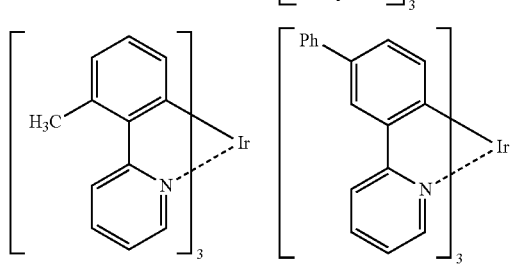
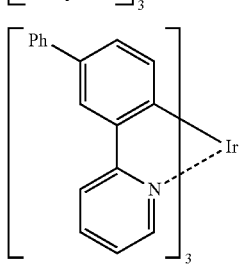
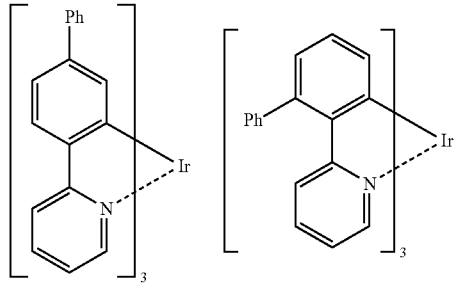
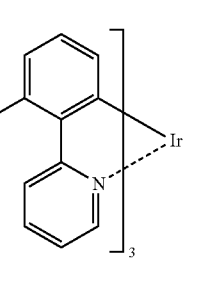
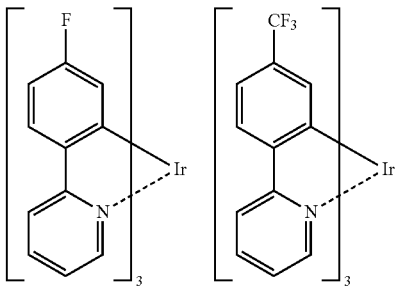
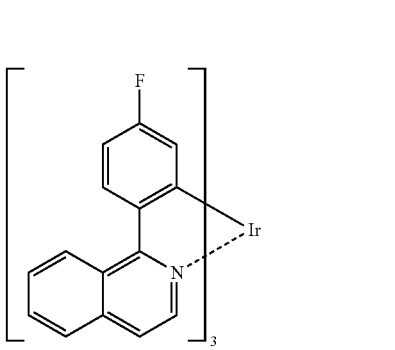
[Ka 30]
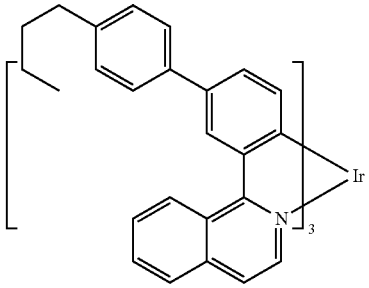
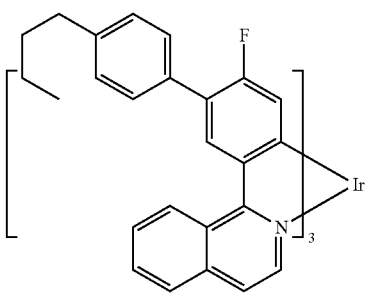
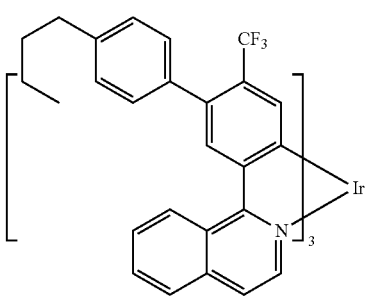

139
-continued
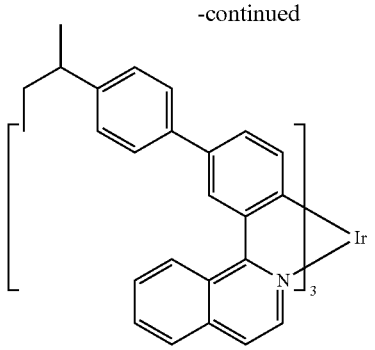
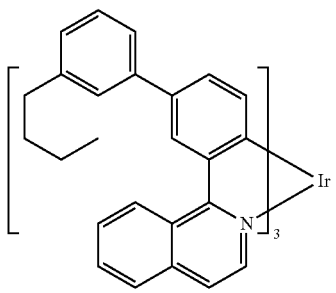
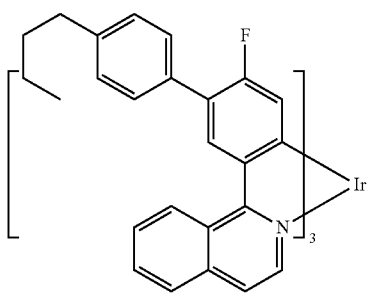
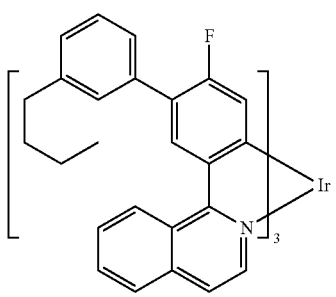
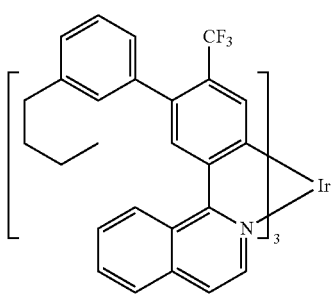
140
-continued
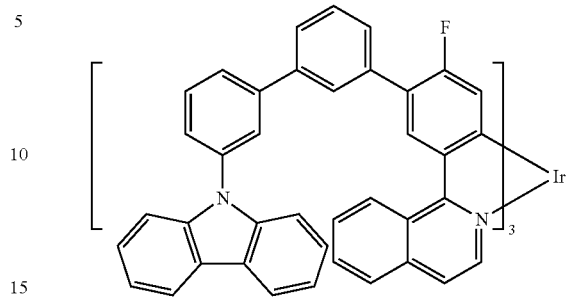
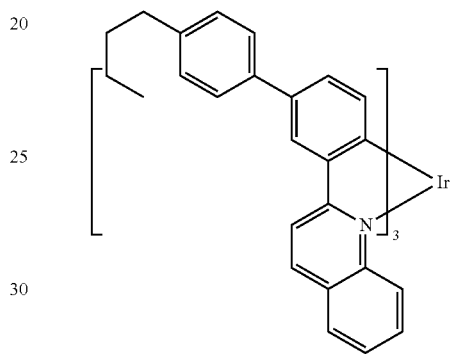
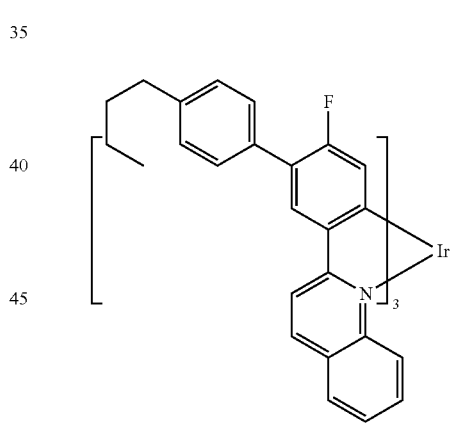
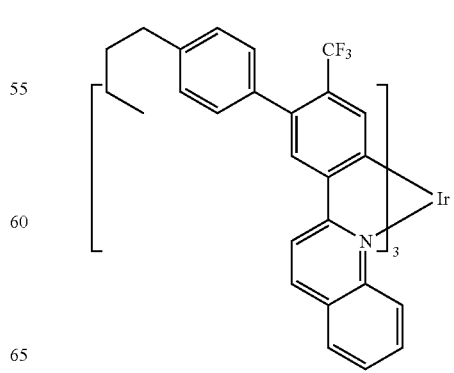

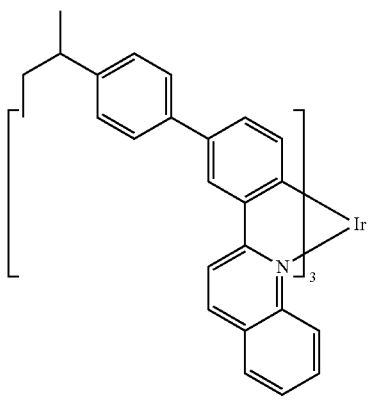
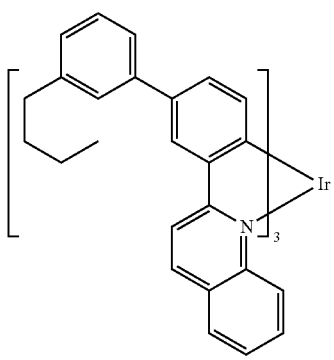
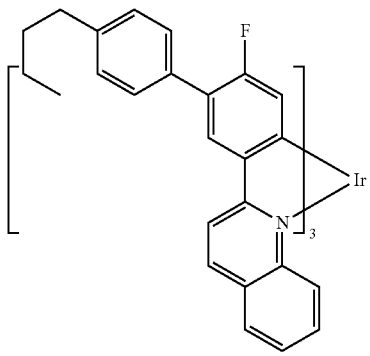
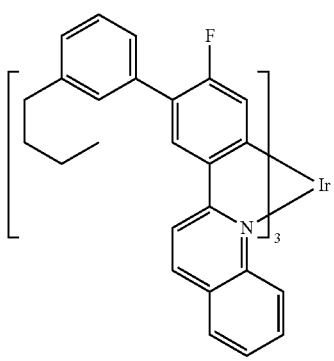
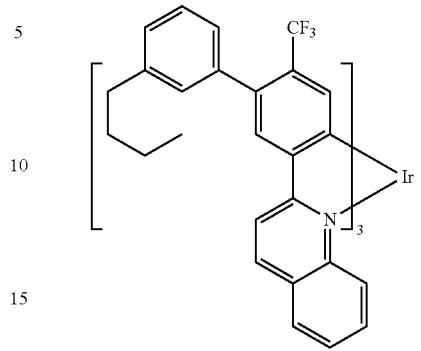
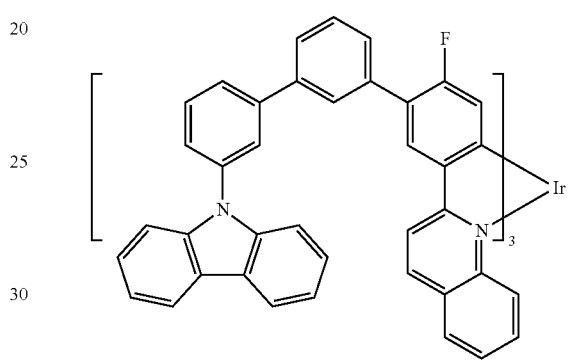
[Ka 31]
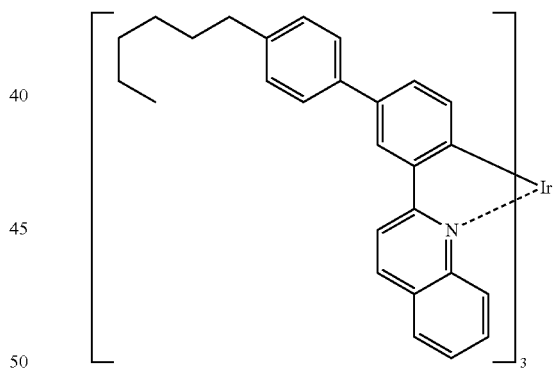
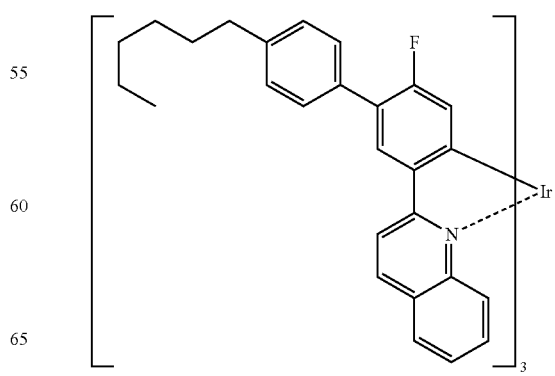

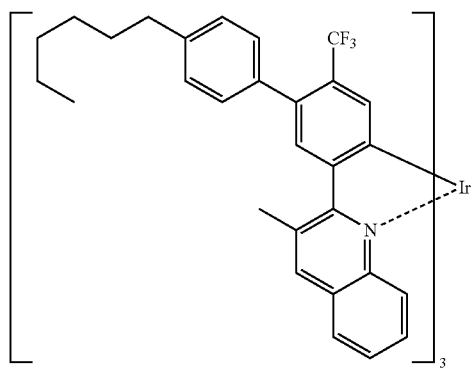
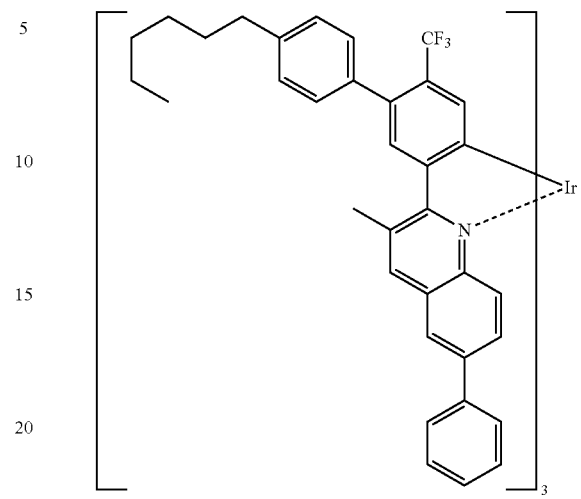
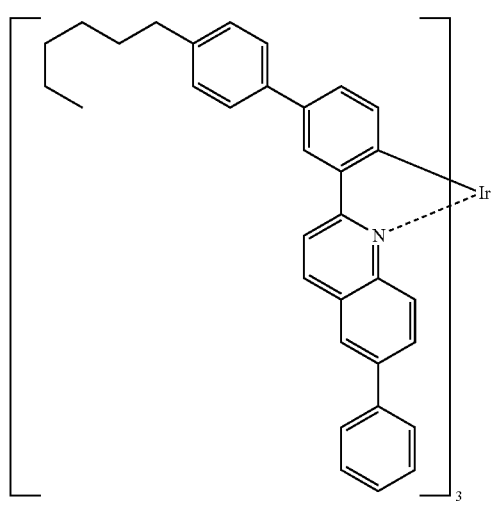
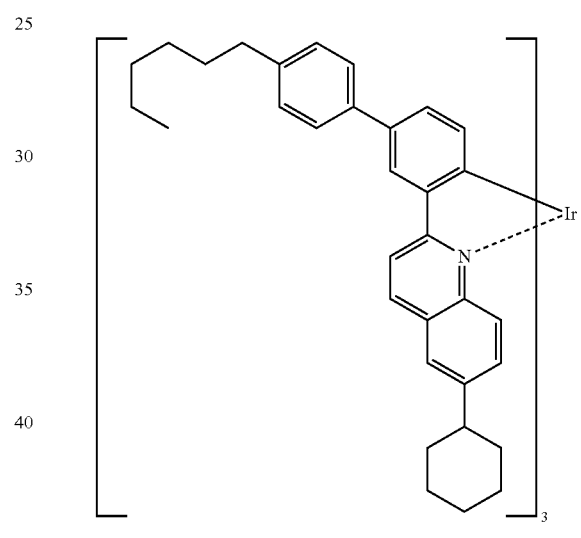
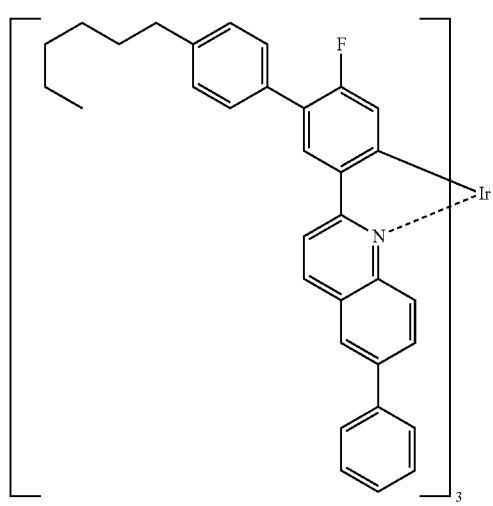
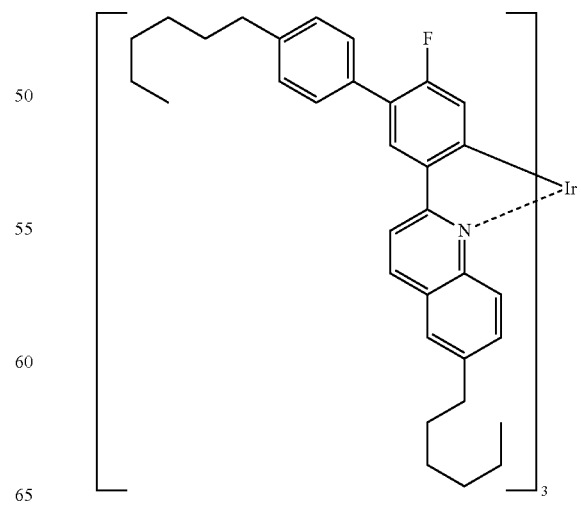

145
-continued
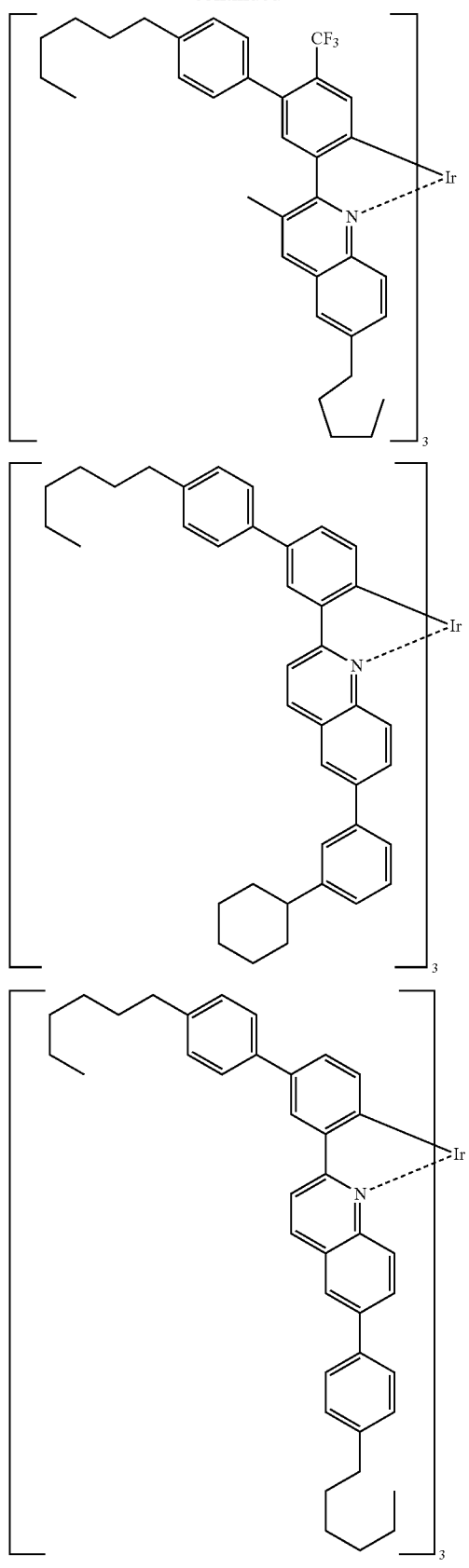
146
-continued
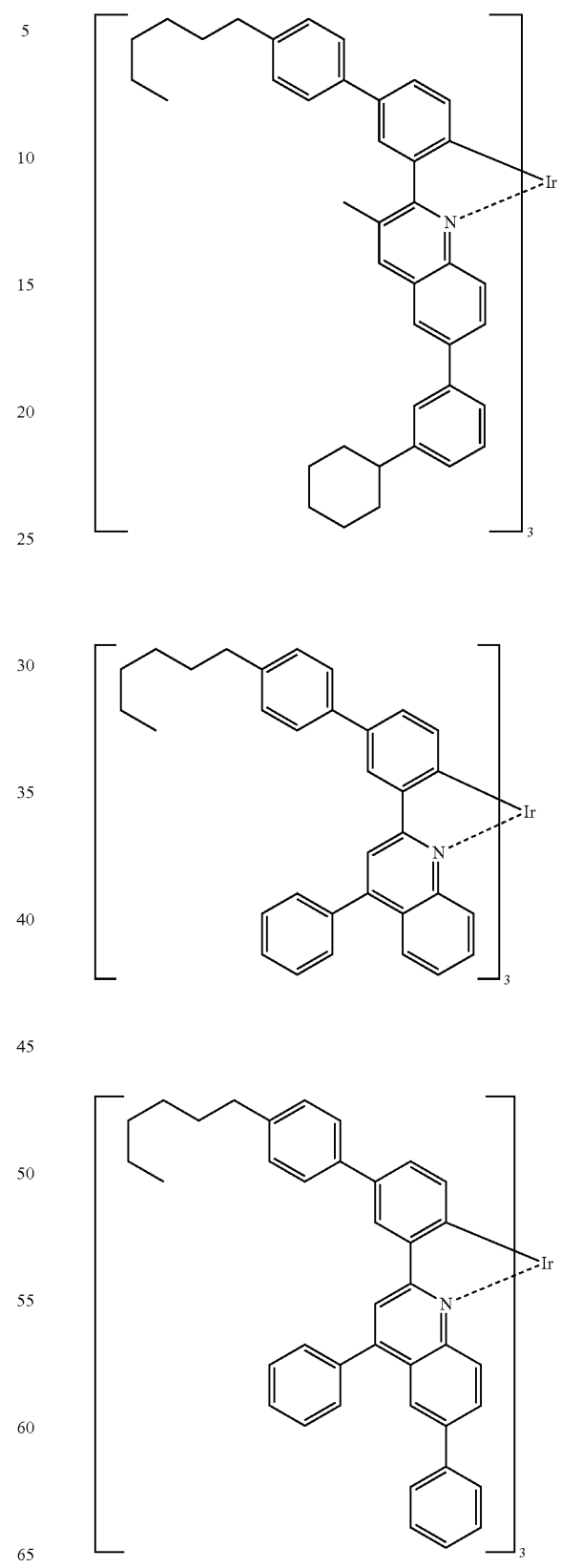

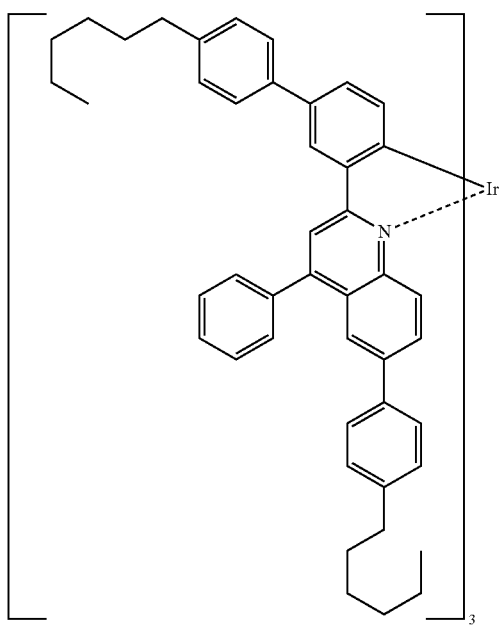
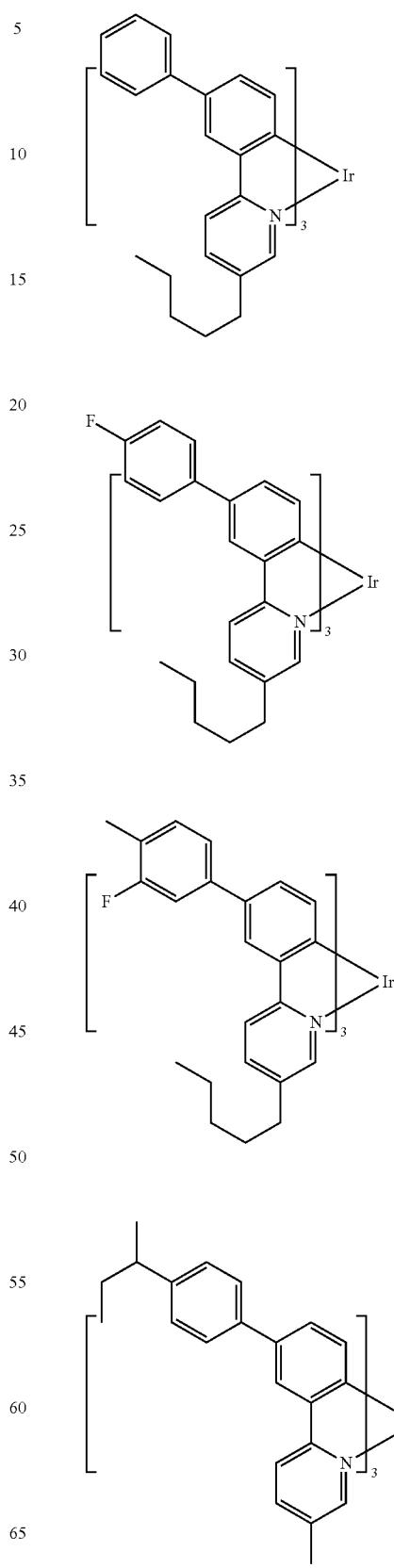
[Ka 32]

149
-continued
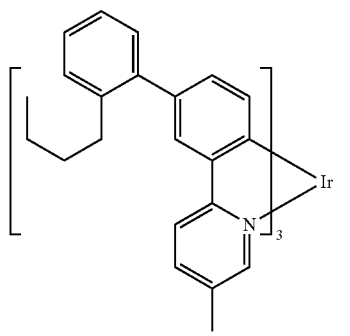
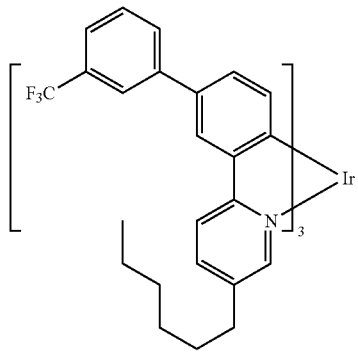
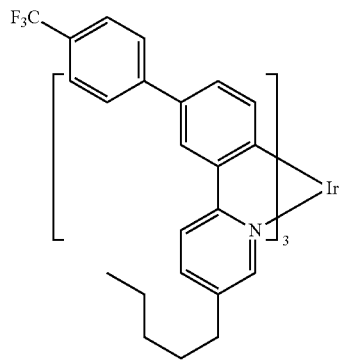
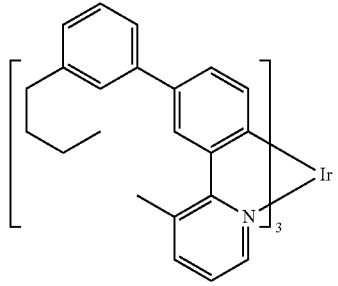
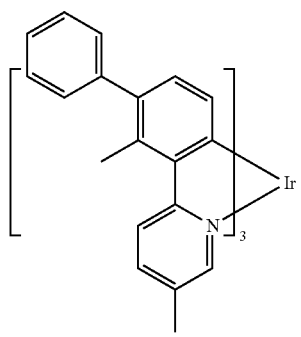
150
-continued
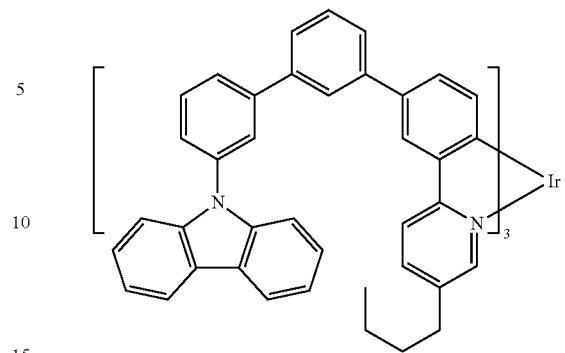
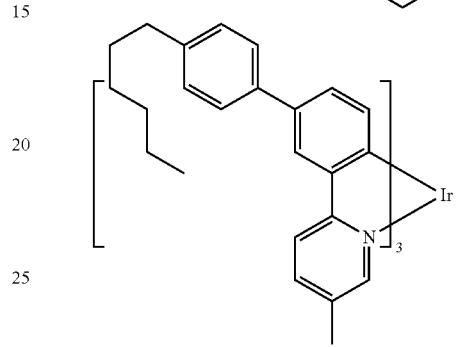
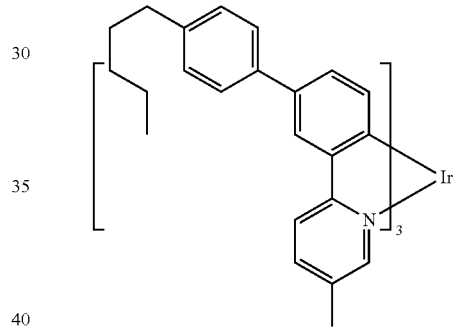
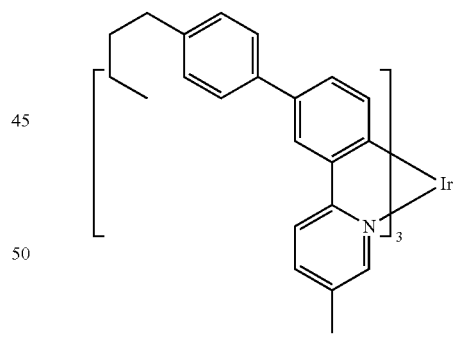
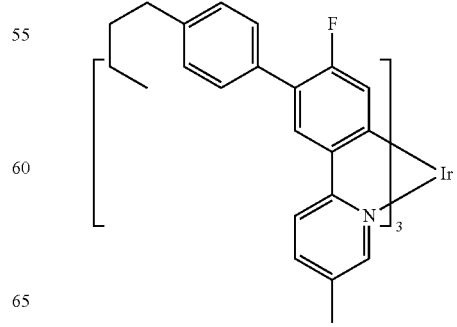

151
-continued
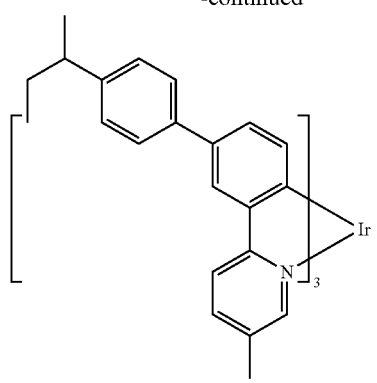
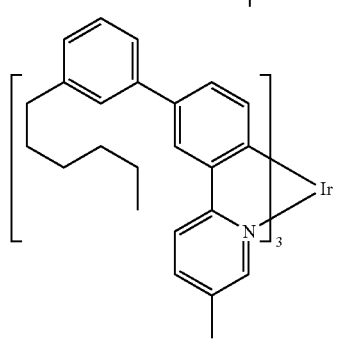
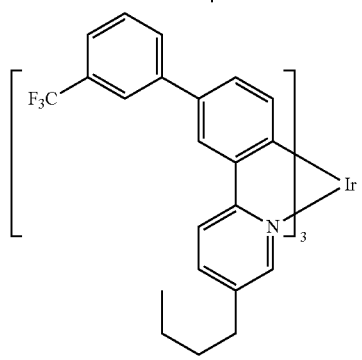
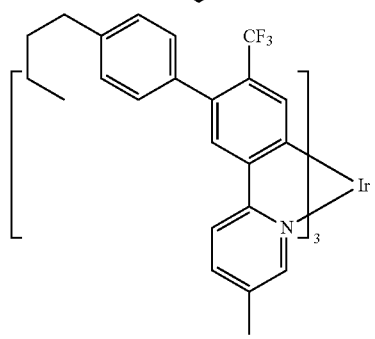
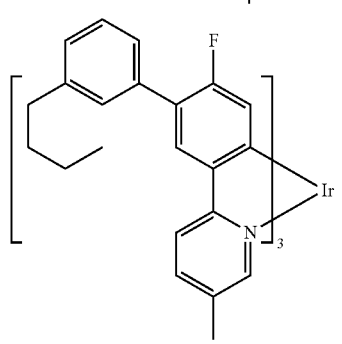
152
-continued
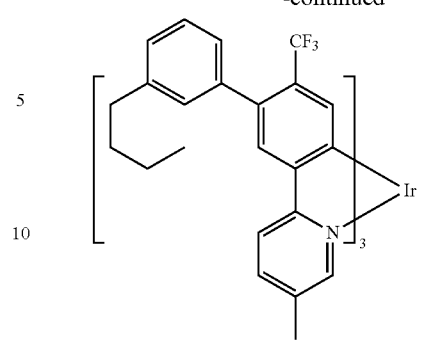
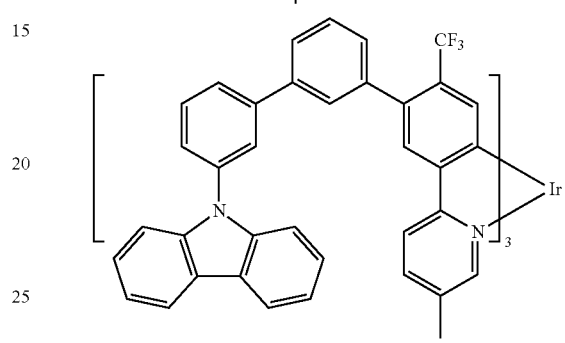
[Ka 33]
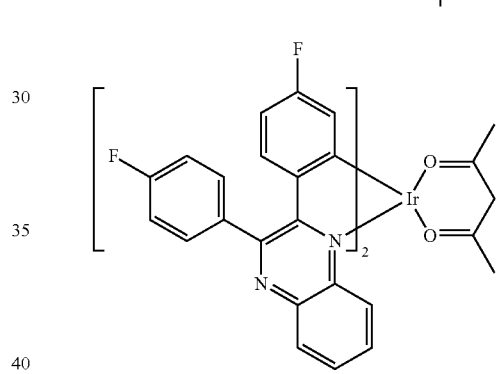
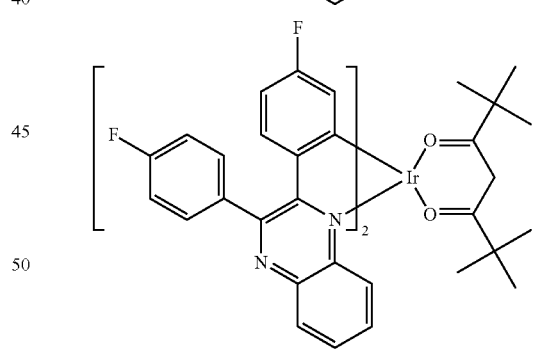
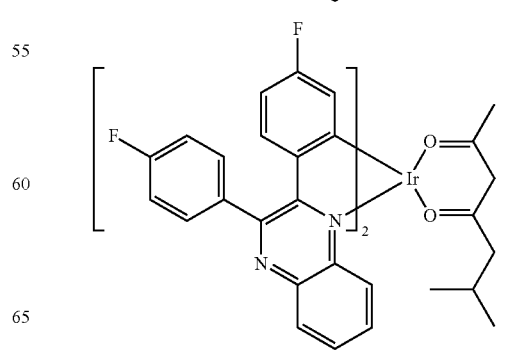

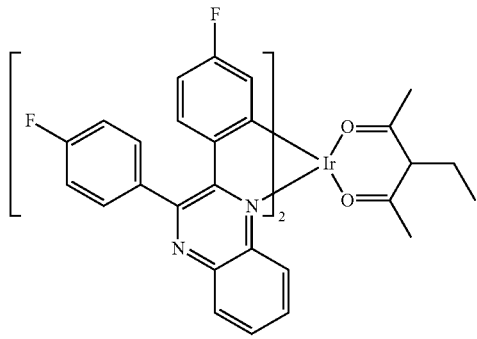

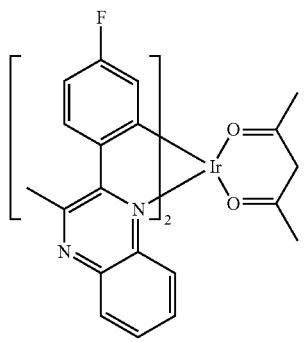

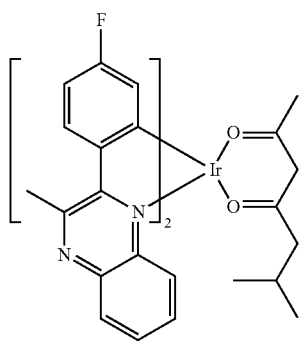

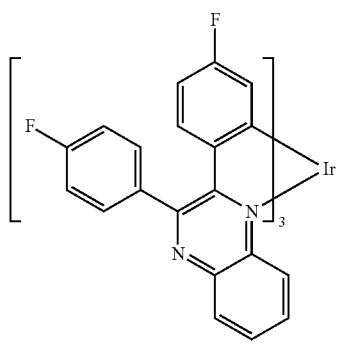

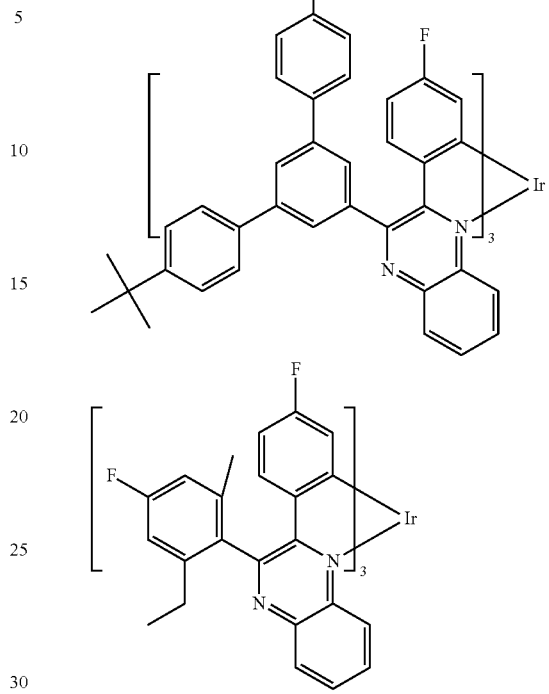

Especially preferred of the organometallic complexes represented by formulae (II), (IIa), (IIb), and (IIc) are compounds which have, as the ligand L and/or L', a 2-arylpyridine-based ligand, i.e., any of a 2-arylpyridine, a 2-arylpyridine having any desired substituent, and a 2-arylpyridie to which any desired group has been fused.

Next, the compounds represented by formula (III) are explained.

In formula (III), $M^d$ represents a metal atom. Examples thereof include the metal atoms enumerated above as examples of the metal atom selected from Groups 7 to 11 of the periodic table. Preferred examples, among these, include ruthenium, rhodium, palladium, silver, rhenium, osmium, iridium, platinum, or gold. Especially preferred examples thereof include divalent metal atoms such as platinum and palladium.

In formula (III), $R^{92}$ and $R^{93}$ each independently represent a hydrogen atom, halogen atom, alkyl group, aralkyl group, alkenyl group, cyano group, amino group, acyl group, alkoxycarbonyl group, carboxyl group, alkoxy group, alkylamino group, aralkylamino group, haloalkyl group, hydroxy group, aryloxy group, aromatic hydrocarbon group, or aromatic heterocyclic group.

When T is a carbon atom, $R^{94}$ and $R^{95}$ each independently represent a substituent, examples of which are the same as the examples of $R^{92}$ and $R^{93}$. As stated above, $R^{94}$ and $R^{95}$ are absent when T is a nitrogen atom.

$R^{92}$ to $R^{95}$ may further have substituents. In this case, the substituents which may be further possessed are not particularly limited, and can be any desired groups.

Furthermore, $R^{92}$ to $R^{95}$ may be bonded to each other to form a ring, and this ring may further have any desired substituent.

Specific examples (T-1 and T-10 to T-15) of the organometallic complexes represented by formula (III) are shown below. However, the organometallic complexes should not be construed as being limited to the following compounds shown as examples. In the following, Me represents methyl and Et represents ethyl.

[Ka 34]

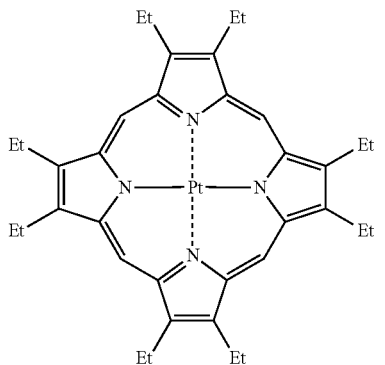
(T-1)

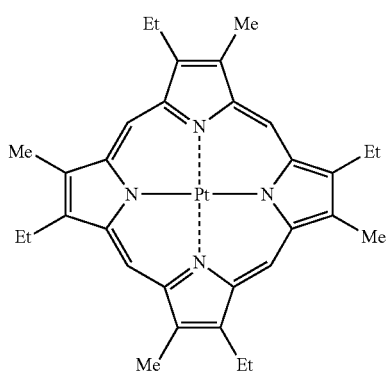
(T-10)

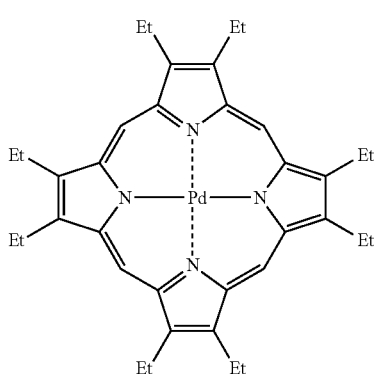
(T-11)

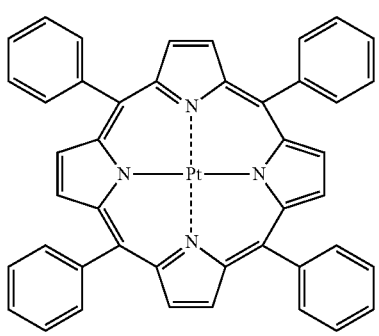
(T-12)

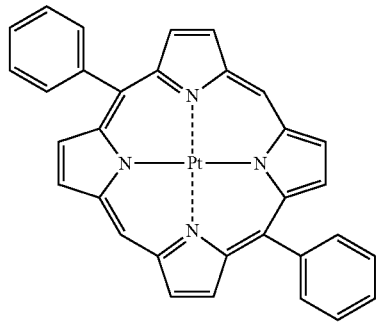
(T-13)

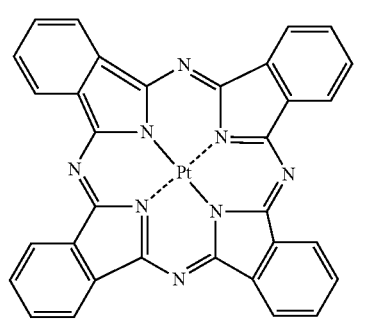
(T-14)

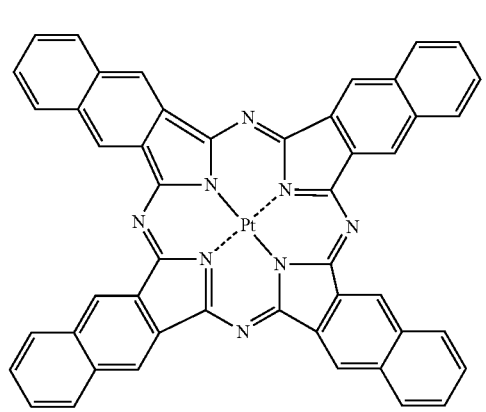
(T-15)

<Charge-Transporting Materials>

Although it is preferred that the composition of the invention should contain the organic compound of the invention as a charge-transporting material, the composition may further contain other charge-transporting materials. Preferred examples of charge-transporting materials usable in combination with the organic compound are shown below. However, the invention is not limited to the following examples.

The charge-transporting materials usable in combination with the organic compound include compounds having hole-transporting ability (hereinafter referred to as "hole-transporting materials") and compounds having electron-transporting ability (hereinafter referred to as "electron-transporting materials"). It is preferred that the composition of the invention should contain a charge-transporting material and a hole-transporting material in a weight ratio which is usually 0:100 or less, preferably 2:98 or less, and is usually 100:0 or higher, preferably 98:2 or higher. Such ranges are preferred because an improved balance between the movement of holes and the movement of electrons is attained and an element having a prolonged working life and a high current efficiency is obtained. Incidentally, the organic compound of the invention belongs to the electron-transporting materials.

(Hole-Transporting Material)
Examples of the hole-transporting material include compounds having a triarylamine or carbazole as a partial structure. Specific examples of the hole-transporting material are shown below. However, the hole-transporting material is not limited to the following examples.
[Ka 35]
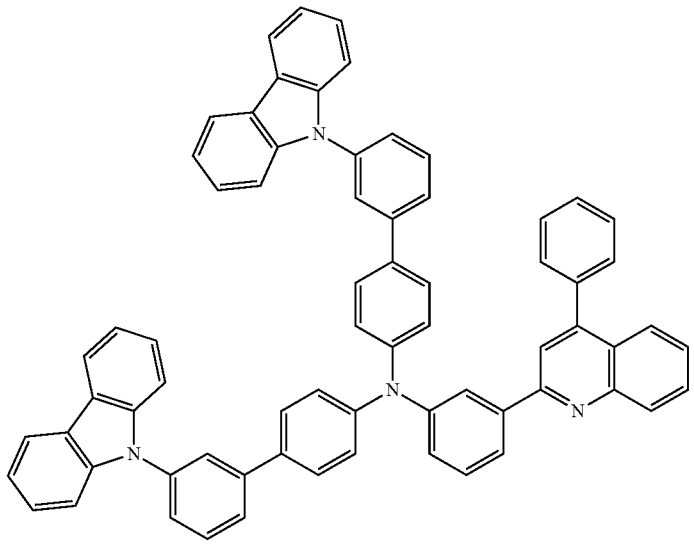
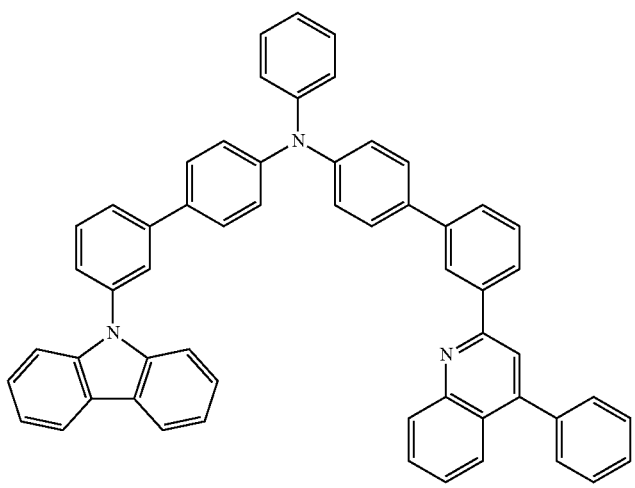

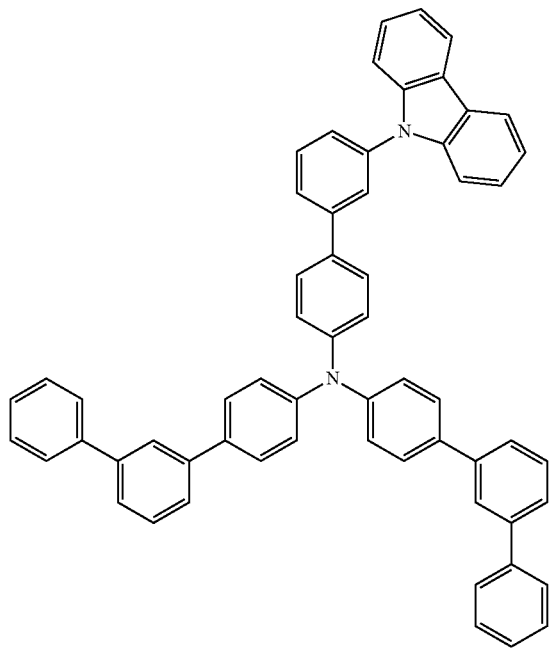
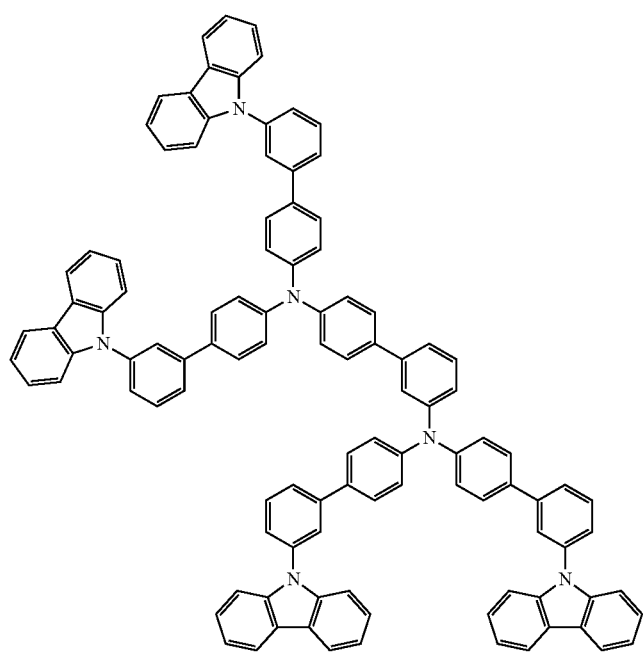

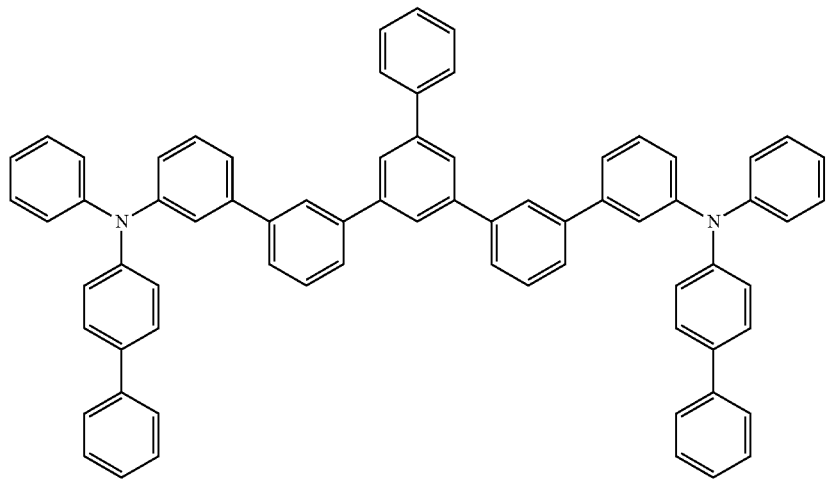
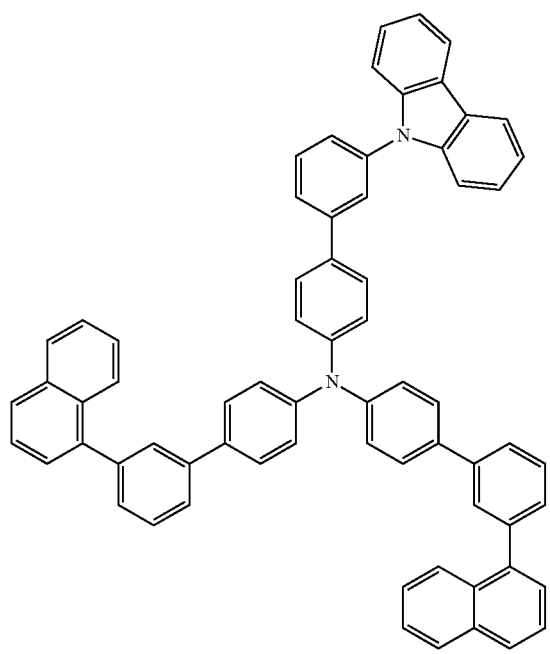

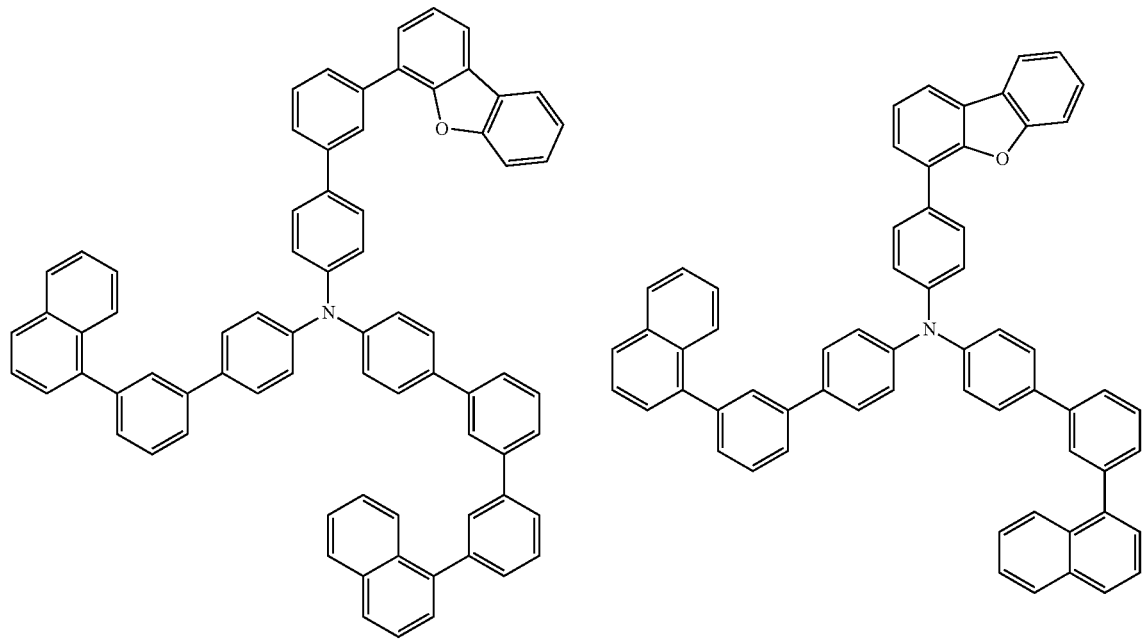
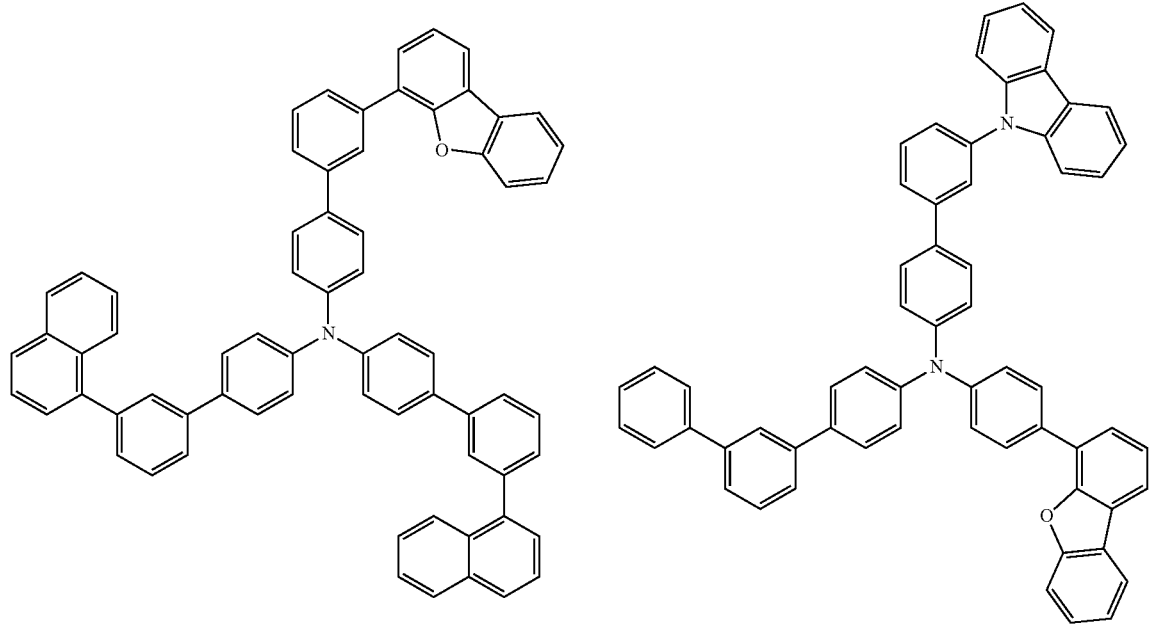

-continued
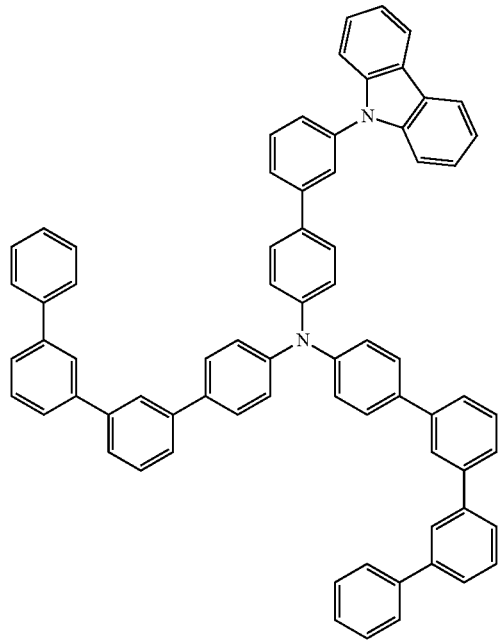
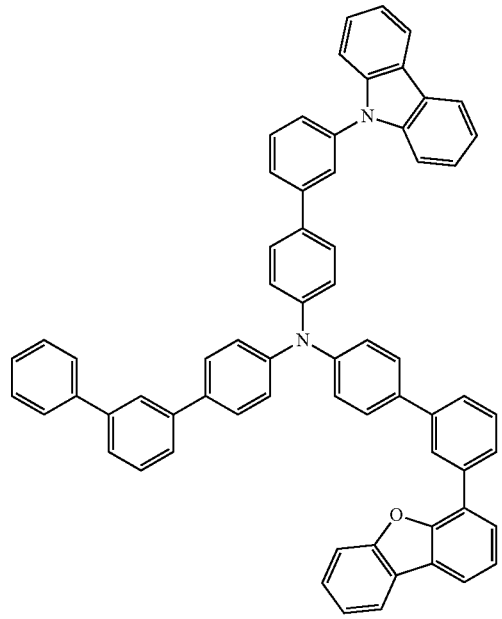
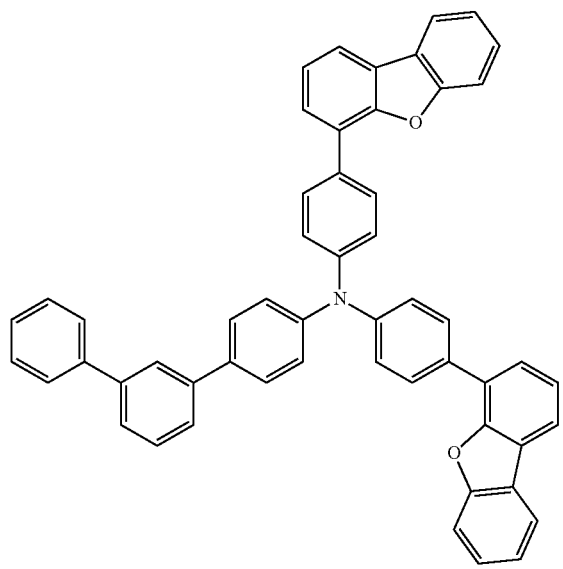
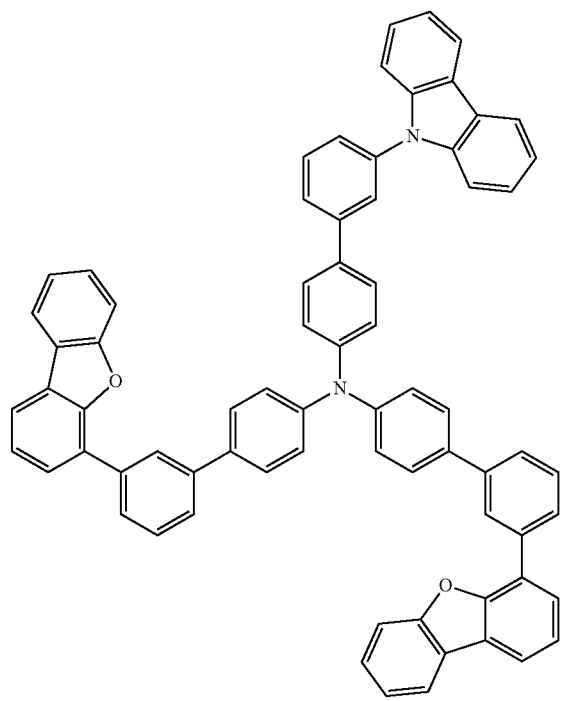
[Ka 36]

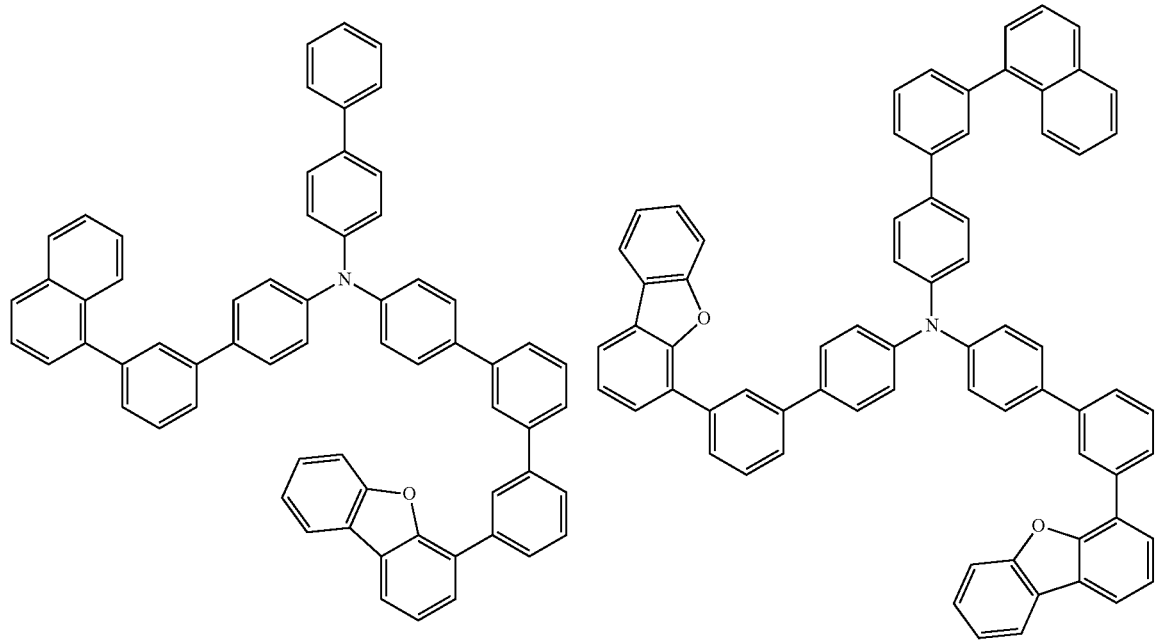
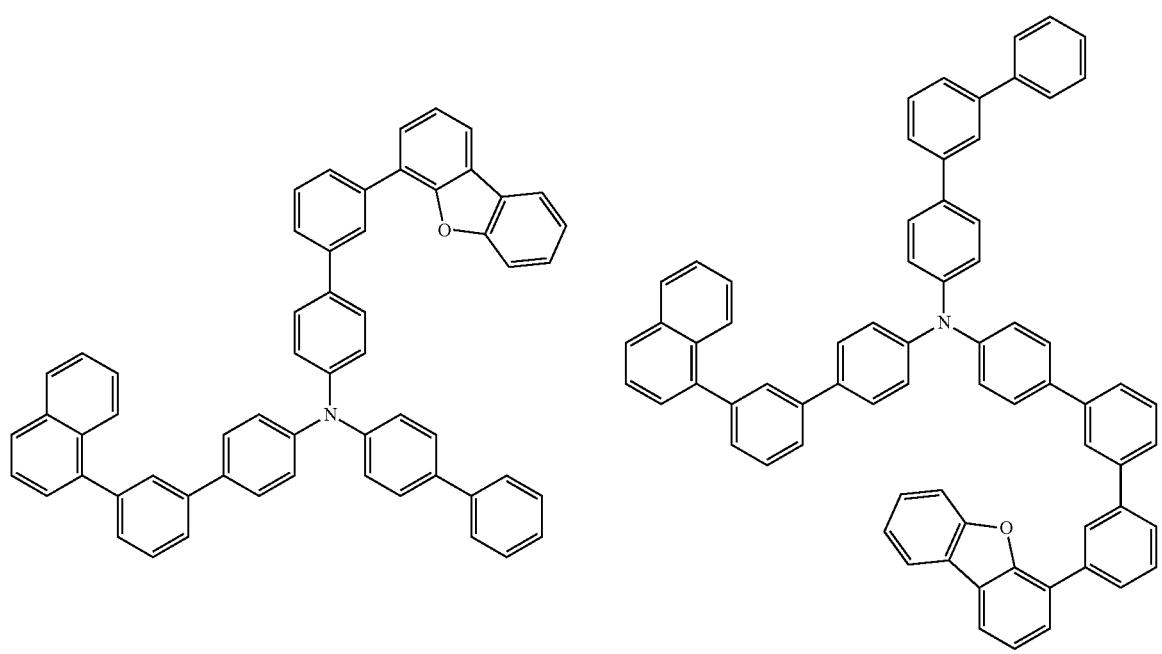

-continued

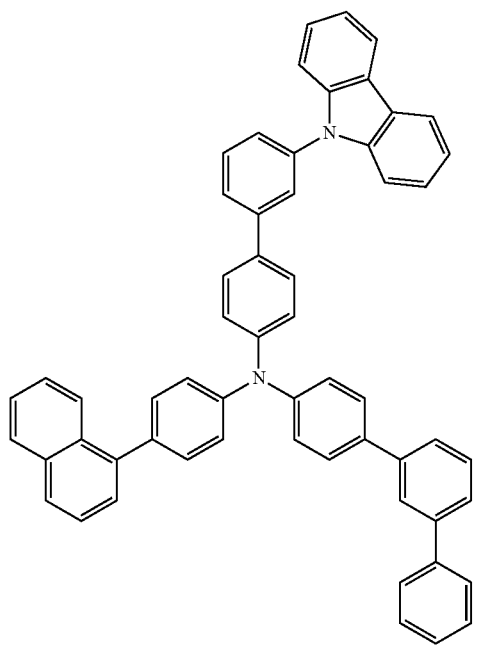
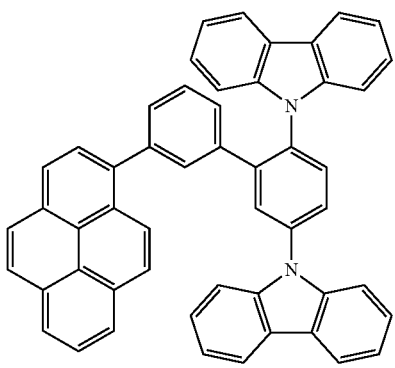
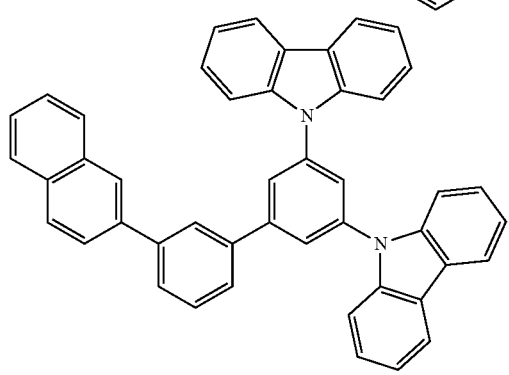
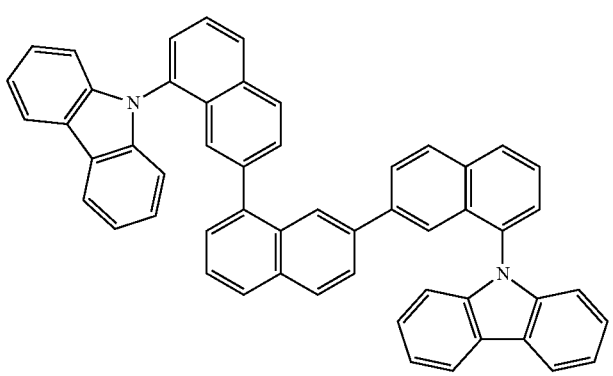
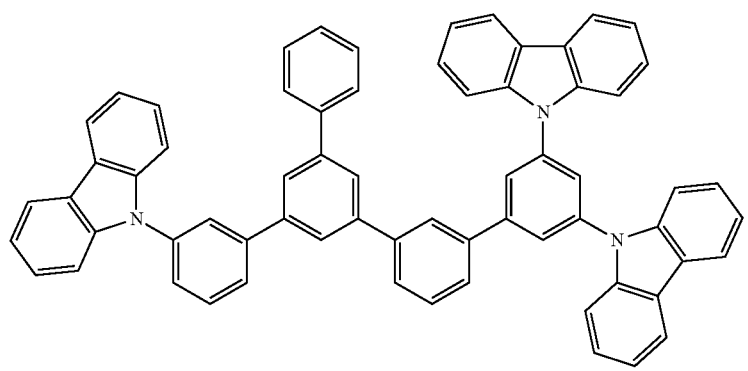

(Electron-Transporting Material)

Examples of the electron-transporting material include compounds having an aromatic heterocycle as a partial structure. Examples of the aromatic heterocycle include the 1,3,5-triazine ring according to the invention, and further include a pyridine ring, quinoline ring, quinoxaline ring, and pyrimidine ring.

Specific examples of the electron-transporting material which may be contained in the composition of the invention are shown below. However, the invention is not limited to the following examples.

<Compounds containing pyridine ring>
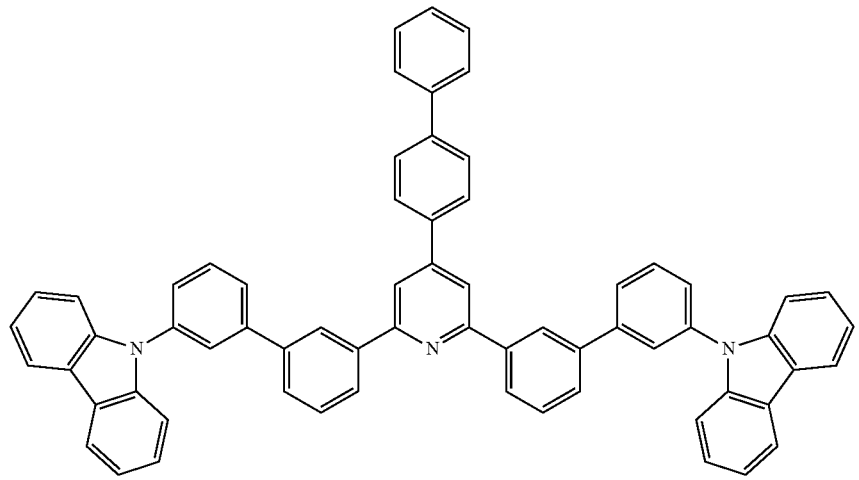
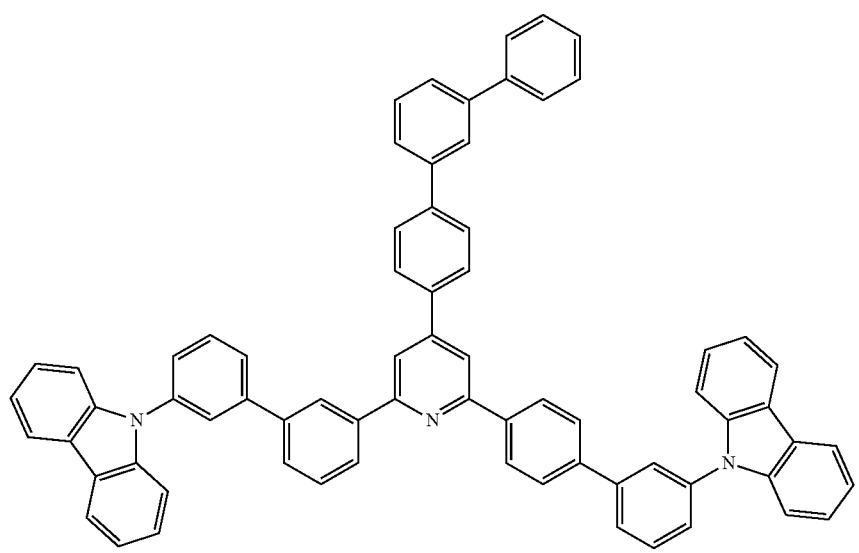
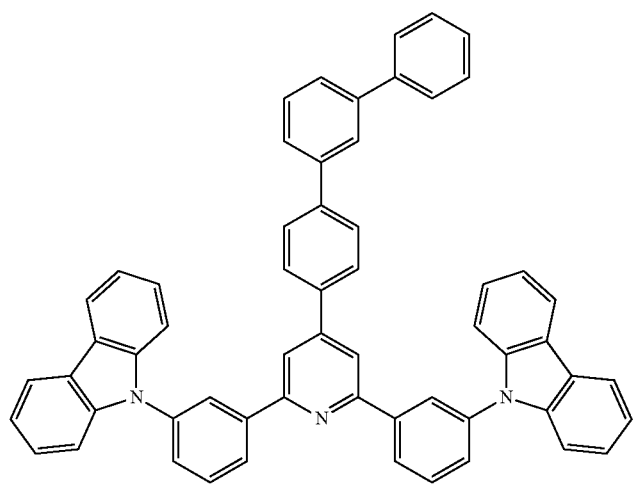

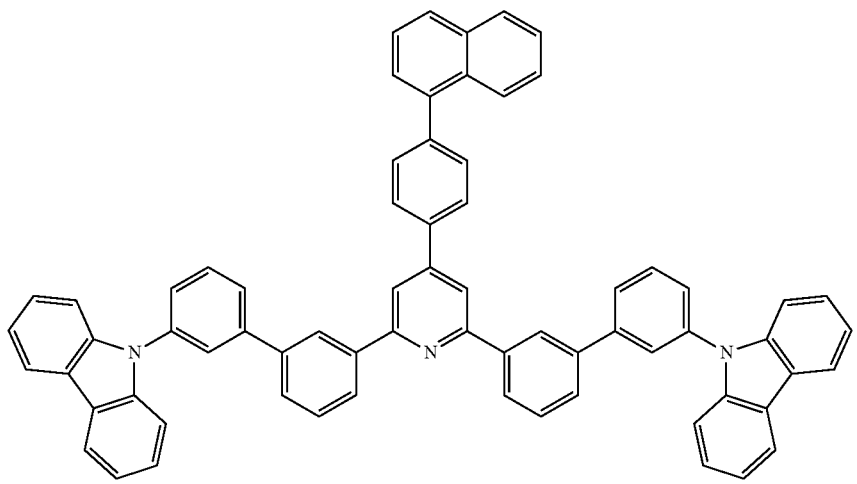
<Compounds containing quinoline ring or quinoxaline ring>
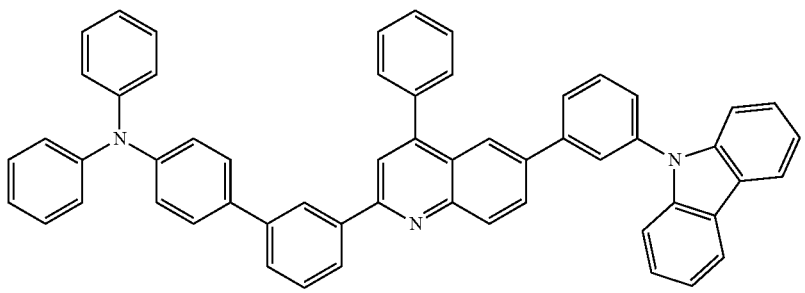
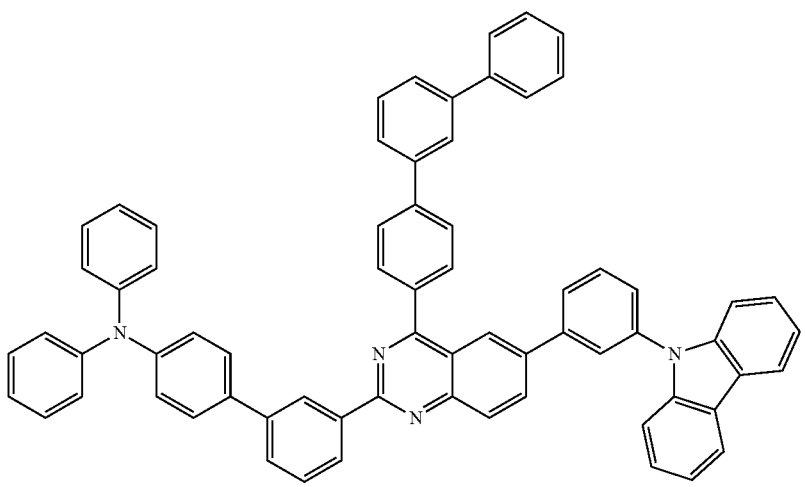

-continued
<Compounds containing pyrimidine ring>
[Ka 39]
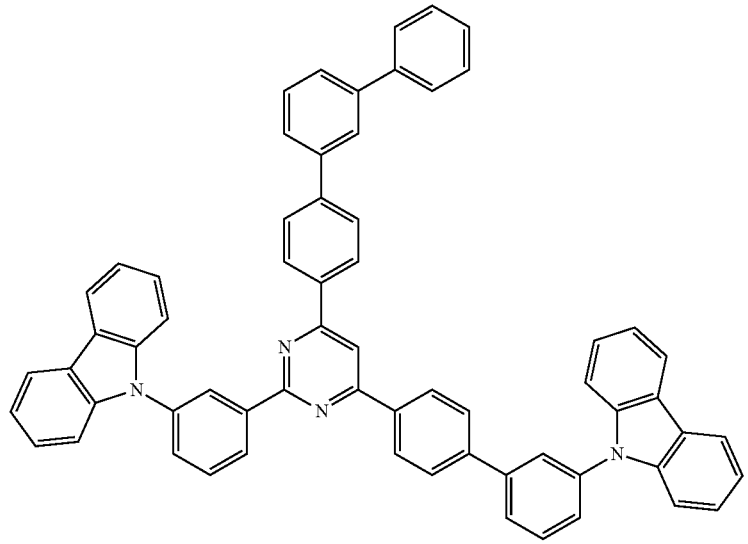
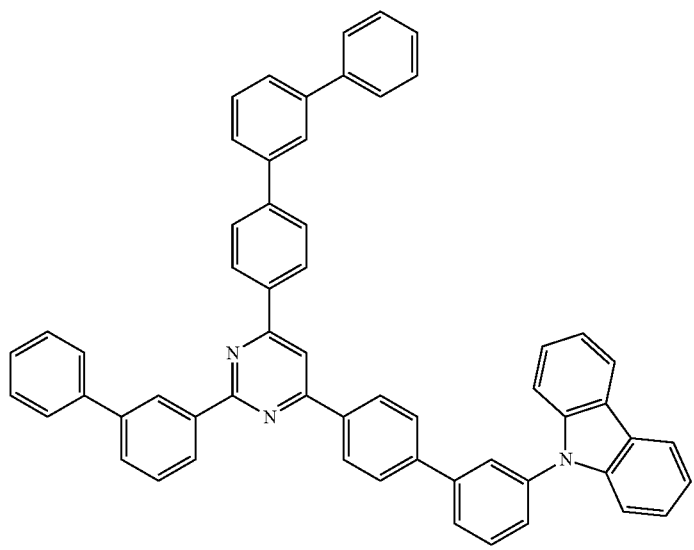
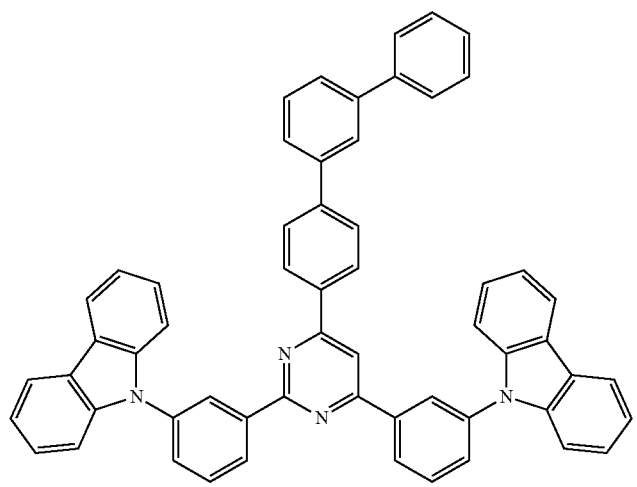

-continued
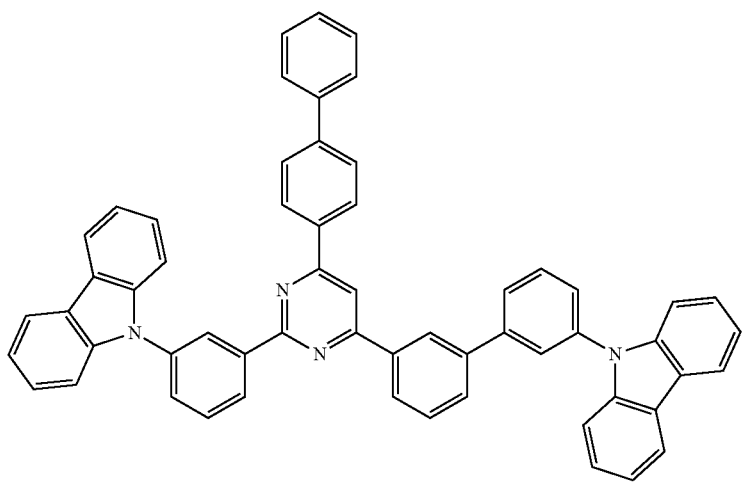
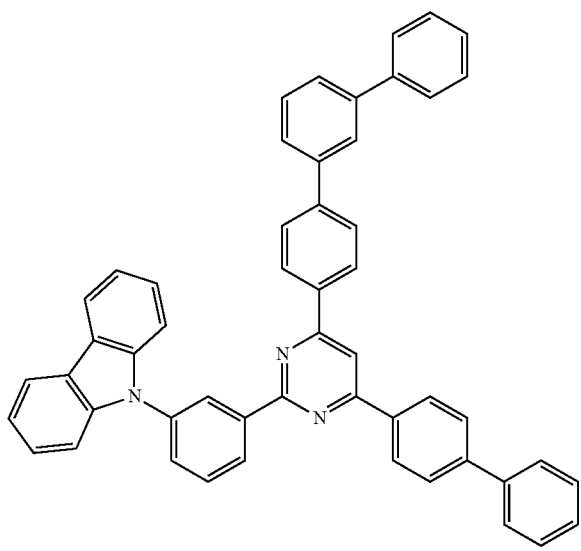
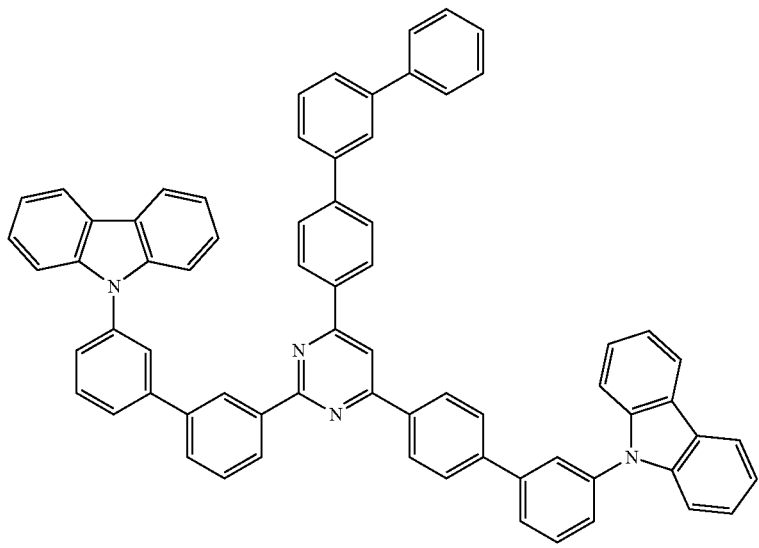

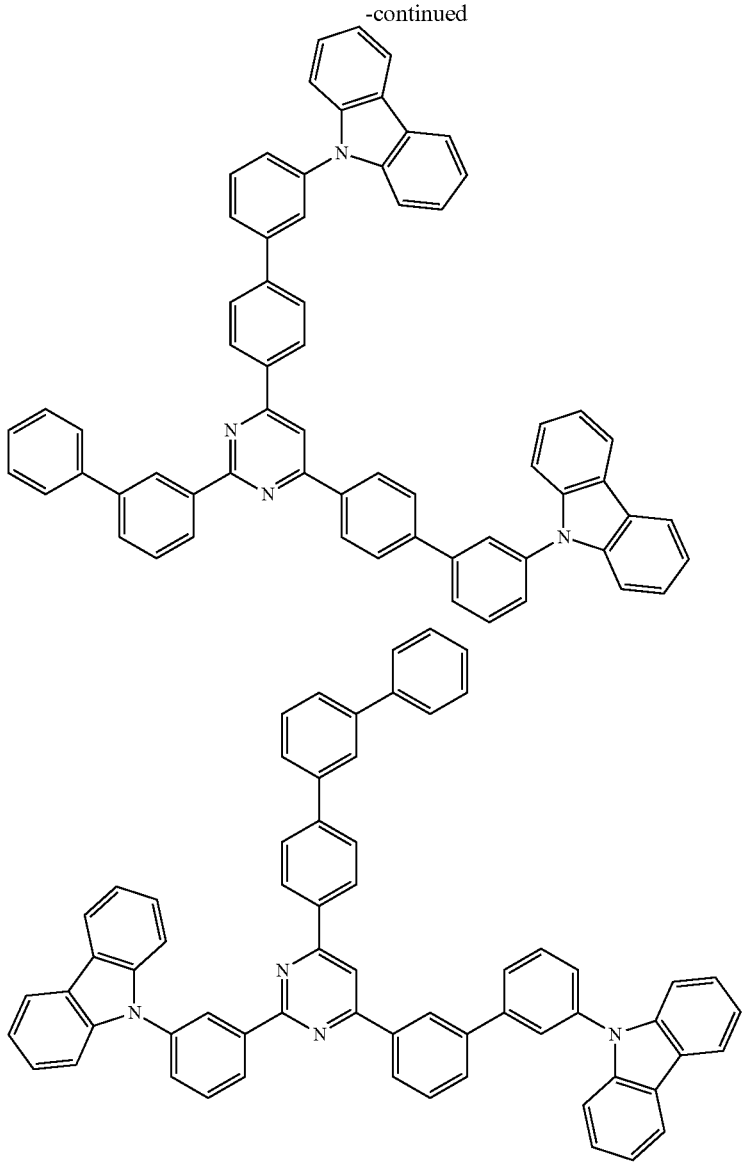

<Other Ingredients>

The composition of the invention may contain ingredients other than the organic compound of the invention, solvent, light-emitting material, and other charge-transporting materials (electron-transporting material and hole-transporting material) according to need. For example, the composition may contain various additives such as, for example, a leveling agent and an antifoamer for the purpose of improving film-forming properties. In the case where two or more layers are to be superposed by a wet film formation method, it is possible to incorporate a photocurable resin or a thermosetting resin beforehand for the purpose of curing and insolubilizing the formed film in order to prevent the layers from mingling with each other.

<Concentration of Materials in the Composition and Proportions Thereof.

The concentration of all materials (solid components) including the charge-transporting materials, light-emitting material, and ingredients which can be added according to need (e.g., leveling agent) in the composition of the invention is usually 0.01% by weight or higher, preferably 0.05% by weight or higher, more preferably 0.1% by weight or higher, even more preferably 0.5% by weight or higher, most preferably 1% by weight or higher, and is usually 80% by weight or less, preferably 50% by weight or less, more preferably 40% by weight or less, even more preferably 30% by weight or less, most preferably 20% by weight or less. In case where the concentration thereof is less than the lower limit, it is difficult to form a thick film in film formation. In case where the concentration thereof exceeds the upper limit, it is difficult to form a thin film.

In the composition of the invention, the weight ratio of the light-emitting material to all charge-transporting materials is usually 0.1/99.9 or higher, more preferably 0.5/99.5 or higher, even more preferably 1/99 or higher, most preferably 2/98 or higher, and is usually 50/50 or less, more preferably 40/60 or less, even more preferably 30/70 or less, most preferably 20/80 or less. In case where the ratio thereof is lower than the lower limit or exceeds the upper limit, there is a possibility that the luminescent efficiency might decrease considerably.

<Properties, etc. of the Composition>
(Moisture Concentration)

In the case where the composition of the invention is used to form a layer by a wet film formation method and to produce organic devices including organic electroluminescent elements, the presence of moisture in the composition to be used results in formation of a thin film which contains moisture and has impaired homogeneity. It is therefore preferred that the moisture content of the composition of the invention should be as low as possible. Furthermore, since organic devices including organic electroluminescent elements generally employ a large number of materials which are considerably deteriorated by moisture (e.g., cathodes), the presence of moisture in the composition of the invention is undesirable because there is a possibility that moisture might remain in the dried thin film to reduce the characteristics of the elements.

Specifically, the content of moisture in the composition of the invention is usually 1% by weight or less, preferably 0.1% by weight or less, more preferably 0.01% by weight or less.

Preferred methods for determining the moisture concentration of the composition of the invention are the methods described in Japanese Industrial Standards "Methods for Determining Moisture Content of Chemical Products" (JIS K0068:2001). For example, the composition can be analyzed by the Karl Fischer's reagent method.

(Evenness)

It is preferred that the composition of the invention should be an even liquid at ordinary temperature, from the standpoint of enabling the composition to show enhanced stability in a wet film formation process, e.g., enhanced stability in ejection from a nozzle in an ink-jet film formation method. The expression "even liquid at ordinary temperature" means that the composition is a liquid constituted of a homogeneous phase and contains no particulate component having a partial diameter of 0.1 µm or larger.

(Viscosity)

With respect to the viscosity of the composition of the invention, in case where the viscosity thereof is extremely low, troubles in film formation steps are apt to arise, such as, for example, an uneven coating surface due to an excessive liquid-film flow and nozzle ejection failures in ink-jet film formation. In case where the viscosity thereof is extremely high, troubles such as nozzle clogging in ink jet film formation are apt to arise. Consequently, the viscosity at 25° C. of the composition of the invention is usually 2 mPa·s or higher, preferably 3 mPa·s or higher, more preferably 5 mPa·s or higher, and is usually 1,000 mPa·s or less, preferably 100 mPa·s or less, more preferably 50 mPa·s or less.

(Surface Tension)

In case where the composition of the invention has a high surface tension, problems arise, such as a decrease in the ability of the film-forming solution to wet the substrate, poor leveling properties of the liquid film, and a higher tendency that the surface of the film being formed becomes uneven during drying. Consequently, the surface tension at 20° C. of the composition of the invention is usually less than 50 mN/m, preferably less than 40 mN/m.

(Vapor Pressure)

In case where the composition of the invention has a high vapor pressure, this composition is apt to have problems such as, for example, a change in solute concentration due to solvent vaporization. Consequently, the vapor pressure at 25° C. of the composition of the invention is usually 50 mmHg or less, preferably 10 mmHg or less, more preferably 1 mmHg or less.

[Thin Film for Organic Electroluminescent Element]

The thin film formed from the composition of the invention by a wet film formation method is less apt to be crystallized and is excellent in terms of luminescent properties and heat resistance, and is usually suitable for use as a layer interposed between the cathode and anode of an organic electroluminescent element.

The thickness of the thin film for organic electroluminescent elements which is to be formed from the composition of the invention is suitably determined according to applications. For example, in the case of use as the luminescent layer of an organic electroluminescent element, the thickness thereof is usually 10 nm or larger, preferably 20 nm or larger, and is usually 300 nm or less, preferably 200 nm or less, as will be described later.

[Organic Electroluminescent Element]

The organic electroluminescent element of the invention includes an anode, a cathode, and one or more organic layers disposed therebetween, and is characterized in that at least one of the organic layers is a layer formed from the composition of the invention. Usually, the element includes a substrate and, disposed thereover, at least an anode, a cathode, and a luminescent layer interposed between these electrodes, and it is preferred that the layer formed from the composition of the invention should be the luminescent layer. It is also preferred that the luminescent layer should be formed from the composition of the invention by a wet film formation method.

FIG. 1 is a diagrammatic view of a section which shows a structure example suitable for the organic electroluminescent element of the invention. In FIG. 1, numeral 1 denotes a substrate, 2 an anode, 3 a hole injection layer, 4 a hole-transporting layer, 5 a luminescent layer, 6 a hole-blocking layer, 7 an electron-transporting layer, 8 an electron injection layer, and 9 a cathode.

[1] Substrate

The substrate 1 serves as the support of the organic electroluminescent element, and a plate of quartz or glass, a metal plate, a metal foil, a plastic film or sheet, or the like is used. Especially preferred are glass plates and plates of transparent synthetic resins such as polyesters, polymethacrylates, polycarbonates, and polysulfones. In the case of using a synthetic resin substrate, attention must be paid on the gas barrier properties thereof. Use of a substrate having too low gas barrier properties is undesirable because there are cases where the surrounding air passes through the substrate to deteriorate the organic electroluminescent element. Consequently, one preferred method is to form a dense silicon oxide film or the like on at least one surface of the synthetic resin substrate to ensure gas barrier properties.

[2] Anode

An anode 2 is disposed on the substrate 1. The anode 2 serves to inject holes into a layer located on the luminescent-layer side (the hole injection layer 3, hole-transporting layer 4, or luminescent layer 5, etc.)

The anode 2 is usually constituted of a metal such as aluminum, gold, silver, nickel, palladium, or platinum, a metal oxide such as an oxide of indium and/or tin, a metal halide such as copper iodide, carbon black, an electroconductive polymer such as poly(3-methylthiophene), polypyrrole, or polyaniline, etc.

Usually, the anode 2 is frequently formed by sputtering, vacuum deposition, or the like. In the case where the anode is formed using fine particles of a metal such as silver, fine particles of copper iodide or the like, carbon black, fine particles of an electroconductive metal oxide, fine particles of an electroconductive polymer, or the like, use can be made of a method in which such fine particles are dispersed in an appropriate binder resin solution and this dispersion is applied to a substrate 1 to thereby form an anode 2. In the case of an electroconductive polymer, it is possible to form an anode 2 by directly forming a thin film on a substrate 1 by electrolytic polymerization or by applying the electroconductive polymer on a substrate 1 (*Appl. Phys. Lett.*, Vol. 60, p. 2711, 1992).

Although the anode 2 is usually of a single-layer structure, the anode 2 can be made, if desired, to have a multilayer structure constituted of a plurality of materials. The thickness of the anode 2 varies depending on required transparency. In the case where transparency is required, it is desirable to adjust the visible light transmittance to usually 60% or higher, preferably 80% or higher. In this case, the thickness of the anode is usually 5 nm or larger, preferably 10 nm or larger, and is usually about 1,000 nm or less, preferably about 500 nm or less. In the case where the anode 2 may be opaque, this anode 2 may have any desired thickness and may be identical with the substrate 1. It is also possible to superpose a different electroconductive material on the anode 2.

It is preferred to subject the anode surface to an ultraviolet (UV)/zone treatment or to a treatment with an oxygen plasma or argon plasma for the purpose of removing impurities adherent to the anode and regulating the ionization potential to improve hole injection properties.

[3] Hole Injection Layer

The hole injection layer 3 is a layer which transports holes from the anode 2 to the luminescent layer 5, and is usually formed on the anode 2.

For forming the hole injection layer 3 according to the invention, either a vacuum deposition method or a wet film formation method may be employed without particular limitations. From the standpoint of diminishing dark spots, however, it is preferred to form the hole injection layer 3 by a wet film formation method.

The thickness of the hole injection layer 3 is usually 5 nm or larger, preferably 10 nm or larger, and is usually 1,000 nm or less, preferably 500 nm or less.

<Formation of Hole Injection Layer by Wet Film Formation Method>

In the case of forming the hole injection layer 3 by a wet film formation method, the hole injection layer 3 is usually formed by mixing materials for constituting the hole injection layer 3 with an appropriate solvent (solvent for hole injection layer formation) to prepare a composition for film formation (composition for hole injection layer formation), applying this composition for hole injection layer formation, by an appropriate technique, to the layer (usually, the anode) which is to underlie the hole injection layer 3, and drying the resultant coating film.

(Hole-Transporting Compound)

The composition for hole injection layer formation usually contains a hole-transporting compound, as a material for constituting the hole injection layer, and a solvent.

The hole-transporting compound may be either a high-molecular compound such as a polymer or a low-molecular compound such as a monomer so long as the high-molecular or low-molecular compound is a compound which has hole-transporting properties and is usually used in the hole injection layers of organic electroluminescent elements. It is, however, preferred that the hole-transporting compound should be a high-molecular compound.

Preferred as the hole-transporting compound is a compound having an ionization potential of 4.5-6.0 eV, from the standpoint of barrier to charge injection from the anode 2 to the hole injection layer 3. Examples of the hole-transporting compound include aromatic amine derivatives, phthalocyanine derivatives, porphyrin derivatives, oligothiophene derivatives, polythiophene derivatives, benzylphenyl derivatives, compounds wherein tertiary amines are connected through a fluorene group, hydrazone derivatives, silazane derivatives, silanamine derivatives, phosphamine derivatives, quinacridone derivatives, polyaniline derivatives, polypyrrole derivatives, polyphenylenevinylene derivatives, polythienylenevinylene derivatives, polyquinoline derivatives, polyquinoxaline derivatives, and carbon.

In the invention, the term "derivatives" has the following meaning. In the case of aromatic amine derivatives, taken as an instance, that term includes both aromatic amines themselves and compounds each including an aromatic amine as the main framework and the derivatives may be either polymers or monomers.

The hole-transporting compound(s) to be contained as a material for the hole injection layer 3 may be any one of such compounds or may be two or more thereof. In the case where two or more hole-transporting compounds are contained, any combination may be employed. It is, however, preferred to use one or more aromatic tertiary amine high-molecular compounds in combination with one or more other hole-transporting compounds.

From the standpoints of amorphousness and visible light transmittance, aromatic amine compounds are preferred of the compounds shown above as examples, and aromatic tertiary amine compounds are especially preferred. Here, aromatic tertiary amine compounds are compounds having an aromatic tertiary amine structure, and include compounds having a group derived from an aromatic tertiary amine.

The aromatic tertiary amine compounds are not particularly limited in the kind thereof. However, from the standpoint of uniform light emission due to surface-smoothing effect, high-molecular compounds having a weight-average molecular weight of 1,000-1,000,000 (polymerization type compounds wherein repeating units are connected to each other) are more preferred. Preferred examples of the aromatic tertiary amine high-molecular compounds include high-molecular compounds having a repeating unit represented by the following formula (IV).

[Ka 40]

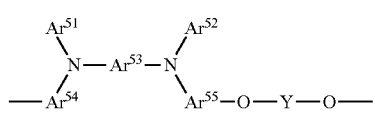

(IV)

(In formula (IV), $Ar^{51}$ and $Ar^{52}$ each independently represent an aromatic hydrocarbon group which may have a substituent or an aromatic heterocyclic group which may have a substituent. $Ar^{53}$ to $Ar^{55}$ each independently represent an aromatic hydrocarbon group which may have a substituent or an aromatic heterocyclic group which may have a substituent. Y represents a linking group selected from the following linking groups. Of the $Ar^{51}$ to $Ar^{55}$, two groups bonded to the same nitrogen atom may be bonded to each other to form a ring.)

[Ka 41]

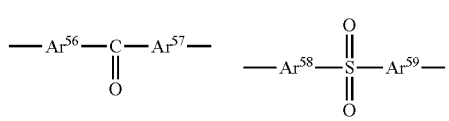

-continued

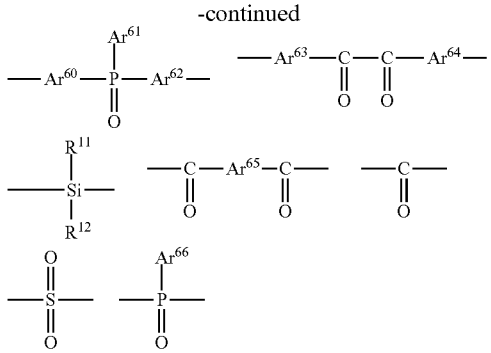

(In the formulae, $Ar^{56}$ to $Ar^{66}$ each independently represent an aromatic hydrocarbon group which may have a substituent or an aromatic heterocyclic group which may have a substituent. $R^{11}$ and $R^{12}$ each independently represent a hydrogen atom or any substituent.)

Preferred as the aromatic hydrocarbon groups and aromatic heterocyclic groups of $Ar^{51}$ to $Ar^{66}$ are groups derived from a benzene ring, naphthalene ring, phenanthrene ring, thiophene ring, and pyridine ring, from the standpoints of the solubility, heat resistance, and hole injection-transport properties of the high-molecular compounds. More preferred are groups derived from a benzene ring and a naphthalene ring.

The aromatic hydrocarbon groups and aromatic heterocyclic groups of $Ar^{51}$ to $Ar^{66}$ may further have a substituent. The molecular weight of the substituent is usually 400 or less, in particular, preferably about 250 or less. Preferred examples of the substituent include alkyl groups, alkenyl groups, alkoxy groups, aromatic hydrocarbon groups, and aromatic heterocyclic groups.

In the case where $R^{11}$ and $R^{12}$ are any substituents, examples of the substituents include alkyl groups, alkenyl groups, alkoxy groups, silyl, siloxy, aromatic hydrocarbon groups, and aromatic heterocyclic groups.

Specific examples of the aromatic tertiary amine high-molecular compounds having a repeating unit represented by formula (IV) include the high-molecular compounds described in WO2005/089024.

Also preferred as the hole-transporting compound is an electroconductive polymer (PEDOT/PSS), which is a derivative of polythiophene, obtained by polymerizing 3,4-ethylenedioxythiophene in high-molecular poly(styrenesulfonic acid). A product obtained by capping the ends of this polymer with a methacrylate or the like may also be employed.

Furthermore, the compound having an insolubilizing group that will be described later in the section "Hole-Transporting Layer" may be used as the hole-transporting compound. In the case of using the compound having an insolubilizing group, the same methods may be used for film formation, etc.

The concentration of the hole-transporting compound in the composition for hole injection layer formation is not limited unless the effects of the invention are considerably lessened. However, from the standpoint of the evenness of film thickness, the concentration thereof is usually 0.01% by weight or higher, preferably 0.1% by weight or higher, more preferably 0.5% by weight or higher, and is usually 70% by weight or less, preferably 60% by weight or less, more preferably 50% by weight or less. In case where the concentration thereof is too high, there is the possibility of resulting in unevenness in film thickness. In case where the concentration thereof is too low, there is a possibility that the hole injection layer formed might have defects.

(Electron-Accepting Compound)

It is preferred that the composition for hole injection layer formation should contain an electron-accepting compound as a constituent material for the hole injection layer.

The electron-accepting compound preferably is a compound which has oxidizing ability and has the ability to accept one electron from the hole-transporting compound described above. Specifically, compounds having an electron affinity of 4 eV or higher are preferred, and compounds having an electron affinity of 5 eV or higher are more preferred.

Examples of such electron-accepting compounds include one or more compounds selected from the group consisting of triarylboron compounds, metal halides, Lewis acids, organic acids, onium salts, salts of arylamines with metal halides, and salts of arylamines with Lewis acids. More specific examples thereof include: onium salts substituted with organic groups, such as 4-isopropyl-4'-methyldiphenyliodonium tetrakis (pentafluorophenyl)borate and triphenylsulfonium tetrafluoroborate (WO2005/089024); inorganic compounds having a high valence, such as iron(III) chloride (JP-A-11-251067) and ammonium peroxodisulfate; cyano compounds such as tetracyanoethylene; aromatic boron compounds such as tris (pentafluorophenyl)borane (JP-A-2003-31365); fullerene derivatives; iodine; and sulfonic acid ions such as poly(styrenesulfonic acid) ions, alkylbenzenesulfonic acid ions, and camphorsulfonic acid ions.

These electron-accepting compounds oxidize the hole-transporting compound and can thereby improve the electrical conductivity of the hole injection layer.

The content of the electron-accepting compound in the hole injection layer or in the composition for hole injection layer formation, based on the hole-transporting compound, is usually 0.1% by mole or higher, preferably 1% by mole or higher, but is usually 100% by mole or less, preferably 40% by mole or less.

(Other Constituent Materials)

As materials for the hole injection layer, other ingredients may be incorporated in addition to the hole-transporting compound and electron-accepting compound described above, unless the effects of the invention are considerably lessened. Examples of such other ingredients include various light-emitting materials, electron-transporting compounds, binder resins, and applicability improvers. One of such other ingredients may be used alone, or any desired two or more thereof may be used in combination in any desired proportion.

(Solvent)

It is preferred that the solvent contained in the composition for hole injection layer formation which is to be used in a wet film formation method should include at least one compound in which the above-described constituent materials for the hole injection layer can dissolve. It is preferred that this solvent should have a boiling point which is usually 110° C. or higher, preferably 140° C. or higher, in particular 200° C. or higher, and is usually 400° C. or lower, in particular 300° C. or lower. In case where the boiling point of the solvent is too low, there is a possibility that this composition might be dried at too high a rate, resulting in impaired film quality. In case where the boiling point of the solvent is too high, it is necessary to employ an elevated temperature in the drying step and this drying may adversely affect the other layers and substrate.

Examples of the solvent include ether series solvents, ester series solvents, aromatic hydrocarbon series solvents, and amide series solvents.

Examples of the ether series solvents include: aliphatic ethers such as ethylene glycol dimethyl ether, ethylene glycol diethyl ether, and propylene glycol 1-monomethyl ether acetate (PGMEA); and aromatic ethers such as 1,2-dimethoxybenzene, 1,3-dimethoxybenzene, anisole, phenetole, 2-methoxytoluene, 3-methoxytoluene, 4-methoxytoluene, 2,3-dimethylanisole, and 2,4-dimethylanisole.

Examples of the ester series solvents include aromatic esters such as phenyl acetate, phenyl propionate, methyl benzoate, ethyl benzoate, propyl benzoate, and n-butyl benzoate.

Examples of the aromatic hydrocarbon series solvents include toluene, xylene, cyclohexylbenzene, 3-iropropylbiphenyl, 1,2,3,4-tetramethylbenzene, 1,4-diisopropylbenzene, cyclohexylbenzene, and methylnaphthalene. Examples of the amide series solvents include N,N-dimethylformamide and N,N-dimethylacetamide.

Also usable besides these are dimethyl sulfoxide and the like.

One of these solvents may be used alone, or any desired two or more thereof may be used in combination in any desired proportion.

(Film Formation Method)

After preparation of the composition for hole injection layer formation, this composition is applied, by a wet process, on the layer (usually, the anode 2) which is to underlie the hole injection layer 3. The resultant coating film is dried. Thus, a hole injection layer 3 is formed.

The temperature in the application step is preferably 10° C. or higher but preferably 50° C. or lower, from the standpoint of preventing film defects due to crystal formation in the composition.

The relative humidity in the application step is not limited unless the effects of the invention are considerably lessened. However, the relative humidity is usually 0.01 ppm or higher but is usually 80% or less.

After the application, the film of the composition for hole injection layer formation is dried usually by heating, etc. Examples of heating means usable in the heating step include a clean oven, hot plate, infrared rays, halogen lamp heater, and irradiation with microwaves. Of these, a clean oven and a hot plate are preferred from the standpoint of evenly heating the whole film.

With respect to the heating temperature in the heating step, it is preferred to heat the coating film at a temperature not lower than the boiling point of the solvent used in the composition for hole injection layer formation, unless the effects of the invention are considerably lessened. When the solvent used for the hole injection layer is a mixed solvent composed of two or more solvents, it is preferred to heat the coating film at a temperature not lower than the boiling point of at least one of these solvents. When an increase in the boiling point of the solvent(s) is taken into account, it is preferred that the coating film in the heating step should be heated preferably at 120-410° C.

In the heating step, the heating period is not limited so long as the heating temperature is not lower than the boiling point of the solvent contained in the composition for hole injection layer formation and so long as sufficient insolubilization of the coating film does not occur. However, the heating period is preferably 10 seconds or longer and is usually 180 minutes or shorter. In case where the heating period is too long, components of other layers tend to diffuse. In case where the heating period is too short, an inhomogeneous hole injection layer tends to be formed. The heating may be carried out in two steps.

<Formation of Hole Injection Layer by Vacuum Deposition Method>

In the case of forming the hole injection layer 3 by vacuum deposition, one or more constituent materials for the hole injection layer 3 (the hole-transporting compound and electron-accepting compound described above, etc.) are placed in one or more crucibles disposed in a vacuum vessel (in the case where two or more materials are used, the materials are placed in respective crucibles), and the vacuum vessel is evacuated to about $10^{-4}$ Pa by means of an appropriate vacuum pump. Thereafter, the crucible is heated (in the case where two or more materials are used, the respective crucibles are heated) to vaporize the material while controlling the rate of vaporization (in the case where two or more materials are used, the materials are vaporized while independently controlling the rates of vaporization thereof), to thereby form a hole injection layer 3 on the anode 2 of the substrate which has been placed so as to face the crucible(s). Incidentally, in the case of using two or more materials, it is possible to use a method in which a mixture of these materials is placed in a crucible and is heated and vaporized to form a hole injection layer 3.

The degree of vacuum during the deposition is not limited unless the effects of the invention are considerably lessened. However, the pressure during the deposition is usually $0.1 \times 10^{-6}$ Torr ($0.13 \times 10^{-4}$ Pa) or higher but is usually $9.0 \times 10^{-6}$ Torr ($12.0 \times 10^{-4}$ Pa) or less. The rate of vacuum deposition is not limited unless the effects of the invention are considerably lessened. However, the deposition rate is usually 0.1 Å/sec or higher but is usually 5.0 Å/sec or less. The film formation temperature during the vacuum deposition is not limited unless the effects of the invention are considerably lessened. However, the vacuum deposition is conducted at a temperature of preferably 10-50° C.

[4] Hole-Transporting Layer

When there is a hole injection layer, the hole-transporting layer 4 can be formed on the hole injection layer 3. When there is no hole injection layer 3, the hole-transporting layer 4 can be formed on the anode 2. The organic electroluminescent element of the invention may have a configuration in which the hole-transporting layer has been omitted.

For forming the hole-transporting layer 4, either a vacuum deposition method or a wet film formation method may be used without particular limitations. However, from the standpoint of diminishing dark spots, it is preferred to form the hole-transporting layer 4 by a wet film formation method.

It is preferred that a material which has high hole-transporting properties and is capable of efficiently transporting injected holes should be used for forming the hole-transporting layer 4. From this standpoint, it is preferred that the material should have a low ionization potential, high transparency to visible light, high hole mobility, and excellent stability and be less apt to generate, during production or use, impurities which function as traps. Furthermore, since this hole-transporting layer 4 is in contact with the luminescent layer 5 in many cases, it is preferred that the material should neither quench the light emitted from the luminescent layer 5 nor form an exciplex at the interface between the hole-transporting layer 4 and the luminescent layer 5 to reduce the efficiency.

As such a material for the hole-transporting layer 4, any material which has hitherto been used as a constituent material for hole-transporting layers may be employed. Examples thereof include the compounds shown above as examples of the hole-transporting compound to be used in the hole injection layer 3 described above. Examples thereof further include arylamine derivatives, fluorene derivatives, spiro derivatives, carbazole derivatives, pyridine derivatives, pyrazine derivatives, pyrimidine derivatives, triazine derivatives, quinoline derivatives, phenanthroline derivatives, phthalocyanine derivatives, porphyrin derivatives, silole derivatives, oligothiophene derivatives, fused-ring aromatic derivatives, and metal complexes.

Other examples thereof include polyvinylcarbazole derivatives, polyarylamine derivatives, polyvinyltriphenylamine derivatives, polyfluorene derivatives, polyarylene derivatives, poly(arylene ether sulfone) derivatives containing tetraphenylbenzidine, polyarylenevinylene derivatives, polysiloxane derivatives, polythiophene derivatives, and poly(p-phenylenevinylene) derivatives. These derivatives may be any of alternating copolymers, random polymers, block polymers, and graft copolymers. Furthermore, the derivatives each may be a polymer in which the main chain has been branched to have three or more ends, or may be a so-called dendrimer.

Preferred of those are polyarylamine derivatives and polyarylene derivatives.

The polyarylamine derivatives preferably are polymers which contain a repeating unit represented by the following formula (V), and especially preferably are polymers each made up of repeating units represented by the following formula (V). In this case, the polymer may be one in which the repeating units differ from each other in $Ar^a$ or $Ar^b$.

[Ka 42]

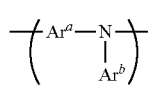

(V)

(In formula (V), $Ar^a$ and $Ar^b$ each independently represent an aromatic hydrocarbon group or aromatic heterocyclic group which may have a substituent.)

Examples of the aromatic hydrocarbon group which may have a substituent include groups derived from 6-membered monocycles or from fused rings each composed of two to five 6-membered monocycles fused together, such as a benzene ring, naphthalene ring, anthracene ring, phenanthrene ring, perylene ring, tetracene ring, pyrene ring, benzpyrene ring, chrysene ring, triphenylene ring, acenaphthene ring, fluoranthene ring, and fluorene ring, and further include groups each made up of two or more such rings linked together through one or more direct bonds.

Examples of the aromatic heterocyclic group which may have a substituent include groups derived from 5- or 6-membered monocycles or from fused rings each composed of two to four 5- or 6-membered monocycles fused together, such as a furan ring, benzofuran ring, thiophene ring, benzothiophene ring, pyrrole ring, pyrazole ring, imidazole ring, oxadiazole ring, indole ring, carbazole ring, pyrroloimidazole ring, pyrrolopyrazole ring, pyrrolopyrrole ring, thienopyrrole ring, thienothiophene ring, furopyrrole ring, furofuran ring, thienofuran ring, benzisooxazole ring, benzisothiazole ring, benzimidazole ring, pyridine ring, pyrazine ring, pyridazine ring, pyrimidine ring, triazine ring, quinoline ring, isoquinoline ring, cinnoline ring, quinoxaline ring, phenanthridine ring, benzimidazole ring, perimidine ring, quinazoline ring, quinazolinone ring, and azulene ring, and further include groups each made up of two or more such rings linked together through one or more direct bonds.

From the standpoints of solubility in organic solvents and heat resistance, it is preferred that $Ar^a$ and $Ar^b$ should each independently be a group derived from a ring selected from the group consisting of a benzene ring, naphthalene ring, anthracene ring, phenanthrene ring, triphenylene ring, pyrene ring, thiophene ring, pyridine ring, and fluorene ring, or be a group which is made up of two or more benzene rings linked together (e.g., biphenyl (biphenylene) or terphenyl (terphenylene)).

Preferred of these are a group derived from a benzene ring (phenyl), a group made up of two benzene rings linked together (biphenyl), and a group derived from a fluorene ring (fluorenyl).

Examples of the substituents which may be possessed by the aromatic hydrocarbon group and aromatic heterocyclic group represented by $Ar^a$ and $Ar^b$ include alkyl groups, alkenyl groups, alkynyl groups, alkoxy groups, aryloxy groups, alkoxycarbonyl groups, dialkylamino groups, diarylamino groups, acyl groups, halogen atoms, haloalkyl groups, alkylthio groups, arylthio groups, silyl, siloxy, cyano, aromatic hydrocarbon ring groups, and aromatic heterocyclic groups.

Examples of the polyarylene derivatives include polymers having, as a repeating unit, an arylene group such as any of the optionally substituted aromatic hydrocarbon groups or aromatic heterocyclic groups which were shown above as examples of the $Ar^a$ and $Ar^b$ contained in formula (V). Preferred as the polyarylene derivatives are polymers having repeating units constituted of the following formula (VI) and/or the following formula (VII).

[Ka 43]

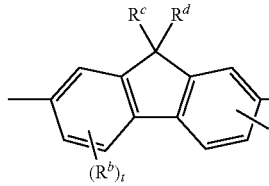

(VI)

(In formula (VI), $R^a$, $R^b$, $R^c$, and $R^d$ each independently represent an alkyl group, alkoxy group, phenylalkyl group, phenylalkoxy group, phenyl, phenoxy, alkylphenyl group, alkoxyphenyl group, alkylcarbonyl group, alkoxycarbonyl group, or carboxy. Symbols t and s each independently represent an integer of 0-3. When t or s is 2 or larger, the multiple $R^a$ or $R^b$ groups contained in the molecule may be the same or different, and any adjoining $R^a$ or $R^b$ groups may have been bonded to each other to form a ring.)

[Ka 44]

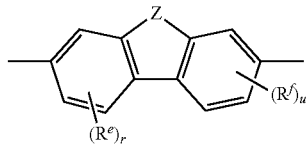

(VII)

(In formula (VII), $R^e$ and $R^f$ each independently have the same meaning as the $R^a$, $R^b$, $R^c$, or $R^d$ contained in formula (VI). Symbols r and u each independently represent an integer of 0-3. When r or u is 2 or larger, the multiple $R^e$ or $R^f$ groups contained in the molecule may be the same or different, and any adjoining $R^e$ or $R^f$ groups may have been bonded to each other to form a ring. Z represents an atom or a group of atoms, the atom or the group constituting a 5- or 6-membered ring.)

Examples of Z include —O—, —$BR^x$—, —$NR^x$—, —$SiR^x_2$—, —$PR^x$—, —$SR^x$—, —$CR^x_2$—, or a group constituted of such atoms or groups bonded to each other. $R^x$ represents a hydrogen atom or any organic group. The term "organic group" in the invention means a group which contains at least one carbon atom.

It is preferred that the polyarylene derivatives should further have a repeating unit represented by the following formula (VIII), besides the repeating units constituted of formula (VI) and/or formula (VII).

[Ka 45]

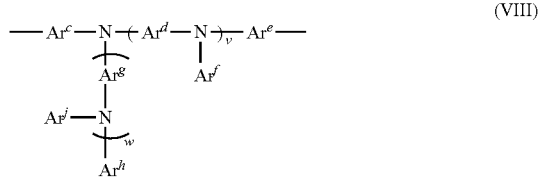

(VIII)

(In formula (VIII), $Ar^c$ to A11 each independently represent an aromatic hydrocarbon group or an aromatic heterocyclic group which each may have a substituent. Symbols v and w each independently represent 0 or 1.)

Examples of $Ar^c$ to $Ar^j$ are the same as those of the $Ar^a$ and $Ar^b$ contained in formula (V).

Specific examples of formulae (VI) to (VIII) and specific examples of the polyarylene derivatives include the same examples as those shown in JP-A-2008-98619.

In the case where the hole-transporting layer 4 is formed by a wet film formation method, a composition for hole-transporting layer formation is prepared and thereafter applied to form a film thereof by a wet process and the coating film is dried by heating, in the same manner as for the formation of the hole injection layer 3.

The composition for hole-transporting layer formation contains a solvent besides the hole-transporting compound described above. The solvent to be used may be the same as the solvent used in the composition for hole injection layer formation. Other conditions including conditions for film formation and conditions for drying by heating may also be the same as in the formation of the hole injection layer 3. Also in the case where the hole-transporting layer is formed by a vacuum deposition method, the conditions for film deposition, etc. may be the same as in the formation of the hole injection layer 3. The hole-transporting layer 4 may contain various light-emitting materials, electron-transporting compounds, binder resins, applicability improvers, etc., besides the hole-transporting compound.

It is also preferred that the hole-transporting layer 4 should be a layer formed by insolubilizing a compound having an insolubilizing group (hereinafter referred to as "insolubilizable compound"), from the standpoint of heat resistance or film-forming properties. The insolubilizable compound is a compound having an insolubilizing group, and is insolubilized to thereby form an insoluble polymer.

The insolubilizing group is a group which reacts by the action of heat and/or irradiation with actinic energy rays and which has the effect of making the reacted compound have reduced solubility in organic solvents or water as compared with the solubility of the unreacted compound. In the invention, it is preferred that the insolubilizing group should be a leaving group or a crosslinkable group.

The term "leaving group" means a group that is eliminated at a temperature of 70° C. or higher from the aromatic hydrocarbon ring to which the group has been bonded and that renders the compound soluble in solvents. The expression "soluble in solvents" means that the compound, in the state of having not reacted by the action of heat and/or irradiation with actinic energy rays, dissolves in toluene at ordinary temperature in an amount of 0.1% by weight or more. The solubility of the compound in toluene is preferably 0.5% by weight or higher, more preferably 1% by weight or higher.

This leaving group preferably is a group which is thermally eliminated without leaving a polar group on the aromatic hydrocarbon ring, and more preferably is a group which is thermally eliminated by means of the reverse Diels-Alder reaction. It is also preferred that the leaving group should be a group which is thermally eliminated at 100° C. or higher, and that the leaving group should be a group which is thermally eliminated at 300° C. or lower.

Examples of the crosslinkable group include: groups derived from cyclic ethers such as oxetane and epoxies; groups derived from an unsaturated double bond, such as vinyl, trifluorovinyl, styryl, acryl, methacryloyl, and cinnamoyl; and groups derived from benzocyclobutane.

The insolubilizable compound may be either a monomer, oligomer, or polymer. One insolubilizable compound may be used alone, or any desired two or more insolubilizable compounds may be used in combination in any desired proportion.

It is preferred to use, as the insolubilizable compound, a hole-transporting compound having a crosslinkable group. Examples of the hole-transporting compound include: nitrogen-containing aromatic compound derivatives such as pyridine derivatives, pyrazine derivatives, pyrimidine derivatives, triazine derivatives, quinoline derivatives, phenanthroline derivatives, carbazole derivatives, phthalocyanine derivatives, and porphyrin derivatives; triphenylamine derivatives; silole derivatives; and oligothiophene derivatives, fused-ring aromatic derivatives, and metal complexes. Preferred of these are: nitrogen-containing aromatic derivatives such as pyridine derivatives, pyrazine derivatives, pyrimidine derivatives, triazine derivatives, quinoline derivatives, phenanthroline derivatives, and carbazole derivatives; and triphenylamine derivatives, silole derivatives, fused-ring aromatic derivatives, metal complexes, and the like. In particular, triphenylamine derivatives are more preferred.

For forming a hole-transporting layer 4 by insolubilizing the insolubilizable compound, use is usually made of a method in which the insolubilizable compound is dissolved or dispersed in a solvent to prepare a composition for hole-transporting layer formation and this composition is applied to form a film thereof by a wet process and insolubilized.

The composition for hole-transporting layer formation may contain an additive which accelerates the insolubilization, besides the insolubilizable compound. Examples of crosslinking type additives which accelerate the insolubilization, for example, include: polymerization initiators and polymerization accelerators, such as alkylphenone compounds, acylphosphine oxide compounds, metallocene compounds, oxime ester compounds, azo compounds, and onium salts; and photosensitizers such as fused-ring hydrocarbons, porphyrin compounds, and diaryl ketone compounds.

The composition may further contain an applicability improver, such as a leaving agent or an antifoamer, an electron-accepting compound, a binder resin, etc.

The composition for hole-transporting layer formation contains the insolubilizable compound in a concentration which is usually 0.01% by weight or higher, preferably 0.05% by weight or higher, more preferably 0.1% by weight or higher, and is usually 50% by weight or less, preferably 20% by weight or less, more preferably 10% by weight or less.

The composition for hole-transporting layer formation which contains the insolubilizable compound in such a concentration is applied on the underlying layer (usually, the hole injection layer 3) to form a film thereof, and the insolubilizable compound is thereafter insolubilized by heating and/or irradiation with actinic energy such as light.

Conditions for the film formation, including temperature and humidity, may be the same as in the wet-process film formation for forming the hole injection layer 3. Techniques for heating after the film formation are not particularly limited. With respect to heating temperature conditions, the temperature is usually 120° C. or higher but is preferably 400° C. or lower. The period of heating is usually 1 minute or longer but is preferably 24 hours or less. Although means for heating are not particularly limited, use may be made of a method in which the multilayer structure having the layer formed above is placed on a hot plate or heated in an oven. For example, use can be made of conditions under which the multilayer structure is heated on a hot plate at 120° C. or higher for 1 minute or longer.

In the case of insolubilization by irradiation with electromagnetic energy such as light, examples of methods therefor include: a method in which the multilayer structure is directly irradiated using a light source for emitting ultraviolet, visible, or infrared light, such as an ultrahigh-pressure mercury lamp, high-pressure mercury lamp, halogen lamp, infrared ray lamp, or the like; or a method in which the multilayer structure is irradiated using a mask aligner or conveyor-type light irradiator which includes any of those light sources built therein. Examples of methods in the case of irradiation with electromagnetic energy other than light include a method in which the multilayer structure is irradiated using an apparatus, i.e., so-called electronic oven, for irradiation with microwaves generated by, for example, a magnetron.

With respect to irradiation period, it is preferred to set conditions necessary for lowering the solubility of the film. However, the multilayer structure is irradiated for a period of usually 0.1 second or longer but preferably 10 hours or less.

Heating and irradiation with electromagnetic energy such as light may be conducted alone or in combination thereof. In the case of employing the combination, the order of conducting the heating and the irradiation is not particularly limited.

The thickness of the hole-transporting layer 4 thus formed is usually 5 nm or larger, preferably 10 nm or larger, and is usually 300 nm or less, preferably 100 nm or less.

[5] Luminescent Layer

A luminescent layer 5 is disposed usually on the hole-transporting layer 4. The luminescent layer 5 is a layer which contains, for example, the light-emitting material described above, and is a layer which, between the electrodes placed in an electric field, is excited by the recombination of holes injected from the anode 2 through the hole injection layer 3 with electrons injected from the cathode 9 through the electron-transporting layer 7 and which thus serves as the main light-emitting source. It is preferred that the luminescent layer 5 should contain a light-emitting material (dopant) and one or more host materials. It is more preferred that the luminescent layer 5 should contain the organic compound of the invention as a host material. Although the luminescent layer 5 may be formed by a vacuum deposition method, it is especially preferred that the luminescent layer 5 should be a layer formed from the composition of the invention by a wet film formation method.

The luminescent layer 5 may contain other materials and components so long as the performance of the invention is not impaired.

In general, in the case of organic electroluminescent elements employing the same materials, a smaller thickness of the layers interposed between the electrodes results in an increase in the intensity of effective electric field and hence in an increase in the quantity of electric current which flows, resulting in a decrease in operating voltage. Consequently, a smaller total thickness of the layers interposed between the electrodes results in a decrease in the operating voltage of the organic electroluminescent element. However, when the total thickness thereof is too small, short-circuiting due to projections of an electrode, e.g., ITO, occurs. Some degree of thickness is therefore necessary.

Consequently, in the invention, when the organic electroluminescent element has organic layers, such as the hole injection layer 3 and the electron-transporting layer 7 which will be described later, besides the luminescent layer 5, the total thickness of the luminescent layer 5 and the other organic layers, e.g., the hole injection layer 3 and the electron-transporting layer 7, is usually 30 nm or larger, preferably 50 nm or larger, more preferably 100 nm or larger, and is usually 1,000 nm or less, preferably 500 nm or less, more preferably 300 nm or less. In the case where layers other than the luminescent layer 5, such as the hole injection layer 3 and the electron injection layer 8 which will be described later, have high electrical conductivity, an increased amount of charges are injected into the luminescent layer 5. In this case, it is possible to use a method in which the operating voltage is lowered while maintaining some degree of total thickness, for example, by increasing the thickness of the hole injection layer 3 and reducing the thickness of the luminescent layer 5.

Therefore, the thickness of the luminescent layer 5 is usually 10 nm or larger, preferably 20 nm or larger, and is usually 300 nm or less, preferably 200 nm or less. In the case where the element of the invention has the luminescent layer 5 as the only layer interposed between the anode and the cathode, the thickness of this luminescent layer 5 is usually 30 nm or larger, preferably 50 nm or larger, and is usually 500 nm or less, preferably 300 nm or less.

[6] Hole-Blocking Layer

A hole-blocking layer 6 is superposed and formed on the luminescent layer 5 so that the hole-blocking layer 6 is in contact with the cathode-side boundary of the luminescent layer 5. Especially when a phosphorescent material is used as a light-emitting substance or a blue light-emitting material is used, the disposition of a hole-blocking layer 6 is effective.

The hole-blocking layer 6 has the function of confining holes and electrons in the luminescent layer 5 to improve the luminescent efficiency. Namely, the hole-blocking layer 6 not only serves to prevent the holes which have moved from the luminescent layer 5 from reaching the electron-transporting layer 7 and to thereby increase the probability of recombination with electrons within the luminescent layer 5 and confine the resultant excitons in the luminescent layer 5, but also serves to efficiently transport, toward the luminescent layer 5, the electrons which have been injected from the electron-transporting layer 7.

Examples of the properties required of the material which constitutes the hole-blocking layer 6 include: to have a high electron mobility and a low hole mobility; to have a large energy gap (difference between HOMO and LUMO); and to have a high excited triplet energy level (T1).

Examples of materials for the hole-blocking layer which satisfy such requirements include metal complexes such as mixed-ligand complexes, e.g., bis(2-methyl-8-quinolinolato)(phenolato)aluminum and bis(2-methyl-8-quinolinolato)(triphenylsilanolato)aluminum, and dinuclear metal complexes, e.g., bis(2-methyl-8-quinolato)aluminum-p-oxobis(2-methyl-8-quinolilato)aluminum, styryl compounds such as distyrylbiphenyl derivatives (JP-A-11-242996), triazole derivatives such as 3-(4-biphenylyl)-4-phenyl-5-(4-tert-butylphenyl)-1,2,4-triazole (JP-A-7-41759), and phenanthroline derivatives such as bathocuproine (JP-A-10-79297).

Furthermore, the compound having at least one pyridine ring substituted at the 2-, 4-, and 6-positions which is described in WO2005/022962 is also preferred as a hole-blocking material.

The thickness of the hole-blocking layer 6 is usually 0.3 nm or larger, preferably 0.5 nm or larger, and is usually 100 nm or less, preferably 50 nm or less.

Although the hole-blocking layer 6 also can be formed by the same method as for the hole injection layer 3, a vacuum deposition method is usually used.

[7] Electron-Transporting Layer

An electron-transporting layer 7 is disposed between the hole injection hole-blocking layer 6 and the electron injection layer 8 for the purpose of further improving the luminescent efficiency of the element. The electron-transporting layer 7 is constituted of a compound which, between the electrodes placed in an electric field, is capable of efficiently transporting, toward the luminescent layer 5, the electrons that have been injected from the cathode 9. It is necessary that the electron-transporting compound to be used for constituting the electron-transporting layer 7 should be a compound into which electrons can be injected at a high efficiency from the cathode 9 or electron injection layer 8 and which has a high electron mobility and is capable of efficiently transporting injected electrons.

Examples of materials which satisfy such requirements include metal complexes such as an aluminum complex of 8-hydroxyquinoline (JP-A-59-194393), metal complexes of 10-hydroxybenzo[h]quinoline, oxadiazole derivatives, distyrylbiphenyl derivatives, silole derivatives, 3- or 5-hydroxyflavone metal complexes, benzoxazole metal complexes, benzthiazole metal complexes, trisbenzimidazolylbenzene (U.S. Pat. No. 5,645,948), quinoxaline compounds (JP-A-6-207169), phenanthroline derivatives (JP-A-5-331459), 2-t-butyl-9,10-N,N'-dicyanoanthraquinonediimine, n-type hydrogenated amorphous silicon carbide, n-type zinc sulfide, and n-type zinc selenide.

The thickness of the electron-transporting layer 7 is as follows. The lower limit thereof is usually about 1 nm, preferably about 5 nm, and the upper limit thereof is usually about 300 nm, preferably about 100 nm.

Although the electron-transporting layer 7 may be formed by a wet film formation method or a vacuum deposition method in the same manner as for the hole injection layer 3, a vacuum deposition method is usually used.

[8] Electron Injection Layer

The electron injection layer 8 serves to efficiently inject, into the luminescent layer 5, the electrons injected from the cathode 9. From the standpoint of efficient electron injection, it is preferred that the material to be used for forming the electron injection layer 8 should be a metal having a low work function, and use is made of an alkali metal such as sodium or cesium or an alkaline earth metal such as barium or calcium. It is preferred that the thickness of the electron injection layer 8 should be 0.1-5 nm.

To interpose an ultrathin insulating film (0.1-5 nm) of LiF, $MgF_2$, $Li_2O$, $Cs_2CO_3$, or the like between the cathode 9 and the electron-transporting layer 7 is also an effective method for improving the efficiency of the element (*Appl. Phys. Lett.*, Vol. 70, p. 152, 1997; JP-A-10-74586; *IEEE Trans. Electron. Devices*, Vol. 44, p. 1245, 1997; *SID 04 Digest*, p. 154).

Furthermore, to dope an organic electron-transporting material represented by a nitrogen-containing heterocyclic compound, such as bathophenanthroline, or by a metal complex, such as an aluminum complex of 8-hydroxyquinoline, with an alkali metal such as sodium, potassium, cesium, lithium, or rubidium (described in JP-A-10-270171, JP-A-2002-100478, JP-A-2002-100482, etc.) is preferred because this doped material has improved electron injection-transport properties and is capable of combining these properties and excellent film quality. The thickness of the layer in this case is usually 5 nm or larger, preferably 10 nm or larger, and is usually 200 nm or less, preferably 100 nm or less.

The electron injection layer 8 may be formed by a wet film formation method or a vacuum deposition method in the same manner as for the luminescent layer 5. In the case of a vacuum deposition method, an evaporation source is placed in a crucible or metallic boat disposed in a vacuum vessel, and this vacuum vessel is evacuated to about $10^{-4}$ Pa with an appropriate vacuum pump. Thereafter, the crucible or the metallic boat is heated to vaporize the evaporation source to form an electron injection layer on the substrate placed so as to face the crucible or metallic boat.

For vacuum-depositing an alkali metal, use is made of an alkali metal dispenser obtained by filling nichrome with an alkali metal chromate and with a reducing agent. By heating this dispenser in a vacuum vessel, the alkali metal chromate is reduced and the alkali metal is vaporized. In the case where an organic electron-transporting material and an alkali metal are co-deposited, the procedure is as follows. The organic electron-transporting material is placed in a crucible disposed in a vacuum vessel, and this vacuum vessel is evacuated to about $10^{-4}$ Pa with an appropriate vacuum pump. Thereafter, each crucible and the dispenser are simultaneously heated to vaporize the materials and form an electron injection layer on the substrate disposed so as to face the crucible and the dispenser.

In this operation, the materials are co-deposited evenly along the thickness direction of the electron injection layer 8. However, there may be a concentration distribution in the film thickness direction.

[9] Cathode

The cathode 9 serves to inject electrons into a layer located on the luminescent-layer side (the electron injection layer 8 or the luminescent layer 5, etc.). The material used as the anode 2 can be used as the cathode 9. However, from the standpoint of efficient electron injection, a metal having a low work function is preferred, and use is made of an appropriate metal such as, for example, tin, magnesium, indium, calcium, aluminum, or silver or an alloy thereof. Specific examples thereof include alloy electrodes having a low work function, such as magnesium-silver alloys, magnesium-indium alloys, and aluminum-lithium alloys.

The thickness of the cathode 9 is usually the same as the anode 2. To further superpose thereon a layer of a metal having a high work function and stable to the air for the purpose of protecting the cathode constituted of a metal having a low work function enhances the stability of the element. Metals usable for this purpose are aluminum, silver, copper, nickel, chromium, gold, platinum, etc.

[10] Other Constituent Layers

The explanations given above were mainly on elements having the layer configuration shown in FIG. 1. However, the organic electroluminescent element of the invention may have any desired layers, besides the layers explained above, between the anode 2 and the luminescent layer 5 and between the cathode 9 and the luminescent layer 5 unless the performance of the element is impaired thereby. Furthermore, any layer other than the luminescent layer 5 may be omitted.

To dispose an electron-blocking layer between the hole-transporting layer 4 and the luminescent layer 5 for the same purpose as the hole-blocking layer 6 is also effective. The electron-blocking layer not only serves to prevent the electrons which have moved from the luminescent layer 5 from reaching the hole-transporting layer 4 and to thereby increase the probability of recombination with holes within the luminescent layer 5 and confine the resultant excitons in the luminescent layer 5, but also serves to efficiently transport, toward the luminescent layer 5, the holes which have been injected from the hole-transporting layer 4.

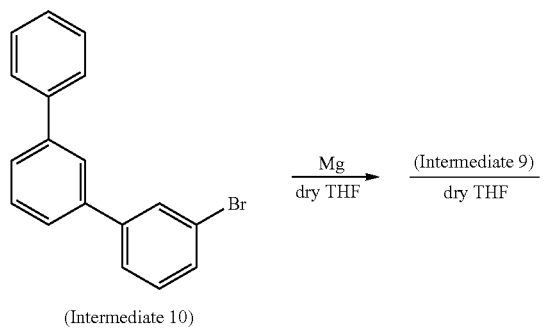

(Intermediate 10)

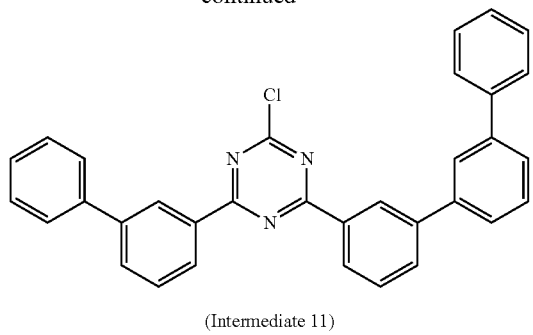

(Intermediate 11)

Examples of the properties required of the electron-blocking layer include: to have high hole-transporting properties; to have a large energy gap (difference between HOMO and LUMO); and to have a high excited triplet energy level (T1). In the case where the luminescent layer 5 is formed by a wet film formation method, it is preferred that the electron-blocking layer also should be formed by a wet film formation method, because this process facilitates the element production.

Consequently, it is preferred that the electron-blocking layer also should have suitability for wet-process film formation. Examples of materials usable for such an electron-blocking layer include copolymers of dioctylfluorene and triphenylamine which are represented by F8-TFB (WO2004/084260).

Incidentally, the structure which is the reverse of the structure shown in FIG. 1 is possible. Namely, it possible to superpose a cathode 9, electron injection layer 8, electron-transporting layer 7, hole-blocking layer 6, luminescent layer 5, hole-transporting layer 4, hole injection layer 3, and anode 2 in this order on a substrate 1. It is also possible to dispose an organic electroluminescent element of the invention between two substrates, at least one of which is highly transparent.

Furthermore, a structure constituted of a stack of stages each having the layer configuration shown in FIG. 1 (i.e., a structure composed of a plurality of stacked light-emitting units) is also possible. In this case, when a charge generation layer made of, for example, $V_2O_5$ is used in place of the interfacial layers located between the stages (i.e., between the light-emitting units) (when the anode is ITO and the cathode is aluminum, the interfacial layers are these two layers), then the barrier between the stages is reduced. This configuration is more preferred from the standpoints of luminescent efficiency and operating voltage.

The organic electroluminescent element of the invention is applicable to either single elements, or elements of a structure in which the elements have been disposed in an array arrangement, or a structure in which anodes and cathodes have been disposed in an X-Y matrix arrangement.

[Display Device and Lighting Device]

The display device and lighting device of the invention employ the organic electroluminescent element of the invention described above. The display device and lighting device of the invention are not particularly limited in the type and structure thereof, and can be assembled using the organic electroluminescent element of the invention in accordance with ordinary methods.

EXAMPLES

The invention will be explained below in more detail by reference to Examples. However, the invention should not be construed as being limited to the following Examples, and the invention can be modified at will unless the modifications depart from the spirit of the invention.

Synthesis of Organic Compounds of the Invention

Synthesis Example for Compound (C-1)

Synthesis of Intermediate 2

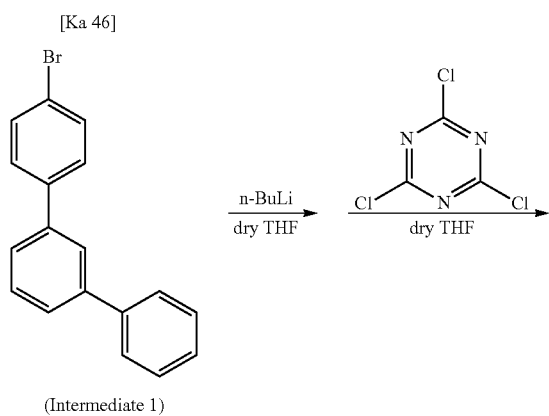

(Intermediate 1)

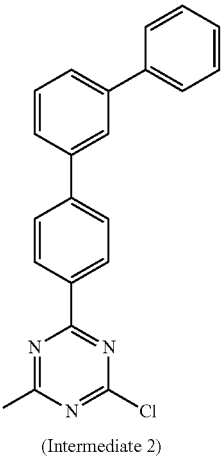

(Intermediate 2)

A solution of intermediate 1 (21.0 g, 67.9 mmol) in dry tetrahydrofuran (THF) (210 mL) was cooled to −78° C. Thereafter, a hexane solution of n-butyllithium (1.6 M, 42 mL) was added dropwise thereto, and the resultant mixture was stirred for 1 hour to obtain a lithium reagent. To a solution of cyanuric chloride (25.0 g, 136 mmol) in dry THF (250 mL) was dropwise added the lithium reagent prepared previously. This mixture was stirred for 3 hours. The resultant reaction solution was poured into ice water (300 mL), and the pH thereof was regulated to below 4 with 1 N hydrochloric acid. This mixture was extracted twice with methylene chloride (100 mL). The organic layer was washed twice with saturated aqueous sodium chloride solution (100 mL) and dried with magnesium sulfate. Thereafter, the solvent was distilled off under reduced pressure. The residue was purified by silica gel column chromatography using an eluent composed of hexane/methylene chloride=3/1. Thus, intermediate 2 (12.5 g, 49%) was obtained. Incidentally, the intermediate 1 was synthesized according to the method described in JP-A-2010-206191.

Synthesis of Intermediate 4

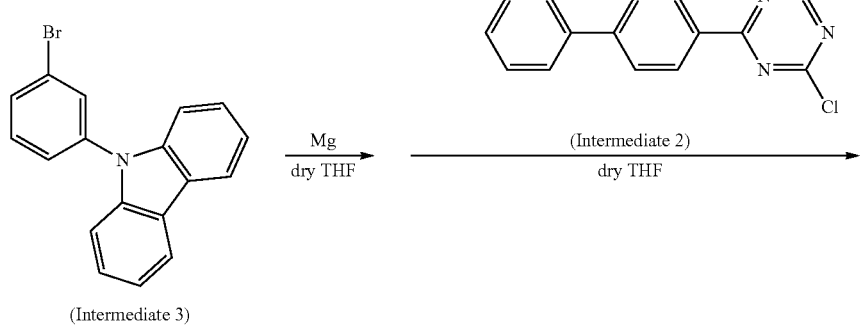

For example, the display device and lighting device of the invention can be produced by methods such as those described in *Yuki EL Disupurei* (Ohmsha, Ltd., published on Aug. 20, 2004, written by TOKITO Shizuo, ADACHI Chihaya, and MURATA Hideyuki).

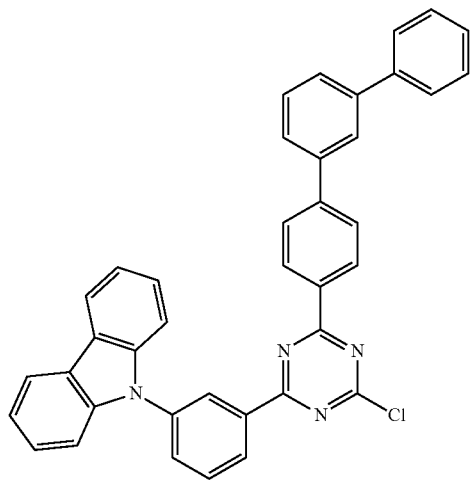

(Intermediate 4)

A solution of intermediate 3 (21.0 g, 65.2 mmol) in dry THF (45 mL) was added dropwise to magnesium pieces so that gentle refluxing occurred. This mixture was stirred at 60° C. for 1 hour to obtain a Grignard reagent. To a solution of intermediate 2 (11.9 g, 32.0 mmol) in dry THF (120 mL) was dropwise added the Grignard reagent prepared previously. This mixture was stirred at 45° C. for 6 hours. The resultant reaction solution was poured into ice water (200 mL), and this mixture was extracted with methylene chloride (400 mL). The organic layer was washed twice with saturated aqueous sodium chloride solution (100 mL) and dried with magnesium sulfate. Thereafter, the solvent was distilled off under reduced pressure. The residue was purified by silica gel column chromatography using an eluent composed of hexane/methylene chloride=2/1. Thus, intermediate 4 (13.4 g, 73%) was obtained. Incidentally, the intermediate 3 was synthesized according to the method described in JP-A-2010-206191.

Synthesis of Compound (C-1) of the Invention

[Ka 48]

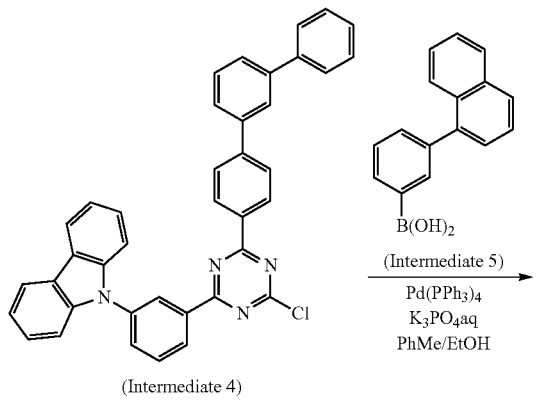

(Intermediate 4)

B(OH)$_2$
(Intermediate 5)

Pd(PPh$_3$)$_4$
K$_3$PO$_4$aq
PhMe/EtOH

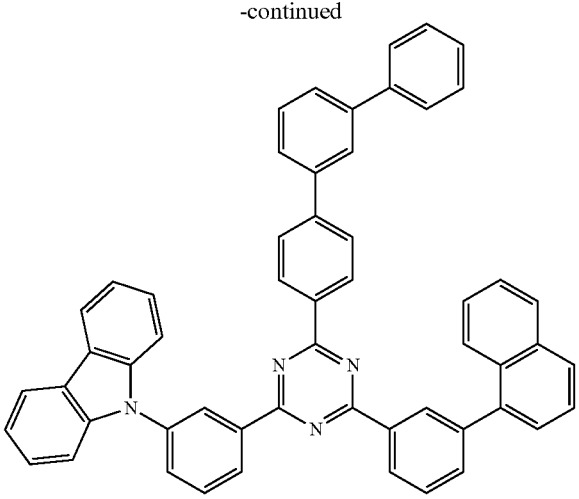

(Compound (C-1))

A toluene/ethanol mixture solution (2:1, 30 mL) which had undergone nitrogen bubbling was added to intermediate 4 (2.00 g, 3.41 mmol) and intermediate 5 (1.11 g, 4.47 mmol). Thereto were further added Pd(PPh$_3$)$_4$ (200 mg, 0.172 mmol) and an aqueous tripotassium phosphate solution (2.0 M, 5 mL) which had undergone nitrogen bubbling, in this order. Thereafter, the resultant mixture was stirred for 4 hours while heating the mixture with refluxing. After the mixture was returned to room temperature, distilled water was added thereto and the resultant mixture was extracted with toluene. The organic layer was washed with saturated aqueous sodium chloride solution and dried with magnesium sulfate. Thereafter, the solvent was distilled off under reduced pressure. The residue was purified by silica gel column chromatography using an eluent composed of hexane/methylene chloride=2/1. Thus, compound (C-1) (1.71 g, 67%) was obtained. The results of analysis by $^1$H NMR spectroscopy are shown below. Analysis by differential scanning calorimetry (DSC analysis) revealed that compound (C-1) had a glass transition temperature of 113° C. Incidentally, the intermediate 5 was synthesized according to the method described in WO2011/024922.
$^1$H NMR: δ [ppm] 8.99 (m, 1H), 8.90-8.80 (m, 5H), 8.18 (d, 2H), 7.95-7.91 (m, 3H), 7.87 (m, 1H), 7.81-7.30 (m, 5H), 7.77-7.36 (m, 24H).
Synthesis Example for Compound (C-2) of the Invention
[Ka 49]
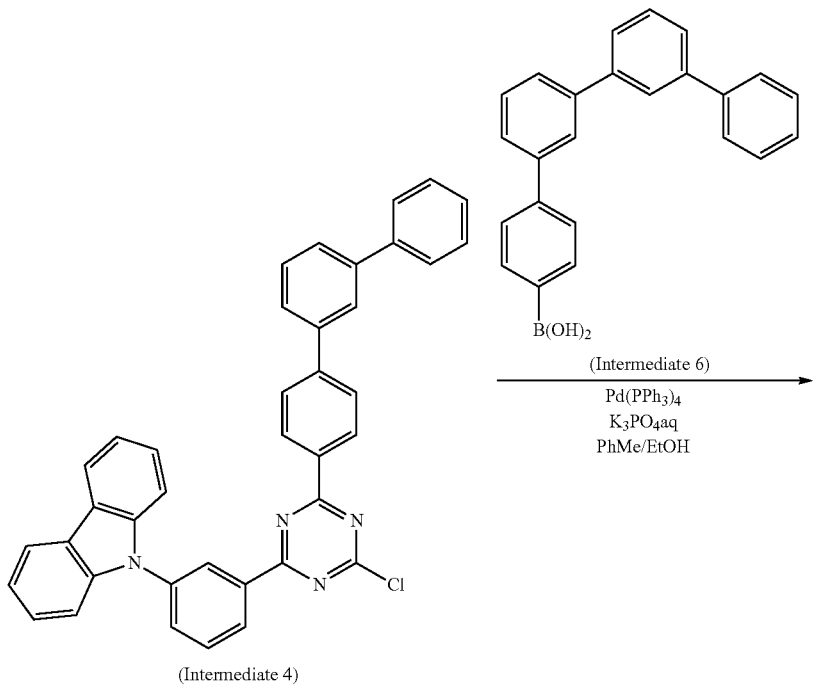
(Intermediate 4)
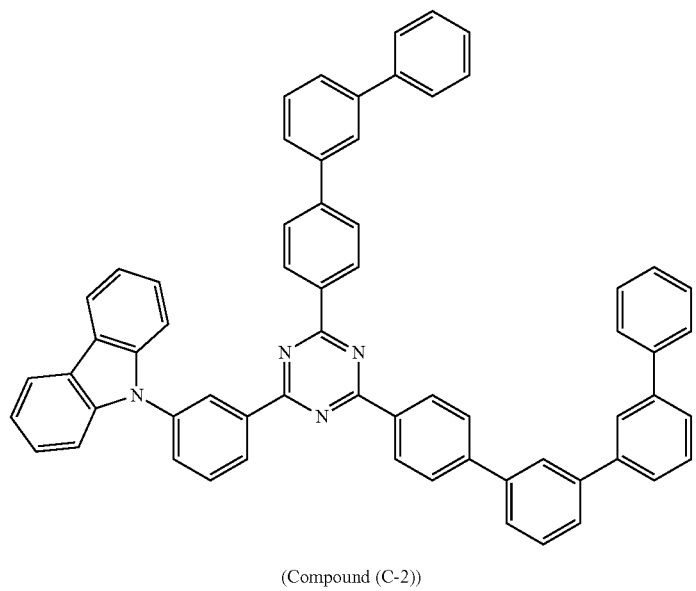
(Compound (C-2))

A toluene/ethanol mixture solution (2:1, 45 mL) which had undergone nitrogen bubbling was added to intermediate 4 (2.60 g, 4.44 mmol) and intermediate 6 (2.02 g, 5.77 mmol). Thereto were further added Pd(PPh$_3$)$_4$ (260 mg, 0.225 mmol) and an aqueous tripotassium phosphate solution (2.0 M, 7 mL) which had undergone nitrogen bubbling, in this order. Thereafter, the resultant mixture was stirred for 4 hours while heating the mixture with refluxing. After the mixture was returned to room temperature, distilled water was added thereto and the resultant mixture was extracted with toluene. The organic layer was washed with saturated aqueous sodium chloride solution and dried with magnesium sulfate. Thereafter, the solvent was distilled off under reduced pressure. The residue was purified by silica gel column chromatography using an eluent composed of hexane/methylene chloride=3/1 to 7/3. Thus, compound (C-2) (2.59 g, 68%) was obtained. The results of analysis by $^1$H NMR spectroscopy are shown below. Analysis by differential scanning calorimetry (DSC analysis) revealed that compound (C-2) had a glass transition temperature of 110° C.

$^1$H NMR: δ [ppm] 9.02 (m, 1H), 8.95-8.91 (m, 1H), 8.89-8.85 (m, 4H), 8.21 (d, 2H), 7.96 (t, 1H), 7.90 (t, 1H), 7.88-7.83 (m, 7H), 7.70-7.32 (m, 25H).

Synthesis Example for Compound (C-3) of the Invention (2.00 g, 3.41 mmol) and intermediate 7 (1.22 g, 4.44 mmol). Thereto were further added Pd(PPh$_3$)$_4$ (198 mg, 0.171 mmol) and an aqueous tripotassium phosphate solution (2.0 M, 5 mL) which had undergone nitrogen bubbling, in this order. Thereafter, the resultant mixture was stirred for 4 hours while heating the mixture with refluxing. After the mixture was returned to room temperature, distilled water was added thereto and the resultant mixture was extracted with toluene. The organic layer was washed with saturated aqueous sodium chloride solution and dried with magnesium sulfate. Thereafter, the solvent was distilled off under reduced pressure. The residue was purified by silica gel column chromatography using an eluent composed of hexane/methylene chloride=2/1. Thus, compound (C-3) (1.41 g, 53%) was obtained. The results of analysis by $^1$H NMR spectroscopy are shown below. Analysis by differential scanning calorimetry (DSC analysis) revealed that compound (C-3) had a glass transition temperature of 103° C.

$^1$H NMR: δ [ppm] 8.49-8.44 (m, 4H), 8.34 (t, 1H), 8.19 (d, 2H), 7.84 (t, 1H), 7.71-7.19 (m, 28H), 7.08-7.05 (m, 1H), 6.99 (t, 1H).

Synthesis Example for Compound (C-4) of the Invention

Synthesis of Intermediate 9

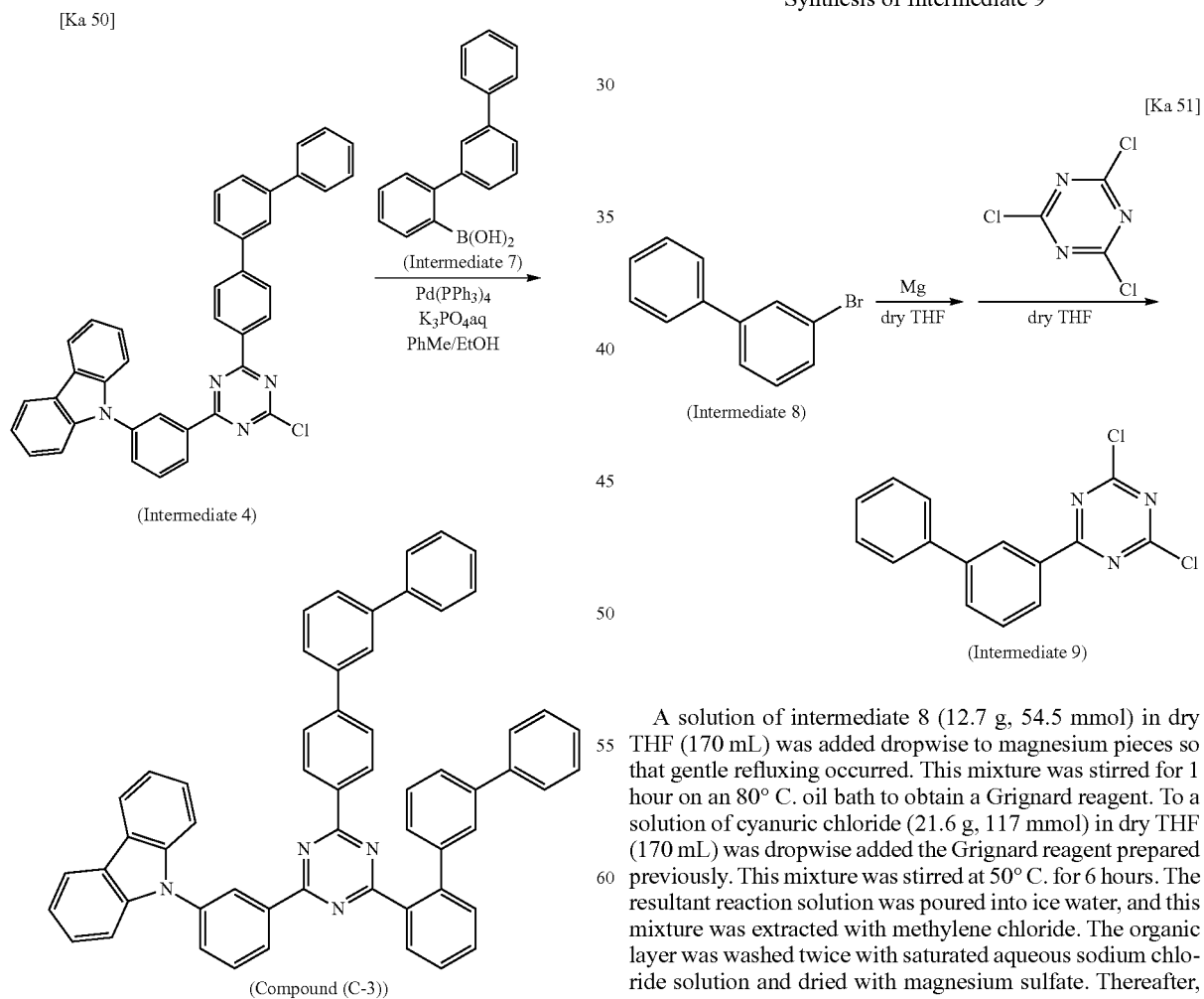

A solution of intermediate 8 (12.7 g, 54.5 mmol) in dry THF (170 mL) was added dropwise to magnesium pieces so that gentle refluxing occurred. This mixture was stirred for 1 hour on an 80° C. oil bath to obtain a Grignard reagent. To a solution of cyanuric chloride (21.6 g, 117 mmol) in dry THF (170 mL) was dropwise added the Grignard reagent prepared previously. This mixture was stirred at 50° C. for 6 hours. The resultant reaction solution was poured into ice water, and this mixture was extracted with methylene chloride. The organic layer was washed twice with saturated aqueous sodium chloride solution and dried with magnesium sulfate. Thereafter, the solvent was distilled off under reduced pressure. The residue was purified by silica gel column chromatography using an eluent composed of hexane/methylene chloride=4/1

A toluene/ethanol mixture solution (2:1, 30 mL) which had undergone nitrogen bubbling was added to intermediate 4 to 3/1 and then subjected to suspension washing in methanol to thereby obtain intermediate 9 (8.98 g, 55%). Incidentally, the intermediate 8 was purchased from Tokyo Kasei Kogyo Co., Ltd. (product No. B2001; 3-bromobiphenyl).

Synthesis of Intermediate 11

[Ka 52]

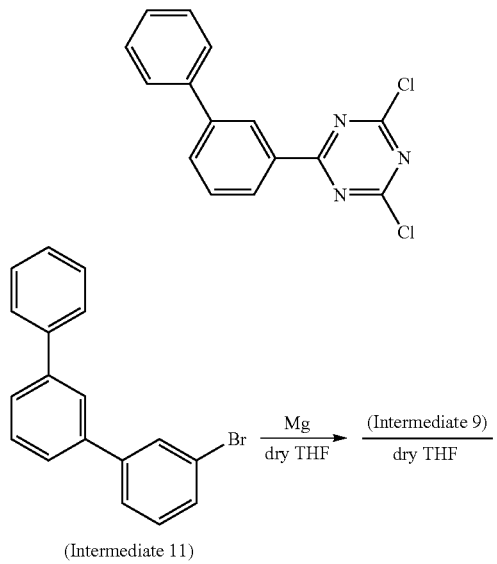

(Intermediate 11)

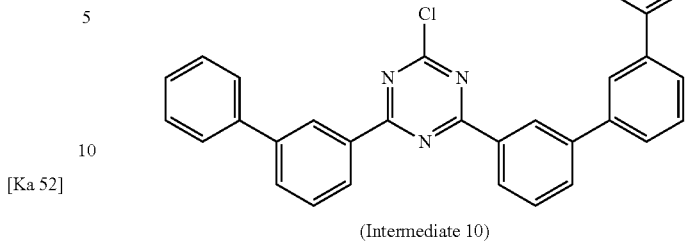

(Intermediate 10)

A solution of intermediate 10 (10.1 g, 32.7 mmol) in dry THF (80 mL) was added dropwise to magnesium pieces so that gentle refluxing occurred. This mixture was stirred for 1 hour on an 80° C. oil bath to obtain a Grignard reagent. To a solution of intermediate 9 (8.98 g, 29.7 mmol) in dry THF (80 mL) was dropwise added the Grignard reagent prepared previously. This mixture was stirred at 50° C. for 4 hours. The resultant reaction solution was poured into ice water, and this mixture was extracted with methylene chloride. The organic layer was washed twice with saturated aqueous sodium chloride solution and dried with magnesium sulfate. Thereafter, the solvent was distilled off under reduced pressure. The residue was purified by silica gel column chromatography using an eluent composed of hexane/methylene chloride=3/1 to 2/1 and then subjected to suspension washing in methanol to thereby obtain intermediate 11 (6.72 g, 46%). Incidentally, the intermediate 10 was synthesized according to the method described in JP-A-2010-206191.

Synthesis Example for Compound (C-4) of the Invention

[Ka 53]

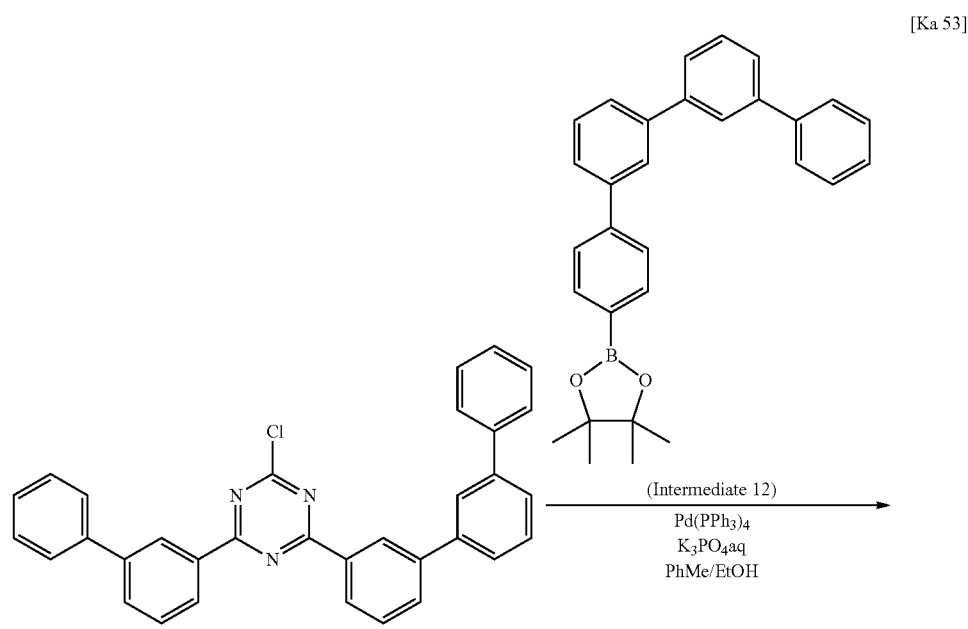

-continued

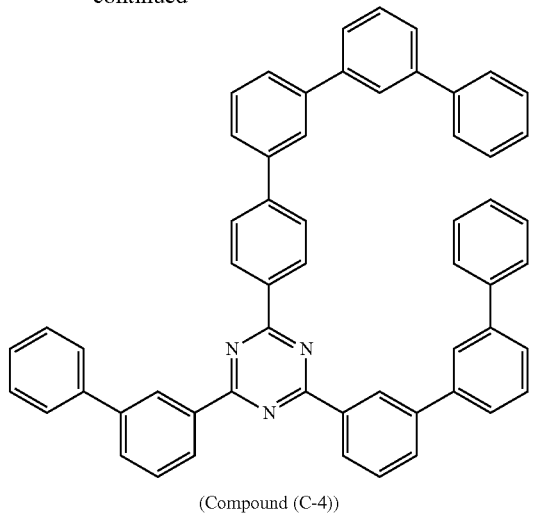

(Compound (C-4))

A toluene/ethanol mixture solution (2:1, 56 mL) which had undergone nitrogen bubbling was added to intermediate 11 (2.86 g, 5.77 mmol) and intermediate 12 (3.24 g, 7.50 mmol). Thereto were further added Pd(PPh$_3$)$_4$ (333 mg, 0.288 mmol) and an aqueous tripotassium phosphate solution (2.0 M, 9 mL) which had undergone nitrogen bubbling, in this order. Thereafter, the resultant mixture was stirred for 3 hours while heating the mixture with refluxing. After the mixture was returned to room temperature, distilled water was added thereto and the resultant mixture was extracted with toluene. The organic layer was washed with saturated aqueous sodium chloride solution and dried with magnesium sulfate. Thereafter, the solvent was distilled off under reduced pressure. The residue was purified by silica gel column chromatography using an eluent composed of hexane/methylene chloride=3/1 to 7/3 and then subjected to suspension washing in an ethyl acetate/ethanol solution. Thus, compound (C-4) (2.14 g, 48%) was obtained. The results of analysis by $^1$H NMR spectroscopy are shown below. Analysis by differential scanning calorimetry (DSC analysis) revealed that compound (C-4) had a glass transition temperature of 79° C.

$^1$H NMR: δ [ppm] 9.06 (m, 1H), 9.03 (m, 1H), 8.89 (d, 2H), 8.82-8.78 (m, 2H), 7.97-7.95 (m, 2H), 7.91-7.83 (m, 5H), 7.77-7.36 (m, 26H).

Synthesis Example for Compound (C-5) of the Invention

[Ka 54]

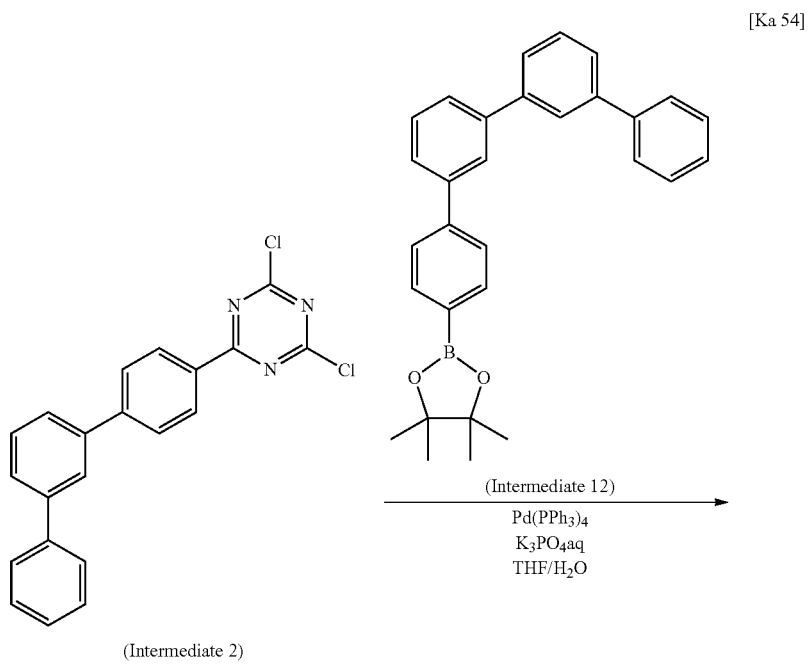

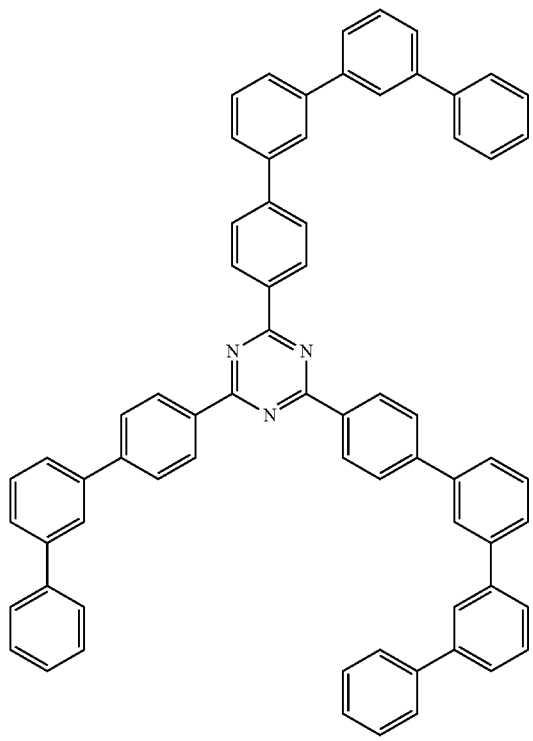

(Compound (C-5))

To intermediate 2 (13.3 g, 35.1 mmol) and intermediate 12 (36.4 g, 84.3 mol) were added tetrahydrofuran (525 mL) and an aqueous potassium carbonate solution (2.0 M, 105 mL) in this order. Thereafter, nitrogen bubbling was conducted. Thereto was further added Pd(PPh$_3$)$_4$ (4.06 g, 3.51 mmol). This mixture was stirred at 50° C. for 5.5 hours and then heated with refluxing for 3 hours. The resultant mixture was temporarily returned to room temperature, allowed to stand overnight, subsequently reheated, and then heated with refluxing for 5.5 hours. After the reaction mixture was returned to room temperature, distilled water was added thereto. This mixture was extracted with methylene chloride. The organic phase was washed with saturated aqueous sodium chloride solution and dried with magnesium sulfate. Thereafter, the solvent was distilled off under reduced pressure. The residue was purified by silica gel column chromatography and then further subjected to reprecipitation from methylene chloride/methanol. Thus, compound (C-5) (15.9 g, 49%) was obtained. The results of analysis by $^1$H NMR spectroscopy are shown below. Analysis by differential scanning calorimetry (DSC analysis) revealed that compound (C-5) had a glass transition temperature of 93° C.

$^1$H NMR: δ [ppm] 8.92-8.89 (m, 6H), 7.98 (t, 2H), 7.93-7.87 (m, 9H), 7.74-7.55 (m, 21H), 7.51-7.45 (m, 6H), 7.42-7.36 (m, 3H).

Synthesis Example for Compound (C-6) of the Invention

[Ka 55]

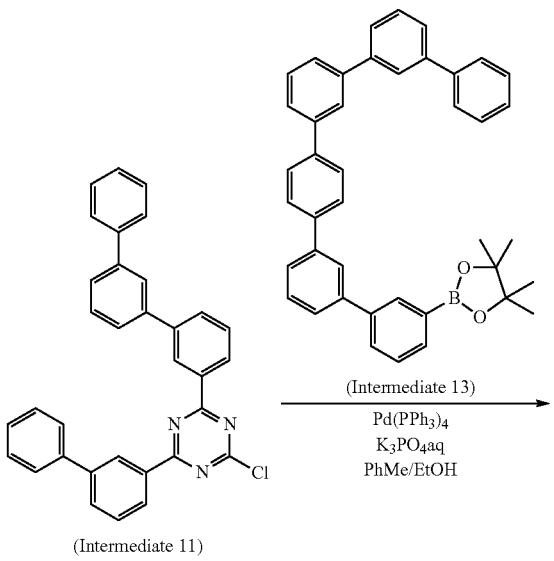

-continued

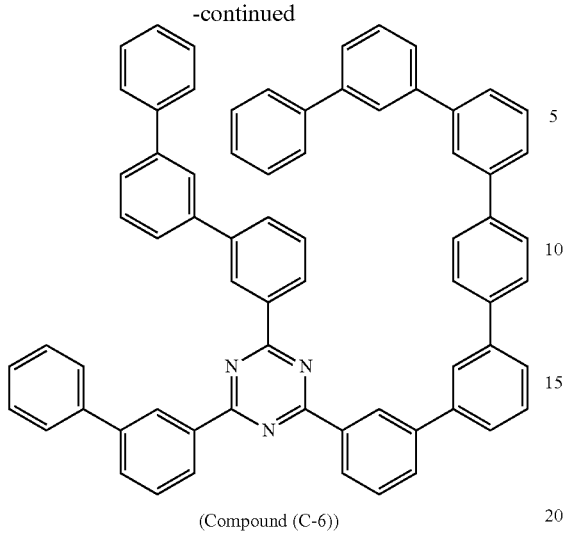

(Compound (C-6))

To intermediate 11 (2.23 g, 4.50 mmol) and intermediate 13 (3.16 g, 5.00 mmol) were added a toluene/ethanol mixture solution (2:1, 36 mL) and an aqueous tripotassium phosphate solution (2.0 M, 5.5 mL) in this order. Thereafter, nitrogen bubbling was conducted. Thereto was further added Pd(PPh$_3$)$_4$ (0.16 g, 0.14 mmol). This mixture was stirred for 4 hours while heating the mixture with refluxing. After the reaction mixture was returned to room temperature, the insoluble matter was taken out by filtration and washed with toluene, distilled water, and ethanol. The filtrate and washings which resulted from these operations were put together and concentrated under reduced pressure, and ethanol was added to the concentrate. The solid generated was taken out by filtration and washed with water and ethanol. The washed solids were put together and dried. Thus, compound (C-6) (2.0 g, 48%) was obtained. The results of analysis by $^1$H NMR spectroscopy are shown below. Analysis by differential scanning calorimetry (DSC analysis) revealed that compound (C-6) had a glass transition temperature of 92° C.

$^1$H NMR: δ [ppm] 9.10 (t, 1H), 9.08 (t, 1H), 9.04 (t, 1H), 8.83-8.78 (m, 3H), 8.01 (t, 1H), 7.95-7.34 (m, 40H).

Synthesis Example for Compound (C-7) of the Invention

Synthesis of Intermediate 15

[Ka 56]

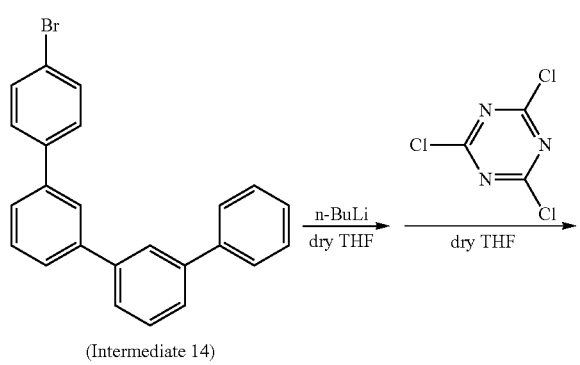

(Intermediate 14)

-continued

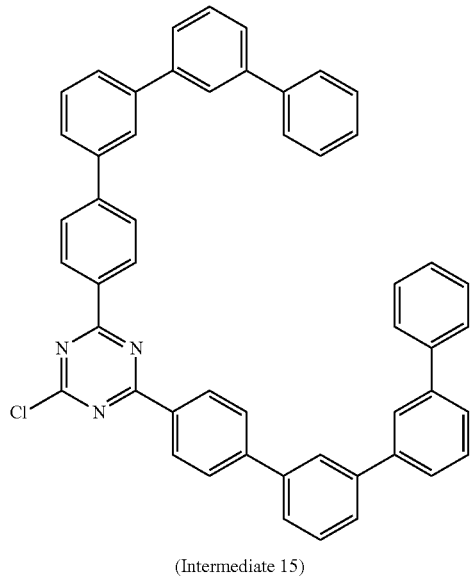

(Intermediate 15)

A solution of intermediate 14 (23 g, 60 mmol) in dry tetrahydrofuran (THF) (100 mL) was cooled to −75° C. Thereafter, a hexane solution of n-butyllithium (1.65 M, 37 mL) was added dropwise thereto. This mixture was stirred at −75° C. for 5 hours and then cooled to −90° C. to obtain a lithium reagent. To a solution of cyanuric chloride (5.0 g, 27 mmol) in dry THF (50 mL) was dropwise added at −90° C. to −70° C. the lithium reagent prepared previously. The resultant mixture was stirred at −70° C. for 2 hours and then allowed to stand at room temperature for 12 hours. This reaction solution was poured into ice water, and the resultant mixture was neutralized with 1 N hydrochloric acid and then extracted with methylene chloride. The organic layer was washed with distilled water and dried with magnesium sulfate. Thereafter, the solvent was distilled off under reduced pressure. The residue was washed with methylene chloride to obtain intermediate 15 (8.4 g, 43%). Incidentally, the intermediate 14 was synthesized by reacting intermediate 10 with p-bromoiodobenzene, according to the method described in JP-A-2010-206191.

Synthesis Example for Compound (C-7) of the Invention

[Ka 57]

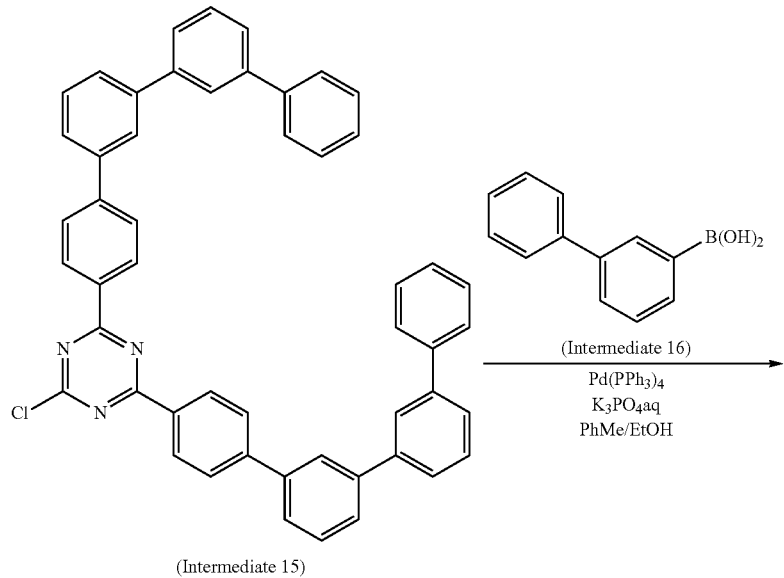

(Intermediate 15)

(Intermediate 16)

Pd(PPh₃)₄
K₃PO₄aq
PhMe/EtOH

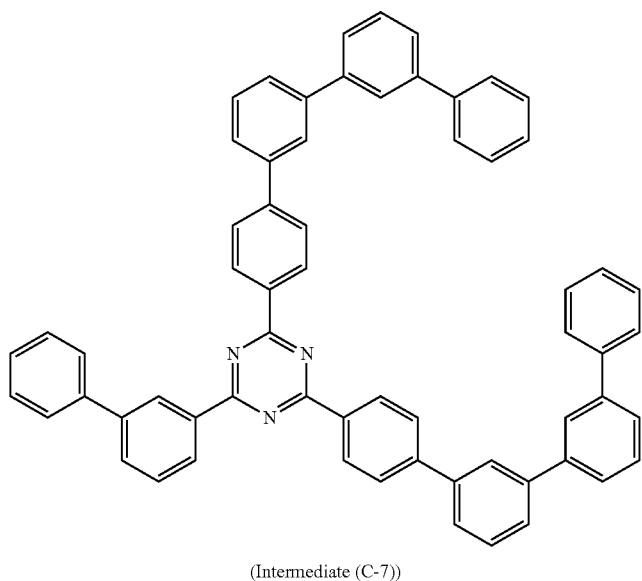

(Intermediate (C-7))

A toluene/ethanol mixture solution (2:1, 318 mL) was added to intermediate 15 (7.5 g, 10 mmol) and intermediate 16 (2.25 g, 11.3 mmol), and nitrogen bubbling was conducted. Thereto were further added Pd(PPh₃)₄ (0.36 g, 0.31 mmol) and an aqueous tripotassium phosphate solution (2.0 M, 13 mL) which had undergone nitrogen bubbling, in this order. Thereafter, the resultant mixture was stirred for 2.5 hours while heating the mixture with refluxing. After the mixture was returned to room temperature, distilled water was added thereto and the resultant mixture was separated into an organic phase and an aqueous phase. The organic phase was washed with saturated aqueous sodium chloride solution and dried with magnesium sulfate. Thereafter, the solvent was distilled off under reduced pressure. The residue was purified by silica gel column chromatography and recrystallized from toluene. Thus, compound (C-7) (4.50 g, 52%) was obtained. The results of analysis by $^1$H NMR spectroscopy are shown below. Analysis by differential scanning calorimetry (DSC analysis) revealed that compound (C-7) had a glass transition temperature of 90° C.

$^1$H NMR: δ [ppm] 9.03 (t, 1H), 8.90 (d, 4H), 8.81-8.78 (m, 1H), 7.98 (t, 2H), 7.90-7.84 (m, 7H), 7.78-7.36 (m, 28H).

Synthesis Example for Compound (C-8) of the Invention

Synthesis of Intermediate 17

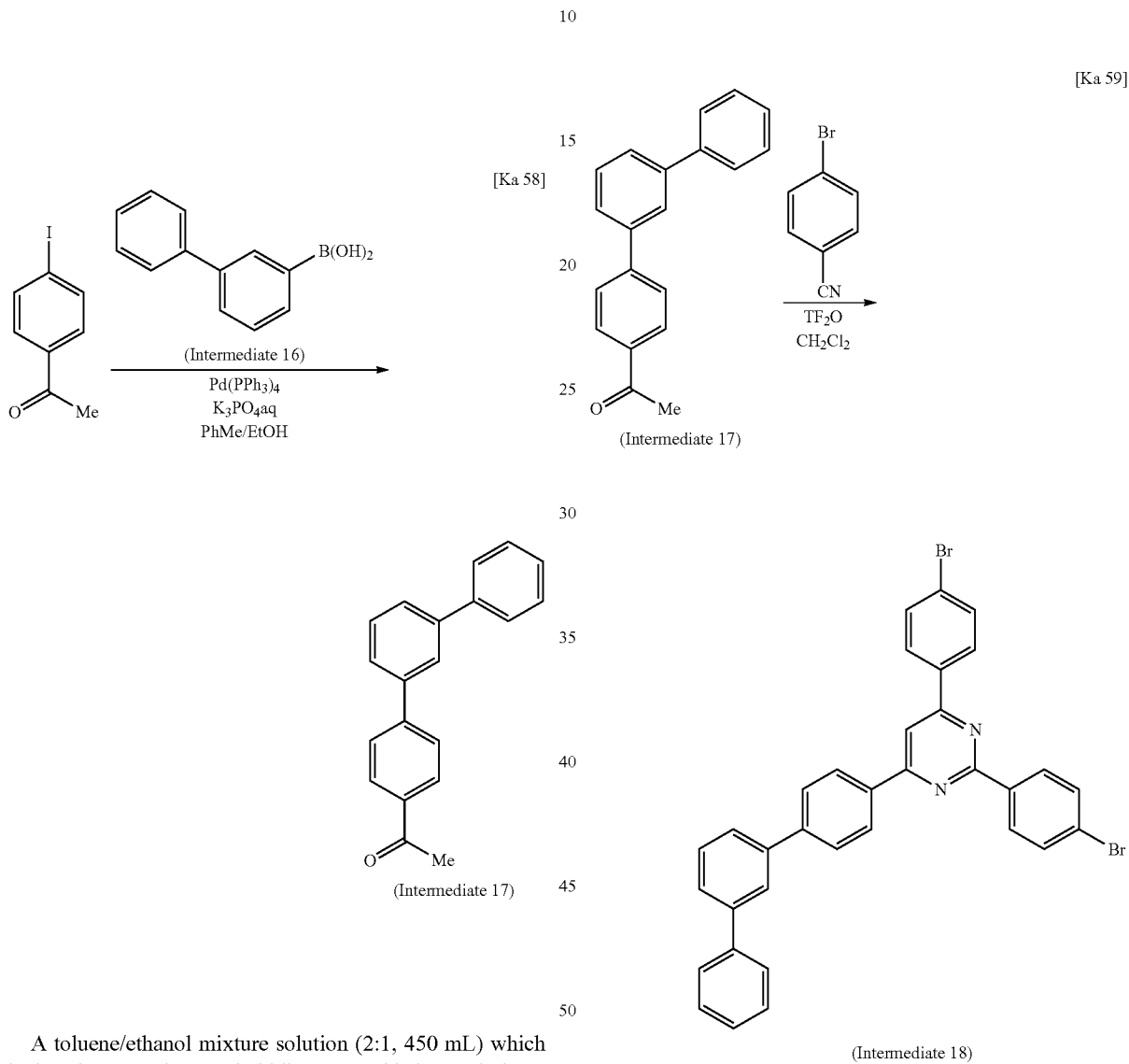

A toluene/ethanol mixture solution (2:1, 450 mL) which had undergone nitrogen bubbling was added to 4'-iodoacetophenone (20.6 g, 83.8 mmol; manufactured by Tokyo Kasei Kogyo Co., Ltd. (product No. I0305)) and intermediate 16 (19.9 g, 101 mmol). Thereto were added Pd(PPh$_3$)$_4$ (1.94 g, 1.68 mmol) and an aqueous tripotassium phosphate solution (2.0 M, 105 mL) which had undergone nitrogen bubbling, in this order. Thereafter, the resultant mixture was stirred for 2 hours while heating the mixture with refluxing. After the mixture was returned to room temperature, distilled water was added thereto and the resultant mixture was extracted with toluene. The organic layer was washed with saturated aqueous sodium chloride solution and dried with magnesium sulfate. Thereafter, the solvent was distilled off under reduced pressure. The residue was purified by silica gel column chromatography to obtain intermediate 17 (21.4 g, 94%).

Synthesis Example for Intermediate 18

A solution in methylene chloride (160 mL) of intermediate 17 (20.0 g, 73.4 mmol), 4-bromobenzonitrile (28.1 g, 154 mmol; manufactured by Tokyo Kasei Kogyo Co., Ltd. (product No. B1426)), and trifluoromethanesulfonic acid anhydride (15 mL) was stirred for 19 hours. An aqueous sodium hydrogen carbonate solution was added to the reaction solution to neutralize the reaction solution. Thereafter, methylene chloride was added thereto, and the residue was taken out by suction filtration to obtain intermediate 18 (2.9 g, 6%).

Synthesis Example for Compound (C-8) of the Invention

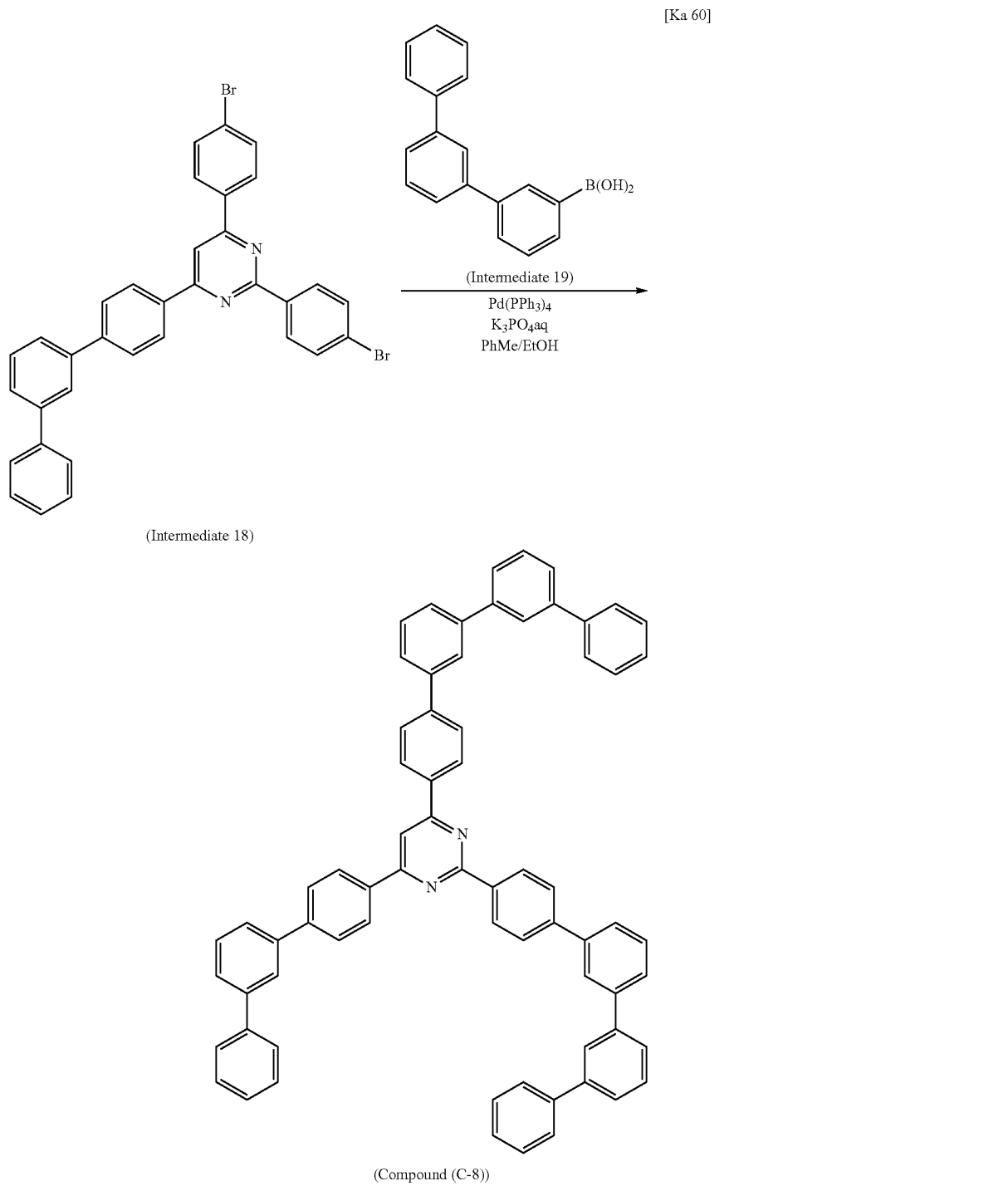

A toluene/ethanol mixture solution (2:1, 18 mL) which had undergone nitrogen bubbling was added to intermediate 18 (618 mg, 1.00 mmol) and intermediate 19 (685 mg, 2.50 mmol). Thereto were added Pd(PPh$_3$)$_4$ (58 mg, 0.05 mmol) and an aqueous tripotassium phosphate solution (2.0 M, 3 mL) which had undergone nitrogen bubbling, in this order. Thereafter, the resultant mixture was stirred for 1.5 hours while heating the mixture with refluxing. After the mixture was returned to room temperature, distilled water was added thereto and the resultant mixture was extracted with toluene. The organic layer was washed with saturated aqueous sodium chloride solution and dried with magnesium sulfate. Thereafter, the solvent was distilled off under reduced pressure. The residue was purified by silica gel column chromatography. Thus, compound (C-8) (330 mg, 36%) was obtained. The results of analysis by $^1$H NMR spectroscopy are shown below. Analysis by differential scanning calorimetry (DSC analysis) revealed that compound (C-8) had a glass transition temperature of 95° C.

$^1$H NMR: δ [ppm] 8.86 (d, 2H), 8.43 (dd, 4H), 8.12 (s, 1H), 7.98-7.95 (m, 2H), 7.91-7.85 (m, 9H), 7.73-7.54 (m, 21H), 7.51-7.46 (m, 6H), 7.42-7.36 (m, 3H).

Synthesis Example for Compound (C-9) of the Invention

Synthesis Example for Intermediate 21

[Ka 61]

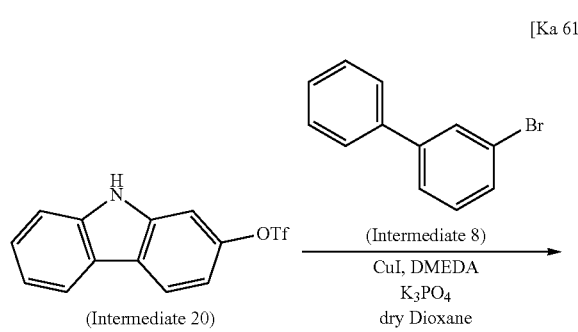

Synthesis of Intermediate 22

[Ka 62]

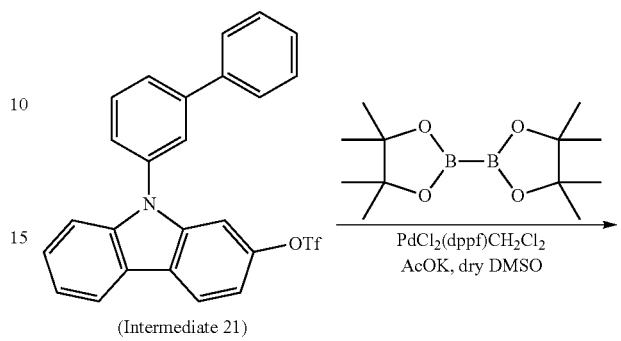

A solution in dehydrated dioxane (150 mL) of intermediate 20 (11.6 g, 36.7 mmol; manufactured by Aldrich Co. (9H-carbazol-2-yl trifluoromethanesulfonate); product No. 639206), and intermediate 8 (9.42 g, 40.4 mmol) was subjected to nitrogen bubbling. Thereto were added CuI (1.40 g, 7.35 mmol), DMEDA (1.6 mL, 14.5 mmol), and tripotassium phosphate (31.2 g, 147 mmol) in this order. This mixture was heated with refluxing for 7 hours. After the resultant reaction mixture was returned to room temperature, this mixture was extracted with methylene chloride. The organic phase was washed with distilled water and dried with magnesium sulfate. Thereafter, the solvent was distilled off under reduced pressure. The residue was purified by silica gel column chromatography to obtain intermediate 21 (11.6 g, 67%).

A solution of intermediate 21 (11.6 g, 24.8 mmol) and bis(pinacolatodiborane) (7.54 g, 29.7 mmol) in dehydrated DMSO (100 mL) was subjected to nitrogen bubbling at 60° C. Thereafter, PdCl$_2$(dppf)CH$_2$Cl$_2$ (606 mg, 0.743 mmol) and potassium acetate (31.2 g, 147 mmol) were added thereto in this order, and the resultant mixture was stirred at 100° C. for 7.5 hours. After the mixture was returned to room temperature, this mixture was extracted with methylene chloride, and the organic phase was washed with distilled water and dried with magnesium sulfate. Thereafter, the solvent was distilled off under reduced pressure. The residue was purified by silica gel column chromatography to obtain intermediate 22 (6.58 g, 60%).

Synthesis of Intermediate 23

[Ka 63]

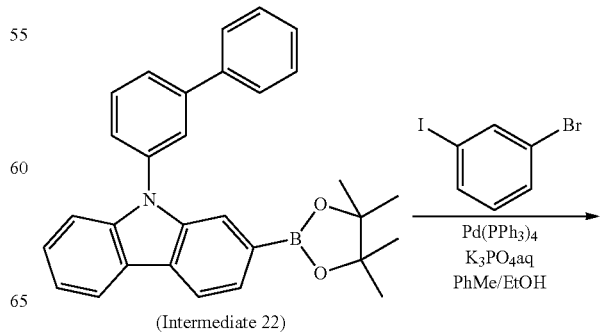

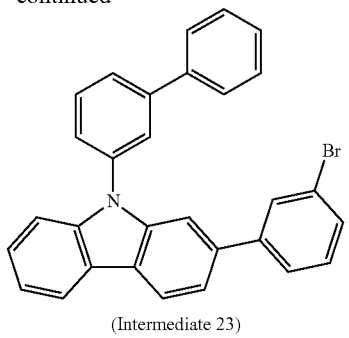

(Intermediate 23)

A toluene/ethanol mixture solution (2:1, 112 mL) which had undergone nitrogen bubbling was added to intermediate 22 (6.58 g, 14.8 mmol) and 3-bromoiodobenzene (4.39 g, 15.5 mmol). Thereto were added Pd(PPh$_3$)$_4$ (510 mg, 0.44 mmol) and an aqueous tripotassium phosphate solution (2.0 M, 19 mL) which had undergone nitrogen bubbling, in this order. Thereafter, the resultant mixture was stirred for 4 hours while heating the mixture with refluxing. After the mixture was returned to room temperature, distilled water was added thereto and the resultant mixture was extracted with toluene. The organic layer was washed with distilled water and dried with magnesium sulfate. Thereafter, the solvent was distilled off under reduced pressure. The residue was purified by silica gel column chromatography to obtain intermediate 23 (6.59 g, 94%).

Synthesis of Intermediate 24

[Ka 64]

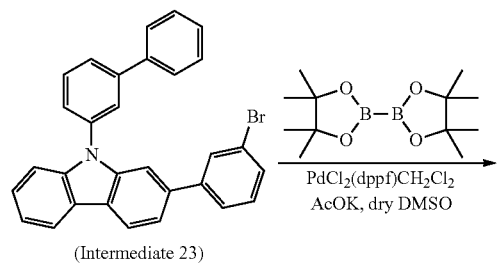

A solution of intermediate 23 (6.59 g, 13.9 mmol) and bis(pinacolatodiborane) (3.88 g, 15.3 mmol) in dehydrated DMSO (100 mL) was subjected to nitrogen bubbling. Thereafter, PdCl$_2$(dppf)CH$_2$Cl$_2$ (340 mg, 0.42 mmol) and potassium acetate (6.82 g, 69.5 mmol) were added thereto in this order, and the resultant mixture was stirred at 100° C. for 5 hours. After the mixture was returned to room temperature, distilled water was added thereto and this mixture was extracted with methylene chloride. The organic phase was washed with distilled water and dried with magnesium sulfate. Thereafter, the solvent was distilled off under reduced pressure. The residue was purified by silica gel column chromatography to obtain intermediate 24 (3.63 g, 50%).

Synthesis of Intermediate 25

[Ka 65]

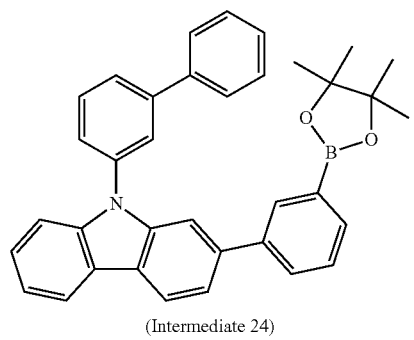

A toluene/ethanol mixture solution (2:1, 54 mL) which had undergone nitrogen bubbling was added to intermediate 24 (3.63 g, 6.96 mmol) and 4-bromoiodobenzene (2.07 g, 7.31 mmol). Thereto were added Pd(PPh$_3$)$_4$ (241 mg, 0.21 mmol) and an aqueous tripotassium phosphate solution (2.0 M, 9 mL) which had undergone nitrogen bubbling, in this order. Thereafter, the resultant mixture was stirred for 2 hours while heating the mixture with refluxing. Furthermore, Pd(PPh$_3$)$_4$ (500 mg) was added thereto, and this mixture was stirred for 2 hours while heating the mixture with refluxing. After the mixture was returned to room temperature, distilled water was added thereto and the resultant mixture was extracted with toluene. The organic layer was washed with distilled water and dried with magnesium sulfate. Thereafter, the solvent was distilled off under reduced pressure. The residue was purified by silica gel column chromatography to obtain intermediate 25 (3.21 g, 84%).

Synthesis of Intermediate 26

Synthesis of Intermediate 27

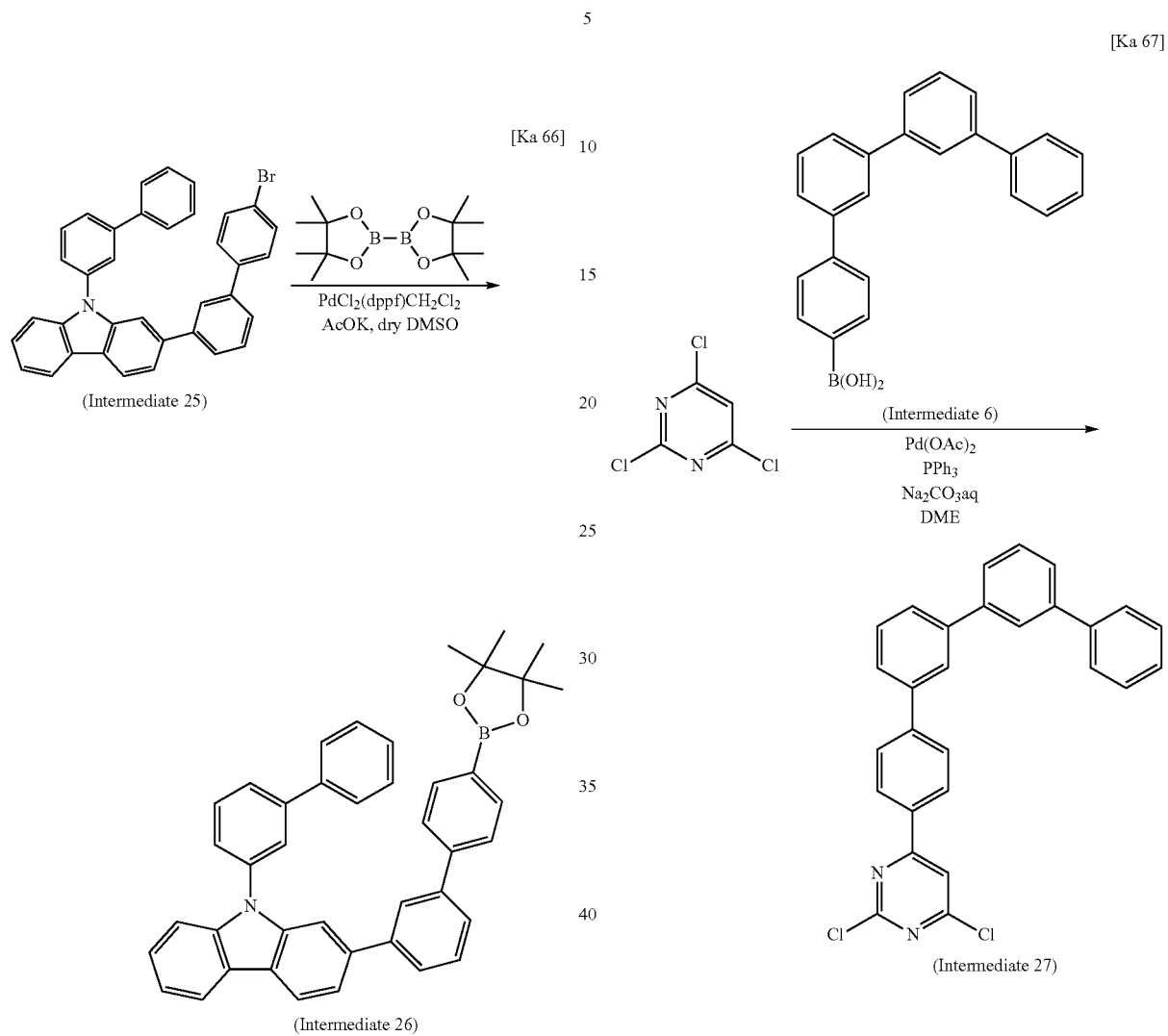

A solution of intermediate 25 (3.21 g, 5.83 mmol) and bis(pinacolatodiborane) (1.78 g, 7.00 mmol) in dehydrated DMSO (50 mL) was subjected to nitrogen bubbling. Thereafter, PdCl$_2$(dppOCH$_2$Cl$_2$ (143 mg, 0.17 mmol) and potassium acetate (2.86 g, 29.3 mmol) were added thereto in this order, and the resultant mixture was stirred at 95° C. for 4 hours. After the mixture was returned to room temperature, distilled water was added thereto and this mixture was extracted with methylene chloride. The organic phase was washed with distilled water and dried with magnesium sulfate. Thereafter, the solvent was distilled off under reduced pressure. The residue was purified by silica gel column chromatography to obtain intermediate 26 (1.29 g, 37%).

2,4,6-Trichloropyrimidine (25.0 g, 136 mmol; manufactured by Tokyo Kasei Kogyo Co., Ltd. (product No. T0417)), intermediate 6 (25.4 g, 72.6 mmol), DME (500 mL), and an aqueous sodium carbonate solution (2.0 M, 113 mL) were introduced in this order. Thereafter, nitrogen bubbling was conducted for 15 minutes. Thereto were added Pd(OAc)$_2$ (0.49 g, 2.17 mmol) and PPh$_3$ (1.14 g, 4.35 mmol) in this order. The temperature of the oil bath was gradually elevated to 100° C., and the reaction solution was heated with refluxing for 7 hours. After the resultant mixture was returned to room temperature, distilled water was added thereto and the resultant mixture was extracted with methylene chloride. The organic phase was washed with distilled water and dried with magnesium sulfate. Thereafter, the solvent was distilled off under reduced pressure. The residue was purified by silica gel column chromatography to obtain intermediate 27 (19.1 g, 58%).

Synthesis of Intermediate 28

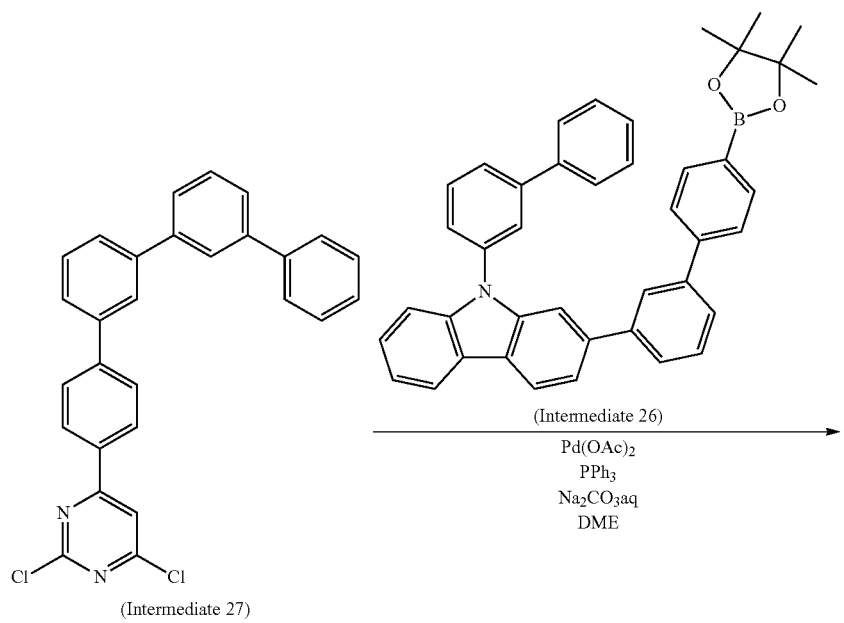

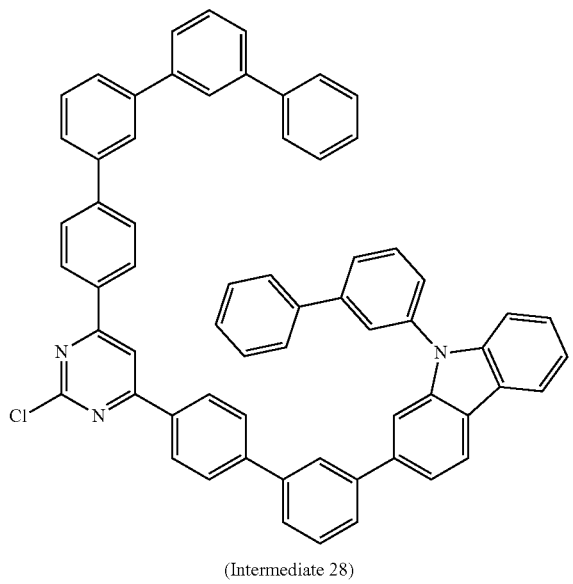

DME (20 mL) which had undergone nitrogen bubbling, Pd(OAc)$_2$ (24 mg, 0.11 mmol), PPh$_3$ (57 mg, 0.22 mmol), and an aqueous tripotassium phosphate solution (2.0 M, 4 mL) which had undergone nitrogen bubbling were introduced, in this order, into a flask which contained intermediate 27 (0.98 g, 2.2 mmol) and intermediate 26 (1.29 g, 2.2 mmol). Thereafter, the resultant mixture was heated at 100° C. with refluxing for 6 hours. After the reaction mixture was returned to room temperature, distilled water was added thereto and this mixture was extracted with methylene chloride. The organic phase was washed with distilled water and dried with magnesium sulfate. Thereafter, the solvent was distilled off under reduced pressure. The residue was purified by silica gel column chromatography to obtain intermediate 28 (1.21 g, 63%).

Synthesis Example for Compound (C-9) of the Invention

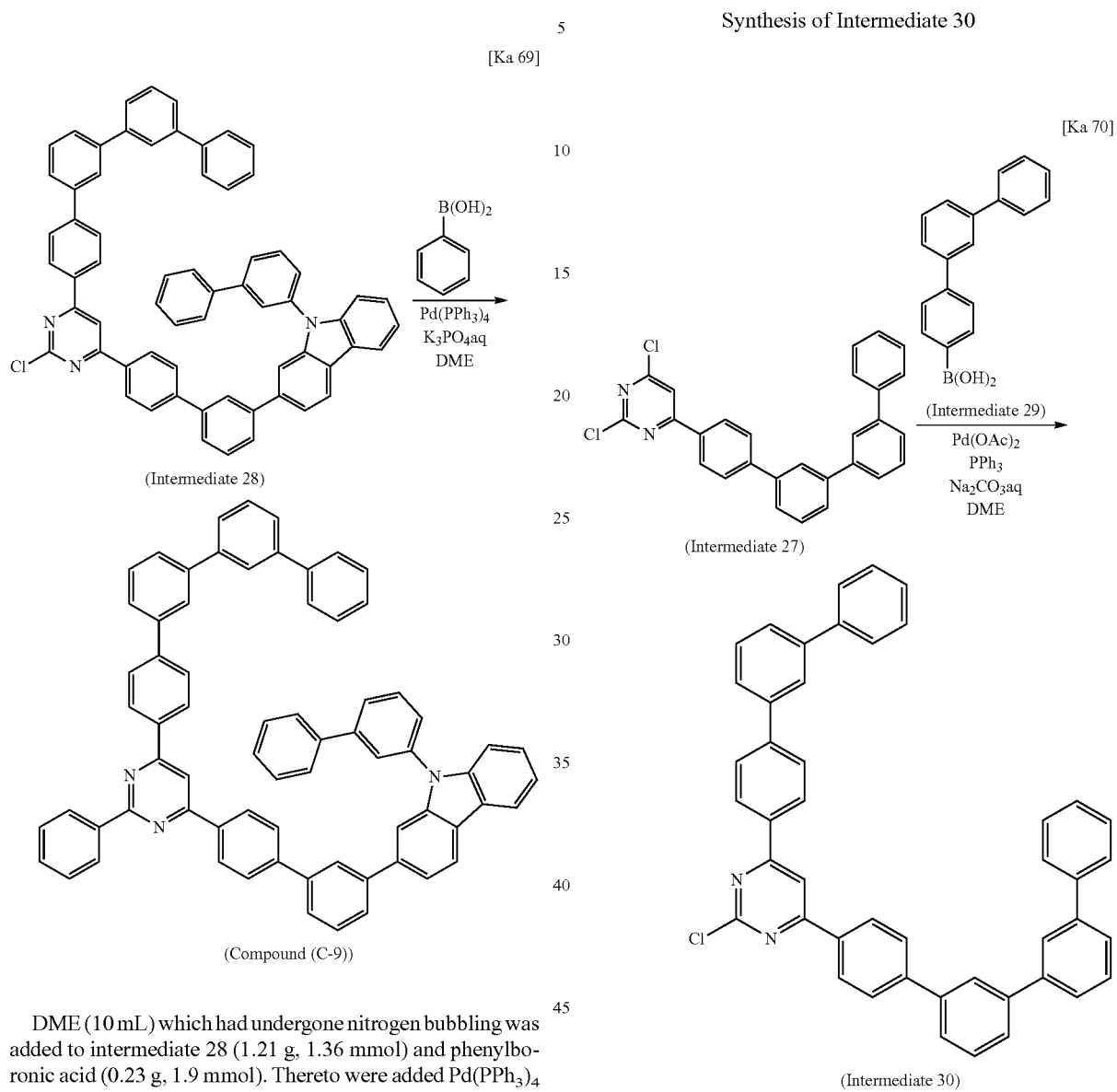

DME (10 mL) which had undergone nitrogen bubbling was added to intermediate 28 (1.21 g, 1.36 mmol) and phenylboronic acid (0.23 g, 1.9 mmol). Thereto were added Pd(PPh$_3$)$_4$ (0.15 g, 0.13 mmol) and an aqueous tripotassium phosphate solution (2.0 M, 2 mL) which had undergone nitrogen bubbling, in this order. Thereafter, the resultant mixture was stirred for 3 hours while heating the mixture with refluxing. After the mixture was returned to room temperature, distilled water was added thereto and the resultant mixture was extracted with methylene chloride. The organic phase was washed with distilled water and dried with magnesium sulfate. Thereafter, the solvent was distilled off under reduced pressure. The residue was purified by silica gel column chromatography. Thus, compound (C-9) (0.96 g, 76%) was obtained. The results of analysis by $^1$H NMR spectroscopy are shown below. Analysis by differential scanning calorimetry (DSC analysis) revealed that compound (C-9) had a glass transition temperature of 125° C.

$^1$H NMR: δ [ppm] 8.78-8.76 (m, 2H), 8.41 (t, 4H), 8.25 (d, 1H), 8.19 (d, 1H), 8.10 (s, 1H), 7.96-7.92 (m, 2H), 7.90-7.80 (m, 6H), 7.74-7.30 (m, 30H).

Synthesis Example for Compound (C-10) of the Invention

Synthesis of Intermediate 30

DME (250 mL) which had undergone nitrogen bubbling, Pd(OAc)$_2$ (198 mg, 0.88 mmol), PPh$_3$ (463 mg, 1.77 mmol), and an aqueous sodium carbonate solution (2.0 M, 46 mL) which had undergone nitrogen bubbling were introduced, in this order, into a flask which contained intermediate 27 (12.0 g, 26.5 mmol) and intermediate 29 (8.07 g, 29.4 mmol). Thereafter, the resultant mixture was heated at 100° C. with refluxing for 6 hours. After the reaction mixture was returned to room temperature, the mixture was concentrated under reduced pressure and the residue was extracted with methylene chloride. The organic phase was washed with distilled water and dried with magnesium sulfate. Thereafter, the solvent was distilled off under reduced pressure. The residue was purified by silica gel column chromatography to obtain intermediate 30 (8.15 g, 48%).

Synthesis Example for Compound (C-10) of the Invention

[Ka 71]

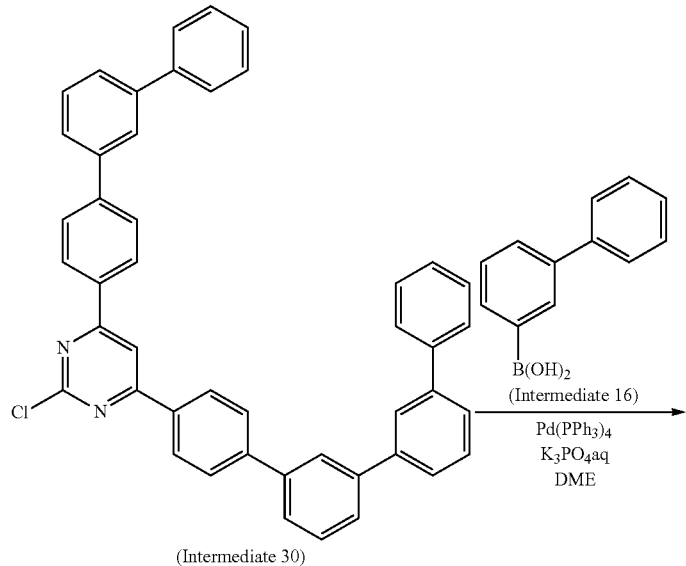

(Intermediate 30)

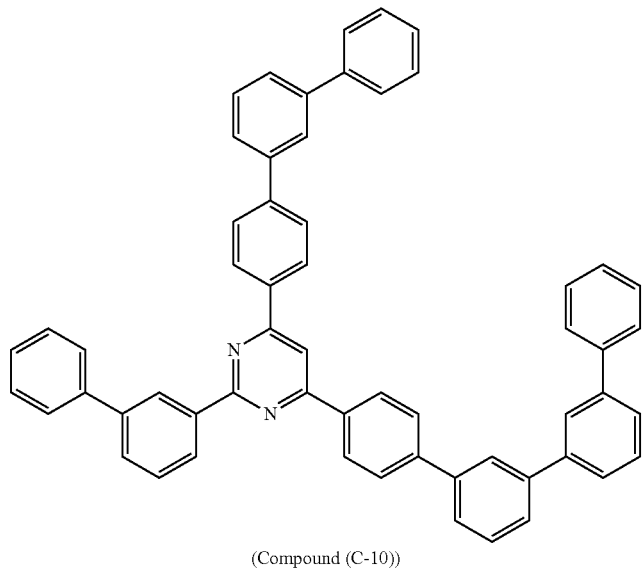

(Compound (C-10))

DME (20 mL) which had undergone nitrogen bubbling, Pd(OAc)$_2$ (26 mg, 0.12 mmol), PPh$_3$ (61 mg, 0.23 mmol), and an aqueous sodium carbonate solution (2.0 M, 4 mL) which had undergone nitrogen bubbling were introduced, in this order, into a flask which contained intermediate 30 (1.5 g, 2.3 mmol) and intermediate 16 (0.60 g, 3.0 mmol). Thereafter, the resultant mixture was heated at 100° C. with refluxing for 6 hours. After the reaction mixture was temporarily returned to room temperature, Pd(PPh$_3$)$_4$ (0.13 g) and an aqueous tripotassium phosphate solution (2.0 M, 4 mL) which had undergone nitrogen bubbling were added thereto in this order. The resultant mixture was heated with refluxing for further 3.5 hours. After the reaction mixture was returned to room temperature, the mixture was extracted with methylene chloride. The organic phase was washed with distilled water and dried with magnesium sulfate. Thereafter, the solvent was distilled off under reduced pressure. The residue was purified by silica gel column chromatography. Thus, compound (C-10) (0.82 g, 45%) was obtained. The results of analysis by $^1$H NMR spectroscopy are shown below. Analysis by differential scanning calorimetry (DSC analysis) revealed that compound (C-10) had a glass transition temperature of 85° C.

$^1$H NMR: δ [ppm] 8.99 (t, 1H), 8.76-8.74 (m, 1H), 8.43 (dd, 4H), 8.13 (s, 1H), 7.95 (t, 1H), 7.91-7.85 (m, 6H), 7.78-7.75 (m, 3H), 7.71-7.46 (m, 20H), 7.42-7.37 (m, 3H).

Synthesis Example for Compound (C-11) of the Invention

[Ka 72]

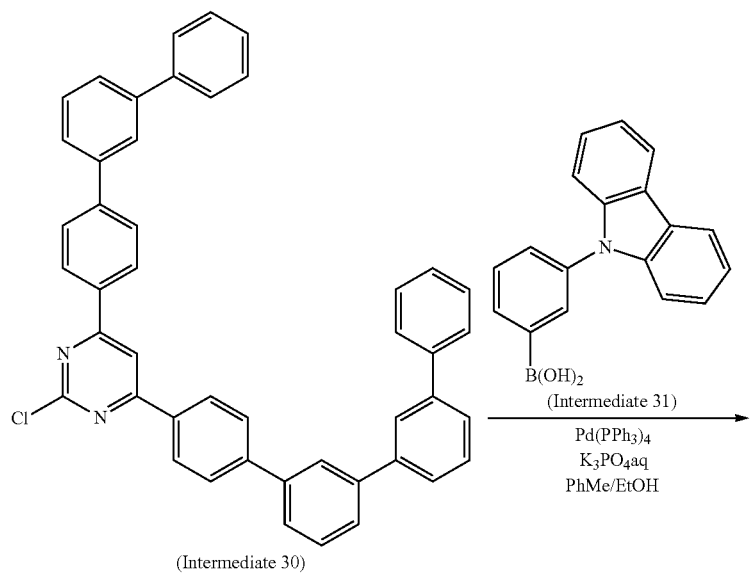

(Intermediate 30)

(Intermediate 31)

Pd(PPh₃)₄
K₃PO₄aq
PhMe/EtOH

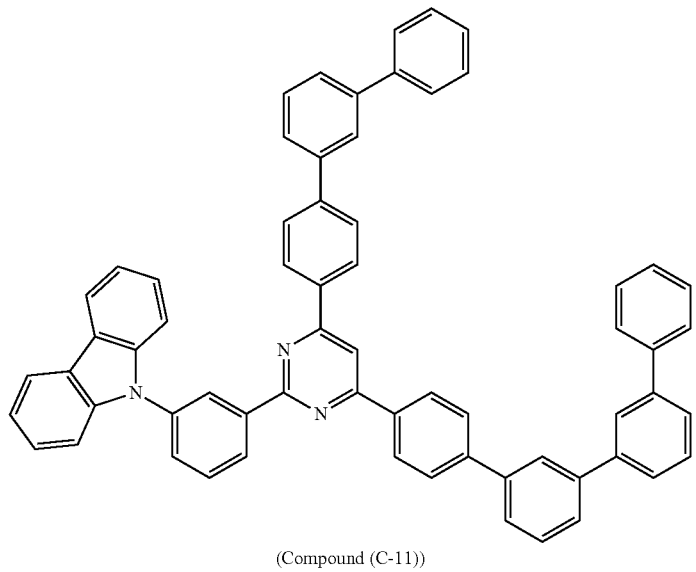

(Compound (C-11))

DME (20 mL) which had undergone nitrogen bubbling, Pd(PPh₃)₄ (89 mg, 0.077 mmol), and an aqueous tripotassium phosphate solution (2.0 M, 3 mL) which had undergone nitrogen bubbling were introduced, in this order, into a flask which contained intermediate 30 (1.0 g, 1.5 mmol) and intermediate 31 (0.58 g, 2.0 mmol). The resultant mixture was heated with refluxing for 3 hours. After the reaction mixture was returned to room temperature, the mixture was extracted with methylene chloride. The organic phase was washed with distilled water and dried with magnesium sulfate. Thereafter, the solvent was distilled off under reduced pressure. The residue was purified by silica gel column chromatography. Thus, compound (C-11) (0.40 g, 31%) was obtained. The results of analysis by $^1$H NMR spectroscopy are shown below. Analysis by differential scanning calorimetry (DSC analysis) revealed that compound (C-11) had a glass transition temperature of 109° C.

$^1$H NMR: δ [ppm] 8.97 (m, 1H), 8.89-8.86 (m, 1H), 8.39 (dd, 4H), 8.19 (d, 2H), 8.16 (s, 1H), 7.93 (t, 1H), 7.88-7.80 (m, 7H), 7.74-7.30 (m, 26H).

Synthesis Example for Comparative Compound (C-12)

Comparative compound (C-12) was synthesized by the method shown in WO2006/62062 (the patent document includes a statement to the effect that the glass transition temperature is 159° C.)

Synthesis Example for Comparative Compound (C-13)

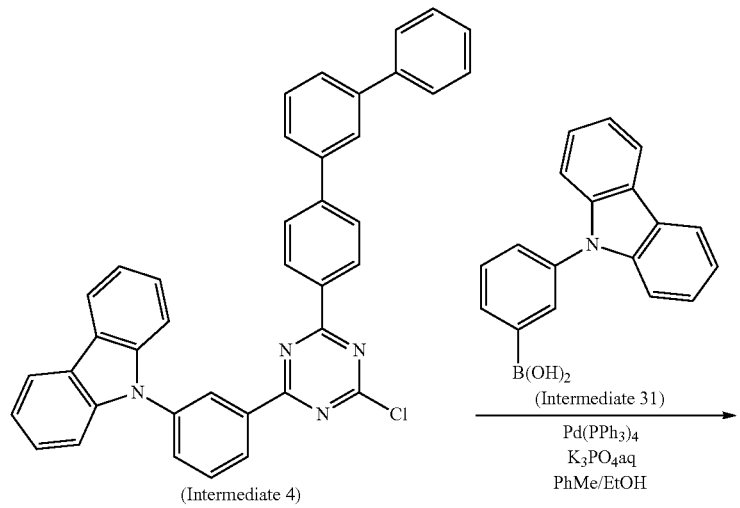

[Ka 73]

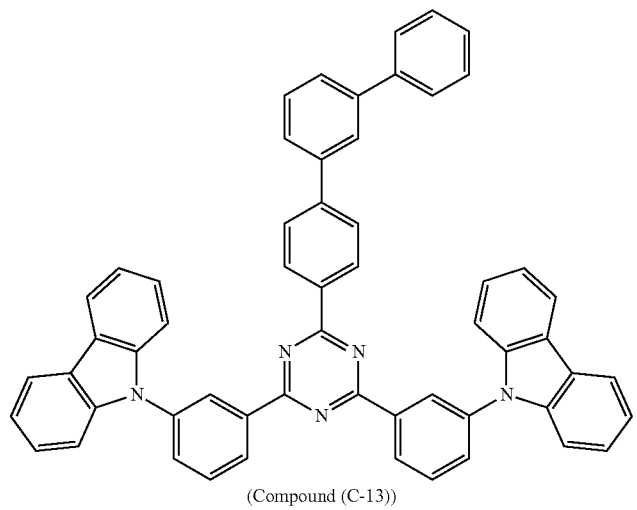

(Compound (C-13))

A toluene/ethanol mixture solution (2:1, 297 mL) which had undergone nitrogen bubbling was added to intermediate 4 (21.5 g, 36.7 mmol) and intermediate 31 (11.4 g, 44.0 mmol). Thereto were further added Pd(PPh$_3$)$_4$ (1.00 g, 0.865 mmol) and an aqueous tripotassium phosphate solution (2.0 M, 50 mL) which had undergone nitrogen bubbling, in this order. Thereafter, the resultant mixture was stirred for 6 hours while heating the mixture with refluxing. After the mixture was returned to room temperature, suction filtration was conducted. The solid obtained by the filtration was dissolved in methylene chloride, and suction filtration was conducted again. The filtrate was distilled under reduced pressure to remove the solvent therefrom, and the residue was purified by silica gel column chromatography using a developer composed of hexane/methylene chloride=1/1 to 1/2. Thus, compound (C-13) (18.6 g, 71%) was obtained. The results of analysis by $^1$H NMR spectroscopy are shown below. Analysis by differential scanning calorimetry (DSC analysis) revealed that compound (C-13) had a glass transition temperature of 129° C.

$^1$H NMR: δ [ppm] 8.98 (m, 2H), 8.87-8.84 (m, 2H), 8.79 (d, 2H), 8.18 (d, 4H), 7.86 (t, 1H), 7.82-7.78 (m, 6H), 7.66-7.60 (m, 4H), 7.56-7.29 (m, 16H).

Synthesis Example for Comparative Compound (C-14)

Synthesis of Intermediate 33

[Ka 74]

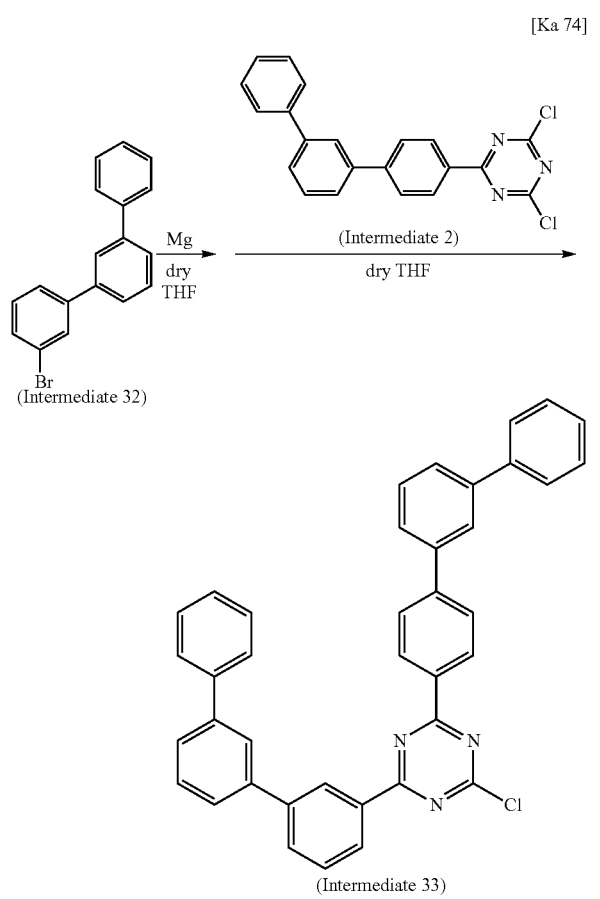

A solution of intermediate 32 (6.74 g, 21.8 mmol) in dry THF (60 mL) was added dropwise to magnesium pieces (578 mg, 23.8 mmol) so that gentle refluxing occurred. This mixture was stirred for 30 minutes to obtain a Grignard reagent. This Grignard reagent was added dropwise to a solution in dry THF (40 mL) of intermediate 2 (7.50 g, 19.8 mmol), and the resultant mixture was stirred at 45-55° C. for 3 hours. The resultant reaction solution was poured into ice water, and this mixture was extracted with methylene chloride. The organic layer was washed with saturated aqueous sodium chloride solution and dried with magnesium sulfate. Thereafter, the solvent was distilled off under reduced pressure. The residue was subjected to suspension washing in hexane/methylene chloride=1/10, and the crystals were subjected to suspension washing in ethanol. The crystals were taken out by filtration to thereby obtain intermediate 33 (6.45 g, 57%). Incidentally, the intermediate 32 was synthesized according to the method described in JP-A-2010-206191.

Synthesis of Compound (C-14)

[Ka 75]

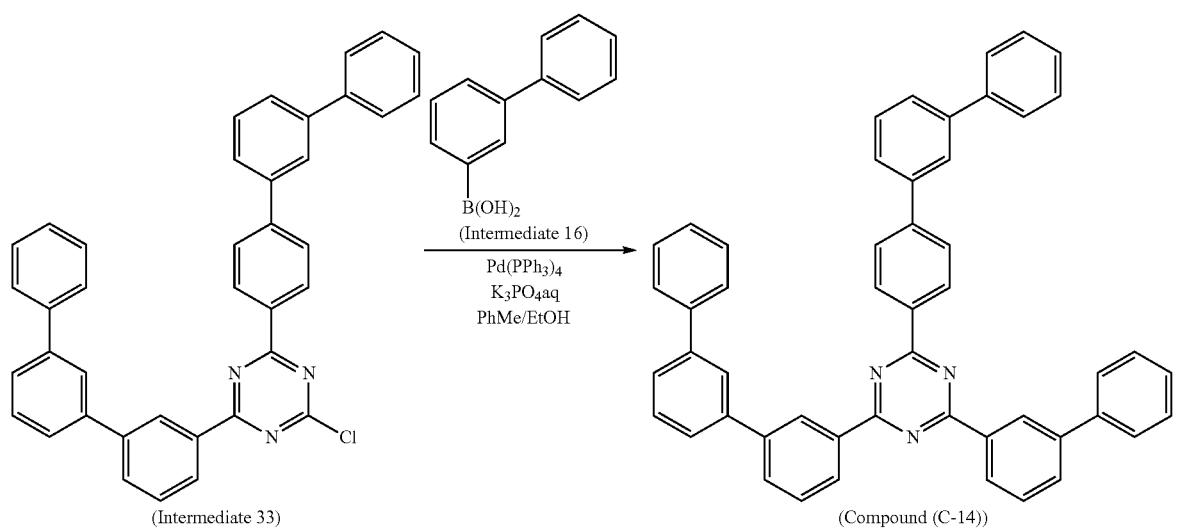

A toluene/ethanol mixture solution (2:1, 15 mL) which had undergone nitrogen bubbling was added to intermediate 33 (571 mg, 0.998 mmol) and intermediate 16 (258 mg, 1.30 mmol). Thereto were further added Pd(PPh$_3$)$_4$ (58.0 mg, 0.0502 mmol) and an aqueous tripotassium phosphate solution (2.0 M, 1.5 mL) which had undergone nitrogen bubbling, in this order. Thereafter, the resultant mixture was stirred for 3 hours while heating the mixture with refluxing. After the mixture was returned to room temperature, distilled water was added thereto and the resultant mixture was extracted with toluene. The organic layer was washed with distilled water and dried with magnesium sulfate. Thereafter, the solvent was distilled off under reduced pressure. The residue was purified by silica gel column chromatography using an eluent composed of hexane/methylene chloride=3/1 to 3/2. Thus, compound (C-14) (285 mg, 41%) was obtained. The results of analysis by $^1$H NMR spectroscopy are shown below. Analysis by differential scanning calorimetry (DSC analysis) revealed that compound (C-14) had a glass transition temperature of 73° C.

$^1$H NMR: δ [ppm] 9.07 (t, 1H), 9.04 (t, 1H), 8.89 (d, 2H), 8.83-8.79 (m, 2H), 7.96-7.84 (m, 6H), 7.77-7.55 (m, 14H), 7.52-7.47 (m, 6H), 7.44-7.37 (m, 3H).

Synthesis Example for Comparative Compound (C-15)

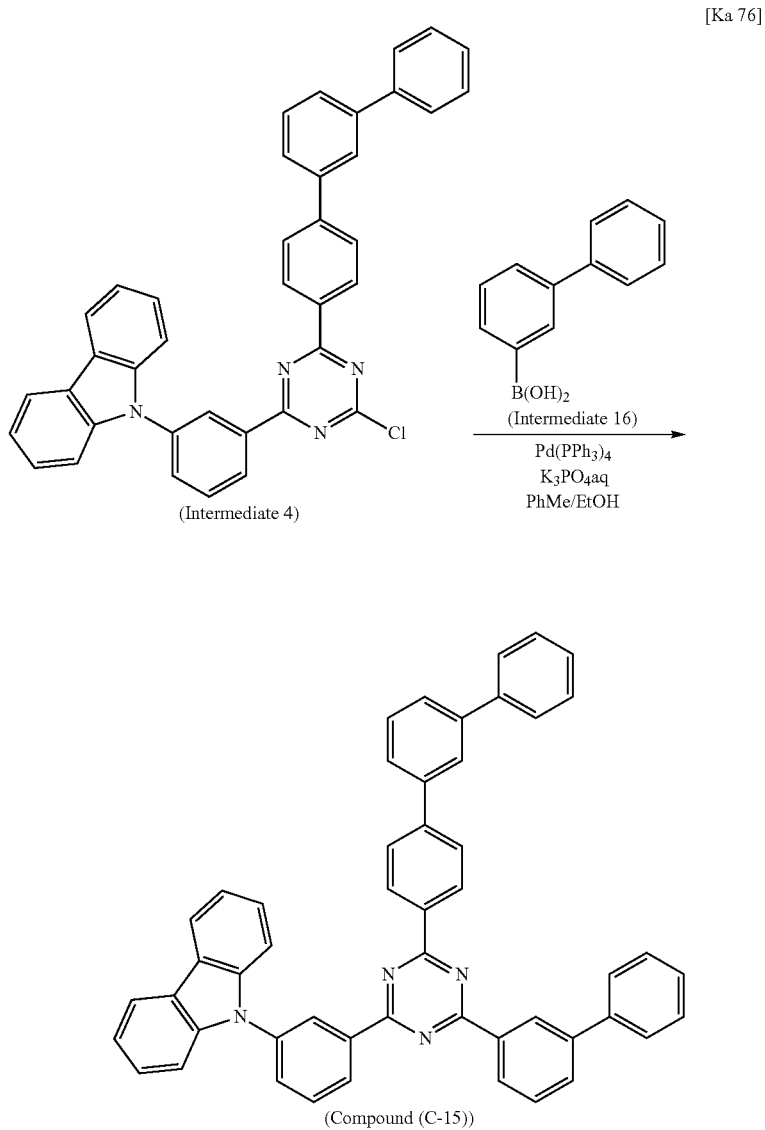

A toluene/ethanol mixture solution (2:1, 24 mL) which had undergone nitrogen bubbling was added to intermediate 4 (1.50 g, 2.56 mmol) and intermediate 16 (0.66 g, 3.33 mmol). Thereto were further added Pd(PPh$_3$)$_4$ (150 mg, 0.128 mmol) and an aqueous tripotassium phosphate solution (2.0 M, 4 mL) which had undergone nitrogen bubbling, in this order. Thereafter, the resultant mixture was stirred for 3 hours while heating the mixture with refluxing. After the mixture was returned to room temperature, distilled water was added thereto and the resultant mixture was extracted with toluene. The organic layer was washed with saturated aqueous sodium chloride solution and dried with magnesium sulfate. Thereafter, the solvent was distilled off under reduced pressure. The residue was purified by silica gel column chromatography using an eluent composed of hexane/methylene chloride=7/3. Thus, compound (C-15) (1.20 g, 67%) was obtained. The results of analysis by $^1$H NMR spectroscopy are shown below. Analysis by differential scanning calorimetry (DSC analysis) revealed that compound (C-15) had a glass transition temperature of 94° C.

$^1$H NMR: δ [ppm] 9.02 (m, 1H), 9.00 (m, 1H), 8.92-8.89 (m, 1H), 8.85 (d, 2H), 8.77-8.74 (m, 1H), 8.20 (d, 2H), 7.90 (t, 1H), 7.86-7.83 (m, 5H), 7.74-7.72 (m, 2H), 7.68-7.62 (m, 5H), 7.58-7.32 (m, 13H).

Synthesis of Comparative Compound (C-16)

Synthesis of Intermediate 35

[Ka 77]

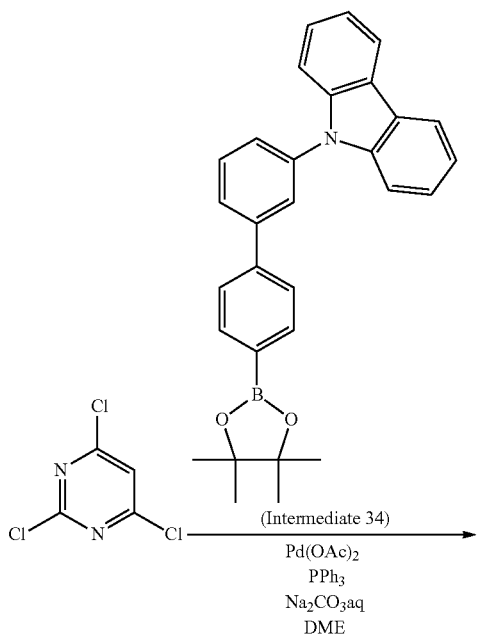

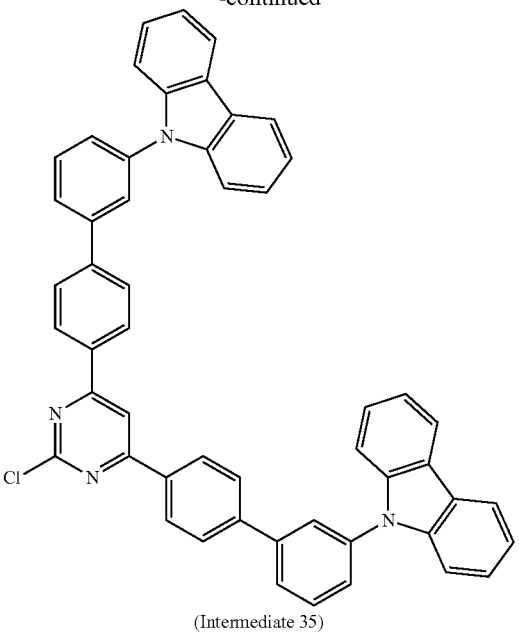

(Intermediate 35)

2,4,6-Trichloropyrimidine (4.58 g, 25.0 mmol), intermediate 34 (17.8 g, 40.0 mmol), DME (125 mL), and an aqueous sodium carbonate solution (2.0 M, 70 mL) were introduced in this order. Thereafter, nitrogen bubbling was conducted for 15 minutes. Thereto were added Pd(OAc)$_2$ (56 mg, 0.25 mmol) and PPh$_3$ (196 mg, 0.75 mmol) in this order. This mixture was heated with refluxing for 1 hour and 15 minutes. Thereto was added Pd(PPh$_3$)$_4$ (50 mg). This mixture was reacted for further 1 hour and 20 minutes. Thereafter, the arylboronic acid pinacolate ester (4.0 g) was additionally added thereto, and this mixture was heated with refluxing for further 2 hours. After the reaction mixture was returned to room temperature, suction filtration was conducted to take out the precipitate. This residue was purified by silica gel column chromatography to obtain 7.3 g of a colorless solid. An examination by NMR spectroscopy revealed that the colorless solid was the compound in which only one (carbazolylphenyl)phenyl group had reacted (yield, 63%). In order to obtain intermediate 35, the following operation was further conducted. The solid (3.5 g, 9.27 mmol), intermediate 34 (3.70 g, 10.2 mmol), DME (45 mL), and an aqueous sodium carbonate solution (2.0 M, 20 mL) were added in this order. Thereafter, nitrogen bubbling was conducted at 50° C. for 10 minutes. Thereto were added Pd(OAc)$_2$ (62 mg, 0.28 mmol) and PPh$_3$ (146 mg, 0.56 mmol) in this order. This mixture was heated with refluxing for 1.5 hours. Intermediate 34 (1.80 g) was additionally added thereto, and this mixture was heated with refluxing for 1.5 hours. Thereafter, intermediate 34 (0.40 g) was further added additionally, and this mixture was heated with refluxing for 30 minutes. After the reaction mixture was returned to room temperature, suction filtration was conducted to take out the precipitate. Thus, intermediate 35 was obtained as a crude reaction product (9.33 g).

Synthesis of Compound (C-16)

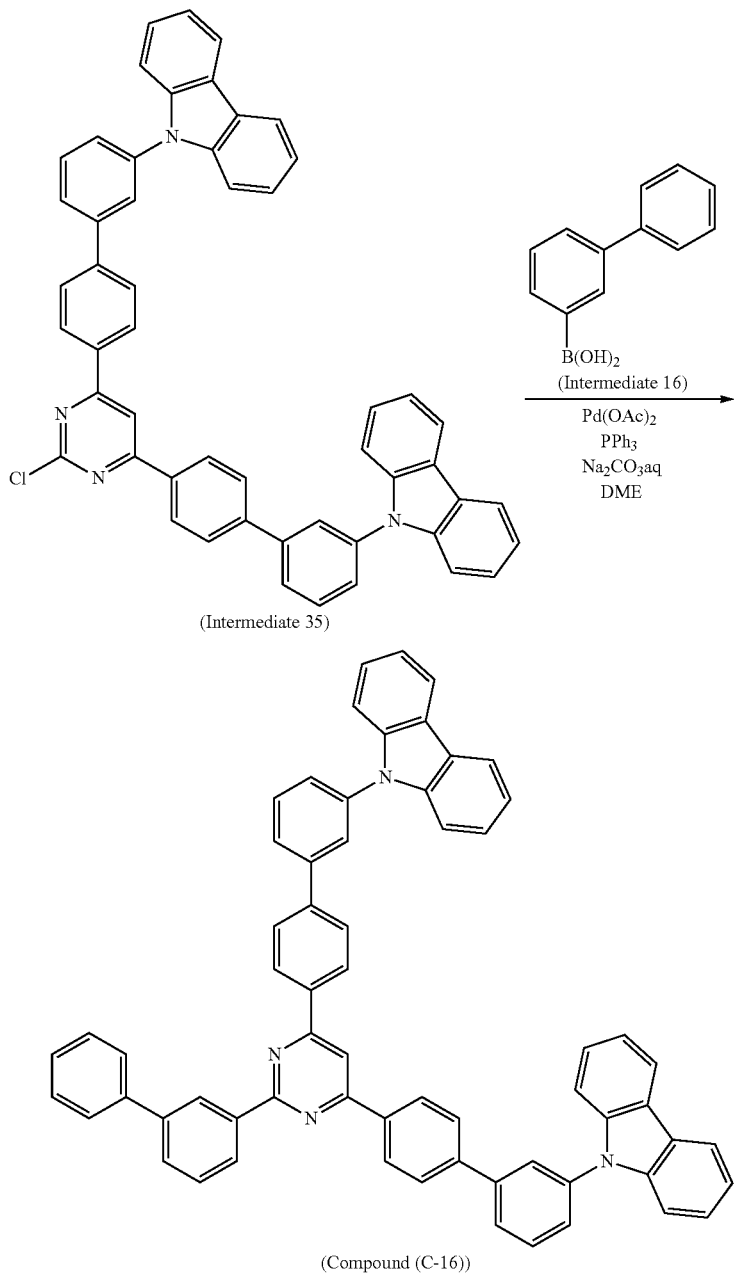

Intermediate 35 (3.00 g, 4.03 mmol), intermediate 16 (0.96 g, 4.84 mmol), THF (40 mL), and an aqueous sodium carbonate solution (2.0 M, 20 mL) were introduced in this order. Thereafter, nitrogen bubbling was conducted for 15 minutes. Thereto were added Pd(OAc)$_2$ (45 mg, 0.20 mmol) and PPh$_3$ (105 mg, 0.4 mmol) in this order. This mixture was heated with refluxing for 3 hours. After the mixture was returned to room temperature, distilled water was added thereto and the resultant mixture was extracted with methylene chloride. The organic layer was washed with saturated aqueous sodium chloride solution and dried with magnesium sulfate. Thereafter, the solvent was distilled off under reduced pressure. The residue was purified by silica gel column chromatography. Thus, compound (C-16) (2.90 g, 83%) was obtained. The results of analysis by $^1$H NMR spectroscopy are shown below. Analysis by differential scanning calorimetry (DSC analysis) revealed that compound (C-16) had a glass transition temperature of 142° C.

$^1$H NMR: δ [ppm] 8.97 (m, 1H), 8.75-8.72 (m, 1H), 8.42 (d, 4H), 8.17 (d, 4H), 8.10 (s, 1H), 7.91-7.71 (m, 13H), 7.65-7.60 (m, 3H), 7.52-7.37 (m, 11H), 7.33-7.29 (m, 4H).

Synthesis of Comparative Compound (C-17)

Synthesis of Intermediate 37

[Ka 79]

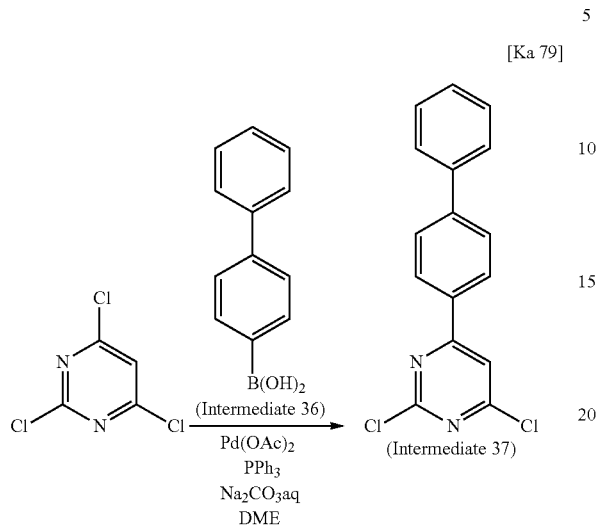

2,4,6-Trichloropyrimidine (8.00 g, 43.6 mmol), intermediate 36 (4.32 g, 21.8 mmol; manufactured by Tokyo Kasei Kogyo Co., Ltd. (4-biphenylboronic acid)), DME (109 mL), and an aqueous sodium carbonate solution (2.0 M, 32 mL) were introduced in this order. Thereafter, nitrogen bubbling was conducted for 20 minutes. Thereto were added Pd(OAc)$_2$ (245 mg, 1.09 mmol) and PPh$_3$ (0.57 g, 2.18 mmol) in this order. This mixture was heated with refluxing for 3.5 hours. After the mixture was returned to room temperature, distilled water was added thereto and the resultant mixture was extracted with methylene chloride. The organic layer was washed with saturated aqueous sodium chloride solution and dried with magnesium sulfate. Thereafter, the solvent was distilled off under reduced pressure. The residue was purified by silica gel column chromatography to obtain intermediate 37 (4.8 g, 37%).

Synthesis of Intermediate 38

[Ka 80]

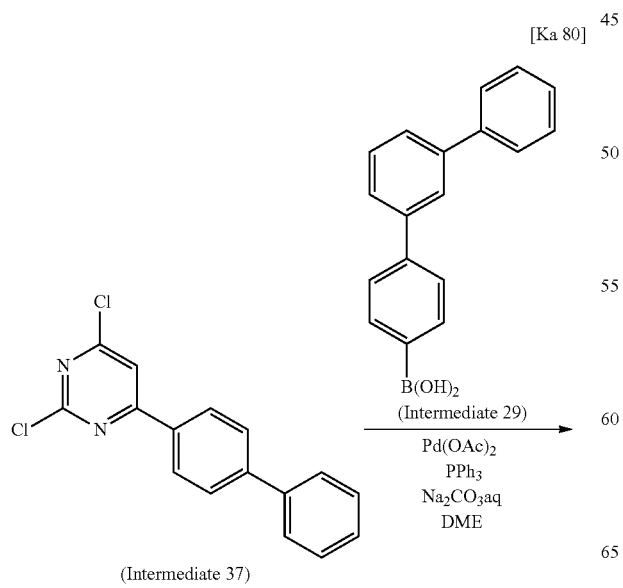

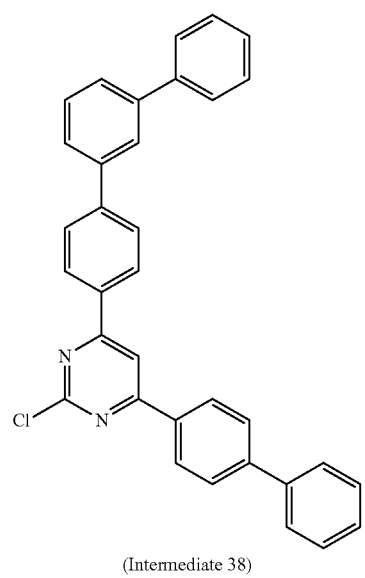

(Intermediate 38)

Intermediate 37 (3.65 g, 12.1 mmol), intermediate 29 (2.77 g, 10.1 mmol), DME (61 mL), and an aqueous sodium carbonate solution (2.0 M, 15 mL) were introduced in this order. Thereafter, nitrogen bubbling was conducted for 30 minutes. Thereto were added Pd(OAc)$_2$ (113 mg, 0.51 mmol) and PPh$_3$ (0.27 g, 1.01 mmol) in this order. This mixture was heated with refluxing for 7 hours. After the mixture was returned to room temperature, distilled water was added thereto and the resultant mixture was extracted with methylene chloride. The organic layer was washed with saturated aqueous sodium chloride solution and dried with magnesium sulfate. Thereafter, the solvent was distilled off under reduced pressure. The residue was purified by silica gel column chromatography to obtain intermediate 38 (3.16 g, 63%).

Synthesis of Compound (C-17)

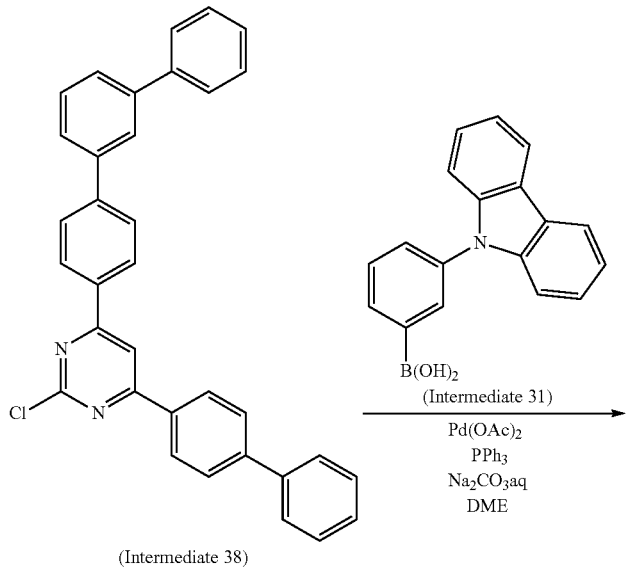

(Intermediate 38)

[Ka 81]

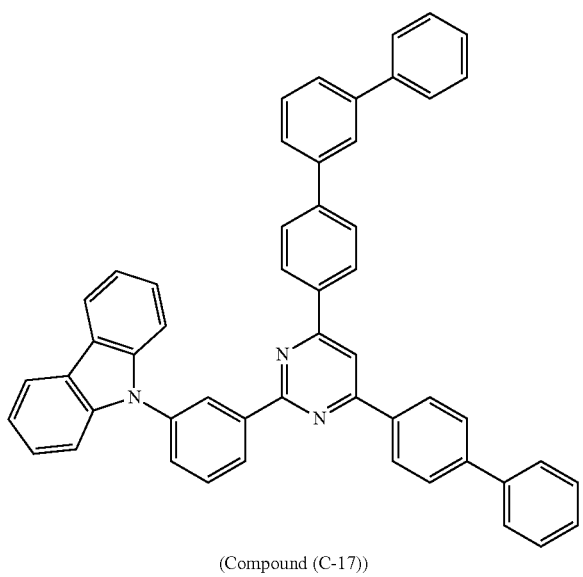

(Compound (C-17))

Intermediate 38 (3.16 g, 6.39 mmol), intermediate 31 (2.20 g, 7.67 mmol), DME (32 mL), and an aqueous sodium carbonate solution (2.0 M, 10 mL) were introduced in this order. Thereafter, nitrogen bubbling was conducted for 30 minutes. Thereto were added Pd(OAc)$_2$ (72 mg, 0.32 mmol) and PPh$_3$ (0.17 g, 0.64 mmol) in this order. This mixture was heated with refluxing for 3 hours. After the mixture was returned to room temperature, distilled water was added thereto and the resultant mixture was extracted with methylene chloride. The organic phase was washed with saturated aqueous sodium chloride solution and dried with magnesium sulfate. Thereafter, the solvent was distilled off under reduced pressure. The residue was purified by silica gel column chromatography. Thus, compound (C-17) (4.1 g, 91%) was obtained. The results of analysis by $^1$H NMR spectroscopy are shown below. Analysis by differential scanning calorimetry (DSC analysis) revealed that compound (C-17) had a glass transition temperature of 108° C.

$^1$H NMR: δ [ppm] 8.96 (t, 1H), 8.88-8.86 (m, 1H), 8.39-8.36 (m, 4H), 8.19 (d, 2H), 8.14 (s, 1H), 7.87 (t, 1H), 7.83-7.61 (m, 12H), 7.57-7.30 (m, 13H).

[Storage Stability Test of Compositions]

The following compounds, which are included in the compounds shown above as examples, were dissolved in an organic solvent to prepare compositions by the methods shown below. Incidentally, the compound (C-18) was obtained according to the method disclosed in JP-A-2006-188493.

[Ka 82]
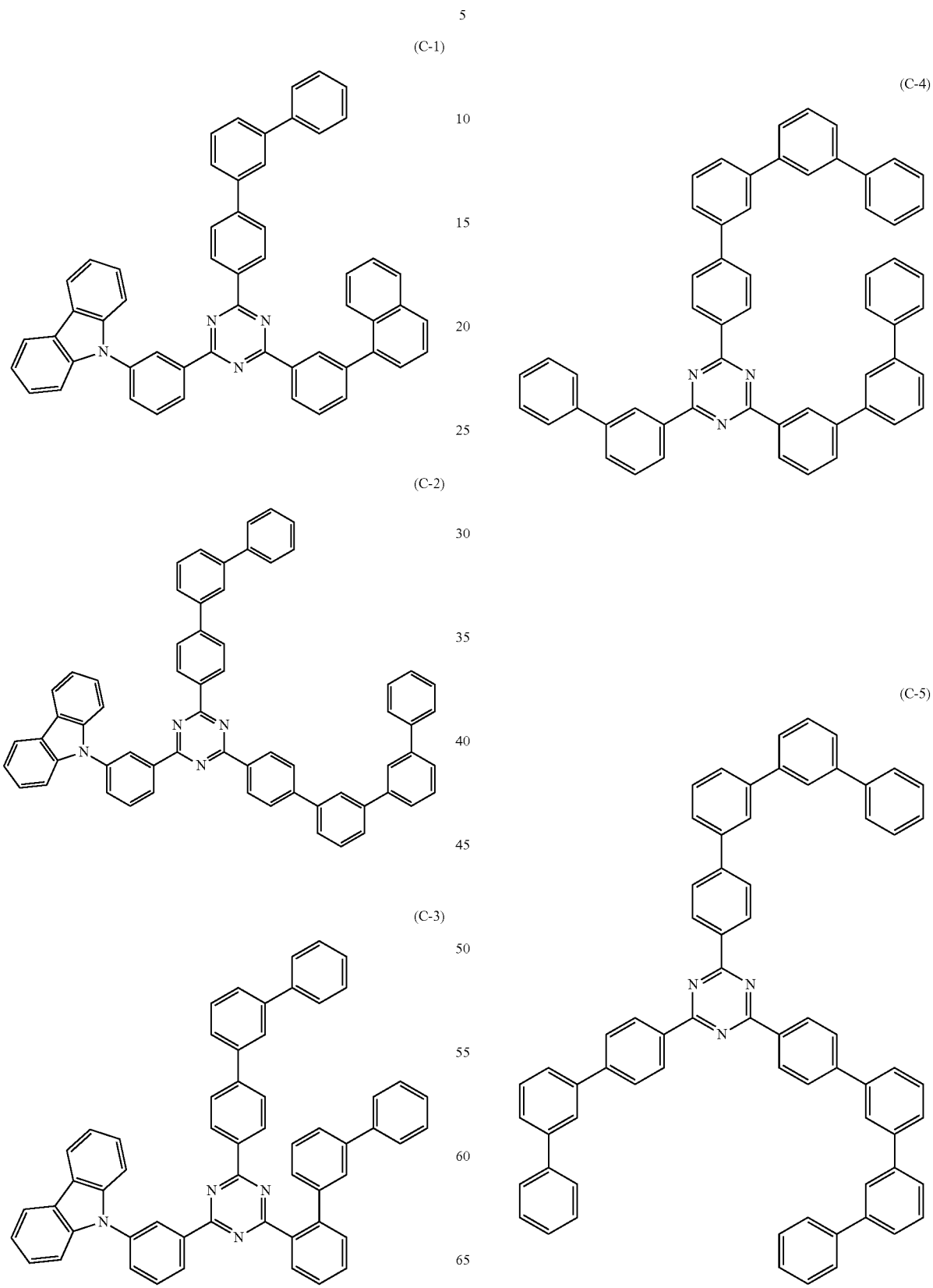

(C-6)
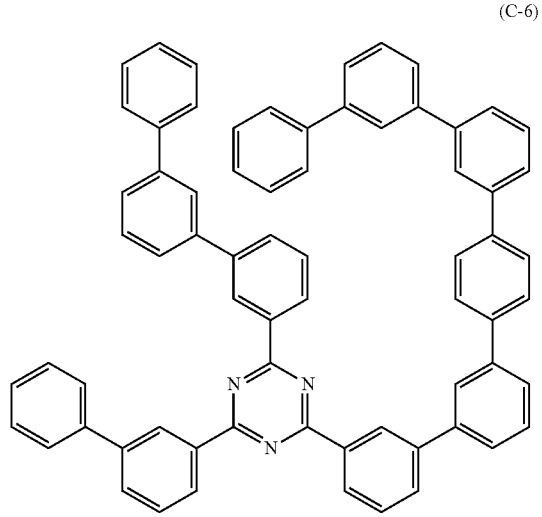
(C-7)
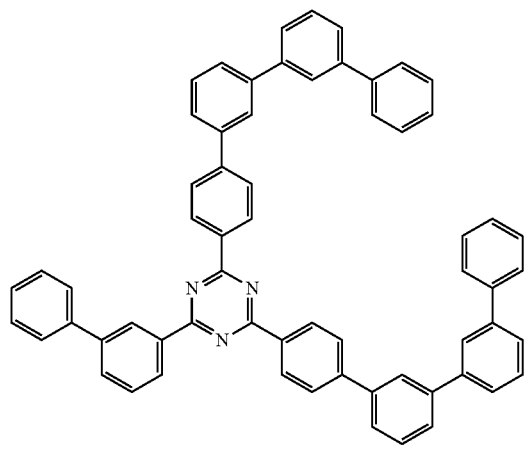
(C-8)
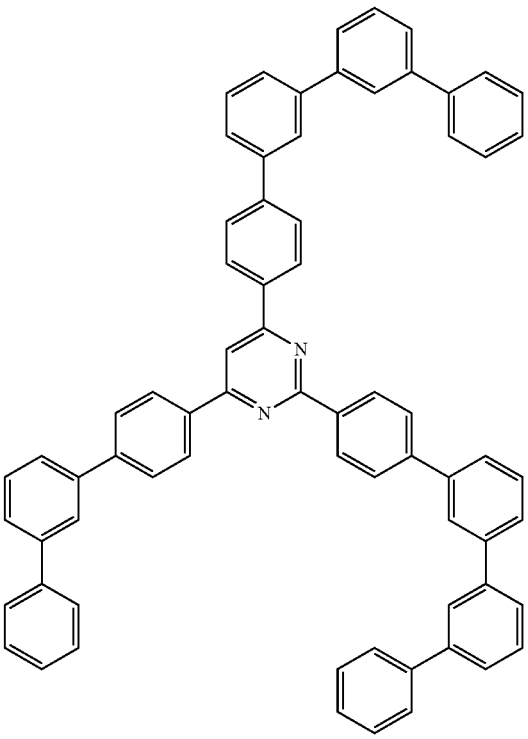
(C-9)
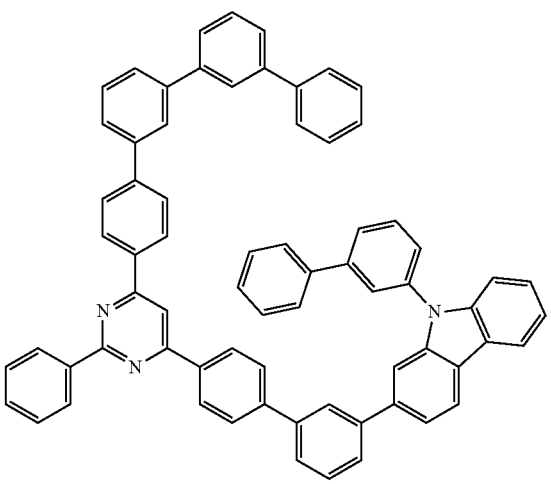

(C-10)
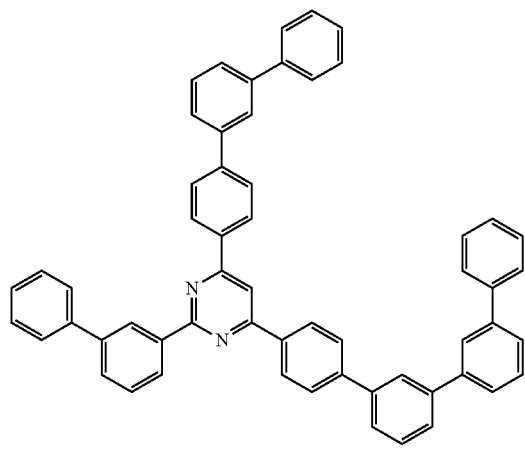
(C-11)
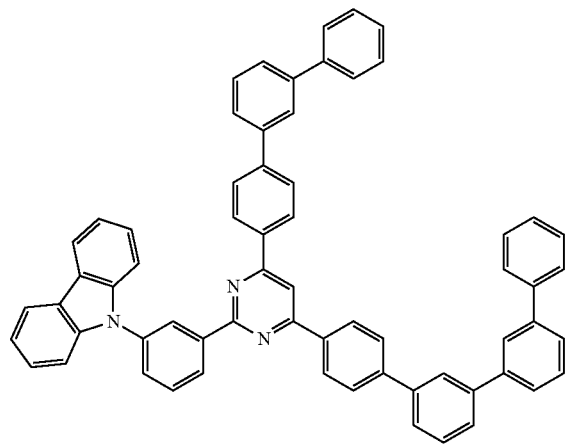
[Ka 83]
(C-12)
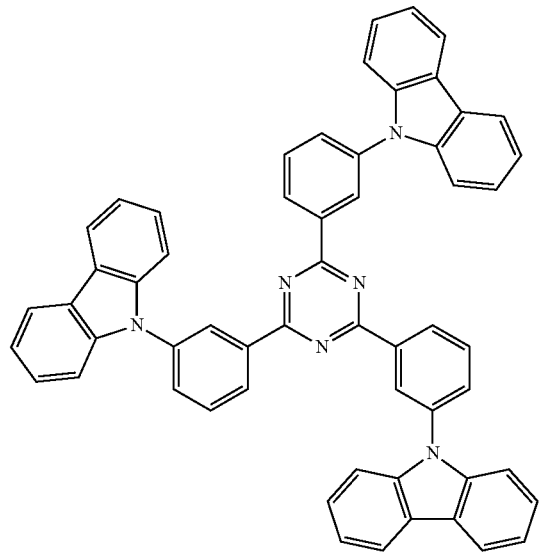
(C-13)
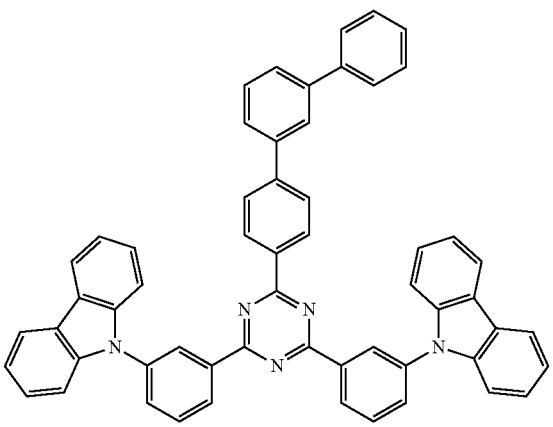
(C-14)
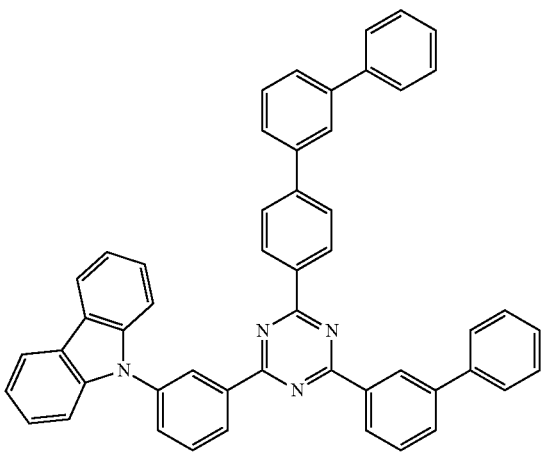
(C-15)

-continued (C-16)

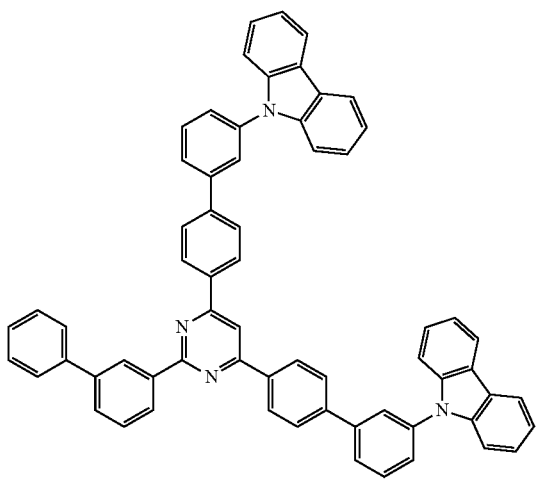

(C-17)

(C-18)

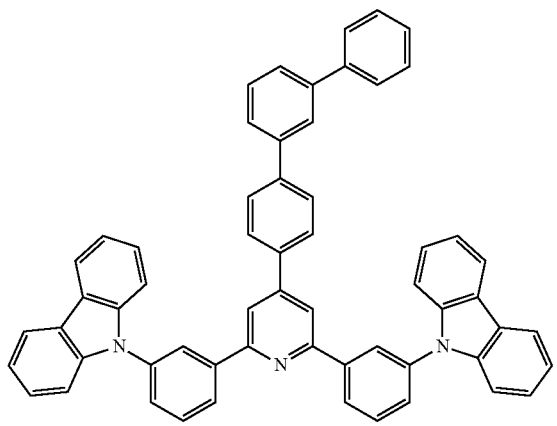

Example 1

Five milligrams of compound (C-1) was weighed out and introduced into a 5-mL sample tube, and cyclohexylbenzene was added thereto to adjust the total amount to 400 mg. Thereafter, the mixture was heated to 60° C. using a hot plate to completely dissolve the compound (C-1). Thus, a composition having a solid concentration of 1.25% by weight was prepared. The composition prepared was placed in the dark having a room temperature of about 15-20° C., and the period required for a solid to separate out therein was measured. Whether a solid had separated out was visually ascertained using a 10-power magnifying lens. The results thereof are summarized in Table 1 together with the molecular weight and glass transition temperature of compound (C-1).

Examples 2 to 11

Compositions were prepared in the same manner as in Example 1, except that the compound (C-1) was replaced by each of compounds (C-2) to (C-11). The period required for a solid to separate out therein was measured in the same manner. Whether a solid had separated out was visually ascertained using a 10-power magnifying lens. The results thereof are summarized in Table 1 together with the molecular weights and glass transition temperatures of compounds (C-2) to (C-11).

Comparative Examples 1 to 6

It was attempted to prepare compositions in the same manner as in Example 1, except that the compound (C-1) was replaced by each of comparative compounds (C-12) to (C-17). With respect to comparative compounds (C-12), (C-15), and (C-16) among these, heating with the hot plate was conducted for 30 minutes but it was ascertained that a solid remained on the bottom of each sample tube. Compositions having a concentration of 1.25% by weight were unable to be prepared from these comparative compounds. With respect to the compositions which were able to be prepared, the period required for a solid to separate out therein was measured in the same manner as in Example 1. Whether a solid had separated out was visually ascertained using a 10-power magnifying lens. The results thereof are summarized in Table 1 together with the molecular weight, number of carbazolyl groups, and glass transition temperature of each of compounds (C-12) to (C-17).

Incidentally, comparative compound (C-12) is outside the scope of the invention because the molecule thereof has three carbazolyl groups therein. Comparative compound (C-13) is outside the scope of the invention because the number of carbazolyl groups is 2. Comparative compound (C-14) is outside the scope of the invention because some of the substituents corresponding to the A, B, and C contained in general formula (1) do not satisfy general formulae (2-1) to (2-5)

and because the molecular weight thereof is less than 750. Comparative compound (C-15) is outside the scope of the invention because some of the substituents corresponding to the A, B, and C contained in general formula (1) do not satisfy general formulae (2-1) to (2-5) and because the molecular weight thereof is less than 750. Comparative compound (C-16) is outside the scope of the invention because the number of carbazolyl groups is 2. Comparative compound (C-17) is outside the scope of the invention because some of the substituents corresponding to the A, B, and C contained in general formula (1) do not satisfy general formulae (2-1) to (2-5).

Reference Example 1

A composition was prepared in the same manner as in Example 1, except that the compound (C-1) was replaced by compound (C-18). The period required for a solid to separate out therein was measured in the same manner. Whether a solid had separated out was visually ascertained using a 10-power magnifying lens. The results thereof are summarized in Table 1 together with the molecular weight, number of carbazolyl groups, and glass transition temperature of compound (C-18). Although compound (C-18) is outside the scope of the invention because this compound has a pyridine framework, this compound is shown for the purpose of comparison in the low solubility due to a 1,3,5-triazine framework.

Production of Organic Electroluminescent Elements

Example 12

An organic electroluminescent element shown in FIG. 1 was produced in the following manner.

A substrate constituted of a glass substrate 1 and, formed thereon, a transparent conductive film of indium-tin oxide (ITO) deposited in a thickness of 70 nm (sputtering-coated product; manufactured by Geomatec Co., Ltd.) was subjected to patterning into stripes having a width of 2 mm using an ordinary technique of photolithography and etching with hydrochloric acid. Thus, an anode 2 was formed. The ITO substrate which had undergone the patterning was cleaned by subjecting the substrate to ultrasonic cleaning with an aqueous surfactant solution, rinsing with ultrapure water, ultrasonic cleaning with ultrapure water, and rinsing with ultrapure water in this order, subsequently dried by bringing the cleaned ITO substrate into contact with compressed air, and then subjected to ultraviolet/ozone cleaning.

Next, a coating liquid for hole injection layer formation was prepared, the coating liquid containing the arylamine polymer represented by the following structural formula

TABLE 1

|  | Compound | Molecular weight | Number of carbazolyl groups | Glass transition temperature (° C.) | Solid concentration of composition | Number of days to solid separating-out |
|---|---|---|---|---|---|---|
| Example 1 | C-1 | 752.90 | 1 | 113 | 1.25 wt % | 28 days |
| Example 2 | C-2 | 855.03 | 1 | 110 | 1.25 wt % | >60 days |
| Example 3 | C-3 | 778.94 | 1 | 103 | 1.25 wt % | >60 days |
| Example 4 | C-4 | 765.94 | 0 | 79 | 1.25 wt % | >60 days |
| Example 5 | C-5 | 918.13 | 0 | 93 | 1.25 wt % | >60 days |
| Example 6 | C-6 | 918.13 | 0 | 92 | 1.25 wt % | >60 days |
| Example 7 | C-7 | 842.04 | 0 | 90 | 1.25 wt % | >60 days |
| Example 8 | C-8 | 917.14 | 0 | 95 | 1.25 wt % | >60 days |
| Example 9 | C-9 | 930.14 | 1 | 125 | 1.25 wt % | 8 days |
| Example 10 | C-10 | 764.95 | 0 | 85 | 1.25 wt % | 35 days |
| Example 11 | C-11 | 854.05 | 1 | 109 | 1.25 wt % | >60 days |
| Comparative Example 1 | C-12 | 804.94 | 3 | 159 | residual solid | — |
| Comparative Example 2 | C-13 | 791.94 | 2 | 129 | 1.25 wt % | 1 day |
| Comparative Example 3 | C-14 | 689.84 | 0 | 73 | 1.25 wt % | 1 day |
| Comparative Example 4 | C-15 | 702.84 | 1 | 94 | residual solid | — |
| Comparative Example 5 | C-16 | 867.05 | 2 | 142 | residual solid | — |
| Comparative Example 6 | C-17 | 701.85 | 1 | 108 | 1.25 wt % | 2 days |
| Reference Example 1 | C-18 | 789.96 | 2 | 124 | 1.25 wt % | >60 days |

As apparent from Table 1, it can be seen that the compounds of the invention have high solubility in the organic solvent and the compositions thereof have high storage stability. A comparison between Comparative Example 2 and Reference Example 1 indicates that the 1,3,5-triazine framework itself brings about low solubility.

(HIT-1), 4-isopropyl-4'-methyldiphenyliodonium tetrakis(pentafluorophenyl)borate, which is represented by structural formula (A-1), and ethyl benzoate. This coating liquid was applied on the anode by spin coating under the following conditions to form a hole injection layer 3 having a thickness of 30 nm.

[Ka 84]

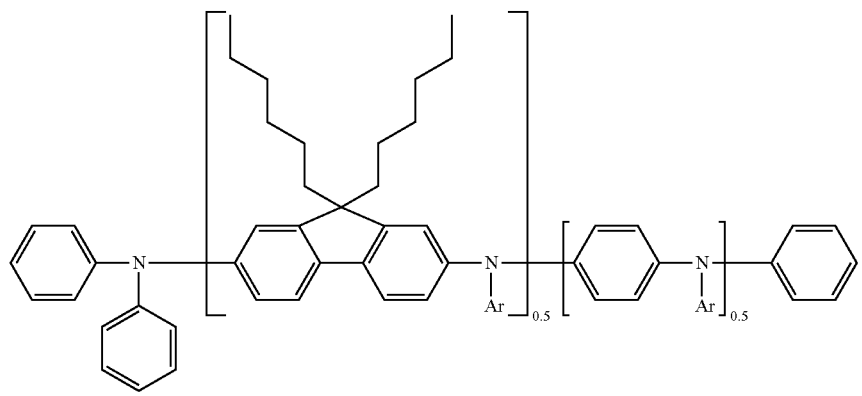
(HIT-1)

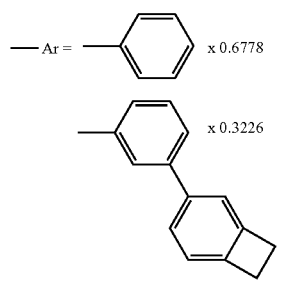

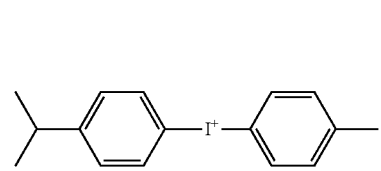

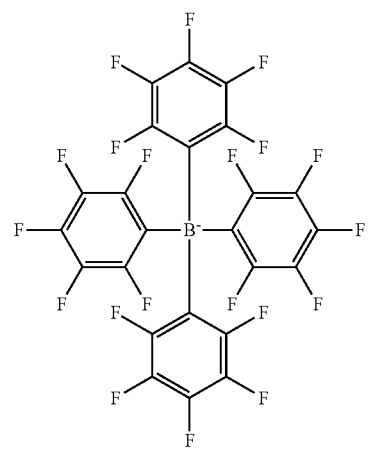
(A-1)

<Coating Liquid for Hole Injection Layer Formation>

| Solvent | ethyl benzoate |
|---|---|
| Concentrations in coating liquid | HIT-1: 2.0% by weight |
| | A-1: 0.4% by weight |

<Conditions of Forming Hole Injection Layer 3>

| Spinner rotation period | 30 sec |
|---|---|
| Spin coating atmosphere | in the air |
| Heating conditions | in the air; 230° C.; 1 hr |

Subsequently, a coating liquid for hole transporting layer formation which contained the compound represented by the following structural formula (HIT-2) was prepared. This coating liquid was applied on the hole injection layer 3 by spin coating and heated under the following conditions to thereby polymerize the compound. Thus, a hole transporting layer 4 having a thickness of 15 nm was formed.

[Ka 85]

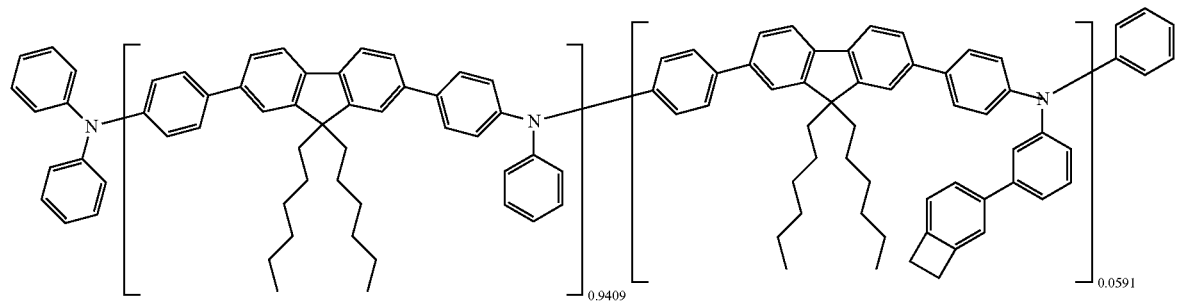

(HIT-2)

<Coating Liquid for Hole Transporting Layer Formation>

| Solvent | cyclohexylbenzene |
|---|---|
| Concentration in coating liquid | HIT-2: 1.0% by weight |

<Conditions for Forming Hole Transporting Layer 4>

| Spinner rotation period | 120 sec |
|---|---|
| Spin coating atmosphere | in dry nitrogen |
| Heating conditions | 230° C.; 1 hour; in nitrogen |

Next, a coating liquid for luminescent-layer formation which contained compound (C-1) and the following compounds (H-1) and (D-1) was prepared. This coating liquid was applied by spin coating and heated under the following conditions to thereby form a luminescent layer 5 having a thickness of 48 nm on the hole transporting layer 4. Incidentally, the compounds (H-1) and (D-1) were prepared respectively by the methods disclosed in JP-A-2010-206191 and JP-A-2010-202644.

[Ka 86]

(H-1)

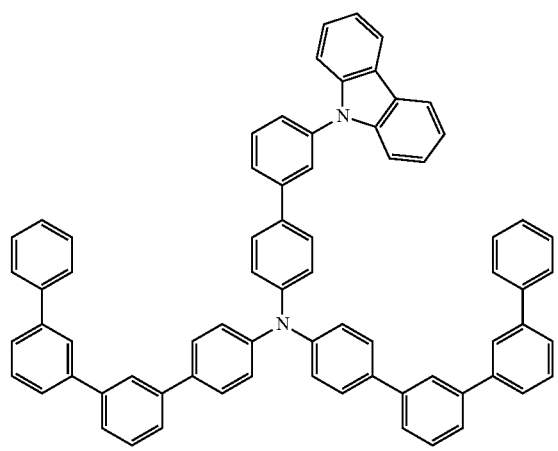

(D-1)

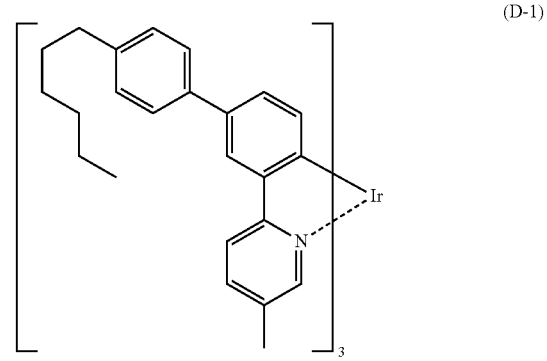

<Coating Liquid for Luminescent-Layer Formation>

| Solvent | cyclohexylbenzene |
|---|---|
| Concentrations in coating liquid | C-1: 1.2% by weight |
| | H-1: 3.6% by weight |
| | D-1: 0.48% by weight |

<Conditions for Forming Luminescent Layer 5>

| Spinner rotation period | 120 sec |
|---|---|
| Heating conditions | 120° C.; 20 min |

The substrate on which up to the luminescent layer 5 had been formed was transferred to a vacuum deposition apparatus, which was evacuated until the degree of vacuum within the apparatus became at least $2.0 \times 10^{-4}$ Pa. Thereafter, the compound represented by the following structural formula (HB-1) was deposited on the luminescent layer 5 by vacuum deposition at a deposition rate of 0.8-1.2 Å/sec. Thus, a hole-blocking layer 6 having a thickness of 10 nm was obtained.

[Ka 87]

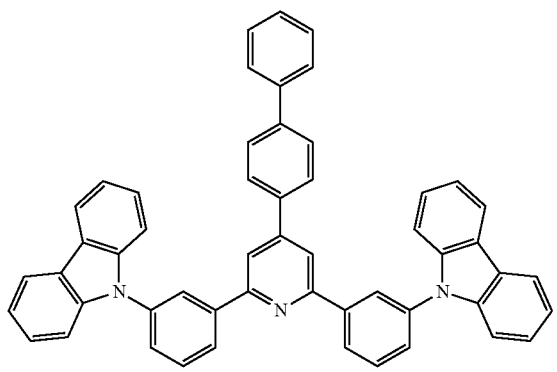

(HB-1)

Furthermore, the organic compound (E-1) having the structure shown below was deposited on the hole-blocking layer 6 by vacuum deposition at a deposition rate of 0.8-1.2 Å/sec. Thus, an electron-transporting layer 7 having a thickness of 20 nm was obtained.

[Ka 88]

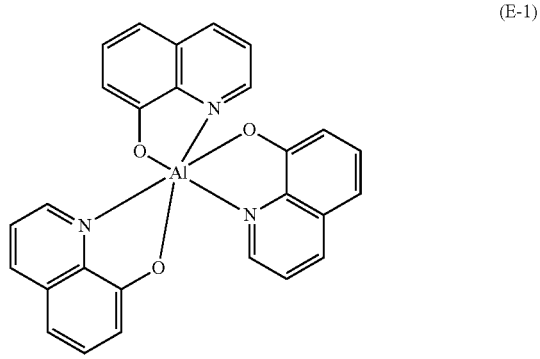

(E-1)

Here, the substrate on which up to the electron-transporting layer 7 had been formed was conveyed under vacuum to a chamber connected to the chamber in which the hole-blocking layer 6 and the electron-transporting layer 7 had been vacuum-deposited. A shadow mask in the form of stripes with a width of 2 mm was brought, as a mask for cathode deposition, into close contact with the surface of the electron-transporting layer 7 so that these stripes were perpendicular to the ITO stripes of the anode 2.

First, using a molybdenum boat, lithium fluoride (LiF) was deposited at a deposition rate of 0.1-0.4 Å/sec to form a film having a thickness of 0.5 nm as an electron injection layer 8 on the electron-transporting layer 7. Next, aluminum was heated in the same manner by means of a molybdenum boat to form an aluminum layer having a thickness of 80 nm as a cathode 9, at a deposition rate of 0.7-5.3 Å/sec.

Subsequently, sealing was conducted in the following manner in order to prevent the element from being deteriorated by the action of atmospheric moisture, etc. during storage. In a gloved nitrogen box, a photocurable resin (30Y-437, manufactured by ThreeBond Co., Ltd.) was applied in a width of 1 mm to the periphery of a glass plate having a size of 23 mm×23 mm, and a moisture getter sheet (manufactured by Dynic Corp.) was disposed in a central part. The substrate on which up to the cathode had been formed was laminated thereto so that the side having the deposited layers faced the desiccant sheet. Thereafter, only the region where the photocurable resin had been applied was irradiated with ultraviolet light to cure the resin.

Thus, an organic electroluminescent element which had a light-emitting area portion with a size of 2 mm×2 mm was obtained. Properties of this element are shown in the following Table 2.

Examples 13 to 15

Organic electroluminescent elements were produced in the same manner as in Example 12, except that each of compounds (C-2), (C-4), and (C-5) was used as a luminescent layer 5 in place of the compound (C-1). Properties of the elements obtained are shown in the following Table 2.

Comparative Example 7

An organic electroluminescent element was produced in the same manner as in Example 12, except that compound (H-2) was used as a luminescent layer 5 in place of the compound (C-1). Properties of the element obtained are shown in the following Table 2. Incidentally, compound (H-2) is outside the scope of the invention because this compound has a pyridine framework.

[Ka 89]

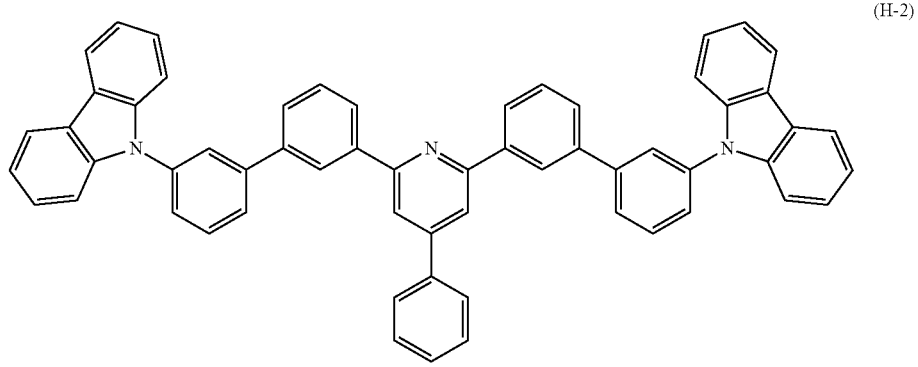

(H-2)

TABLE 2

|  | Compound | Relative working life to LT$_{80}$ | Color of luminescence |
|---|---|---|---|
| Example 12 | C-1 | 2.5 | green |
| Example 13 | C-2 | 2 | green |
| Example 14 | C-4 | 3 | green |
| Example 15 | C-5 | 4 | green |
| Comparative Example 7 | H-2 | 1 | green |

[Measurement of Working Life]

The working life of each organic EL element produced was measured by a method in which a constant direct current (20 mA/cm$^2$) was caused to flow through the element during the test and the element in this state was examined for change in luminance by means of a photodiode. The period required for the luminance to decrease to 80% of the luminance value measured at initiation of the test was determined. The working life is given in terms of value relative to the working life of Comparative Example 7 which was taken as 1.

As apparent from Table 2, it was found that all the elements of Examples 12 to 15 had an improved working life as compared with Comparative Example 7. Furthermore, since the compositions employing the compounds of the invention have high storage stability as shown in Table 1, the compounds of the invention and the compositions containing these compounds are considered to be exceedingly useful for efficiently producing organic electroluminescent elements using a coating liquid application process.

Example 16

An organic electroluminescent element was produced in the same manner as in Example 12, except that compounds (C-4), (H-3), and (D-2) were used as a luminescent layer 5 in place of the compounds (C-1), (H-1), and (D-1), respectively. Properties of the element obtained are shown in the following Table 3. Incidentally, the compound (H-3) was synthesized by the method described in JP-A-2011-26237, and the compound (D-2) was synthesized by the method shown below.

[Ka 90]

(H-3)

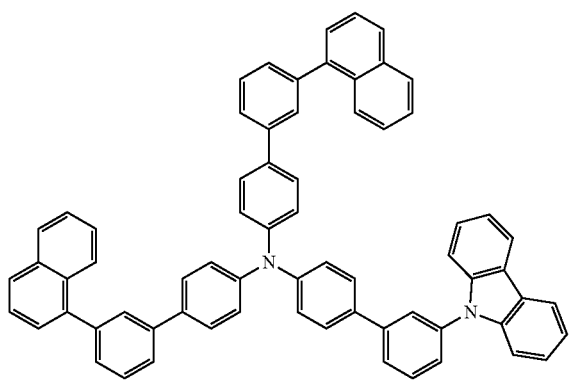

(D-2)

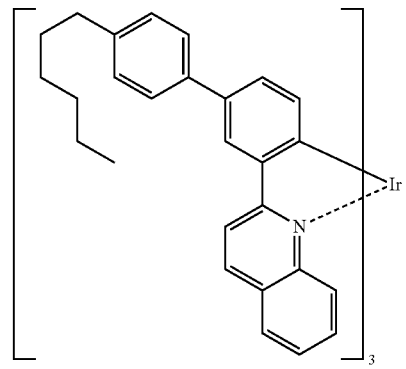

Synthesis of Compound D-2

Synthesis of Intermediate 39

[Ka 91]

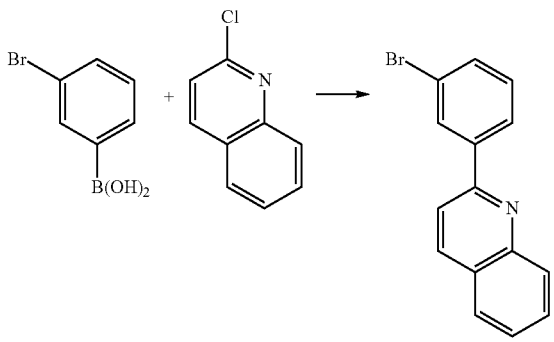

(Intermediate 39)

Sodium carbonate (43.5 g, 411 mmol) was added to a mixture of 3-bromophenylboronic acid (25.0 g, 124 mmol), 1-chloroquinoline (20.3 g, 124 mmol), and toluene (250 mL). Nitrogen bubbling was conducted for 30 minutes while stirring the resultant mixture. Pd(PPh$_3$)$_4$ (4.31 g, 3.73 mmol) was added thereto, and this mixture was stirred at 130° C. for 3.5 hours. After the disappearance of the starting materials was ascertained by TLC, the reaction mixture was extracted twice with toluene. The organic layer was washed with saturated aqueous sodium chloride solution and concentrated under reduced pressure. The residue was purified by silica gel column chromatography to obtain intermediate 39 (28.4 g; yield, 80%).

Synthesis of Intermediate 40

[Ka 92]

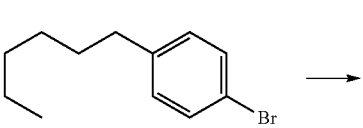

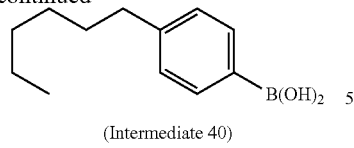

(Intermediate 40)

In a nitrogen atmosphere, an n-hexane solution of n-butyllithium (1.67 M, 131 mL, 218 mmol) was added dropwise to a solution in dry THF (300 mL) of 4-bromohexylbenzene (50.0 g, 207 mmol) at −75° C., and this mixture was stirred. After 2 hours, trimethoxyborane (64.6 g, 622 mmol) was added dropwise thereto. This mixture was stirred for further two hours. Thereafter, 1 N dilute hydrochloric acid (300 mL) was added dropwise thereto, and the resultant mixture was stirred for 30 minutes. This mixture was extracted with ethyl acetate, and the organic layer was washed with saturated aqueous sodium chloride solution, dried with sodium sulfate, and then concentrated under reduced pressure. Thus, intermediate 40 (42.5 g; yield, 99%) was obtained as a colorless solid.

Synthesis of Intermediate 41

[Ka 93]

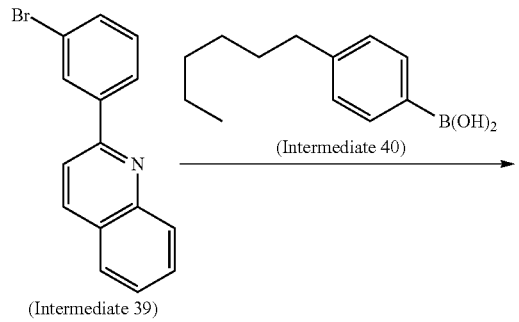

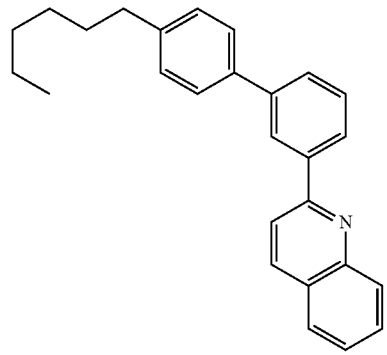

(Intermediate 41)

In a nitrogen atmosphere, a toluene/ethanol mixture solution (2:1, 360 mL) of intermediate 39 (13.5 g, 47.5 mmol) and intermediate 40 (10.8 g, 52.8 mmol), water (120 mL), and tripotassium phosphate (33.5 g, 158 mmol) were introduced, and nitrogen bubbling was conducted for 30 minutes while stirring the mixture. Pd(PPh$_3$)$_4$ (2.5 g, 2.18 mmol) was added thereto, and this mixture was stirred at 130° C. for 3.5 hours. After the disappearance of the starting materials was ascertained by TLC, the reaction mixture was extracted twice with toluene. The organic layer was washed once with saturated aqueous sodium chloride solution and concentrated under reduced pressure. The residue was purified by silica gel column chromatography to obtain intermediate 41 (17.2 g; yield, 98%).

Synthesis of Intermediate 42

[Ka 94]

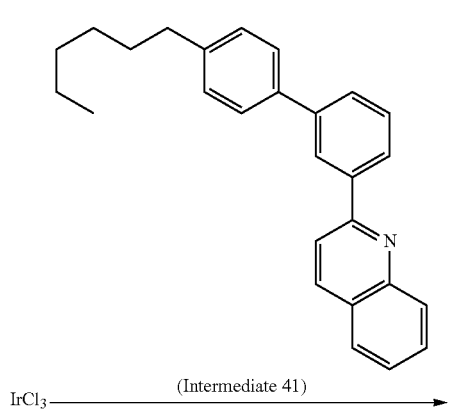

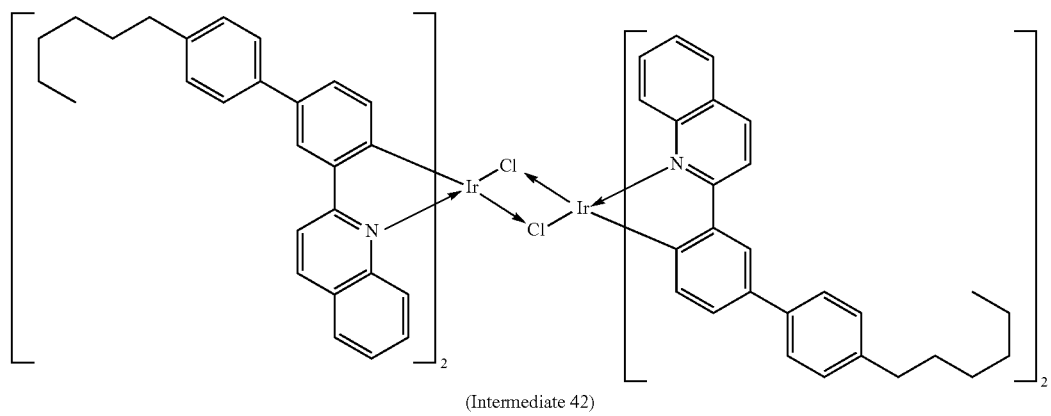

(Intermediate 42)

In a nitrogen atmosphere, 2-ethoxyethanol (200 mL) and water (66 mL) were added to intermediate 41 (13.5 g, 36.9 mmol) and $IrCl_3$ n-hydrate (6.85 g, 18.5 mmol), and this mixture was stirred at 135° C. for 10 hours. Thereafter, the mixture was extracted with dichloromethane, and the organic layer was washed with saturated aqueous sodium chloride solution, dried with sodium sulfate, and then concentrated under reduced pressure. Thus, intermediate 42 (11.9 g; yield, 66%) was obtained as a red solid.

Synthesis of Intermediate 43

In a nitrogen atmosphere, intermediate 42 (11.9 g, 6.22 mmol), sodium acetylacetonate (3.80 g, 31.0 mmol), and 2-ethoxyethanol (100 mL) were introduced in this order, and the resultant mixture was stirred at 135° C. for 9 hours. Thereafter, the mixture was extracted with dichloromethane, and the organic phase was washed with saturated aqueous sodium chloride solution, dried with sodium sulfate, and then concentrated under reduced pressure. The residue was dissolved in dichloromethane and purified by basic silica gel column chromatography. Thus, intermediate 43 (7.75 g; yield, 61%) was obtained as a red solid.

[Ka 95]

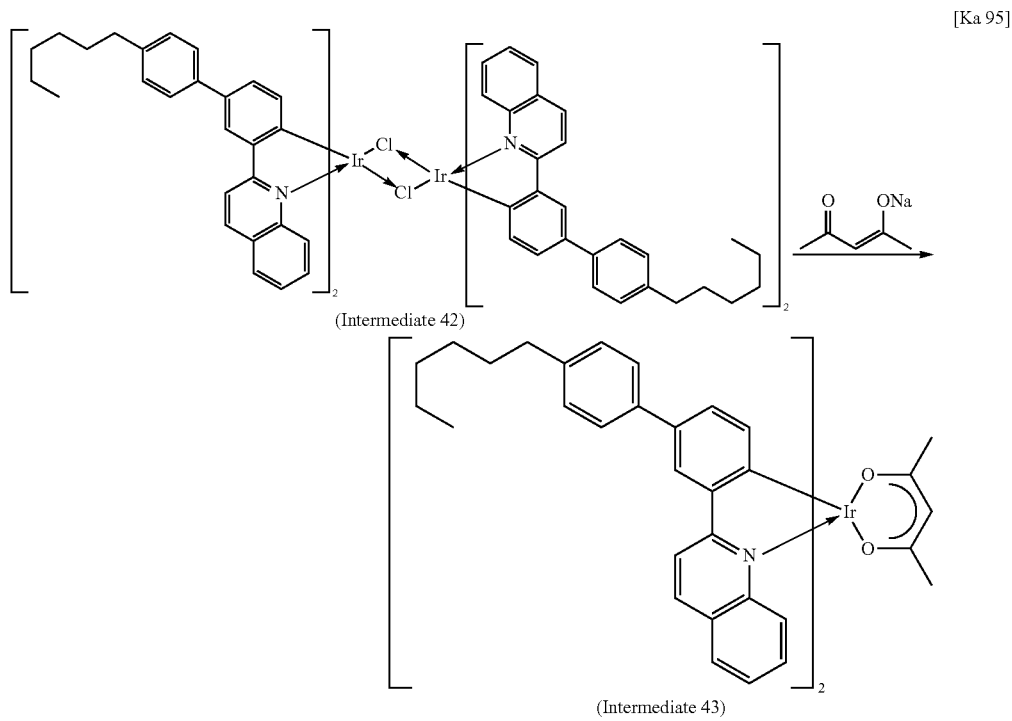

Synthesis of Compound (D-2)

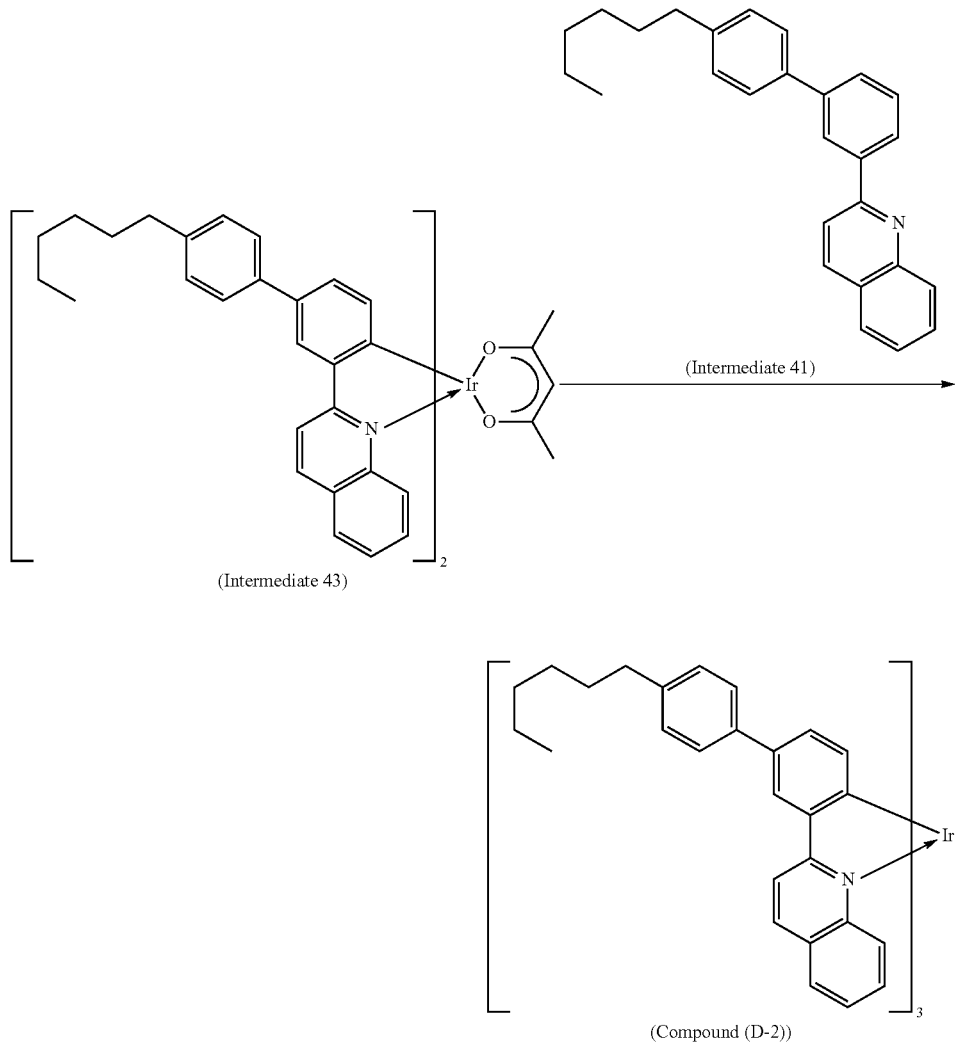

In a nitrogen atmosphere, glycerol (230 mL) was added to intermediate 43 (7.00 g, 3.56 mmol) and intermediate 41 (13.6 g, 37.2 mmol), and this mixture was stirred at 190° C. for 17 hours. Thereafter, the mixture was extracted with dichloromethane, and the organic layer was washed with saturated aqueous sodium chloride solution, dried with sodium sulfate, and then concentrated under vacuum. The residue was dissolved in dichloromethane and subjected twice to purification by basic silica gel column chromatography. The residue was dissolved in toluene and subjected to suspension washing in methanol, and the precipitate was taken out by suction filtration. Thus, compound (D-2) (2.93 g; yield, 69%) was obtained as a red solid. The results of analysis by $^1$H NMR spectroscopy are shown below.

$^1$H NMR: δ [ppm] 8.18 (d, 3H), 8.09 (d, 3H), 8.07 (d, 3H), 7.97 (s, 3H), 7.67 (d, 3H), 7.47 (d, 6H), 7.20 (t, 3H), 7.16 (d, 6H), 6.96 (d, 3H), 6.72 (t, 3H), 6.61 (d, 3H), 2.59 (t, 6H), 1.30 (m, 24H), 0.89 (t, 9H).

Examples 17 to 20

Organic electroluminescent elements were produced in the same manner as in Example 16, except that each of compounds (C-8), (C-9), (C-10), and (C-11) was used as a luminescent layer 5 in place of the compound (C-4). Properties of the elements obtained are shown in the following Table 3.

Comparative Example 8

An organic electroluminescent element was produced in the same manner as in Example 16, except that compound (H-4) was used as a luminescent layer 5 in place of the compound (C-4). Properties of the element obtained are shown in the following Table 3. Incidentally, compound (H-4) is outside the scope of the invention because the molecule thereof has two carbazolyl groups therein.

[Ka 97]

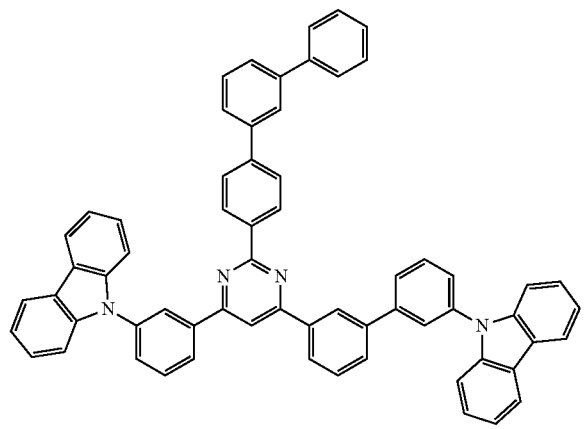

(H-4)

TABLE 3

| | Compound | Relative working life to LT$_{80}$ | Color of luminescence |
|---|---|---|---|
| Example 16 | C-4 | 4 | orange |
| Example 17 | C-8 | 10 | orange |
| Example 18 | C-9 | 3 | orange |
| Example 19 | C-10 | 10 | orange |
| Example 20 | C-11 | 4 | orange |
| Comparative Example 8 | H-4 | 1 | orange |

<Measurement of Working Life>

The working life of each organic EL element produced was measured by a method in which a constant direct current (30 mA/cm$^2$) was caused to flow through the element during the test and the element in this state was examined for change in luminance by means of a photodiode. The period required for the luminance to decrease to 80% of the luminance value measured at initiation of the test was determined. The working life is given in terms of value relative to the working life of Comparative Example 8 which was taken as 1.

It was found from Table 3 that all the elements of Examples 16 to 20 had an improved working life as compared with Comparative Example 8. Furthermore, since the compositions employing the compounds of the invention have high storage stability as shown in Table 1, the compounds of the invention and the compositions containing these compounds are considered to be exceedingly useful for efficiently producing organic electroluminescent elements using a coating liquid application process.

While the invention has been described in detail and with reference to specific embodiments thereof, it will be apparent to one skilled in the art that various changes and modifications can be made therein without departing from the spirit and scope thereof.

This application is based on a Japanese patent application filed on Apr. 7, 2011 (Application No. 2011-085501), the contents thereof being incorporated herein by reference.

INDUSTRIAL APPLICABILITY

The invention is suitable for use not only as materials for organic devices including organic electroluminescent elements but also in various fields where organic electroluminescent elements are used, such as, for example, the fields of flat panel displays (e.g., displays for OA computers, and wall-mounting TVs), light sources which take advantage of the feature of a surface light emitter (e.g., the light sources of copiers and the backlights of liquid-crystal displays or instruments), display boards, marker lamps, lighting devices, etc.

DESCRIPTION OF REFERENCE NUMERALS AND SIGNS

1 Substrate
2 Anode
3 Hole injection layer
4 Hole-transporting layer
5 Luminescent layer
6 Hole-blocking layer
7 Electron-transporting layer
8 Electron injection layer
9 Cathode

The invention claimed is:

1. An organic compound which is represented by formula (3), has a molecular weight of 750 or more and 2,000 or less, and has one or no carbazolyl group in the molecule:

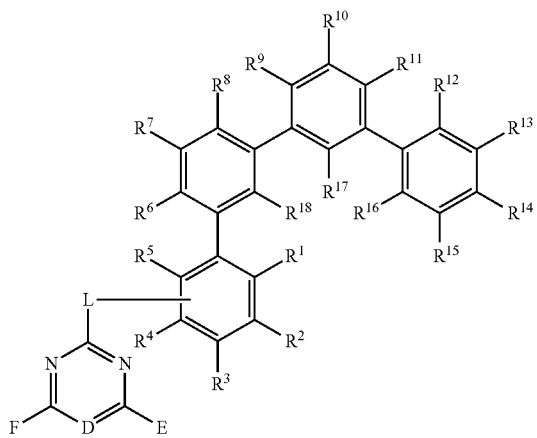

(3)

wherein

D represents CH or a nitrogen atom;
E and F each independently are selected from substituents represented by formulae (4-1) to (4-6):

$$—X^6 \quad (4\text{-}1)$$

$$—Ar^{16}—X^7 \quad (4\text{-}2)$$

$$—Ar^{17}—Ar^{18}—X^8 \quad (4\text{-}3)$$

$$—Ar^{19}—Ar^{20}—Ar^{21}—X^9 \quad (4\text{-}4)$$

$$—Ar^{22}—Ar^{23}—Ar^{24}—Ar^{25}—X^{10} \quad (4\text{-}5)$$

$$—Ar^{26}—Ar^{27}—Ar^{28}—Ar^{29}—Ar^{30}—X^{11} \quad (4\text{-}6)$$

wherein Ar$^{16}$ represents a 1,2-phenylene group or 1,3-phenylene group, which may have a substituent, Ar$^{17}$ to Ar$^{30}$ each independently represent a 1,2-phenylene group, 1,3-phenylene group, or 1,4-phenylene group, which may have a substituent, and X$^6$ to X$^{11}$ each independently represent an aromatic hydrocarbon group which may have a substituent, a carbazolyl group which may have a substituent, a dibenzofuranyl group which may have a substituent, or a dibenzothienyl group which may have a substituent,
with the proviso that E and F each contain at least one of a 1,2-phenylene group and a 1,3-phenylene group;
L represents a direct bond or a divalent aromatic hydrocarbon group which may have a substituent, and forms a bond with any one of the substitution positions of $R^1$ to $R^5$;
$R^1$ to $R^5$ each independently represent a bond with L, a hydrogen atom, a phenyl group which may have a substituent, a dibenzofuranyl group which may have a substituent, a dibenzothienyl group which may have a substituent, an alkyl group, a silyl group, a fluorine atom, or a perfluoroalkyl group; and $R^6$ to $R^{18}$ each represent a hydrogen atom, a phenyl group which may have a substituent, a dibenzofuranyl group which may have a substituent, a dibenzothienyl group which may have a substituent, an alkyl group, a silyl group, a fluorine atom, or a perfluoroalkyl group; with the proviso that when D is represented by a nitrogen atom, E and F are not the same groups.

2. The organic compound according to claim 1, wherein in formulae (4-3) to (4-6), the substituents represented by $Ar^{17}$ to $Ar^{30}$ each independently are a 1,3-phenylene group or a 1,4-phenylene group.

3. The organic compound according to claim 1, wherein in formulae (4-2) to (4-6), the substituents represented by $Ar^{16}$, $Ar^{18}$, $Ar^{21}$, $Ar^{25}$, and $Ar^{30}$ are 1,3-phenylene groups.

4. A charge-transporting material which comprises the organic compound according to claim 1.

5. A composition for organic electroluminescent element which comprises the organic compound according to claim 1 and a solvent.

6. An organic electroluminescent element which comprises an anode, a cathode, and one or more organic layers disposed between the anode and the cathode, wherein at least one of the organic layers is a layer formed from the composition for organic electroluminescent element according to claim 5.

7. The organic electroluminescent element according to claim 6, wherein the layer formed from the composition for organic electroluminescent element is a luminescent layer.

8. A display device which comprises the organic electroluminescent element according to claim 6.

9. A lighting device which comprises the organic electroluminescent element according to claim 6.

* * * * *